United States Patent
Bandman et al.

(12) 
(10) Patent No.: US 6,183,968 B1
(45) Date of Patent: Feb. 6, 2001

(54) COMPOSITION FOR THE DETECTION OF GENES ENCODING RECEPTORS AND PROTEINS ASSOCIATED WITH CELL PROLIFERATION

(75) Inventors: Olga Bandman, Mountain View; Preeti Lal, Santa Clara; Jennifer L. Hillman, Mountain View; Henry Yue; Roopa Reddy, both of Sunnyvale; Karl J. Guegler, Menlo Park; Mariah R. Baughn, San Leandro, all of CA (US)

(73) Assignee: Incyte Pharmaceuticals, Inc., Palo Alto, CA (US)

( * ) Notice: Under 35 U.S.C. 154(b), the term of this patent shall be extended for 0 days.

(21) Appl. No.: 09/276,531

(22) Filed: Mar. 25, 1999

Related U.S. Application Data

(60) Provisional application No. 60/079,677, filed on Mar. 27, 1998.

(51) Int. Cl.⁷ .................................................. C12Q 1/68
(52) U.S. Cl. ................................................ 435/6; 536/24.3
(58) Field of Search ................................. 435/6; 536/24.3

(56) References Cited

U.S. PATENT DOCUMENTS 4,358,535 * 11/1982 Falkow et al. ............................ 435/6

* cited by examiner

*Primary Examiner*—Scott W. Houtteman
(74) *Attorney, Agent, or Firm*—Incyte Genomics, Inc.; Lynn E. Murry

(57) ABSTRACT

The present invention relates to a composition comprising a plurality of polynucleotide probes. The composition can be used as hybridizable array elements in a microarray. The present invention also relates to a method for selecting polynucleotide probes for the composition.

7 Claims, No Drawings

SEQUENCE LISTING (1) GENERAL INFORMATION:

(iii) NUMBER OF SEQUENCES:134

(2) INFORMATION FOR SEQ ID NO:    1:

(i) SEQUENCE CHARACTERISTICS:
       (A) LENGTH: 1419 base pairs
       (B) TYPE: nucleic acid
       (C) STRANDEDNESS: single
       (D) TOPOLOGY: linear (vii) IMMEDIATE SOURCE:
       (A) LIBRARY: PROSTUT05
       (B) CLONE: 843193

(xi) SEQUENCE DESCRIPTION: SEQ ID NO: 1 :

```
caactggcca ggagcctctg ttacattgtg gctaaggagc tgcctgccag gggcagccat      60
tgggccaccg ctgatagtgc ctgtcctctt ggtactgcct ctgcctccct ccgctaagga     120
ggcaccttgc ctgcctgctg tcccatagtg cccagcccca gcccagccc cagctccagc     180
ccatagagga gggaggaaca ctggaagggc cctgagcacc aggggcaag gccgggaaga     240
agatgggtat gagctcagga ttccacagtt agtgcttcaa agaaatgctc atgggaccct     300
gcaggagctt tcagagtccc ccacatgctc tctggtgacc ctaactcgca gcaccatctg     360
ctctgtgccc atgtgctggg caaggggtct ttcaaggcca gtggggagga tgaggaagga     420
atctggttgt cctggctaat ggagcatgtc cttggagttc tgggggagat gacaggctct     480
ggtctaagag gtagggacag gggttctgtc cctaatgagc tgtgtgcccc gtgcacctcc     540
ttcatagaat acgaggacgg gatagaaccc tgagggctcc ttccagctcc cagagtcctg     600
attccagggg ctgtgctctg tcaataagtg tccccagcc tgggcagacc ccagtccctt     660
ctgtaaggta gacgcaaagc aaagaggtta tgaccggctc acccaggggc ctgggaaggc     720
tatggccata tgcccacttc actctgcagg acaagtggcc tgtccccact atattcacct     780
cctcacccct ctcccttgga tggaccagtg gtggtgtcac ccaaagcaaa ttgacactat     840
ttttccttg gtaaccgcaa aggggagaa tcacccgtct cctaatttta accagtacgt     900
gagggaccag ggcgccatga ccgaccagct gagcaggcgg cagatccgcg agtaccaact     960
ctacagcagg accagtggca agcacgtgca ggtcaccggg cgtcgcatct ccgccaccgc    1020
cgaggacggc aacaagtttg ccaagctcat agtggagacg gacacgtttg gcagccggt    1080
tcgcatcaaa ggggctgaga gtgagaagta catctgtatg aacaagaggg gcaagctcat    1140
cgggaagccc agcgggaaga gcaaagactg cgtgttcacg gagatcgtgc tggagaacaa    1200
ctatacggcc ttccagaacg cccggcacga gggctggttc atggccttca cgcggcaggg    1260
gcggccccgc caggcttccc gcagccgcca gaaccagcgc gaggcccact tcatcaagcg    1320
ctctaccaag gccagctgcc cttccccaac cacgcccgag aagcagaagc agttcgattt    1380
gtnggcttcc gcccccannc gccggaccaa gcgcacacg                           1419
```

(2) INFORMATION FOR SEQ ID NO:    2:

(i) SEQUENCE CHARACTERISTICS:
       (A) LENGTH: 468 base pairs
       (B) TYPE: nucleic acid
       (C) STRANDEDNESS: single
       (D) TOPOLOGY: linear (vii) IMMEDIATE SOURCE:
              (A) LIBRARY: BRAINOT12
              (B) CLONE: 1417346

(xi) SEQUENCE DESCRIPTION: SEQ ID NO: 2 :

aggacgctgt gaaatgccgt gtggttgacc ggcaggagga gggcaacggg gactcagggg      60
gctccttcca gaacggccac gcccagctca tgaccgactt cgagaaggac gtggatctgg     120
cctgtagatc agtgctgaac aaggacatcg cggcctgccg cactgccacc atcacgggca     180
cactgaagcg gccgtctctg cccgaggagg agaagctgaa gctggcccat gccaggggc      240 cgcccaccaa tttcaanagc ctgcnggcna acgtgtcnaa gntgcacntg cagggcntna     300
nccngnttat cccgggcggg cccntaccn ggaactnccn caaancantt caagtgacnc      360
nctcnaagga ngganccaag ggccccnna atnnccnnc ttnnangaac nnngtnnccc       420
gngggaantt ttnctnaaan agnaagtncn ngagnccccc ncaaacat                  468

(2) INFORMATION FOR SEQ ID NO:    3:

(i) SEQUENCE CHARACTERISTICS:
              (A) LENGTH: 2351 base pairs
              (B) TYPE: nucleic acid
              (C) STRANDEDNESS: single
              (D) TOPOLOGY: linear (vii) IMMEDIATE SOURCE:
              (A) LIBRARY: PENITUT01
              (B) CLONE: 1450775

(xi) SEQUENCE DESCRIPTION: SEQ ID NO: 3 :

GGAGCCGGAG GGGCGCACAC TTGGAGCTGA AGCCCTCTCC AGGGCTCCGG GCCGGTGCCC      60

CAACGGACAG AGGTCGAGGA GGACCCGCAG AGGTGGCAGC GGCCGGGGGC AGGAGGATGG     120

TGCAGAAGGA GAGTCAAGCG ACGTTGGAGG AGCGGGAGAG CGAGCTCAGC TCCAACCCTG     180

CCGCCTCTGC GGGGGCATCG CTGGAGCCGC CGGCAGCTCC GGCACCCGGA GAAGACAACC     240

CCGCCGGGGC TGGGGGAGCG GCGGTGGCCG GGGCTGCAGG AGGGGCTCGG CGGTTCCTCT     300

GCGGTGTGGT GGAAGGATTT TATGGAAGAC CTTGGGTTAT GGAACAGAGA AAAGAACTCT     360

TTAGAAGGCT CCAGAAATGG GAATTAAATA CATACTTGTA TGCCCCAAAA GATGACTACA     420

AACATAGGAT GTTTTGGCGA GAGATGTATT CAGTGGAGGA AGCTGAGCAA CTTATGACTC     480

TCATCTCTGC TGCACGAGAA TATGAGATAG AGTTCATCTA TGCGATCTCA CCTGGATTGG     540

ATATCACTTT TTCTAACCCC AAGGAAGTAT CCACATTGAA ACGTAAATTG GACCAGGTTT     600

CTCAGTTTGG GTGCAGATCA TTTGCTTTGC TTTTTGATGA TATAGACCAT AATATGTGTG     660

CAGCAGACAA AGAGGTATTC AGTTCTTTTG CTCATGCCCA AGTCTCCATC ACAAATGAAA     720

TCTATCAGTA CCTAGGAGAG CCAGAAACTT TCCTCTTCTG TCCCACAGAA TACTGTGGCA     780

CTTTCTGTTA TCCAAATGTG TCTCAGTCTC CATATTTAAG GACTGTGGGT GAAAAGCTTC     840

TACCTGGAAT TGAAGTGCTT TGGACAGGTC CCAAAGTTGT TTCTAAAGAA ATTCCAGTAG     900

AGTCCATCGA AGAGGTTTCT AAGATTATTA AGAGAGCTCC AGTAATCTGG GATAACATTC     960

ATGCTAATGA TTATGATCAG AAGAGACTGT TTCTGGGCCC GTACAAAGGA AGATCCACAG    1020

AACTCATCCC ACGGTTAAAA GGAGTCCTCA CTAATCCAAA TTGTGAATTT GAAGCCAACT    1080

ACGTTGCTAT CCACACCCTT GCCACCTGGT ACAAATCAAA CATGAATGGA GTGAGAAAAG    1140

ATGTAGTGAT GACTGACAGT GAAGATAGTA CTGTGTCCAT CCAGATAAAA TTAGAAAATG    1200

AAGGCAGTGA TGAAGATATT GAAACTGATG TACTCTATAG TCCACAGATG GCTCTAAAGC    1260

```
TAGCATTAAC AGAATGGTTG CAAGAGTTTG GTGTGCCTCA TCAATACAGC AGTAGGCAAG    1320

TTGCACACAG TGGAGCTAAA GCAAGTGTAG TTGATGGGAC TCCTTTAGTT GCAGCACCCT    1380

CTTTAAATGC CACAACCGTA GTAACAACAG TTTATCAGGA GCCCATTATG AGCCAGGGAG    1440

CAGCCTTGAG TGGTGAGCCT ACTACTCTGA CCAAGGAAGA AGAAAAGAAA CAGCCTGATG    1500

AAGAACCCAT GGACATGGTG GTGGAAAAAC AAGAAGAAAC GGACCACAAG AATGACAATC    1560

AAATACTGAG TGAAATTGTT GAAGCGAAAA TGGCAGAGGA ATTGAAACCA ATGGACACTG    1620

ATAAAGAGAG CATAGCTGAA TCAAAATCCC CAGAGATGTC CATGCAAGAA GATTGTATTA    1680

GTGACATTGC CCCCATGCAA ACTGATGAAC AGACAAACAA GGAGCAGTTT GTGCCAGGTC    1740

CAAATGAAAA GCCTTTGTAC ACTGCGGAAC CAGTGACCCT GGAGGATTTG CAGTTACTTG    1800

CTGATCTATT CTACCTTCCT TACGAGCATG GACCCAAAGG AGCACAGATG TTACGGGAAT    1860

TTCAATGGCT TCGAGCAAAT AGTAGTGTTG TCAGTGTCAA TTGCAAAGGA AAAGACTCTG    1920

AAAAAATTGA AGAATGGCGG TCACGAGCAG CCAAGTTTGA AGAGATGTGT GGACTAGTGA    1980

TGGGAATGTT CACTCGGCTC TCCAATTGTG CCAACAGGAC AATTCTTTAT GACATGTACT    2040

CCTATGTTTG GGATATCAAG AGTATAATGT CTATGGTGAA GTCTTTTGTA CAGTGGTTAG    2100

CGTTTGCTGC CAATTGATGG GGCAAATGAT CTCTTTTTTC AGCCACCTCC ACTGACTCCT    2160

ACCTCCAAAG TTTATACTAT CAGACCTTAT TTTCCTAAGG ATGAGGCATC CGTGTACAAG    2220

ATTTGCAGAG AAATGTATGA CGATGGAGTG GGTTTACCCT TTCAAAGTCA ACCTGATCTT    2280

ATTGGAGACA AGTTAGTAGG AGGGCTGCTT TCCCTCAGCC TGGATTACTG CTTTGTCCTA    2340

GAAGATGAAG A                                                        2351

(2) INFORMATION FOR SEQ ID NO:    4:

(i) SEQUENCE CHARACTERISTICS:
        (A) LENGTH: 887 base pairs
        (B) TYPE: nucleic acid
        (C) STRANDEDNESS: single
        (D) TOPOLOGY: linear (vii) IMMEDIATE SOURCE:
        (A) LIBRARY: LUNGTUT03
        (B) CLONE: 1472268

(xi) SEQUENCE DESCRIPTION: SEQ ID NO: 4 :

agaatttgaa ggccttaggg aatttagtct aatttgatac ttccattact gctctgcgga     60
tagccttcat tagattaatt gtaggagttt attttgttta atttttttaa atgaacttta    120
tattataaat atcacatgat taaagagaaa aatagaatat agcaaggtat aaagtaaaag    180
ggaaaagtca gcctggagac cttgtttaaa agacagattt cttcgctttt cccccaaatt    240
gtgattcagg tggcctagga atgtatctag gagtgtggag attgtaaaat tccccaggtg    300
gacttctgca tccagatttt agaatcattt tttaaatgcc ttattttaca CATGaagcaa    360
ttgaGTCCCA GAGAGGTAGA GTGATTTTTG CAAGGTGTCA TTGCAAATAA AGACAAAAC     420

TGGTGGTTCT GTTTGAGGGT GACCAGTTTG TTGGTATTTT CATTATGAGT CATTCTTTTG    480

CTTGAAACAA AATctTTGCT GATCCTTGAA CCTGGTGTTT GACAGGTGCT ATATCAATAT    540

Ttgtaannnn nnnnnnnnnn nnnnnnnnnt ccaaATACTG AAACCCAAAC CATGGACACTG   600

GTTTTCCAGA AATACTTCCT GCTATTTTAA TATATTATCA ATTAAGAAAA ACAGTTATTA    660

AAactttttg aagacctggc nnnnnnnnnn nnnnnnnnnn nnnnnnnnnn nnnnnnnnnn    720
nnnnnnnnnn nnnnnnnnnn nnnnnnnnnn nnnnnnnnnn nnnnnnnnnn nnnnnnnnnn    780
```

| | | |
|---|---|---|
| nnnnnnnnnn nnnnnnnnnn nnnnnnnnnn ngcatgtngn ccaataattc cccagctaac | 840 |
| tttgggaggg ctaaagggtn ggggataatt caccctgagg ccccaag | 887 |

(2) INFORMATION FOR SEQ ID NO: 5:

(i) SEQUENCE CHARACTERISTICS:
        (A) LENGTH: 1350 base pairs
        (B) TYPE: nucleic acid
        (C) STRANDEDNESS: single
        (D) TOPOLOGY: linear (vii) IMMEDIATE SOURCE:
        (A) LIBRARY: PANCTUT01
        (B) CLONE: 1514169

(xi) SEQUENCE DESCRIPTION: SEQ ID NO: 5 :

| | |
|---|---|
| tnaaccccac accgggttat tgttaaaatt tttttgtaaa acaggttntc ccaatgttgc | 60 |
| ccaagcttgt tatggaactc cttgccccctt aggnattctc ccaatctaag ctncccaaag | 120 |
| ttgtcgggat tnacaggtgt ggccactgca cagggccagg acaaggattc ttaatcccac | 180 |
| tccaggatgg gaaacccatg gccgagtggg aagaaaccag ctgaggtcac ATCACCAGAG | 240 |
| GAGGGAGAGT GTGGCCCCTG ACTCAGTCCA TCAGCTTGTG TAGCTGAGGT CTGGGCCAGG | 300 |
| TCTAACCAGG CTCCCCACTC CTCCCAACCT GAGCCTGCCC TCTGATCTCT GCCTGTTCCT | 360 |
| CTGTCCCACA GGGGGCaaaG GCTACGGGTC AGAGAGCGGG GAGGAGGACT TTGCTGCCTT | 420 |
| TCGAGcctgg ctgcgcTGCT ATGGCATGCC AGGCATGAGC TCCCTGCAGG ACCGGCATGG | 480 |
| CCGTACCATC TGGTTCCAGG TTGGGCCCTA CTGTTCACAC AGGCAGAGAC CCCAGGAGGC | 540 |
| TGATGGGTGG AAACGTGGGG TCACAATAAC TGGGGTGGTG ATGCTCAGGG TCTGTCTAGA | 600 |
| CCCTCCAAGG ACCACACTGT TCCTGAGGGT CACACCCCTC CCCTCCCatg cgtcccaggg | 660 |
| ttgcagctag tggaagtagc ccaaggcagg tagcccaagt gaaagtagcc aagggcagag | 720 |
| cagctttgct gatgtggact ctaacatggg ggatgtccta gaggcttcct aagggagaag | 780 |
| ctacactgat ctggatgggt gtgtgtgagt cctgcctctc caaggaatac cgcccctgtg | 840 |
| ccaacccagg ctgattcctg aattatcccc atccCATTTT AGGGGGATcc tggaccgttg | 900 |
| gcacccaaag gtaAGCTACT CCTAATGTAa taggctaaga GAGCAGAAAG GACTTcacgc | 960 |
| ctgcaAGGGC Tacagcaccc ttctccacCC TATCCCCCTG CAAcctggg agtcacCCCT | 1020 |
| GGGCAGGATA GGACCCTCCA ACTCAACAC CAGTGTCCTG CAGGGCGCAA GTCCCGCAAA | 1080 |
| AAGAAATCCA AGGCCACACA GCTGAGTCCT GAGGACAGAG TGGAGGTATG GCTGCCTGCT | 1140 |
| CCCGCCTCCT CCCCTGCACT CTGCAGCCCT GGCTGCCCCT CCCAGGCAGC TGCCTTACCC | 1200 |
| TAAGAGGGCG GGGGGAGTGG TGGGCCCTAA CCAACCTCTG AactgctTTC TGaGCCCCTC | 1260 |
| AGGGACCCGT GTCTCCTCCA TCCAGGACGC TTTGCCTCCA AGCaaggccc cttccaggac | 1320 |
| acgaaggtca aggctgacat ccttaagang | 1350 |

(2) INFORMATION FOR SEQ ID NO: 6:

(i) SEQUENCE CHARACTERISTICS:
        (A) LENGTH: 102 base pairs
        (B) TYPE: nucleic acid
        (C) STRANDEDNESS: single
        (D) TOPOLOGY: linear (vii) IMMEDIATE SOURCE:
        (A) LIBRARY: PROSTUT09
        (B) CLONE: 1647183

(xi) SEQUENCE DESCRIPTION: SEQ ID NO: 6 :

| TGGGCCTTTC TCTTCCTCAT GTTTAGTGTT TCATAAAAAT GTGTCCATAT TACTCATTTC | 60 |
| TTTCTTAAAT AGTAATATTA TGTGGAATTA GTACACTCAG CC | 102 |

(2) INFORMATION FOR SEQ ID NO:    7:

(i) SEQUENCE CHARACTERISTICS:
        (A) LENGTH: 1233 base pairs
        (B) TYPE: nucleic acid
        (C) STRANDEDNESS: single
        (D) TOPOLOGY: linear (vii) IMMEDIATE SOURCE:
        (A) LIBRARY: BRSTTUT08
        (B) CLONE: 1730180

(xi) SEQUENCE DESCRIPTION: SEQ ID NO: 7 :

| aancgggggn cccaanttgg aggcccggca aaaccggcaa aattttaaaa tttttttggaa | 60 |
| gtttttaggg ctttcaaaat ncccantttg nggggcaacc cccccagggg gncttttaa | 120 |
| acaaactttt ttaanggnct ttccccgggg gctttccggt taaatggttt tgnggtgttg | 180 |
| gncaaatttn ggtnggaaga gcagacagaa cagatagata gaagaaaaga aaagggtcac | 240 |
| ttggcactag gtcttcacag gtaaagattc agagtgtgat aggaagcaca ggctcaggca | 300 |
| CCCGGGTCTA ATCAATGACA ATCTCGCTTC TAGGCCTTTT GGTGGCATTT TCTAGTCTAC | 360 |
| CTCTAAGCTC TAGGGAATCG TGTGGCTAAA ATCTTCCCTC CTGCTGAGAC TCAGAGAATA | 420 |
| CCATGTTGGC CAAGATCTCT AAAACAATCA AACCTGGCAG TATTGAGTTA CCTTCCTCTT | 480 |
| ATCATAAAGT CTTTCCTCAC TTCCTCCTTA TTGTGAACTT TCTTAAGAAG TGAGTCCAGG | 540 |
| AGGAAGCAGT GACATGAATT TATTAACTTG ACTCAGACTT CTAAAGACAA CACAAACTGG | 600 |
| GCGCCCCATT CAGAGAGTGA CAGGGAAACC CCGTGGCATA ATTAGTTacc tACGAGTTTC | 660 |
| CAAATAGGAT TTGAAGGAG ACATACAAAC TAGGTCGCCG GCGTGGCACA TGGCTTCCCT | 720 |
| GAAGCCAGCA TTGCCCTGgc CAAGGAAGCT TTGCAGAACA GATGAGATTT CAGCTGGgac | 780 |
| tTGCAGCCAA GTGGGATTTG GCCTTTTGGG GAGAAGGGAA AGGGCATTCA AAGGCCAGGG | 840 |
| ACAGAGTATG GTCAAAGGCA TGGAGATGAG GAAGAGGGGA CCAGAGCAGA GGGTCAGGTT | 900 |
| GGAAAGCGAG TTGGGGTCAA TCTGCAAAGG GGCTGACGTG Ccaggtaaan nnnnnnnnnn | 960 |
| nnnnnnnnnn nnnnnnnnnn nnnnnnnnnn nnnnnnnnnn nnnnnnnnnn nnnnnnnnnn | 1020 |
| nnnnnnnnnn nnnnnnnnnn nnnnnnnnnn nnnnnnnnnn nnnnnnnng gctggccaat | 1080 |
| aactccagag acagctgcta atactgtgca tttaacaaat tggtgatttt aagccctggg | 1140 |
| cgacacacgt aacctagact ttgaatgttc catgggtctg caagcaatgc catgaaattg | 1200 |
| gactggccac catacccacc catgtgcntg gag | 1233 |

(2) INFORMATION FOR SEQ ID NO:    8:

(i) SEQUENCE CHARACTERISTICS:
        (A) LENGTH: 3556 base pairs
        (B) TYPE: nucleic acid
        (C) STRANDEDNESS: single
        (D) TOPOLOGY: linear (vii) IMMEDIATE SOURCE:
        (A) LIBRARY: LIVRTUT01
        (B) CLONE: 1753826

(xi) SEQUENCE DESCRIPTION: SEQ ID NO: 8 :

| cggacggtgg cggacgcgtg ggcggacgcg tgggcttgct tttgggagcc agcggtatgg | 60 |

-continued

| | |
|---|---|
| cgtcgggctg caagattggc ccgtccatcc tcaacagcga cctggccaat ttaggggccg | 120 |
| agtgcctccg gatgctagac tctggggccg attatctgca cctggacgta atggacgggc | 180 |
| attttgttcc caacatcacc tttggtcacc ctgtggtaga aagccttcga aagcagctag | 240 |
| gccaggaccc tttctttgac atgcacatga tggtgtccaa gccagaacag tgggtaaagc | 300 |
| caatggctgt agcaggagcc aatcagtaca cctttcatct cgaggctact gagaacccag | 360 |
| gggctttgat taaagacatt cgggagaatg ggatgaaggt tggccttgcc atcaaaccag | 420 |
| gaacctcagt tgagtatttg gcaccatggg ctaatcagat agatatggcc ttggttatga | 480 |
| cagtggaacc ggggtttgga gggcagAAAT TCATGGAAGA TAtgatgcca aaggttcact | 540 |
| ggttgaggac ccagttccca tctttggata tataggtccg atggtggagt aggtcctgac | 600 |
| actgtccata aatgtgcaga ggcaggagct aacatgattg tgtctggcca gtGCTATTAT | 660 |
| GAGGAgtgaa gcccccagat ctgtGATCAA TCTATTAAGA AATGTTtgct cagaagctgc | 720 |
| tcagaAACGT TCTCTTGATC GGTGAAACCA TAAGGAGCCC AGTGTTCCTG TTCATGAAAT | 780 |
| CTCCCTTTTA CTGGAAAACA GGAATATTGA CTACCAAATC ACAATGCAAT TGAAGCCGTA | 840 |
| CTGCTTTTTT GAGCAGTTAT TCATTCCAGT GATTAAAACT GATTGTGCAG AATATTCTAA | 900 |
| GAGGTCAGAA ATTGGTGTGT ATAACTACAT TTTTAGTGAT GCAATTTATT GATTAGTGAG | 960 |
| TAAGATACTG TTTTTATTGA GAGATTTGAT TTTTATAAAG TAAAAATACG GCTGCATTAG | 1020 |
| GGTTACAAAC AGAAAAGTGT CTTAATGTCT AAGGAGGGCA TATTAGCTAC ACTACAAAAA | 1080 |
| CAAATTTTGT CTGTACTTCT GAAAAGAATT TTGTTGTTTC TCAGCTGTTT TCCAAAAGCA | 1140 |
| AAGGAAGTCT TTATGGTTTT TTTCTATTTC AtgttattgT gatttgTTTA Taagtttggg | 1200 |
| tggggtgcat accatattct tggttcttaa aatctatcac ttttcacctt acacttgatg | 1260 |
| tgtgaaaact ataaaaacaa tgtgtgaaac ccaggggttc taaaatacaa gcatagattt | 1320 |
| tatcagggtg ttttgtcaaa gcaggttatt cagtgattcc tccccaccat tcttaagaac | 1380 |
| gttaaataat gctgttgtgt tagctctgag tagaaaggaa aaagtaaaac ctctgtttgg | 1440 |
| aggtaatatt gggttgaatt ctgactgccc ctttctagct ggacctttaa caaatcaccc | 1500 |
| aatcttttn cgtgtttctc taaagtcatt tatacattaa atgtaattat agcaactgtg | 1560 |
| gggttctgtt gagaattaag agctaacact atatatgtaa agtttccagt actagtccca | 1620 |
| gaatttagaa tatgctcaac acaaagtaaa cagcattata taagtttata tttttgtgag | 1680 |
| ttataaagta ctttgatata ttctcattaa atctgtaaat cacctctata agtaagtggt | 1740 |
| aataataaag cagatatttt tgtccccatt taaaaaatga agaaattaat gcttaatagg | 1800 |
| gtggtaccct ggaaaggatc tgggaagtgg tagaatttct ggtctgtact tttacaaatg | 1860 |
| gagcccttgg gagggtgggt taggtaaaag aagcttTTTA CTTAacgttg tcttattTCc | 1920 |
| aGTCTAATTT TACGCTGTAG CAGAACCAGA TGGCTGAGAA AATTCTGGAA CTATGGATCT | 1980 |
| TgacCCCAAG GATATATTAT TTTATTCCAA GAAAGATCAG GTAGGCGAAA AGATGACAGG | 2040 |
| ATACAGAGTC AATCCATAAA CTAAATATTT ATAACTGTTC TGAATTATAC AGAGTCTAAA | 2100 |
| AATATGTGTC AGCTACTTCA TTCCTGTAAA TACTCTTGCT GTGTTATAAA TATGGCAAGA | 2160 |
| AATAAACATG ACCAATATCA ATAGACTTCT TGAGGCTACT ATAAGTTTTG AGAAATAAGG | 2220 |
| TTCAAAAAAT AAGAATGCTA ACACTTAAGC ACAGACTAGA GCTTGCTTGG GTTTCTTCCT | 2280 |
| GCATTACAAG GTAAAATTT GTTAATGTTT GTTTTTATTC AGCTTGGgaA AGCTTTGTGC | 2340 |
| CATGAATACG TCGCATTTAA TAACAAGCAA CACACGGCAT ATAGAAATAA CTTTAATTAA | 2400 |
| AAAACTTACA TAGAAGATTA TAATATCAGA CGTGACAAAG ATTTGAGTTT ATTTGCCTGG | 2460 |

```
ACAACTTGGG TTTGTCTGGC TtttgTTTTC TTTTTCTTTA AAAATAAATG TACAGTAAAA      2520

CTACAAGCAA AAGTTTGTCA GTAttgaatt gaaTTTTTTA CCCCTTAAAA GGACTAGTAT      2580

AATTTCCAAT CTCTAACAAA AACTTAGTGT CAAATCTCAC AGATAAGGCC AAATGGCCAA      2640

TATTTTCAGT TATGTGGGTA GTACAACTTG AGTAACCTTT TTTACATGAC AAAAAGTGAG      2700

TTATATAAAT TGTCCTCAAC TTTCACATAG GAAAAAAATG GTTTAATAGC TTCAAAAGGA      2760

ATTTTCTTTC ATGTATACTC TTCAGTATCC AATATTGAAG CTTTGTTCTT TGAAAAATTT      2820

TAATTTCCAA TCTAGGATGC AAGCAAGAAT ATATGTTTAT TTGAATAGAG TAAGCTATGG      2880

CAAAGAATGA CCAAATTAGC TAGAAATAGA AATCAGCCAG AATTAACTAA TTTCTTGCTA      2940

ATCTAGAAAT ACAATCATCT TTTTTTTTTT TTTCAAATTT TATACTGATA GGGCTTTACT      3000

GTTTGTGGCT CATTTTAAAA CTGGTGTCTT CTCTTCATGA GACACATTAA TTGGTAAAAC      3060

TCAAATTGAG TTTTCAAAGA TGTGATAGTA TTAAAGTGCA CCAATATTTG ACTCAAATTT      3120

GCTTGCTTTA TTTTGTTAGG AGTAAACAGA AAGTAGCCTG TGTTTAGTCC CAAAGATAGC      3180

AGTGATTTTG AATAAAGGAG TTTTGTGTTG CCTGGATATA TGAATTTCTG TAAATAACTT      3240

CTGTTGGTTA AAcatgttaa aacaacaaca acaacaacaa aaaacttCTG TCTCTATATT      3300

CAGGACGTTC AGATGTCTTT TATTAGTGGA AACCTGTGTT TTATCTATTC TGCAGCTTAC      3360

ATTTCATAGG GTAGTTCATA CATGCATTTC CAAGGGGAGT GGGTCATTGC CAGTGTTTTA      3420

AAAACTACat agnnnnnnnn nnnnnnnnnn nnnnnnnnnn tatacaCACA TATTTGTATA      3480

TTCTAATATA TTACTAAGGC AATTTTAATG AATTACCATG TATATAAAAA AATAGCTGTC      3540

ACTTggcaca caggtt                                                     3556

(2) INFORMATION FOR SEQ ID NO:    9:

(i) SEQUENCE CHARACTERISTICS:
         (A) LENGTH: 774 base pairs
         (B) TYPE: nucleic acid
         (C) STRANDEDNESS: single
         (D) TOPOLOGY: linear (vii) IMMEDIATE SOURCE:
         (A) LIBRARY: MENTUNON3
         (B) CLONE: 1773002

(xi) SEQUENCE DESCRIPTION: SEQ ID NO: 9 :

tagcctacac ncncttgngn caccccccang gccttnacaa ccattcattg ccttcccnnn       60
ctcnnaatca ctcannngga aattgtggan ccgnaataac caattttcac acccggaaac      120
cacntattga cccaangatt tacngncnaa gctcctaant ccgactccnc taacagngna      180
aagctgngta acgcctgcag ggtcccggtc cggaaattcc ccgggtcgcc ccacgcgtcc      240
ggagaactac agttgtcttg agaaatgcta aaaggtactt tctttacTCT GTGTTTCTGC      300

AGCTTAAAAA CAATATTGCT Tttcatgctt TTTGGAAAAC TATTTTAACT ggatatttat      360
gaaACTCATT TTTCAAATAG AACTTGACAA AACTTTACCT CCTACATATT TGGTAATGAA      420

AGGAATAGCA GAGGCAAATt gaacaataaa aatgaAACCA AAGGTATCTT CCCAACTGTA      480

TAGTAGGCTC AAGGGTAaat gttgaaatat ctctattgga gaacagaagt taaatatatt      540
accacattTT TGGATGCTCT TGCTCTGGAC TTTTGAAAGT GAAGGTATAT AAGTCAAATA      600

ACTTCATTTC CAAGTATGTT TTATCACCTT TAGGTTCGTG ATTGCTGTCC TTGTTCAGTC      660

CCTTAAAGGT AAATACTGTa ctaattaaaa atattttgca gataatagca tgtatgaact      720
ttcagtcttt agctttttct ctagtcacat aaacaaaaaa acactgtcaa tttc           774
```

(2) INFORMATION FOR SEQ ID NO:   10:

(i) SEQUENCE CHARACTERISTICS:
        (A) LENGTH: 541 base pairs
        (B) TYPE: nucleic acid
        (C) STRANDEDNESS: single
        (D) TOPOLOGY: linear (vii) IMMEDIATE SOURCE:
        (A) LIBRARY: PROSTUT12
        (B) CLONE: 1810626

(xi) SEQUENCE DESCRIPTION: SEQ ID NO: 10 :

```
aggaaatcca aacaactgcc attgatttat tcatttattt cacaaatatt tactgaacgc    60
atccagcatg ctctgtgggg tgctgtgctg gggctggggg tgccaggatg agaaacagcc   120
gtgtggctgt gctcttggct tcaccagcca gacgagtgtt gcctttgcaa ggagaaagga   180
ctcacaaggc ttacacattt gctgccctca gttttgccct ttctcaaata aatctcacac   240
atccaatctc cttgttgccc attagggagt atataatgaa attaagtaaa tgaggaattg   300
cctaaaacta agggagtttc acctccatgt aggtagaaga atgtgaaatg ggtctgtgtc   360
cagaagccca gatcagaaat ggtccatagc aaggtgggggg nnnngttnnc ccnngnatt    420
gngggggngnt gnaaaaacnt tnntttcccn ncccttgna angggaaac cccccncca     480
aaaaaanngg tttttttttgg gggcccccccc nacnaaaann ttttcctntt gggnaaattt 540
t                                                                  541
```

(2) INFORMATION FOR SEQ ID NO:   11:

(i) SEQUENCE CHARACTERISTICS:
        (A) LENGTH: 250 base pairs
        (B) TYPE: nucleic acid
        (C) STRANDEDNESS: single
        (D) TOPOLOGY: linear (vii) IMMEDIATE SOURCE:
        (A) LIBRARY: BRAINOT09
        (B) CLONE: 2158529

(xi) SEQUENCE DESCRIPTION: SEQ ID NO: 11 :

```
AGACGGCATC ACGGACAAGA AGCTGAAGGA GCGGGCAGGG GCCTCCCTGT GGAGCTCCTG    60
CGTGGTGCTG CCGCTGCTGG CGCTGACCTG GATGTCGGCT GTGCTCGCCG TCACCGACCG   120
CCGCTCCGCC CTCTTCCAGA TCCTCTTCGC TGTCTTCGAC TCGCTGGAGG GCTTCGTCAT   180
CGTCATGGTG CACTGTATCC TCCGTAGAGA GGTCCAGGAC GCTGTGAAAT GCCGTGTGGT   240
TGACCGGCAG                                                         250
```

(2) INFORMATION FOR SEQ ID NO:   12:

(i) SEQUENCE CHARACTERISTICS:
        (A) LENGTH: 1563 base pairs
        (B) TYPE: nucleic acid
        (C) STRANDEDNESS: single
        (D) TOPOLOGY: linear (vii) IMMEDIATE SOURCE:
        (A) LIBRARY: PANCTUT02
        (B) CLONE: 2236316

(xi) SEQUENCE DESCRIPTION: SEQ ID NO: 12 :

```
ccgcgatcta gaactagtga agcttaggaa ctaaattaaa ccaagtgtgt tgaaaagctg    60
aatgcacagc agaaacttgt gactgacagt gatggaggtc agtaatctgt gtctataaaa   120
```

```
catccangca gatgtcatct cataantttc catccacagc ctctcccttg tctgtctttt      180
gctgcctgtt acaggttgta gaactcatga caggtggagc tcaaactcca gtcaccaatg      240
cgaataaaat cttctattta aatttgctgg cccaatatcg gctggccagt caagtgaaag      300
aggaggtgga acatttccta aaaggccTGA ATGAATTGGT CCCTGAGAAC CTTTTGGCTA      360

TTTTTGATGA GAATGAGCTt gaGGTAAGTG ATTGCAATTC AGACTCCCAT TCTTAACTTG      420

GCATTTTTGT AGCTTACAGG AACCAGCTTG GTGTACCTTC TCTTATGAGA TGCAGCTGGA      480

AAGCCATTTA TGCAAGAGGT GGTTTCACTT TTGTCGCTCC TCCATTCATT GACCCTTCAG      540

CCTTTAAAAA ATTAGAATGT GAAAATTAGT AGCAAAGAGT GCAGAGATAT TAGCTTAAGG      600

GATAAATAAA TGAAAGTAGc aaGTAGCTCA TTATTTATGA AGAGTAATAA TTAATACTCA      660

TTTATTCATC AAGTatcacc gtgcctggcc cagcaattag aattttaaca ctggcagtta      720
tgaataatat gaaggagagg tagatttctg agtgattctg gtttaaccag ctgggtggat      780
ggtggttcca cgtattcagg tggcaaacag gaaaaacatg tgttcgaaga agaatggagg      840
taggtggtct cttaagaatg gttaagaggc ttgggagtca gactgcttgg gtttgcatcc      900
cagctttgcc cgttttctgg ctATCaaact tgtcagCTAT TATTTGTTGA GTACGTACTA      960

TTTGATTTAT GACCACAGGC AGCTGAGCCT CAGTGTTGGT GCCTAGTGTA CAAGATTGTT     1020

AAAGAATAAA GTTATTTTGC AAAGTGTaac CCATTTTTAG CACTGACATA GCACTGACAG     1080

TAGCTGCTGA TCTCATTATG GGCTAAAATA AGACAATATT CAAAGGTCAG AGATATCTAG     1140

CCAGAATCTG ATGGAGGCTG GATTTCAGAT TTTGTTACAG AATTAGACAG AGGAACACAG     1200

AGGGGACAGG CTCAGTTAGG GTGGAGGTGT GGGGTAGGGA AGCAGGACTT GATATAAATT     1260

ATTGGAATCA TTGTCTTTTA AACCAGTGGT TTATGTCAGG GTATAGCGTT TCAAGGGATT     1320

TGAGGGTCAG ATGGGGAAAT GTAGCCCCtt taTTTTGCCA GTGTGAAGCA GATACCCTGC     1380

TTTTCTTTAC AGTAGCGGAG TCAGCTTAAG AGCTTTAAAG GTCCTAAACT TCAAAAACAT     1440

TACAGTGCCC CATCCTCCGC CTTAATGTAA TTCAAAATAC AAACAATACT AAACTGTAAA     1500

ATAAATGTAA CAAAGTCCAA TAAAGTTTTt attttttcct catgaaaang nnnngaaaaa     1560
aaa                                                                  1563

(2) INFORMATION FOR SEQ ID NO:    13:

(i) SEQUENCE CHARACTERISTICS:
        (A) LENGTH: 517 base pairs
        (B) TYPE: nucleic acid
        (C) STRANDEDNESS: single
        (D) TOPOLOGY: linear (vii) IMMEDIATE SOURCE:
         (A) LIBRARY: PANCTUT02
         (B) CLONE: 2237722

(xi) SEQUENCE DESCRIPTION: SEQ ID NO: 13 :

anaggaaccc tccggcctag aagttcagat gtcttgccaa tatatctgtg cttcacaact       60
tgcctactct ctctgacccc taacattttc acatactttt ccaattctgc ctgtcataaa      120
tttgctgctt ccccctaagt agaatgttga ttcctgtcaa acacacagcc tagccctgat      180
tcctcctctt ctctcaagca gtgatattgt caacaatgat aaacaactac tatgtactga      240
gtgttttttt atgtgctgct cacactttat acacatgtat agattcattc ttcatcatag      300 attttttcagc tagctggcat ttattagccc cactttgcat atgtaggaac acaggctcaa      360
ggaaagaaag caacttccca caatttccca ggctagtaaa agtcagagat ggaattcaag      420
```

```
cccagatcat tccaagtttg tgctcttcct gtgacacgac actgcctcag tcagggcatc    480
agagaggaag ttagaaagca gatggtgaga ggggagt                              517
```

(2) INFORMATION FOR SEQ ID NO: 14:

(i) SEQUENCE CHARACTERISTICS:
        (A) LENGTH: 1209 base pairs
        (B) TYPE: nucleic acid
        (C) STRANDEDNESS: single
        (D) TOPOLOGY: linear (vii) IMMEDIATE SOURCE:
        (A) LIBRARY: NGANNOT01
        (B) CLONE: 2314835

(xi) SEQUENCE DESCRIPTION: SEQ ID NO: 14 :

```
ctctcagCTC TGCCCATCAC ACCTCTGCCC TAAGTTGGgg ctcagttTTT GTGTCTTCCT     60

CTCCATAGCC ATCTTCTACA CTGTCTCTGG CTGATGGTCC CTTACGCTGT TGAGAAACCT    120

CCGCATCACA CCATCCACAG TCCGCAGTGT TCTAGAATTA GCTGGGGGA GTTGGAAGTG    180

GGCCCGGTGC CAGGGCAGGG GTGGGGCTGG TCCCGCTGAT GGGGCCTTCG CTCCTACCCT    240

CCTCAGCTGA GTGATGAACT GAAGCAGCAC TTGAACCGGA CTCTGGCTGA GAACTACGGG    300

CAGCCCGGAG CCACGCAGAT CACCGCCTCA GTGGACCGAC TCCAGCAgga tttcaagtgc    360
tgcggaagaa cagctcagcc gactggcagc acagcacgta catcctgttg cgggaggccg    420
agggccgcca ggtgcccgac agctgctgca agacagtggt ggcgcgctgc ggccagcggg    480 cccaccccte caacatctat aaggtggagg gaggctgcct caccaagctg gagcagttcc    540
tggCCGACCA CCTGCTGCTT ATGGGGGCAG TGGGCATCGG GGTGGCCTGC CTGCAGATCT    600

GCGGGATGGT TCTCACCTGC TGCTTGCACC AGAGGCTCCA GCGGCATTTT TACTAATGGC    660

CAACCACCTC CTCTTCCAAC TGCCCCTCAA GACAACATGT GGCCACATGC CATCTGCAAG    720

GCctgccaga gttAGCACCA GCTCCACTAG GGCCATAGAT GCCCCCTCCT TTGTGCCTAG    780

CTCCTGCGAA TCCACCGAGT GCCTGAGACC ATAGCTTCTA CTGTGCCCAC CCAGGCAGAG    840

ACCctcggcc ccctctcctc catTTCTGAG CCCCCATGGC CAGATCCTGG GCAGGGAAAT    900

GATCCTTTCA GGagacaACC AGAGCCCctc accaggaacg ggggcacccg tggactacgg    960
gagggtggcg gttgggttct ctgctccctc ccagctcctg aacctggaac aatcggcaga   1020
aaacccagga accccggcac tcctgcattc agcacgggat tccccaccc atgcccagaa    1080 gccctgacct tgctgtttct ggaaaaagca tggggtgggg cagggaggct ggcatttccc   1140
ccagaagacc ttgcccttttn cctgcccact ctccacactc ctcacctcna nnnnntaata   1200 aaatcatnc                                                            1209
```

(2) INFORMATION FOR SEQ ID NO: 15:

(i) SEQUENCE CHARACTERISTICS:
        (A) LENGTH: 556 base pairs
        (B) TYPE: nucleic acid
        (C) STRANDEDNESS: single
        (D) TOPOLOGY: linear (vii) IMMEDIATE SOURCE:
        (A) LIBRARY: BRAITUT21
        (B) CLONE: 2519631

(xi) SEQUENCE DESCRIPTION: SEQ ID NO: 15 :

```
aggcgagtgg agcggaggac ccgagcggct gaggagagag gaggcggcgg cttagctgct     60
```

-continued

| | |
|---|---|
| acggggtccg gccggcgccc tcccgagggg ggctcaggag gaggaaggag gacccgtgcg | 120 |
| agaatgcctc tgccctggag ccttgcgctc ccgctgctgc tctcctgggt ggcaggtggt | 180 |
| ttcgggaacg cggccagtgc aaggcatcac gggttgttag catcggcacg tcagcctggg | 240 |
| gtctgtcact atggaactaa actggcctgc tgctacggct ggagaagaaa cagcaaggga | 300 |
| gtctgtgaag ctacatgcga acctggatgt aagtttggtg agtgcgtggg accaaacaaa | 360 |
| tgcagatgct ttccaggata caccgggaaa acctgcagtc aagatgtgaa tgagtgtgga | 420 |
| atgaaacccc gggcccatgc caacacagat gtgtgaatac acacggaagc tacaagtggc | 480 |
| ttttttgggc cccctttttnc cccatgcaat ctatgcaatg ctactgttga ctctagacat | 540 |
| gtgcatgata aactgt | 556 |

(2) INFORMATION FOR SEQ ID NO: 16:

(i) SEQUENCE CHARACTERISTICS:
        (A) LENGTH: 4245 base pairs
        (B) TYPE: nucleic acid
        (C) STRANDEDNESS: single
        (D) TOPOLOGY: linear (vii) IMMEDIATE SOURCE:
        (A) LIBRARY: BRAITUT21
        (B) CLONE: 2526432

(xi) SEQUENCE DESCRIPTION: SEQ ID NO: 16 :

| | |
|---|---|
| gggnccccg actngaaaag cggcaattna gngaaccgca ntttantgtg aggtagctca | 60 |
| ntcagtaagc accncaaggg tttacacttn tttcctccgg gctggccggc cagcgagtac | 120 |
| gactacgtga gcttccagtc ggacatcggc ccgtaccaga gcgggcgctt ctacaccaag | 180 |
| ccacctcagt gcgtggacat ccccgcggac ctgcggctgt gccacaacgt gggctacaag | 240 |
| aagatgGTGC TGCCCAACCT GCTGGAGCAC GAGACCATGG CGGAGGTGAA GCAGCAGGCC | 300 |
| AGCAGCTGGG TGCCCCTGCT CAACAAGAAC TGCCACGCCG GCACCCAGGT CTTCCTCTGC | 360 |
| TCGCTCTTCG CGCCCGTCTG CCTGGACCGG CCCATCTACC CGTGTCGCTg gctCTGCGAG | 420 |
| GCCGTGCGCG ACTCGTGCGA GCCGGTCATG CAGTTCTTCG GCTTCTACTG GCCCGAGATG | 480 |
| CTTAAGTGTG ACAAGTTCCC CGAGGGGGAC GTCTGCATCG CCATGACGCC GCCCAATGCC | 540 |
| ACCGAAGCCT CCAAGCCCCA AGGCACAACG GTGTGTCCTC CCTGTGACAA CGAGTTGAAA | 600 |
| TCTGAGGCCA TCATTGAACA TCTCTGTGCC AGCGAGTTTG CACTGAGGAT GAAAATAAAA | 660 |
| Gaagtgaaaa aagaaaatgg cgacaagaag attgtcccca agaagaagaa gccCCTGAAG | 720 |
| TTGGGGCCCA TCAAGAAGAA GGACCTGAAG AAGCTTGTGC TGTACCTGAA GAATGGGGCT | 780 |
| GACTGTCCCT GCCACCAGCT GGACAACCTC AGCCACCACT TCCTCATCAT GGGCCgcaag | 840 |
| gtgaaGAGCC AGTACTTGCT GACGGCCATC CACAAGTGGG ACAAGAAAAA CAAGGAGTTC | 900 |
| AAAAACTTca tgaagaaaat gaaaaaccat gagtgcccca cctttcagtc cgtgtttaag | 960 |
| tgattctccc ggggcaggg tgggaggga gcctcgggtg gggtactaac ggtgtggaca | 1020 |
| gtgcccggg aacccgtgg gtcacacaca cgcactgcgc ctgtcagtag tggacattgt | 1080 |
| aatccagtcg gcttgttctt gcagcattcc cgctcccttc cctcgcatag ccacgctcca | 1140 |
| aaccccaggg tagccatggc cgggtaaagc aagggccatt tagattagga aggttttaa | 1200 |
| gatccgcaat gtggagcagc agccactgca caggaggagg tgacaaacca tttccaacag | 1260 |
| caacacagcc actaaaacac aaaaaggggg attgggcgga aagtgagagc cagcagcaaa | 1320 |
| aactacattt tgcaacttgT TGGTGTGGAT CTATTGGCTG ATCTATGCCT TTCAACTAGA | 1380 |

-continued

| | | |
|---|---|---|
| AAATTCTAAT GATTGGCAAG TCACGTTGTT TTCAGGTCCA GAGTAGTTTC TTTCTGTCTG | 1440 |
| CTTTAAATGG AAACAGACTC ATACCACACT TACAATTAAG GTCAAGCCCA GAAAGTGATA | 1500 |
| AGTGCAGGGA GGAAAAGTGC AAGTCCATTA TGTAATAGTG ACAGCAAAGG GACCAGGGGA | 1560 |
| GAGGCATTGC CTTCTCTGCC CACAGTCTTT CCGTGTGATT GTCTTTGAAT CTGAATCAGC | 1620 |
| CAGTCTCAGA TGCCCCAAAG TTTCGGTTCC TATGAGCCCG GGGCATGATC TGATCCCCAA | 1680 |
| GACATGTGGA GGGGCAGCCT GTGCCTGCCT TTGTGTCAGA AAAAGGAAAC CACAGTGAGC | 1740 |
| CTGAGAGAGA CGGCGATTTT CGGGCTGAGA AGGCAGTAGT TTTCAAAACA CATAGTTAAA | 1800 |
| Aaagaaacaa atgaaaaaaa ttttagaaca gtccagcaaa ttgctagtca gggtgaattg | 1860 |
| tgaaattggg tgaagagctt aggattctaa tctcatgttt tttccttttc acatttttaa | 1920 |
| aagaacaatg acaaacaccc acttattttt caaggtttta aaacagtcta cattgagcat | 1980 |
| ttgaaaggcg tgctagaaca aggtctcctg atccgtccga ggctgcttcc cagaggagca | 2040 |
| gctctcccca ggcatttgcc aagggaggcg gatttccctg gtagtgtagc tgtgtggctt | 2100 |
| tccttcctga agagtccgtg ggttgcccta gaacctaaca cccccctagca aaactcacag | 2160 |
| agctttccgt ttttttcttt cctgtaaaga aacatttcct ttgaacttga ttgcctatgg | 2220 |
| atcaaagaaa ttcagaacag cctgcctgtc ccccgcact ttttacatat atttgtttca | 2280 |
| tttctgcaga tggaaagttg acatgggtgg ggtgtcccca tccagcgaga gagtttcaaa | 2340 |
| agcaaaacat ctctgcagtt tttcccaagt accctgagat acttcccaaa gcccttatgt | 2400 |
| ttaatcagcg atgtatataa gccagttcac ttagacaact ttacccttct tgtccaatgt | 2460 |
| acaggaagta gttctaaaaa aaatgcatat taatttcttc ccccaaagcc ggattcttaa | 2520 |
| ttctctgcaa cactttgagg acatttatga ttgtccctct gggccaatgc ttatacccag | 2580 |
| tgaggatgct gcagtgaggc tgtaaagtgg gcccccctgcg gccctagcct gacccggagg | 2640 |
| aaaggatggt agattctgtt aactcttgaa gactccagta tgaaaatcag catgcccgcc | 2700 |
| tagttaccta ccggagagtt atcctgataa attaacctct cacagttagt gatcctgtcc | 2760 |
| ttttaacacc ttttttgtgg ggttctctct gacctttcat cgtaaagtgc tggggacctt | 2820 |
| aagtgatttg cctgtaattt tggatgatta aaaaatgtgt atatatatta gctaattaga | 2880 |
| aatattctac ttctctgttg tcaaactgaa attcagagca agttcctgag tgcgtggatc | 2940 |
| tgggtcttag ttctggttga ttcactcaag agttcagtgc tcatacgtat ctgctcattt | 3000 |
| tgacaaagtg cctcatgcaa ccgggccctc tctctgcggc agagtcctta gtggagggt | 3060 |
| ttacctggaa cattagtagt taccacagaa tacggaagag caggtgactg tgctgtgcag | 3120 |
| ctctctaaat gggaattctc aggtaggaag caacagcttc agaaagagct caaaataaat | 3180 |
| tggaaatgtg aatcgcagct gtgggtttta ccaccgtctg tctcagagtc ccaggaccct | 3240 |
| tgagtgtcat tagttacttt attgaaggtt ttagacccat agcagctttg tctctgtcac | 3300 |
| atcagcaatt tcagaaccaa aagggaggct ctctgtaggc acagagctgc actatcacga | 3360 |
| gcctttgttt ttctccacaa agtatctaac aaaaccaatg tgcagactga ttggcctggt | 3420 |
| cattggtctc cgagagagga ggtttgcctg tgatttccta attatcgcta gggccaaGGT | 3480 |
| GGGATTTGTA AAGCTTTACa gtAATCATTC TGGATAGAGT CCTGGGAGGT CCTTGGCAGA | 3540 |
| ACTCAGTTAA atCTTTGAAG AataTTTGTA GTTatcttag AAGATAGCAT GGGAGGTGAG | 3600 |
| GATTCCAAAA ACATTTTATT TTTAAAATAT CCTGTGTAAC ACTTGGCTCt tgTACCTGT | 3660 |
| GGGTTAGCAT CAAGTTCTCC CCAGGGTAGA ATTCAATCAG AGCTCCAGTT TGCATTTGGA | 3720 |
| TGTGTAAATT ACAGTAATCC CATTTCCCAA ACCTAAAATC TGTTTTTCTC ATCAGACTCT | 3780 |

```
GAGTAACTGG TTGCTGTGTC ATAACTTCAT AGATGCAGGA GGCTCAGGTG ATCTGTTTGA      3840

GGAGAGCACC CTAGGCAGCC TGCAGGGAAT AACATACTGG CCGTTCTGAC CTGTTGCCAG      3900

CAGATACACA GGACATGGAT GAAATTCCCG TTTCCTCTAG TTTCTTCCTG TAGTACTCCT      3960

CTTTTAGATC CTAAGTCTCT TACAAAAGCT TTGAATACTG TGAAAATGTT TTACATTCCA      4020

TTTCATTTGT GTTGTTTTTT TAACTGCATT TTACCAGATG TTTTGAtgtt atcgcttATG      4080

TTAATAGTAA TTCCCGtatg tgttcatttt attttcatgc tttttcagcC ATGTatcaat      4140
attcacttga ctaaaatcac tcaattaatc caaaaaanan angnnnnnnn nnnnnnnnn      4200 nannnaanna nngggnaaa annaannggg gggcgcccca nanta                      4245

(2) INFORMATION FOR SEQ ID NO:    17:

(i) SEQUENCE CHARACTERISTICS:
          (A) LENGTH: 50 base pairs
          (B) TYPE: nucleic acid
          (C) STRANDEDNESS: single
          (D) TOPOLOGY: linear (vii) IMMEDIATE SOURCE:
          (A) LIBRARY: BRSTTUT14
          (B) CLONE: 2742507

(xi) SEQUENCE DESCRIPTION: SEQ ID NO: 17 :

CCTAATTAGT TAATGTAATC ACATGGTTCA AAGAGTATA TATAGTCAAA                  50

(2) INFORMATION FOR SEQ ID NO:    18:

(i) SEQUENCE CHARACTERISTICS:
          (A) LENGTH: 1464 base pairs
          (B) TYPE: nucleic acid
          (C) STRANDEDNESS: single
          (D) TOPOLOGY: linear (vii) IMMEDIATE SOURCE:
          (A) LIBRARY: UTRSTUT05
          (B) CLONE: 2883288

(xi) SEQUENCE DESCRIPTION: SEQ ID NO: 18 :

gnaaaccnct tntccccgng gcgttggccc gattcattna atgcagntgg cacgaacagg       60
tttccccgnc tggaaangcg ggccagttga gcgcaancgc aaattaattg tgagttngcn      120
nnnnnnnnnn nnnnnnnnnn nnagatttgg tgcgtggtga atttcttcag ctcgggtcaa      180
aagaaaatga gaatgaaaga tttgcacact accttgaaga gacattcaag aagaccgcca      240
gcctgatagc caacagtTGT AAAGCAGTAT GTCTCTGTTC TAGGATGTCC CGACCCAGTG      300

GTGCATGAGA TCGCCTATCA GTACGGAAAA AATGTAGGAA TAGCTTTTCA GCTAATAGAT      360

GATGTATTGG ACTTCACCTC GTGTTCTGAC CAGATGGGCA AACCAACATC AGCTGATCTG      420

AAGCTCGGGT TAGCCACTGG TCCTGTCCTG TTTGCCTGTC AGCAGTTCCC AGAAATGAAT      480

GCTATGATCA TGCGACGGTT CAGTTTGCCT GGAGATGTAG ACAGAGCTCG ACAGTATGTA      540

CTACAGAGTG ATGGTGTGCA ACAAACAACC TACCTCGCCC AGCAGTACTG CCATGAAGCA      600

ATAAGAGAGA TCAGTAAACT TCGACCATCC CCAGAAAGAG ATGCCCTCAT TCAGCTTTCA      660

GAAATTGTAC TCAAGAGA TAAATGACAA CTCTTTCTGT TCTTTCTGGC AGCTATCTTA      720

CCAGACTGTG CCTAAAGAAT TTTGTGGAAT ACACTTTGTT TGCTTCATGT GCAGATAACC      780

AAAAATCATT TTAAAGATA TCAAACTTAT TGATGGGCAA TTTATTTTTT TTTATTGCAA      840

AAGTTTTTTC AGAAAACTTT TTAAATGTAA TTAATAAACC ACCtgAATCT GTCATTCTAG      900
```

-continued

| | |
|---|---|
| TCCTATAAAT TATAATcaAG GTATCTTGAT GGTTATATGT GGTATTGTTT ACACTGTTAA | 960 |
| TATCCACATG TAAGGCCATT ACACAAATAA ATAACCAATG TTAAAATTCA AATGGTTTGT | 1020 |
| CTTGATTTAC cgtaggagta AAGGTCAGAA AAATGTGAag tctgcattga agtccacatg | 1080 |
| agTTATATTT TAACAGTatc caaaatttca tataggagaa tggtttatta taaaagactg | 1140 |
| tacataaaat ttagacaaca ggttatattc aanttagggg gngcaatcca cttgnaaaaa | 1200 |
| aggggaaagt tgtatnggga nctancntgn tccccnaatg ganacctttg nntggttgtt | 1260 |
| aaaannttn cncnaggggg nnantnttgg cctnntngan anntggctcc nccattggnn | 1320 |
| nttgnggnnc gcaaaaaang gggtcnttgn ntttttncn nnaaanaana ctgntttng | 1380 |
| ccnctngttc ttncncgttc ccantgtnnc ngtttnaaan ctctagntng cccnccggn | 1440 |
| gtacnatgnn gttgtnagtt tggt | 1464 |

(2) INFORMATION FOR SEQ ID NO: 19:

(i) SEQUENCE CHARACTERISTICS:
        (A) LENGTH: 1992 base pairs
        (B) TYPE: nucleic acid
        (C) STRANDEDNESS: single
        (D) TOPOLOGY: linear (vii) IMMEDIATE SOURCE:
        (A) LIBRARY: KIDNFET01
        (B) CLONE: 2952523

(xi) SEQUENCE DESCRIPTION: SEQ ID NO: 19 :

| | |
|---|---|
| GCTGAGCAAG GGCGTGTGCA CCATGACGGC TGCCTTCCTG CACTTCTTCT TTCTCTCCTC | 60 |
| CTTTTGCTGG GTGCTTACCG AGGCCTGGCA GTCCTACCTG GCTGTCATTG GGCGGATGCG | 120 |
| CACCCGCCTC GTTCGCAAGC GCTTCCTCTG CCTGGGCTGG GGTCTGCCTG CCCTGGTGGT | 180 |
| GGCCGTGTCT GTTGGCTTTA CCCGAACGAA AGGATACGGT ACATCCAGCT ACTGCTGGCT | 240 |
| CTCCCTGGAG GGCGGCCTGC TCTACGCCTT TGTGGGCCCT GCAGCCGTCA TTGTCCTGGT | 300 |
| GAACATGCTC ATCGGAATCA TCGTCTTCAA CAAGCTCATG GCACGTGATG CATCTCCGA | 360 |
| CAAATCCAAG AAGCAGAGGG CCGGGGCCTC ACTCTGGAGC TCCTGCGTGG TGCTGCCCCT | 420 |
| GCTGGCGCTC ACCTGGATGT CTGCCGTCCT GGCTATGACA GACCGCCGTT CCGTCCTCTT | 480 |
| CCAGGCCCTC TTTGCTGTCT TCAACTCCGC GCAGGGCTTT GTCATCACTG CTGTGCACTG | 540 |
| CTTCCTGCGC CGAGAGGTCC AGGATGTGGT GAAGTGCCAG ATGGGGGTGT GCCGGGCTGA | 600 |
| TGAGAGCGAA GACTCCCCTG ACTCGTGTAA GAACGGGCAG CTGCAGATCC TGTCAGACTT | 660 |
| TGAAAAGGAT GTGGATCTGG CTTGTCAAAC AGTGCTGTTC AAGGAGGTCA ACACTTGCAA | 720 |
| CCCGTCCACC ATCACGGGCA CACTATCCCG CCTGTCCCTG GATGAGGATG AGGAGCCCAA | 780 |
| GTCCTGCCTC GTGGGCCCTG AGGGCAGCCT CAGCTTCTCA CCACTGCCTG GAATATCCT | 840 |
| GGTGCCCATG GCAGCCTCAC CAGGGCTGGG GGAGCCTCCG CCCCCACAGG AGGCCAACCC | 900 |
| TGTTTACATG TGTGGGGAGG GTGGCCTGCG GCAGCTGGAC CTCACATGGC TGCGGCCCAC | 960 |
| TGAGCCAGGC TCTGAGGGAG ACTACATGGT GCTGCCCCGG CGGACTTTGA GCCTGCAGCC | 1020 |
| TGGCGGTGGG GGTGGAGGTG GTGAGGATGC CCCCAGGGCC CGGCCGGAGG GGACCCCCCG | 1080 |
| GCGAGCTGCC AAGACAGTGG CCCACACTGA AGGCTACCCC AGCTTCCTGT CCGTGGACCA | 1140 |
| CTCGGGCCTG GGGCTGGGCC CTGCCTATGG ATCTCTCCAG AATCCCTATG GAATGACCTT | 1200 |
| CCAACCGCCA CCGCCGACAC CCAGCGCCCG CCAAGTGCCC GAGCCAGGGG AGCGCACCGG | 1260 |
| GACCATGCCT CGCACCGTGC CCGGCTCTAC CATGAAGATG GGCTCCCTGG AGCGAAAGAA | 1320 |

```
ATTACGGTAT TCAGACCTGG ACTTTGAGAA GGTGATGCAC ACCCGGAAAC GGCATTCAGA    1380

ACTCTACCAC GAGCTCAACC AGAAGTTCCA CACTTTCGAC CGCTACCGCA GCCAGTCCAC    1440

GGCCAAGAGG GAGAAGCGGT GGAGTGTGTC CTCGGGTGGG GCGGCCGAGC GGAGCGTGTG    1500

CACCGATAAG CCCAGCCCTG GGGAGCGCCC CAGCTTGTCC AACATCGGC GCCATCAGAG    1560

CTGGAGCACC TTCAAATCTA TGACACTGGG CTCGCTGCCC CCCAAGCCCC GAGAACGGCT    1620

GACTCTGCAC CGGGCAGCAG CCTGGGAGCC CACAGAACCA CCGGATGGTG ACTTCCAGAC    1680

AGAGGTGTGA GTGCCACGCT GGACTGCCCA CTGCATATAA ATATATATAT CTCTCTATTT    1740

TCACACTCCA CTTTGGAACT ACCCAGGAGC CAGCGCCCTC TCCCCTCTCC CGAGGGCTGG    1800

GCAGGGAGGC GCCGTGGACT CAGCCAGGCT GGGGGAGCCG GACATGGCTT GGCCTGGGGT    1860

CCCAGGGCCC TTCCTTGTTT CTCAGAGGCC CCTCAGCCAC TGGAACCCCA TCTTCAGCCC    1920

AGCCTGTCCG TCCCTGTCCC GGGCTGGGGA GGGGGGAGGG GAACTTTGTT GGGAATAAAC    1980

TTCACTCTGT GG                                                        1992
```

(2) INFORMATION FOR SEQ ID NO:   20:

(i) SEQUENCE CHARACTERISTICS:
        (A) LENGTH: 796 base pairs
        (B) TYPE: nucleic acid
        (C) STRANDEDNESS: single
        (D) TOPOLOGY: linear (vii) IMMEDIATE SOURCE:
        (A) LIBRARY: THYMNON04
        (B) CLONE: 3190833

(xi) SEQUENCE DESCRIPTION: SEQ ID NO: 20 :

```
ggcggggccc ccaccttttc tgacatcagc gctgccttgg tccctcttcc cgagccgggg     60
atggtcgcag tcttcgtgtg cccagggacc ctgcagaagg tgctggagcc cacctcgaca    120
cacgagtcag agcaccagtc tggcgcatgg tgcaaggacc cgctgcaggc ggtgaccgca    180
tctacgtgat gccctggatc ccctaccgca cggacacact gactgagtat gcctcgtggg    240
aggactacgt ggccgcccgc cacaccacca cctaccgcct gcccaaccgc gtggatggca    300 caggcttttgt ggtctacgat ggtgccgtct tctacaacaa ggagcgcacg cgcaacatcg    360
tcaagtatga cctacggacg cgcatcaaga gcggggagac ggtcatcaat accgccaact    420
accatgacac ctcgccctac cgctggggcg gaaagaccga cattgacctg gcggtggaac    480
gagaacgggc tgtgggtcat ctacgccact gagggcaaca acgggcggct ggtggtgagc    540
cagctgaacc cctacacact gcgctttgag ggcagtggga gacgggttac gacaagcgct    600
cggaatccaa cgccttcatg gtgtgtgggg tcctgtacgt ctgcgttccg tgtagtggan    660
gatgacacgg agcggctggc aaccgcgnng gaattatgnc cnttnaagan ncaattgccc    720
aacccgnnnn gaagctngnn aagccnnaac tttcnccaaa cccctaagc aattnnaact    780 tccntcgggt naanna                                                    796
```

(2) INFORMATION FOR SEQ ID NO:   21:

(i) SEQUENCE CHARACTERISTICS:
        (A) LENGTH: 2101 base pairs
        (B) TYPE: nucleic acid
        (C) STRANDEDNESS: single
        (D) TOPOLOGY: linear (vii) IMMEDIATE SOURCE:
        (A) LIBRARY: BRAINOT19
        (B) CLONE: 3245612

(xi) SEQUENCE DESCRIPTION: SEQ ID NO: 21 :

```
angctgagca agggcgtgtg caccatgacg gctgccttcc tgcacttctt ctttctctcc      60
tccttttgct gggtgcttac cgaggcctgg cagtcctacc tggctgtcat tgggcggatg     120
cgcacccgcc tcgttcgcaa gcgcttcctc tgcctgggct ggggtctgcc tgccctggtg     180
gtggccgtgt ctgttggctt tacccgaacg aaaggatacg gtacatccag ctactgctgg     240
ctctccctgg agggcggcct gctctacgcc tttgtgggcc ctgcagccgt cattgtcctg     300
gtgaacatgc tcatcggaat catcgtcttc aacaagctca tggcacgtga tggcatctcc     360
gacaaatcca agaagcagag ggccgggtcg gagcggtgcc cctgggccag cctgctcctc     420
ccctggctca gcgtgtggag cggtccccag ccccctgctc agctcagcct cggccaggaa     480
cgccatggcc tcactctgga gctcctgcgt ggtgctgccc ctgctggcgc tcacctggat     540
gtctgccgtc ctggctatga cagaccgccg ttccgtcctc ttccaggccc tctttgctgt     600
cttcaactcc gcgcagggct ttgtcatcac tgctgtgcac tgcttcctgc gccgagaggt     660
ccaggatgtg gtgaagtgcc agatgggggt gtgccgggct gatgagagcg aagactcccc     720
tgactcgtgt aagaacgggc agctgcagat cctgtcagac tttgaaaagg atgtggatct     780
ggcttgtcaa acagtgctgt tcaaggaggt caacacttgc aacccgtcca ccatcacggg     840
cacactatcc cgcctgtccc tggatgagga tgaggagccc aagtcctgcc tcgtgggccc     900
tgagggcagc ctcagcttct caccactgcc tgggaatatc ctggtgccca tggcagcctc     960
accagggctg ggggagcctc cgcccccaca ggaggccaac cctgtttaca tgtgtgggga    1020
gggtggcctg cggcagctgg acctcacatg gctgcggccc actgagccag gctctgaggg    1080
agactacatg gtgctgcccc ggcggacttt gagcctgcag cctggcggtg ggggtggagg    1140
tggtgaggat gccccagggg cccggccgga ggggaccccc cggcgagctg ccaagacagt    1200
ggcccacact gaaggctacc ccagcttcct gtccgtggac cactcgggcc tggggctggg    1260
ccctgcctat ggatctctcc agaatcccta tggaatgacc ttccaaccgc caccgccgac    1320
acccagcgcc cgccaagtgc ccgagccagg ggagcgcacc gggaccatgc ctcgcaccgt    1380
gcccggctct accatgaaga tgggctccct ggagcgaaag aaattacggt attcagacct    1440
ggactttgag aaggtgatGC ACACCCGGAA ACGGCATTCA GAACTCTACC ACGAGCTCAA    1500
CCAGAAGTTC CACACTTTCG ACcgctACCG CAGCCAGTCC ACGGCCAAGA GGGAGAAGCG    1560
GTGGAGTGTG TCCTCGGGTG GGCggCCga gcggagcgtg tgcaCCGATA AGCCCAGCCC    1620
TGGGGAGCGC CCCAGCTTGT CCCAACATCG GCGCCATCAG AGCTGGAGCA CCTTCAAATC    1680
TATGACACTG GgctcgctGC CCCccaAGCC CCGAGAACGG CTGACTCTGC ACCGGgcaGC    1740
AGCCTGGGAG CCCACAGAAC CACCGGATGG TGACTTCCAG ACAGAGGTGT GAGTGCCACG    1800
CTGGACTGCC CACTGCATAT AAATATATAT ATCTCTCTAT TTTCACACTC CACTTTGGAA    1860
CTACCCAGGA GCCAGCGCCC TCTCCCCTCT CCCGAGGGCT GGGCAGGGAG GCGCCGTGGA    1920
CTCAGCCAGG CTGGGGAGC CGGACATGGC TTGGCCTGGG GTCCCAGGGC CCTTCCTTGT     1980
TTCTCAGAGG CCCCTCAGCC ACTGGAACCC CATCTTCAGC CCAGCCTGTC CGTCCCTGTC    2040
CCGGGCTGGG GAGGGGGGAG GGGAACTTTG TTGGGAATAA ACTTCACtct gtggaaaaaa    2100
a                                                                   2101
```

(2) INFORMATION FOR SEQ ID NO:    22:

(i) SEQUENCE CHARACTERISTICS:

(A) LENGTH: 2138 base pairs
(B) TYPE: nucleic acid
(C) STRANDEDNESS: single
(D) TOPOLOGY: linear (vii) IMMEDIATE SOURCE:
(A) LIBRARY: BRAINOT20
(B) CLONE: 3270974

(xi) SEQUENCE DESCRIPTION: SEQ ID NO: 22 :

```
aatttnaacc ncccccaggna aaagggnggn ccttcaaaag cggnttttaa cccctnaaaa      60
ttgtgcccna aatgtgggggg tcgactctag aggatccccc tttgtcagcc accaccgcca     120
gtaacgccat ggcgtctctt tggagctcct gtgtggtgtt gcccttctg gctttgacgt      180
gGATGTCTGC GGTTCTGGCC ATGACAGATa gaCGCTCCAT ATTGTTTCAA ATACTTTTTG     240
CTGTGTTTGA TTCATTGCAA GGCTTTGTTA TAGTCATGGT CCACTGCATT CTTCGGAGAG     300
AGGTTCAGGA TGCATTTAGA TGCCGATTGA GAAACTGTCA GGATCCCATC AATGCAGATT     360
CTTCGAGTTC GTTTCCTAAt agGCATGCTC AAATCATGAC AGACTTTGAA AAGGATGTAG     420
ACATTGCCTG TCGATCAGTT CTTCATAAGG ATATTGGTCC TTGCCGAGCA GCCACAATAA     480
CAGGAACACT TTCTAGGATT TCTCTAAATG ATGATGAAGA AGAAAAGGGA ACAAACCCTG     540
AAGGGCTAAG CTATTCAACA TTGCCTGGAA ATGTCATTTC ctaagtcatC ATCCAGCAAC     600
CCACAGGTTT GCACATGCCC ATGAGTATGA ATgagcttag caatccatgt TTGAAAAAAG     660
AAAATAGTGA ATTGCGGAGA ACTGTGTACT TATGTACGga tgataatttg agaggggctG     720
ACATGGACAT AGTCCATCCT CAAGAAAGaa tgatggaaag tgactatatt gtgatgccca     780
gaagttctgt aaataaccag ccttcaatga agaagaaag caaaatgaat aTTGGCATGG      840
AAACCTTGCC GCATGAAAGG CTATTGCACT ACAAAGTAAA CCCTGAATTC AATATGAATC     900
CCCCTGTAAT GGACCAGTTC AATATGAACT TAGAGCAACA TCTCGCACCC CAGGAACATA     960
TGCAGAATTT GCCCTTTGAA CCTCGCACAG CTGTGAAGAA TTTCATGGCC TCTGAGTTGG    1020
ATGATAATGC AGGACtatcA AGAAGTGAAA CTGGATCAAC GATATCAATG AGTTCTTTAG    1080
AGAGAAGAAA ATCACGATAT TCAGACCTTG ACTTTGAGAA GGTCATGCAT ACAAGGAAGA    1140
GGCATATGGA ACTATTTCAA GAACTAAATC AGAAATTTCA AACTTTGgaC AGATTTCGGG    1200
ATATACCAAA TACAAgcAGT ATGgaAAACC CCGCACCAAG CAAGAATCCA TGGGACACTT    1260
TCAAAAACCC CAGTGAATAC CCGCATTACA CCACAATCAA TGTCTTAGAC ACAGAGGCAA    1320
AGGATGCTTT GGAACTGAGG CCAGCAGAGT GGGAGAAGTG TCTGAATTTG CCTCTGGATG    1380
TGCAAGAGGG TGACTTTCAA ACAGAAGTTT AAAAAAATCA AAATGGActA AGGTAGAGAC    1440
AaaacTTTAT TGCACTGACA CTTAAGACTT GGGAAGCCTG ACATTTCTAT CTGGACAGTG    1500
TGACTATCTT ATGTCAGGAC CTTCATGTGC CAAACgtcAG TGGTGTTTTC ATATGGTAAC    1560
TTCTCACTAG TCAGGCTAGT GGAGAGATGA CCAGGTGTAC AGTTCTGACC ATCCTGTGTT    1620
GTAAGTACCC GTGGAATGGA TTTGTAAGGT AATCTTTATA GATAAACCTC AAGCAACGAT    1680
TCATGTTGTA ACCGCTTCAT ATGGTTTAGT TTTCAAAAAA cttCACCATG AAGCACAATG    1740
TATATATTTA TGCAGTTTTT AAAGTTTATA ACAGTCTGTT TGGCCATTAC TACACTTTTT    1800
ACTTTATAAT ATAAAAGCAA AGTTTTTGTC attAAATGAA TGTTTGTTGA GCTACATTCT    1860
TCATTGCTTT AAATGCAAta aAGTAATAAT CTCACTTTTA TATGAATAAT ATATTTCACA    1920
tctttattat tgcagttttc tctagaaagc tctgagaagc tttctctgct gcagctgtgt    1980
ataaaatatt taaaatgttg tatggtgtaa ataaactttt gtctacatat caaaaaaaaa    2040
```

```
aaaaaaattt ttgggtccca nccctttnga tnccnannnt gtaaanaaag gggngncggnc    2100 ccccncnggn ctntnagggn gagcactccn tnnngnnc                             2138

(2) INFORMATION FOR SEQ ID NO:   23:

(i) SEQUENCE CHARACTERISTICS:
        (A) LENGTH: 2833 base pairs
        (B) TYPE: nucleic acid
        (C) STRANDEDNESS: single
        (D) TOPOLOGY: linear (vii) IMMEDIATE SOURCE:
        (A) LIBRARY: FIBRANT01
        (B) CLONE: 150629

(xi) SEQUENCE DESCRIPTION: SEQ ID NO: 23 :

CCTTCGACCG CCCCCCGAGT AATTGACCCA GGACTCATTT TCAGGAAAGC CTGAAAATGA      60

GTAAAATAGT GAAATGAGGA ATTTGAACAT TTTATCTTTG GATGGGGATC TTCTGAGGAT     120

GCAAAGAGTG ATTCATCCAA GCCATGTGGT AAAATCAGGA ATTTGAAGAA ATGGAGATG      180

TTTACATTTT TGTTGACGTG TATTTTTCTA CCCCTCCTAA GAGGGCACAG TCTCTTCACC     240

TGTGAACCAA TTACTGTTCC CAGATGTATG AAAATGGCCT ACAACATGAC GTTTTTCCCT     300

AATCTGATGG GTCATTATGA CCAGAGTATT GCCGCGGTGG AAATGGAGCA TTTTCTTCCT     360

CTCGCAAATC TGGAATGTTC ACCAAACATT GAAACTTTCC TCTGCAAAGC ATTTGTACCA     420

ACCTGCATAG AACAAATTCA TGTGGTTCCA CCTTGTCGTA AACTTTGTGA GAAAGTATAT     480

TCTGATTGCA AAAAATTAAT TGACACTTTT GGGATCCGAT GGCCTGAGGA GCTTGAATGT     540

GACAGATTAC AATACTGTGA TGAGACTGTT CCTGTAACTT TGATCCACA CACAGAATTT      600

CTTGGTCCTC GGAAGAAAAC AGAACAAGTC CAAAGAGACA TTGGATTTTG GTGTCCAAGG     660

CATCTTAAGA CTTCTGGGGG ACAAGGATAT AAGTTTCTGG GAATTGACCA GTGTGCGCCT     720

CCATGCCCCA ACATGTATTT TAAAAGTGAT GAGCTAGAGT TTGCAAAAAG TTTTATTGGA     780

ACAGTTTCAA TATTTTGTCT TTGTGCAACT CTGTTCACAT TCCTTACTTT TTTAATTGAT     840

GTTAGAAGAT TCAGATACCC AGAGAGACCA ATTATATATT ACTCTGTCTG TTACAGCATT     900

GTATCTCTTA TGTACTTCAT TGGATTTTTG CTGGGCGATA GCACAGCCTG CAATAAGGCA     960

GATGAGAAGC TAGAACTTGG TGACACTGTT GTCCTAGGCT CTCAAAATAA GGCTTGCACC    1020

GTTTTGTTCA TGCTTTTGTA TTTTTTCACA ATGGCTGGCA CTGTGTGGTG GGTGATTCTT    1080

ACCATTACTT GGTTCTTAGC TGCAGGAAGA AAATGGAGTT GTGAAGCCAT CGAGCAAAAA    1140

GCAGTGTGGT TCATGCTGT TGCATGGGGA ACACCAGGTT TCCTGACTGT TATGCTTCTT     1200

GCTATGAACA AAGTTGAAGG AGACAACATT AGTGGAGTTT GCTTTGTTGG CCTTTATGAC    1260

CTGGATGCTT CTCGCTACTT TGTACTCTTG CCACTGTGCC TTTGTGTGTT TGTTGGGCTC    1320

TCTCTTCTTT TAGCTGGCAT TATTTCCTTA AATCATGTTC GACAAGTCAT ACAACATGAT    1380

GGCCGGAACC AAGAAAAACT AAAGAAATTT ATGATTCGAA TTGGAGTCTT CAGCGGCTTG    1440

TATCTTGTGC CATTAGTGAC ACTTCTCGGA TGTTACGTCT ATGAGCAAGT GAACAGGATT    1500

ACCTGGGAGA TAACTTGGGT CTCTGATCAT TGTCGTCAGT ACCATATCCC ATGTCCTTAT    1560

CAGGCAAAAG CAAAAGCTCG ACCAGAATTG GCTTTATTTA TGATAAAATA CCTGATGACA    1620

TTAATTGTTG GCATCTCTGC TGTCTTCTGG GTTGGAAGCA AAAGACATG CACAGAATGG     1680

GCTGGGTTTT TTAAACGAAA TCGCAAGAGA GATCCAATCA GTGAAAGTCG AAGAGTACTA    1740

CAGGAATCAT GTGAGTTTTT CTTAAAGCAC AATTCTAAAG TTAAACACAA AAGAAGCAC     1800
```

| | |
|---|---|
| TATAAACCAA GTTCGCACAA GCTGAAGGTC ATTTCCAAAT CCATGGGAAC CAGCACAGGA | 1860 |
| GCTACAGCAA ATCATGGCAC TTCTGCAGTA GCAATTACTA GCCATGATTA CCTAGGACAA | 1920 |
| GAAACTTTGA CAGAAATCCA AACCTCACCA GAAACATCAA TGAGAGAGGT GAAAGCGGAC | 1980 |
| GGAGCTAGCA CCCCCAGGTT AAGAGAACAG GACTGTGGTG AACCTGCCTC GCCAGCAGCA | 2040 |
| TCCATCTCCA GACTCTCTGG GGAACAGGTC GACGGGAAGG GCCAGGCAGG CAGTGTATCT | 2100 |
| GAAAGTGCGC GGAGTGAAGG AAGGATTAGT CCAAAGAGTG ATATTACTGA CACTGGCCTG | 2160 |
| GCACAGAGCA ACAATTTGCA GGTCCCCAGT TCTTCAGAAC CAAGCAGCCT CAAAGGTTCC | 2220 |
| ACATCTCTGC TTGTTCACCC AGTTTCAGGA GTGAGAAAAG AGCAGGGAGG TGGTTGTCAT | 2280 |
| TCAGATACTT GAAGAACATT TTCTCTCGTT ACTCAGAAGC AAATTTGTGT TACACTGGAA | 2340 |
| GTGACCTATG CACTGTTTTG TAAGAATCAC TGTTACGTTC TTCTTTTGCA CTTAAAGTTG | 2400 |
| CATTGCCTAC TGTTATACTG GAAAAAATAG AGTTCAAGAA TAATATGACT CATTTCACAC | 2460 |
| AAAGGTTAAT GACAACAATA TACCTGAAAA CAGAAATGTG CAGGTTAATA ATATTTTTTT | 2520 |
| AATAGTGTGG GAGGACAGAG TTAGAGGAAT CTTCCTTTTC TATTTATGAA GATTCTACTC | 2580 |
| TTGGTAAGAG TATTTTAAGA TGTACTATGC TATTTTACTT TTTTGATATA AAATCAAGAT | 2640 |
| ATTTCTTTGC TGAAGTATTT AAATCTTATC CTTGTATCTG TTATACATAT GTGAAATAAG | 2700 |
| CTTATAAGGA ATTGAGCTGT TTGGAATGCT ATTCGAGTAT TTGACCATGC GAATGTGAGA | 2760 |
| TTTAGCATTT GGTAGCTTTA ACGGAATTTC AAGAAATGGA AAAGAGCTCT TTATCCGTAA | 2820 |
| GAAGGTTGCC AAG | 2833 |

(2) INFORMATION FOR SEQ ID NO: 24:

(i) SEQUENCE CHARACTERISTICS:
        (A) LENGTH: 1027 base pairs
        (B) TYPE: nucleic acid
        (C) STRANDEDNESS: single
        (D) TOPOLOGY: linear (vii) IMMEDIATE SOURCE:
        (A) LIBRARY: ADENINB01
        (B) CLONE: 158253

(xi) SEQUENCE DESCRIPTION: SEQ ID NO: 24 :

| | |
|---|---|
| tgcnggtcga ctctagagga tcccccctacg tcatatcatc gagtgttgca aacctgaccg | 60 |
| tcaggnactt gacaagaaac gtgacagtca cattaaagca catcaacccg agccaggatg | 120 |
| agttaacagt gagatgtgta ttttgggact tgggcagaaa tggtggcaga ggaggctggg | 180 |
| tcagacaatg gctgctctgt caaagacagg aggttgaatg naaaccatct gtacctgtag | 240 |
| ccatctaaca aggcttcggc gttctgctgg acctatctag gacatctgtg ctgcctgctc | 300 |
| aaatgatggc tctgacgtcc attacatata ttggttgtgg gctttcatca atttttctgt | 360 |
| cagtgactct tgtaacctac atagcttttg aatccgagg gattacccctt ccaaaatcct | 420 |
| catccagctg tgtgctgctc tgcttctgct gaacctggac ttcctcctgg actcgtggat | 480 |
| tgctctgtat aagatgcaag gccctgcat ctcagtggct gtatttcttc attaatttct | 540 |
| cttggtctca ttcacatggg atggggctag aagcattcca tatgtacctg ggccttgtca | 600 |
| aaagtattta ataacttta cattccggaa aaaataccat ccctttaaaa tttcctggca | 660 |
| attggtncgg gttggggggg gggtaaccaa gcctggtggg gtttggtgna acccaattna | 720 |
| aanccctgga acttaataat tccccccag gaattaaaac ttaatngggg ggctnttggg | 780 |
| gaattcccccc aattgggggg aaaaaaattt ccccccaaa tggggnttcc aacccgggaa | 840 |

-continued

```
tngaaccttt cctgggccng gggattccaa acaaancaaa tggccaggtn tttcctaaca      900
attaaacggg tgggtggggg aaaatttcnc gngtgaaaat tttggcngga aaggtcaggc      960
atgttcaatg ngggncccg ggttcanggg gtaccgagcn ccaattcggg aaancaggta     1020 naagnng                                                              1027
```

(2) INFORMATION FOR SEQ ID NO: 25:

(i) SEQUENCE CHARACTERISTICS:
        (A) LENGTH: 202 base pairs
        (B) TYPE: nucleic acid
        (C) STRANDEDNESS: single
        (D) TOPOLOGY: linear (vii) IMMEDIATE SOURCE:
        (A) LIBRARY: BMARNOR02
        (B) CLONE: 172065

(xi) SEQUENCE DESCRIPTION: SEQ ID NO: 25 :

```
CCGGCGAAGA GAAAAAGGAA CTTCCCCCAC CCCCTCGGGT GCCGTCGGAG CCCCCCAGCC       60

CACCCCTGGG TGCGGCGCGG GGACCCCGGG CCGAAGAAGA GATTTCCTGA GGATTCTGGT      120

TTTCCTCGCT TGTATCTCCG AAAGAATTAA AAATGGCCGA GAATGTGGTG GAACCGGGGC      180

CGCCTTCAGC CAAGCGGCCT AA                                              202
```

(2) INFORMATION FOR SEQ ID NO: 26:

(i) SEQUENCE CHARACTERISTICS:
        (A) LENGTH: 1835 base pairs
        (B) TYPE: nucleic acid
        (C) STRANDEDNESS: single
        (D) TOPOLOGY: linear (vii) IMMEDIATE SOURCE:
        (A) LIBRARY: EOSIHET02
        (B) CLONE: 319854

(xi) SEQUENCE DESCRIPTION: SEQ ID NO: 26 :

```
gacttggtag ccaaggggga taagatgaag atcgggtgtt ccacaattga ggaatctgaa       60
tccacagaga ccactggtgt ggcttttgtc tcctttgtgg gcatggaatc ggttttaaat      120
gagcgcttct tcaaagacca ccaggctccc ttgaccacct ctgagatcaa gctgaagatg      180
aattctcgag tcgttggggg cataatgact ggagagaaga aagacggctt ctcagatcca      240
atcatctaca ctctggagaa cattcagcca agcagaagtt tgagaggcc catctgtgtt       300 tcctggagca ctgatgtgaa gggtggaaga tggacatcct ttggctgtgt gatcctggaa      360
gcttctgaga catataccat ctgcagctgt aaTCAGATGG CAAATCttgc cattatcaTG      420

GCGTctgggg agctcacgat ggacttttcc ttgtacatca ttagccatGT AGGCATTATC      480

ATCTCCTTGG TGTGCCTCGT CTTGGCCATC GCCACCTTTC TGCTGTGTCG CTCCATCCGA      540

AATCACAACA CCTACCTCCA CCTGCACCTC TGCGTGTGTC TCCTCTTGGC GAAGatCTCT      600

TCctcgccgg tatacacaag aCTGACAACA agatggggct gcgccaTCAT CGCGGGCTTC      660

CTGCACTACC TTTTCCTTGC CTGCTTCTTC TGGATGCTGG TGGAggCTGT GATACTGTTC      720

TTGATGGTCA GAAACCTGAA GGTGGTGAAT TActtcagct ctcgcAACAT CAAGATGCTG      780

CACATCTGTG CCTTTGGTTA TGGGCTGCCG ATGCTGGTGG TGGTGATCTC TGCCAGtgtg      840
cagccacagg gctatggaat gcataatcgc tgctgggctg aatacagaga cagggttcat      900
ctggagtttc ttggggccag tttgcacagt tatagtgatc aactcccttc tcctgacctg      960
gaccttgtgg atcctgaggc agaggctttc cagtgttaat gccgaagtct caacgctaaa     1020
```

```
agacacccag gttactgacc ttcaaggcct ttgcccagct cttcatcctg ggctgcTcct    1080
gggtgctGGG CATTTTTCAG ATTGGACCTG AGGCAGGTGT CATGGCTTAC CTGTTCACCA    1140

TCATCAACAG CCTGCAGGGG GCCTTCATCT TCCTCATCCA CTGTCTGCTC AACGGCCAGG    1200

TACGAGAAGA ATACAAGAGG TGGATCACTG GGAAGACGAA GCCCAGCTCC CAGTCCCAGA    1260

CCTCAAGGAT CTTGCTGTCC TCCATGCCAT CCGCTTCCAA GACGGGTTAA AGTCCTTTCT    1320

TGCTTTCAAA TATGCTATGG AGCCACAGTT GAGGACAGTA GTTTCCTGCA GGAGCCTACC    1380

CTGAAATCTC TTCTCAGCTT AACATGgaAA TGAGgaTCCc aCcaGCCCCA GAACCCTCTG    1440

GGGAAGAATG TTGGGGGcgg TCTTCCTGTG GTTGTATGCA CTGATGAGAA ATCAGgcgTT    1500

TCTGCTCCAA ACGACCATTT tgtCTTCGTG CTCTGCAACT TCTTCAATTC CAGAGTTTCT    1560

GAGAACAGAC CCAAATTCAA TGGCATGACC AAGAACACCT GGCTACCATT TTGTTTTCTC    1620

CTGCCCTTGT TGGTGCATGG TTCTAAGcat GCCCCTCCAg agCCTATCAT ACGCCTGata    1680

CAGAGAACCT CTCAATAAAT GATTTGTCGC CTGTCTGACT GATTTACcct aaaaaaaann    1740
aaantnaaaa ngggngggggg ggnnccgtgg tnngnttnnt nnnnnngggg gnnnnnaggt    1800
ntgtctcccg gggngnaatn nntgttntnn ncgng                                1835

(2) INFORMATION FOR SEQ ID NO:   27:

(i) SEQUENCE CHARACTERISTICS:
        (A) LENGTH: 809 base pairs
        (B) TYPE: nucleic acid
        (C) STRANDEDNESS: single
        (D) TOPOLOGY: linear (vii) IMMEDIATE SOURCE:
        (A) LIBRARY: EOSIHET02
        (B) CLONE: 320551

(xi) SEQUENCE DESCRIPTION: SEQ ID NO: 27 :

aancnncgga ctccattggc gnaggccntc ccgtgggccc caangcctgt tgcccacttt     60 ggcccnccte ccgaaggtta agcanattgg ntttnatcct ttccttggac cagtctgtgc    120
cattttctct gcgaatttag tattgtttat cttggtcttt tggattttga aaagaaaact    180
ttcctccctc aatagtgaag tgtcaaccat ccagaacaca aggatgctgg ctttcaaagc    240
aacagctcag ctcttcatcc tgggctgcac atggtgtctg ggcttgctac aggtgggtcc    300
agctgcccag gTCATGGCCT ACCTCTTCAC CATCatcaac agcctcCAAG GCTTCTTCAT    360

CTTCTTGGTC TACTGCCTCC tcagccagca ggtccagaAA CAATATCAAA AGTGGTttag    420
agagatcgta aaATCAAAAT CTGAGTCTGA GACATACACA CTTTCCagCA AGATGGGTCC    480

TGACTCAAAA CCCAGTGAGG Gggatgtttt tccaggacaa gtgaagagaa aataTTAAAA    540

CTAGAATATT CAACTCCAta TGGAAAATCA TAtccatgGA TCTCTTTGgC ATTATGAAGA    600

ATGAAGCTAA GGAAAAGGGA ATTCATTAAA CATATCATCC TTGGAGAGGA AGTAATCAAC    660

CTTTACTTCC CAAGCTGTTt gttctccaca ataggctctc aacaaatgtg tggtaaattg    720
catttctctt cactaagggn gtattcagcn aaggttggnc ccggggaacc caagnatgcc    780
ccactgcaaa tatttccttg actttttgt                                       809

(2) INFORMATION FOR SEQ ID NO:   28:

(i) SEQUENCE CHARACTERISTICS:
        (A) LENGTH: 1451 base pairs
        (B) TYPE: nucleic acid
        (C) STRANDEDNESS: single
```

(D) TOPOLOGY: linear (vii) IMMEDIATE SOURCE:
          (A) LIBRARY: HNT2AGT01
          (B) CLONE: 491493

(xi) SEQUENCE DESCRIPTION: SEQ ID NO: 28 :

| | | | | | |
|---|---|---|---|---|---|
| ccagctgcag | tagactacag | gagttatgga | acagataaag | tatgttggct | ccgacttgac | 60 |
| acctacttca | tttggagttt | tataggacag | gcaactttga | taattatgct | taatgtaatc | 120 |
| ttccttggga | ttgctttata | taaaatgttt | caccatactg | ctatactgaa | acctgaatca | 180 |
| ggctgtcttg | ataacatcaa | ctatgaggat | aacagaccct | tcatcaagtc | atgggttata | 240 |
| ggtgcaatag | ctcttctctg | cctattagga | ttgacctggg | cctttggact | catgtatatt | 300 |
| aatgaaagca | cagtcatcat | ggcctatctc | ttcaccattt | tcaattctct | acagggaatg | 360 |
| tttatattta | ttttccattg | tgtcctacag | aagaaggtac | gaaaagagta | tgggaaatgc | 420 |
| ctgcgaacac | attgctgtag | tggcaaaagt | acagagagtt | cccattggtt | caagggaaac | 480 |
| atctgggtct | cgaactcctg | gacgctactc | cacaggctca | cagagcgana | ttccgtagaa | 540 |
| tgtggaatga | cacggttcga | aagcagtcag | agtcttcctt | tattactgga | gacataaaca | 600 |
| gttcagcgtc | actcaacaga | gaggggcttc | tgaacaatgc | caggggatac | aagtgtcatg | 660 |
| gatactctac | cactgaatgg | taaccatggc | aatagttaca | gcattgccag | cgggaattac | 720 |
| ctgaggcaac | tgtgtgcaaa | tcatagaccg | tggctataac | cataacgaga | ccgccctaga | 780 |
| gaaaaagatt | ctgaaggaac | tcacttccaa | ctatatccct | tcttacctga | caaccatga | 840 |
| gcgctccagt | gaacagaaca | ggaatctgat | gaacaagctg | gtgaataacc | ttggcagtgg | 900 |
| aagggaagat | gatgccattg | tcctggatga | tgccacctcg | tttaaccacg | aggagagttt | 960 |
| gggcctggaa | ctcattcatg | aggaatctga | tgctcctttg | ctgccccccaa | gagtatactc | 1020 |
| caccgagaac | caccagccac | accattatac | cagaaggcgg | atcccccaag | accacagtga | 1080 |
| gagcttttc | cctttgctaa | ccaacgagca | cacagaagat | ctccagtcac | cccatagaga | 1140 |
| ctctctctat | accagcatgc | cgacactggc | tggtgtggcc | gccacagaga | gtgttaccac | 1200 |
| cagcacccag | accgaactcc | caccggccaa | atgtggtgat | gccgaatgtt | actacaaaag | 1260 |
| catgcaaacc | tagggtccag | aaacaggtcc | atnagtgaaa | acttnnntac | cagctaagnt | 1320 |
| cngggggaaa | ntttatgggnt | ttaanaggtt | ccnccaaaan | aaaagatgg | ggancccctt | 1380 |
| cccgggggg | attttcnaaa | aggggaccgg | gttcattttg | ggnccctagt | ctntagggag | 1440 |
| gttggccccc | g | | | | | 1451 |

(2) INFORMATION FOR SEQ ID NO:   29:

(i) SEQUENCE CHARACTERISTICS:
          (A) LENGTH: 474 base pairs
          (B) TYPE: nucleic acid
          (C) STRANDEDNESS: single
          (D) TOPOLOGY: linear (vii) IMMEDIATE SOURCE:
          (A) LIBRARY: COLNTUT02
          (B) CLONE: 614640

(xi) SEQUENCE DESCRIPTION: SEQ ID NO: 29 :

| | | | | | |
|---|---|---|---|---|---|
| agattattca | tagagcatct | ttcgtggtgg | aggaatctga | gtgcttggag | gccttgcagc | 60 |
| aggaagtggc | atttacaaat | ggtgctcaga | acaagaacac | tgcctgtgtc | cctagccaaa | 120 |
| aagaaactaa | ggacctagca | tgagttccca | ttaaaatctg | tgtggactga | gtcattaaag | 180 |

```
ctaagttaac ggcttcactt ttttctttgg ccaaaaggac aagacatact tcttgatatc    240
tgagaaactg aactgcagat gaatttaaag atagtattgg ggtgcccagt ttctcttaaa    300
aagaaaaagg aggggaaaga gaacaggctt gtctatgttg tatggttctt caaatgttaa    360
tttaagcaaa ataatttgat ttgactcctt gaagcttacc ttggagaact ataatttgat    420
agactatttt atatttttac aatagatttt cttcatcagc tagactagta gaag          474
```

(2) INFORMATION FOR SEQ ID NO:  30:

(i) SEQUENCE CHARACTERISTICS:
        (A) LENGTH: 1083 base pairs
        (B) TYPE: nucleic acid
        (C) STRANDEDNESS: single
        (D) TOPOLOGY: linear (vii) IMMEDIATE SOURCE:
        (A) LIBRARY: COLNTUT02
        (B) CLONE: 615769

(xi) SEQUENCE DESCRIPTION: SEQ ID NO: 30 :

```
ttacatttat ttaaacagaa aacgtgcaca tgagctgcct actcattttc ttcactgcgc    60
ancttgngca ttggggtnnn nnnnnnnnnn nnnnnnnnnn nnnnnnnnnn nnnnnnnnnn    120
nnnnnnnnnn nnnnnnnnnn nnnnnnnnnn nnnnnnnnnn nnnnnnnnnn nnnnnnnnnn    180
nnnnnnnnnn nnnnnnnnnn nnnnnnnnnn nnnnnnnnnn nnnnnnnnnn nnnnnngtac    240
acagtaaaca taggcaattt ttattagtca atgttagaaa atatttttt aaaaaactat     300 gtagtttaca aagcttaaag tatttgctat ctggctttta agaaaatgtt tgcccatccc    360
ttccctggag tcttggagag caaggatggc tctctatacc ttttatagta cctggcattt    420
agtaggtaca tattaaatat ctgttgaaag aagtgaagag cctcaaggcc cagctctaac    480
tcctctttaa tgggaggctc ttttttttgga agggcagggc tagacaggta tgggtcagtt    540
ctcttctgat agtcccagag tctacagcga accaaagatg aaagctctga aggagagaca    600
ccagtactca caggtctcat gtccatgctc cgtccaaggg gacctagcta cttccttacc    660
ccttctcagt ttcaggagaa gaaaagtgtt ggagattggt taagacccct tcccaccaat    720
tgctgtggtg aaccctccag caagggcatg gctactttca ggaaagcaaa gagggtcctc    780
tgcttctcta tccttcccaa aaaacatggg ctggggtaga ccctaaagag cagggcatgg    840
aggactgtgg gaaggactca gccttgctgt agaagctctc tgcaaagcaa gaggcagggt    900
atggtaacaa atgccaattc ctggttaaat tagggtattn ggtaaccaaa ttcccaatt     960 ncccggggtn aaaattgggc tttnnccaag gggaagggt ttcaaagctt ttgtntgggc     1020
aaaattggac caaatgcaat ccccnggggg ntacccnggg ttttatncca aatntncccn    1080
ggg                                                                  1083
```

(2) INFORMATION FOR SEQ ID NO:  31:

(i) SEQUENCE CHARACTERISTICS:
        (A) LENGTH: 703 base pairs
        (B) TYPE: nucleic acid
        (C) STRANDEDNESS: single
        (D) TOPOLOGY: linear (vii) IMMEDIATE SOURCE:
        (A) LIBRARY: PROSTUT01
        (B) CLONE: 713784

(xi) SEQUENCE DESCRIPTION: SEQ ID NO: 31 :

```
gtctggagat gagctgccct gtgacatgcg gatcccatct gacaagcagg acaagcttca    60
```

```
tggctgcctg gagcacctct ttaaccaggt ggactccatc aatgctctcc tcaaggggcc      120
agtcatgagc cgggctttcg aagagaccaa gcatttccct atgaaccaca gcttacaaga      180
gtttaaacag aaagaagagt gtacaatccg tgggccggag cctgatccag attagcatcc      240
aggaggaccc ctgggaacct ccccaactcc atcaagaccc tggtggacaa cattcagaga      300
tatgtggaag atgggaagaa ccagctgctc ctggccttgc tgaagtgcac agacacggag      360
ctgcagctgc gcagagacgc gatcttctgc caggccctgg tggccgccgt gtgcaccttc      420
tccgagcagc tgctggcggc cctgggctac cgctacaaca caatggcga gtacgaggag       480 agcagccgcg acgccagccg caagtggctg agcaggtgg cggccacggg cgtcctgctg        540
cactgccagt ccctnctctc gcnagcnaca gtgaagnagg nacggnccat gctggaggtc      600
atctngntga cgctgtcana gctggacaat ttnaccttct ccctttaagg nagctngncc      660
gnnaactatt ttggncaanc accaaatgtn ttttaccgca ttt                        703

(2) INFORMATION FOR SEQ ID NO:     32:

(i) SEQUENCE CHARACTERISTICS:
        (A) LENGTH: 3487 base pairs
        (B) TYPE: nucleic acid
        (C) STRANDEDNESS: single
        (D) TOPOLOGY: linear (vii) IMMEDIATE SOURCE:
        (A) LIBRARY: PROSTUT01
        (B) CLONE: 714029

(xi) SEQUENCE DESCRIPTION: SEQ ID NO: 32 :

agcgggcaag aagatggcgg gatcagtggc cgacagcaat gccgtggtga aactagatga       60
tggccattta acaactctt tgagctctcc agttcaagcg gacgtgtact tcccacgact       120
gatagttcca ttttgtgggc acattaaagg tggcatgaga ccaggcaaga aggtgttagt      180
gatgggcatc gtagacctca acccagagag cttttgcaatc agcttgaCCT GTGGGGACTC     240

AGAAGACCCT CCTGCCgatg tggcaaTCGA ACTCAAAGCT GTGTTCACAG ATCGGCAGCT      300

ACTCAGAAAT TCTTGTATAT ctggggagag gggtgaaGAA CAGTCagcaa tccCTTACTT      360

TCCATTCATT CCAGACCAGC CATTCAGGGT GGAAATTCTT TGTGAGCACC CACGTTTCCG      420

AGTGTTTGTG GATGGACACC AACTTTTTGA TTTTTACCAT CGCATTCAAA CGTTATCTGC      480

AATTGACACC ATAAAGATAA ATGGAGACCT CCAGATCACC AAGCTTGGCT GATTTAAACC      540

ACCTCTATTT CAAATAGGAT CACGTGCCAC AACTATCTGA CTGTTGGTCT GGAAGAAGTG      600

TCCTAGCAAG ATCGGAGAC TTAAAAAGAA AACAAAAACA AATGGCAAGT TTCACTTAAG       660

GGTGGTTTGC CCTTAAGAAG AAAGCTGTTG GACAAAGAC ACCGAGCCAT TATACCCAGA       720

ATAAAATAAT ACATTTATGC TGGATTTTAT TCAGACCAAa ctaAAATGGA TTTGTGATGA      780

TTTGTGATTT GGTAgcaaat tattcatctt ttcaaAGCAA GGCaatgctt agaAACAGAA      840

GTGCTAAAGA CACTTAAAAA GCCAACAACA ACGGTACAGt gaaatcaatg catttctgca      900
ctaaagtgga attgtgtagc acaaccaata ttttagtcag ggtatttaca tagaatgTAG      960

GTTGTTCAAG GTttgacttt tttttttgtt tttgtttttg ttttgtttt tgttttgcac      1020 agcATAATGT TAATTCAGAT TGttgaagcc ttcttgtagt tattatttat actcaatgta     1080
tgtattaaag aatgaacaat gtctcaagaa cagcaagttg taaactttg aatgtataaa      1140 tatcttaggt ccaaggggag aaaattacat attacaatta tgaaacaggt gaatttctgc    1200
tttaaagaat tgagattctc catacccta aacttaggat ctcttgatat aaactgctgt      1260
```

```
aagtgctttt gggaaacctt tgcaaaacca ttttgataaa actgctttcc aagttattgt    1320
tggttatgta aaattctatt tacattgctt tttctcctta ctgggaatta gcacattatt    1380
ggcttcctta agactaatta tttctctctt gatttatata atagctcatt aagttgttat    1440
taatcaaaaa cacaaagagg tgattgctta gacaattttt aaagtgacta tagtataaac    1500
ttttaaaaga ataatatgaa aatgactgtg gaatgcagtg taaagcagaa gcaaacggcc    1560
ctgaataact tacttggaag taatttatat caacttaagc tgttagctca ttgtataact    1620
tttcttatgt gaccctcacc aatatcccta agtaatgcct tggaagcttt cagagtagaa    1680
gatgcttcct actgtgttgg ctctgaggag atagtaggat tagataggat ccagattagg    1740
aaatgatcca gttagtttat ctgaaaggtt aactcccagg actccaggtc tttgaatcca    1800
gccagtagag tgaatgcttc caattaagct gtaggtgtta ccctgcactt acggaactga    1860
tcaaacaggt gactccaaca ggagggttgc agtactgtaa acgtcaccgc aaggcaaggg    1920
atgcttaaag tcctgggttc tggactttaa aagctacatt ggccctggag ggaggggacc    1980
cttggcattg ctttgatcag gtagtgaggg aagacagggt tctggggtgg gggtgtattt    2040
atatataatt taggttttgt ttgtacagca tactgtgtct tgtaatgaca catccttgtc    2100
ctgctttcct ttttgagtt ttttctttt tttacacaac atgcagaggc actgaagtga    2160
ccatgtcatt ttcaaagtgt caagaatgta gacagtgttt cagtaccaaa gtctaaaata    2220
aactaaaatt atgaattttt tataggtgat acatttggat tcttctcaac tttgaaactg    2280
tttagcacag ttccattgta ttatataaga agacactgta tccaacaaga ctggctgtac    2340
attgaaaagc tttatgtacc agccaactta tttaaccata ttcagcctgt tccgtggggg    2400
ctgttctgtg gttccaggta ttttcaagcc tgtgattaac ttctcatggc ttgtcactta    2460
aaagtcccta aatttgagag acttaaaggg caccttgaaa tacatttgtg gagttttgat    2520
ccaacttatg gtggaagagc cccataggaa gactgttttg agtggccaac cattcccacc    2580
cactgcataa ttcagcagaa actagaggag cagggcgtgt actgattgga attgacacgc    2640
ttattctgtc tacctatcag ctaactcatt agcagccaag cccttaggca gcttagtgtg    2700
aaaatacaat gttaactgtt tgtttctctg tgaggttagt gggaacctct tggataagcc    2760
tattgggatt aatctaaatg atgtgatgat ttgattcagg tatagcccaa attagtaagg    2820
ggctttagct gtaaactgaa aacaatattc acaccctctc ctgggcctgt aaggtctaag    2880
gtgagaattt caggatggaa aatgcAATGT AAAGCTTCCA CAGGAAAGTA TTCGGGTATG    2940

TAAGGTGTTA TTTCTgacca gagccctaGT TCTGCAATAA CCAAAACCAA GGAGTATAAA    3000

TAACAATCAG GCTCTGGGGG AATAGAAAGC AGGCTTTAGA CAATCTGTCC ATTTCTACAG    3060

TAAAATTGGA GTGAGTGTGT ATATCTACTT AAAACTTAAT AGAAGTGACT TCTACTTTTT    3120

GGGCTATTCC AGAAGTATTT TAAAATTATT ATTTAAAATT TTGAAGCCCC ATTTCAAATC    3180

TTGCCGACCT TAGTTCAAAG CCCCCTGAGA GATCACTTTT AGAATTGAGG ATTTGTTAAA    3240

ATGGCAAGTC ATTTCATTTG TGTTAAAAAG AAAATACCCA AAAGGAAGGA GGGAGCCCTG    3300

TTTGCCTTGA GATAAACGGC CTTGGCATTT TCTGGCATTA ATGTAGAAAT AATGTTCCTA    3360

TGATGACATA TTTTCAAAGA AACACTTTCT TATTTACTGT GTGGTGTAAA ATGTTGCTAA    3420

ATGTGTTGTT ACATTATGTC ACTGCTGAAA GTAATTTGCA CTATAataaa ggaattttct    3480
acaaaac                                                              3487
```

(2) INFORMATION FOR SEQ ID NO: 33:

(i) SEQUENCE CHARACTERISTICS:
    (A) LENGTH: 1455 base pairs
    (B) TYPE: nucleic acid
    (C) STRANDEDNESS: single
    (D) TOPOLOGY: linear (vii) IMMEDIATE SOURCE:
    (A) LIBRARY: BRAITUT01
    (B) CLONE: 746308

(xi) SEQUENCE DESCRIPTION: SEQ ID NO: 33 :

```
ggcccggaag tgcgcaggcg ctgggcaaga tggcgggagg ggtgcgcccg ctggcggggc    60
ctccgcgcct tgtgtcgcgt gctgctcttc ctctcgcagt tctgcattct gtcgggcggt   120
gagcaatcgc aggcgctggc tcagtcaata aggatccgg gcccaacacg cacattcaca    180
gtagttccca gggcagcaga aagtactgaa atcccacctt atgtgatgaa gtgtccgagc   240
aatggtttgt gtagcaggct tcctgcagac tgtatagact gcacaacaaa tttctcctgt   300
acctatggga agcctgtcac ttttgactgt gcagtgaaac catctgttac ctgtgttgat   360
caagacttca atcccaaaa gaacttcatc attaacatga cttgcagatt ttgctggcag    420
cttcctgaaa cagattacga gtgtaccaac tccaccagct gcatgacggt gtcctgtcct   480
cggcagcgcc taccctgcca actgcacggt gcgggacCAC GTCCACTGCT TGGGTAACCG   540
tacttttccc aaaatgctat ATTGCAATTG gactggaggc tATAAGTGGT CTACGGCTCT   600
GGCTCTAAGC ATCACCCTCG GTGGGTTTGG AGCAGACcgt ttctacctgG GCCAGTGGCG   660
GGAAGGCCTC GGCAAGCTCT TCAGCTTCGG TGGCCTGGGA ATATGGACGC TGATAGACGT   720
CCTGCTCATT GGAGTTGGCT ATGTTGGACC AGCAGATGGC TCTTTGTACA TTTAGCTGTG   780
GTGTGTGCTT CAGAAAGGAG CAGGGCTTAG AAAAAGCCCT TTTGTCCGTa ggaGTTGATG   840
TGGTGTGAGT GATATATTTC TATGTTTTTA ATGTACAGCA TCTGTACTTT GTTTGCCTTG   900
ATAAAGGTAA GATAAATGAA ACGCTGAACT ATGCTAATCT GGAATTTGTT TTTATTTGCC   960
TGAAATATAT TTTTTTCTGT GAAAAAATTA AAACGTACTT AAGCCAGGAG AATGAATTAT  1020
ACAGTGAttg aaaatccatt taattcctat gactttgtt ttgtattgcc caagtcaaac   1080
tacatcactt gtatctccag cccaaatgtA GTCTGCCTTG AAAAGTCTTT CAGCTGTGAC  1140
TGCAGGAAGT GGGAGTGTTT TTATTGTTAG CTAATTGCTG TGACTGCAGG AAGTGGGAGT  1200
GTTTCTGTTG TTGGCTAATT GAAGTTATTA GGCTCAGCTT CAGTCATGTG TAAGTTTTGC  1260
AGTGTAATAC ATatgTAGTC TGGTCTGTAT ATATGAAAAT TTGAATTAAA CTGCAGAATG  1320
TTTATGTCTA GTTATGGTTT AAATTTTCTT AGTAGTATAT AAAAGGTAAG AGTACTGAAA  1380
AATTAATAAA Attgcaagtt aagaaataaa aangaannaa aaggaannaa tnatnntggn  1440
aaanaannaa aaaag                                                   1455
```

(2) INFORMATION FOR SEQ ID NO:   34:

(i) SEQUENCE CHARACTERISTICS:
        (A) LENGTH: 1750 base pairs
        (B) TYPE: nucleic acid
        (C) STRANDEDNESS: single
        (D) TOPOLOGY: linear (vii) IMMEDIATE SOURCE:
        (A) LIBRARY: BRAITUT01
        (B) CLONE: 746982

(xi) SEQUENCE DESCRIPTION: SEQ ID NO: 34 :

```
gcnccccag gnttttaccc cttaagcctc ccgncccgta agttttgtgg aaattgtgag    60
```

```
ccgactctag aggatccccc tgatgaactc ttaaggcaca tgtttgtgca ttatcactag      120
cagccagtAA CCTCTcctgt gcctctacct agctcccatc tattcattca ccttCTCTCT      180

GACTGCACTT TTCTTTTTTA tgaAAAAAGA GAGATGGGGG AGAAAAAAGA CAAGAGGGAA      240

AGtatttctc ttgattcttg gTTAAATTTG TTTAATAATA ATaatatcct aaatttttta      300
tatttaatct ttttttccct tacaagaact tGaagttttt tttttttaat ttttataatg      360
tACTGATGTG GTTCAGAGAG ATAAAGCACT TTAGTACATA GTCACTCTTT TTAGTACAAA      420

CAAATCATTT GGAATAccta aagattgtag agTCATTCCC TCTATCACTG ACACATCAGT      480

GACGATGGGA AGACATGGAA AACAAGGAGA GAAAAATGAT GTATAATTTG TAGTTTTTAG      540

TGATAGTATT TAAAATATAT CCTCATTTGT GGGgttgagc cctaaacttt aGTTTAGGGT      600

AGGTACTCAA CTTAAAGAAT ATAGGTTTCT TCTTATATCT GTATTCTTTA GATCCTAACC      660

TCTGTCTAct TTTTGCTCAG TAGGAGTCTT GATAGAAGAT ATGAATCTCT GAGAGGTATG      720

TTTATTTGTT AATCCTAACC AGTATAATAA GCAAATACAC TATAATAGAT CCACGTTACT      780

GGAATCTGTA AACCTTGAGG GATAGCTTTC tgcTTAAAAA CACACACACA CACACACACA      840

CACACGGAAA ACCTTTATTT TAAAGTCAAG TTGTGAGCAA ATAGAAATAa gaGACAAAAG      900

GACATCACTC TTATCAAATG TGTGAGCAGT AGAAGAGACC ACATTTACAG TCAATAGAAA      960

TAATGAAAAA AAATTAGGTG TTTAGTGTAT TTTAAACAGT TTTGTTTTGT TTTACTTGAG     1020

GGGGACGTCC CAAAATTAAA GGAATGGAGA ATAATCAAA ATCATGTATA CCATCTTCTA      1080

TTTCCAGCTC CTGATTCCCC ATAGGTAACA TCCCTTAGGA GCGAAGAGTT CAATTAGTAA     1140

TGTTTATGTG TTATGTCAGG AGATGAAACC CTTGTTCTTA GGATCACAGA ATACTAAAGC     1200

ACCTCAAAAA AACAGGTATC ATGTGAAACA GTGGTTGCCA AAAGTGGAGC GAGGATGATT     1260

TCACTAGGCA TTTGGCAATT CTTAGAGACA TTTCCGGTTG TCACAATTGG AGGGATACTA     1320

GTAGCATGAA TTGGGTAGAG GCCAGGGATG TTGCTAAATA GATTATAATA CACAAGGAAA     1380

GCAGCCTCAA AGAATTACCC CTCCCAAAAT GTCAGAAGTG CtaaGGCTGA GAAACCCTGA     1440

TGTAAAGATC AGTCCcaGTT ATAAACTGAA AACAGCTATT TAcaaAGCAG TAAATGCAAG     1500

AAAGAAAAGG AAGTCGCAAA GAGAAAGTGA TGTAATGCAA ATTGAGGATT TTACAAGATC     1560

AGATACTGCT GCTTTAAGTC AAGGGTGAAT AATCTCAACA AACAGCAAAT AGCAATCACT     1620

TTACCAGCTG CATATTGCAC CCACATAGGT AACTCTTCAT TTTAGGAACA AACTGAATTT     1680

GAACACTGAG CCTTTTGAAC TCAGCCATCT CTATATATTC TTTCCTTAAA ATTCATGATT     1740

TTGggcaaaa                                                             1750

(2) INFORMATION FOR SEQ ID NO:    35:

(i) SEQUENCE CHARACTERISTICS:
        (A) LENGTH: 369 base pairs
        (B) TYPE: nucleic acid
        (C) STRANDEDNESS: single
        (D) TOPOLOGY: linear (vii) IMMEDIATE SOURCE:
        (A) LIBRARY: PROSTUT03
        (B) CLONE: 791314

(xi) SEQUENCE DESCRIPTION: SEQ ID NO: 35 :

tgattactga agaaaagaga tggggaatga ttttaacatt tttggcctgc ttagttccaa        60
gagaaatttg atttatggct ggcttttgga aggcaggagc cagtaattct aatcttacct       120
gatttgatcg aatgaccttg agcaagtgac ttgatttcaa tgatctgata ctttcaaaaa       180
```

```
atcccaaagc cctttgaaaa actaggaact gcatcttagt caatcttttta gagaatttttt    240 aagaaatcat acctcaataa agctagtgag atgctttcat atatagaaag ttgataattc       300
atttacattc tacataaaca ttggtcctaa gattttaatt tattttttatc ttactatttt    360 ttgaggatg                                                              369
```

(2) INFORMATION FOR SEQ ID NO:   36:

(i) SEQUENCE CHARACTERISTICS:
        (A) LENGTH: 191 base pairs
        (B) TYPE: nucleic acid
        (C) STRANDEDNESS: single
        (D) TOPOLOGY: linear (vii) IMMEDIATE SOURCE:
        (A) LIBRARY: PROSTUT04
        (B) CLONE: 832357

(xi) SEQUENCE DESCRIPTION: SEQ ID NO: 36 :

```
ttatggatgg tgaagggaat ggtatagaat tggagagatt atcttactga acacctgtag        60
tcccagcttt ctctggaagt ggtggtatttt gagcaggatg tgcacaaagg aattttaatn     120
ncccnaaatn gnttttnanc ntttnnanan nattaaaaacn nnggtttngg ggggaattgg     180
aggggggntc t                                                            191
```

(2) INFORMATION FOR SEQ ID NO:   37:

(i) SEQUENCE CHARACTERISTICS:
        (A) LENGTH: 2038 base pairs
        (B) TYPE: nucleic acid
        (C) STRANDEDNESS: single
        (D) TOPOLOGY: linear (vii) IMMEDIATE SOURCE:
        (A) LIBRARY: PROSTUT05
        (B) CLONE: 838871

(xi) SEQUENCE DESCRIPTION: SEQ ID NO: 37 :

```
ggtcgactct agaggatccc cccccgagt ctgactccag actcgagtcc ctaaactctg         60
tgctacagaa ttttttgctg tcatctgctg gaggatatcc gttctttaat ctatggcaat     120
actcataaat tctctcagga aagccactgg aattatggct tttggttttt gttttttaaaa    180 aagtctattc cctgattatg gtaattgatc tttcctttga GGGCAAGTGC CAGGATAGAA     240

CTTAATCAAT ATTAAAGTCA TATTTCATTC TAATTTCTGT AGTATCTCCT ATCACATTAG     300

ATCTTAGGAA ATACCAAGTT GATAAGTAAA TGATACACTT GGCCCAGATG ACTGACCTTC     360

ATTTTCTGTT GTCAATTATT TCTCCTCTTA ACCCTCAACA TTTCTTTTCT CTCCCTGATT     420

GTCTCTCCTA ATCTCCTTTA TTTTTGTCTT CTTGAGACAT TCActgATCT TTTTCCTTTC     480

TTCTTTTTCC TCATCCTCTA TCATTGATCA GTAAAGACCC TCAAATCTCA TTGTTTTCAC     540

ACATTTCTAG TACAGTCATT CCTTGCCCCA CTGGGTTTTA GTGGACTTCT GGGGTGTCCA     600

CATCATGCTA ATGTTGTGGA CGCAGGTAGT TGTCCTAGTG GATGCCGGAT AGACATATGT     660

GGATTAGGAG TTGCAGGAGG GGTCTGACAA TGGGACTTTG TTGGCATTAA ATGTTCAAGT     720

CTATGCCTGG AAGCTGAGTT TACCCTCAAT TTGCATCTCA AGTCTCGGCT GAGGAAGTGT     780

GTTGAAACTG GCAGCACGT GCAgGGTGGT TAGTCCAGTG GGCcgTTACA ACCTAGCACT      840

TGTCCAGGCA GCTTCCTTGA AAAGAATGTT TATAGAATTA ATGTGCCTGT GTGTTACACa     900
catataaact GACCTATGTT TTCAAAAGTT ACATGGTGAG TGCTGGTTGA AAAGACTTGA     960
```

```
GGAAAATTTT CTCAGATAGC TTTAAAATGA GGCATGTGCT GTCATTGGTA GAGCCTTCGT    1020

TTAGTATGCA ACTGATACTT GAAATATGAC TTTCTCTGTT AGTGGCTTTA AcaggttcCA    1080

GTAATGGTTG TGTGATACTC TTCATTTTAT TAGGGTTCAA CAGTTCATCA AAGGGAAGAG    1140

AAATGTAGGG GCTCCTATTT GAAAAATTTA TGTGTGTTTA TTTACACATA AATATGTAca    1200
tttgnnnnnn nnnnnnnnnn nnnnnnnnnn nnnnnnnnnn nnnnnnnnnn nnnnnnnnnn    1260
nnnnnnnnnn nnnnnnnnnn nnnnnnnnnn nnnnnnnnnn nnnnnnnnnn nnnnnnnnnn    1320
nnnnnnnnnn nnnnnnnnnn nnnnnnnnnn nnnnnnnnnn nnnnnnnnnn nnnnnnnnnn    1380
nnnnnnnnnn nnnnnnnnnn nnnnnnnnnn nnnnnnnnnn nnnnnnnnnn nnnnnnnnnn    1440
nnnnnnnnnn nnnnnnnnnn nnnnnnnnnn nnnnnnnnnn nnnnnnnnnn nnnnnnnnnn    1500
nnngTATGTA CATTTGCATA TCCTATTCCC ATTGAATATT ATCTAAACTT GCCTATATTT    1560

CTTAACTCAG AAGTTACATG CATCCTCCTT AACAAGTGGG TGAGCTAGAT AaatCTCAGG    1620

GGATTAAAAA AGATTCAATT ACTTATCTTT TGGGGTGAAT TGATGagtAA GAAACTGTAA    1680

TAGCAACCCT CTGGACCTAC TAGGCATCTG TAATTGGTAG GCTTTTCCGA CATTTTTTCC    1740

TTCACAGACT TAGCAACCGA AGCACAAGGT GGATTAAATA AATGACTAAA TAAAAGAGAA    1800

ACAGAAAATAT CATATCCTGG CTCCAGATCc aTGATTGTCA GTAGTGTGTT ACAGTGTTTT    1860

TACCAGtaaC AGTTAGCATT GCCTTGATTA TAAGCAAACA AAAGTAGATT CTATttaggc    1920
ttaagcaact atgccaacta ccatgatacc tcaccatacc agatgggga ggaagactga    1980 tatcgaccta gcagtttgat gnaaatgggt tatngggnca ttttccgccc tgnacaga     2038

(2) INFORMATION FOR SEQ ID NO:    38:

(i) SEQUENCE CHARACTERISTICS:
        (A) LENGTH: 563 base pairs
        (B) TYPE: nucleic acid
        (C) STRANDEDNESS: single
        (D) TOPOLOGY: linear (vii) IMMEDIATE SOURCE:
        (A) LIBRARY: PROSTUT05
        (B) CLONE: 838872

(xi) SEQUENCE DESCRIPTION: SEQ ID NO: 38 :

attagtctta tgctgcttct gccattttca tttctgtaga cagaagagaa tttagaatgg      60
tttcactgct gtctagtggg ggacaaatta tannnnnnnn nnnnnnnnnn nnnnnnnnnn     120
nnnnnnnctg acaactgtta acttctcact atgtgccagg gactattgtg agttaactca    180
cttaatcctc atagccaccc tttgaggtac ctataattat tctatagatg aagaagcaca    240
gacagagagg ttaattaaga gcaagtgttg gagttgaact cctgatattt cccccttaa     300 gctgaagtcc atgacctgct tcccaattcc tggcagccac acagttgctc tgctattttt    360
cagtcttcta acttcaacat agttactttt tactcttttt catcctctac cttctttaaa    420
tcacgtctct ttttccttc ttgttttttat cctttctcct ctactttctg tcttactttn    480
tttcntctgt ttttctgcct tttgcttcct tatcctcttc tttgaaatcc atatcttatt    540
tactaaattt tttttgacac ttt                                            563

(2) INFORMATION FOR SEQ ID NO:    39:

(i) SEQUENCE CHARACTERISTICS:
        (A) LENGTH: 616 base pairs
        (B) TYPE: nucleic acid
        (C) STRANDEDNESS: single
        (D) TOPOLOGY: linear
```

(vii) IMMEDIATE SOURCE:
              (A) LIBRARY: BRAITUT03
              (B) CLONE: 859761

(xi) SEQUENCE DESCRIPTION: SEQ ID NO: 39 :

| | | | | | |
|---|---|---|---|---|---|
| aagctggtac | gctgcagncc | ggnccggaat | cccggtcncc | nacggtcngc | cacgtgaact | 60 |
| tcaaagtttc | tgtAAATTTA | TATATTAGTT | GCCtgtcttg | taactaTGAT | AGAGACGGAT | 120 |
| TTTTTTAATT | TTGCCAATCT | TTGTATTTTA | ACAAAAACAT | TGTCTACTTA | GGTTTAAGTT | 180 |
| AATCTTTGAT | CATTTATACG | TAATTTGTTT | tatttgtnnn | nnnnnnnnnn | nnnnnnnatg | 240 |
| tGTCATTTTC | TCCTATCAGT | TTCTGTCTTC | TTGTTTTTAA | ATTATGACTT | TTATTTTTAT | 300 |
| TGTTTTCATA | GATACAACAG | AGAAATGCAT | AATGTCCACt | gaatttatta | aagttccaaa | 360 |
| atcggtcgcg | cgcagtnnnn | nnnnnnnnnn | nnnnnnnnnn | nnnnnnnnnn | nnnnnnnnnn | 420 |
| nnnnnnnnnn | nnnnnnnnnn | nnnnnnnnnn | nnnnnnnnnn | nnnnnnnnnn | nnnnnnnnnn | 480 |
| nnnnnnnnnn | nnnnnnnnnn | nnnnnnnnnn | nnnnnnnnnn | nnnnnnnnnn | nnnnnnnnnn | 540 |
| nngccgaggc | agggagaatt | gctgggaanc | tggggaggca | gaaggttnca | agtgagcgga | 600 |
| gatgggcacc | accgcc | | | | | 616 |

(2) INFORMATION FOR SEQ ID NO:    40:

(i) SEQUENCE CHARACTERISTICS:
              (A) LENGTH: 69 base pairs
              (B) TYPE: nucleic acid
              (C) STRANDEDNESS: single
              (D) TOPOLOGY: linear (vii) IMMEDIATE SOURCE:
              (A) LIBRARY: BRAITUT03
              (B) CLONE: 859956

(xi) SEQUENCE DESCRIPTION: SEQ ID NO: 40 :

| | | | | | |
|---|---|---|---|---|---|
| TGAATTGTTG | GTTGTATGTA | ATCTTAATAT | TATATATTAA | AGTAGGCGTA | CATGGACAGT | 60 |
| AGCTACCAT | | | | | | 69 |

(2) INFORMATION FOR SEQ ID NO:    41:

(i) SEQUENCE CHARACTERISTICS:
              (A) LENGTH: 311 base pairs
              (B) TYPE: nucleic acid
              (C) STRANDEDNESS: single
              (D) TOPOLOGY: linear (vii) IMMEDIATE SOURCE:
              (A) LIBRARY: BRAITUT03
              (B) CLONE: 867581

(xi) SEQUENCE DESCRIPTION: SEQ ID NO: 41 :

| | | | | | |
|---|---|---|---|---|---|
| gggggggaaag | tcTGGCACAG | GAAGAAGCAG | GTCTTGACTG | ACAGGggaat | tacctggGAA | 60 |
| GACAGCTAAC | GAAGGGGCAG | GGGAGGGACA | GAGGACCCGA | GTGTTCAAGG | AGGAGAGCAG | 120 |
| CCAGAAAACC | ACCCAGGCAC | CTCCCGAGCA | GGAAGGCAGC | AGGGGGAGCT | GCGGGGACTC | 180 |
| GTGTGATTTC | AATAGTAGCG | CTTCTGCGGA | GAGACACAGC | GAGGAAACCT | TCTCTATGGA | 240 |
| GAGGAGGCCG | TCGTTCTTCT | CAGGCCAGAC | ATCCTTGCCC | TCCAGTTCAT | AGAAGAGAAA | 300 |
| ATTgagggcc | g | | | | | 311 |

(2) INFORMATION FOR SEQ ID NO:    42:

(i) SEQUENCE CHARACTERISTICS:

(A) LENGTH: 3707 base pairs
(B) TYPE: nucleic acid
(C) STRANDEDNESS: single
(D) TOPOLOGY: linear (vii) IMMEDIATE SOURCE:
(A) LIBRARY: CERVNOT01
(B) CLONE: 936117

(xi) SEQUENCE DESCRIPTION: SEQ ID NO: 42 :

```
atgggttcct catcccttcc tgctgcaaaa gaagttaaca aaaaacaagt gtgctacaaa      60
cacaatttca atgcaagctc agtttcaggg tgttcaaaaa ctgttgatgt gtgttgtcac     120
tttaccaatg ctgctaataa ttcagtctgg agcccatcta tgaagctgaa tctggttcct     180
ggggaaaaca tcacatgcca ggatcccgta ataggtgtcg agagccggg gaaagtcatc      240
cagaagctat gccggttctc aaacgttccc agcagccctg agagtcccat tggcgggacc     300
atcacttaca aatgtgtagg ctcccagtgg gaggagaaga gaaatgactg catctctgcc     360
ccaataaaca gtctgctcca gatggctaag gctttgatca agagcccctc tcaggatgag     420
atgctcccta cacctgaa ggatctttct attagcatag gcaaagcgga acatgaaatc       480
agctcttctc ctggggagtc tgggagccat tattaacatc cttgatctgc tctcaacagt     540
tccaacccaa gtaaattcag aaatgatgac gcacgtgctc tctacggtta atgtcatcct     600
tggcaagccc gtcttgaaca cctggaaggt tttacaacag caatggacca atcagagttc     660
acagctacta cattcagtgg aaagattttc ccaagcatta cagtcaggag atagccctcc     720
tttgtccttc tcccaaacta atgtgcagat gagcagcacg gtaatcaagt ccagccaccc     780
agaaacctat caacagaggt ttgttttccc atactttgac ctctgggca atgtggtcat      840
tgacaagagc tatctagaaa acttgcagtc ggattcatct attgtcacca tggctttccc     900
aactctccaa gccatccttg ctcaggatat ccaggaaaat aactttgcag agagcttagt     960
gatgacaacc actgtcagcc acaatacgac tatgccattc aggatttcaa tgactttta    1020
gaacaatagc cttcaggcgg cgaaacgaag tgtgtcttct ggaacttcag gcttgccaac    1080
aacacagggg ggtgggacag cagtgggtgc tatgttgaag aaggtgatgg ggacaatgtc    1140
acctgtatct gtgaccacct aacatcattc tccatcctca tgtccctga ctccccagat     1200
cctagttctc tcctgggaat actcctggat attatttctt atgttggggt gggcttttcc    1260
atcttgagct tggcagcctg tctagttgtg gaagctgtgg tgtggaaatc ggtgaccaag    1320
aatcggactt cttatatgcg ccacacctgc atagtgaata tcgctgcctc ccttctggtc    1380
gccaacacct ggttcattgt ggtcgctgcc atccaggaca atcgctacat actctgcaag    1440
acagcctgtg tggctgccac cttcttcatc cacttcttct acctcagcgt cttcttctgg    1500
atgctgacac tgggcctcat gctgttctat cgcctggttt tcattctgca tgaaacaagc    1560
aggtccactc agaaagccat tgccttctgt cttggctatg ctgcccact tgccatctcg     1620
gtcatcacgc tgggagccac ccagccccgg gaagtctata cgaggaagaa tgtctgttgg    1680
ctcaactggg aggacaccaa ggccctgctg ctttcgcca tcccagcact gatcattgtg     1740
gtggtgaaca taaccatcac tattgtggtc atcaccaaga tcctgaggcc ttccattgga    1800
gacaagccat gcaagcagga gaagagcagc ctgtttcaga tcagcaagag cattgggtc     1860
ctcacaccac tcttgggcct cacttggggt tttggtctca ccactgtgtt cccagggacc    1920
aaccttgtgt tccatatcat atttgccatc tcaatgtct tccagggatt attcatttta     1980
ctctttggat gcctctggga tctgaaggta caggaagctt tgctgaataa gttttcattg    2040
```

-continued

| | | | | |
|---|---|---|---|---|
| tcgagatggt | cttcacagca | ctcaaagtca | acatccctgg | ggttcatcca cacctgtgtt | 2100 |
| ttctatgagt | tctccaatat | caaggagatt | taacaatttg | tttggtaaaa caggaacgta | 2160 |
| taatgtttcc | accccagaag | caaccagctc | atccctggaa | aactcatcca gtGCTTCTTC | 2220 |
| GTTGCTCAAC | TAAGAACAGG | ATAATCCAAC | CTACGTGACC | TCCCGGGGAC AGTGGCTGTG | 2280 |
| CTTTTAAAAA | GAGATGCTTG | CAAAGCAATG | GGGAACGTGT | TCTCGGGGCA GGTTCCGGG | 2340 |
| AGCAGATGCC | AAAAAGACTT | TTTCATAGAG | AAGAGGCTTT | CTTTTGTAAA GACAGAATAA | 2400 |
| AAATAATTGT | TATGTTTCTG | TTTGTTCCCT | CCCCCTCCCC | CTTGTGTGAT ACCACATGTG | 2460 |
| TATAGTATTT | AAGTGAAACT | CAAGCCCTCA | AGGCCCAACT | TCTCTGTCTA TATTGTAATA | 2520 |
| TAGAATTTCG | AAGAGACATT | TTCACTTTTT | ACACATTGGG | CACAAAGATA AGCTTTGATT | 2580 |
| AAAGTAGTAA | GTAAAAGGCT | ACCTAGGAAA | TACTTCAGTG | aattctnnnn nnnnnnnnnn | 2640 |
| nnnnnnnnnn | nnnnnnaag | ggagggaaac | agggagaaag | ggaaaaagaa gaaaaagaga | 2700 |
| aagatgaaaa | taggaacaaa | taaagacaaa | caacattaag | ggccatattg taagatttcc | 2760 |
| atgttaatga | tctaatAtaa | tCACTCAgtg | caacattGAG | AATTTTTTTT taatggctca | 2820 |
| aAAATGGAAA | CTGAAAGCAA | GTCATGGGGA | ATGAATACTT | TGGGCAGTAT CTTCCtgaTG | 2880 |
| TCTTCTTAGC | TAAGAGGAGG | AAAAAAAGGC | TGAAAAAATA | GGGAGGAAAT TCCTTCATCA | 2940 |
| GAACGACTTC | AAGTGGATAA | CAATATTTAT | AAGAAATGAA | TGGAAGGAAA TATGATCCTC | 3000 |
| CTGAGACTAA | CTTTGTATGT | TAAGGTTTGA | ACTAAGTGAA | TGTATCTGCA GAGGAAGTAT | 3060 |
| TataAAGATA | TGtcatTAGA | TCCAAGTGCT | GATTAAATTt | ttaTAGTTTA TCAGAaaagC | 3120 |
| CTTATATTTT | AGTTTGTTCC | ACATTTTGAA | AGCAAAAAAT | ATATATTTGA TATACCCTTC | 3180 |
| AATTGCCAAA | TTTGATATGT | TGCACTGAAG | ACagacCCTG | TCATATATTT AATGGCTTCA | 3240 |
| AGCAGGTACT | TCTCTGTGCA | TTATAGAATA | GATTTAATA | ATCTTATAGC ATTGTATATT | 3300 |
| ATTATTGCTG | TTGTCACTGT | TATTATTATT | GTGGATACTG | GCCCTTGGTG TGTTGCATAG | 3360 |
| CTCCCTATGT | ATTCTCTGTT | TCcatcTTTA | AGTTCCCAGA | CCAATATACA TTAAGAGTTT | 3420 |
| TGCATGGTCT | AAATTGTGTT | TATTCCAACC | ACGTGGAAAG | CTCCTGGAAA GAAATTTTAC | 3480 |
| ATTCGGTTGT | TCTGTGCTCC | TAATGACACT | TGACCTTGTT | GAACAAATGG CAGAGCCTTT | 3540 |
| CCCAAGGATT | TGATTGTTTG | TGAATTATCT | GCATGTGTGC | TTTTTTTtgG TGTGTATTTC | 3600 |
| ATTAAAAAAT | ATAAATATTT | ATGAAAATTG | CACGCATATT | AGAGTTAACC ATGTACTATT | 3660 |
| GATACAGCAA | CGCTACATTG | CAAATAAAAG | TCCgatccca | aaaggag | 3707 |

(2) INFORMATION FOR SEQ ID NO: 43:

(i) SEQUENCE CHARACTERISTICS:
        (A) LENGTH: 729 base pairs
        (B) TYPE: nucleic acid
        (C) STRANDEDNESS: single
        (D) TOPOLOGY: linear (vii) IMMEDIATE SOURCE:
        (A) LIBRARY: KIDNTUT01
        (B) CLONE: 996903

(xi) SEQUENCE DESCRIPTION: SEQ ID NO: 43 :

| | | | | |
|---|---|---|---|---|
| atantttatt | ttaatattta | caaatattta | caaatatta | tttttaaata aaatgtatat | 60 |
| accatgtagt | atgttgtatt | tatttactca | atgttcttt | aagtgtttca ggctgcatgt | 120 |
| accaagtagt | tcagacgatt | ggctcggatg | gaaaaaatct | tctgcaatta cttccaattc | 180 |
| ctaagtcttc | tggaaatctt | ataccactag | ttcaatcttc | agtcatgtct gatgctttga | 240 |

```
aaggaatac aggaaaacca gttcaagtta cttttcagac tcagatttcc agctcttcca    300
caagtgcatc agttcaattg ccCATTTTTC AGccagccag tTCTTCAAAC TATTTTCTTA    360

CAAGAACAGT AGATACATCA GAAAAGGTA GAGTTACTTC TGTGGGAACT GGAAATTTTT    420

CTTCATCAGT TTCTAAAGTT CAGAGTCATG GTGTGAAAAT TGATGGACTC ACCATGCAAA    480

CATTTGCTGT TCCTCCctca acacaaaaag actCATCTTT TATTGTAGTT AATACCCAGA    540

GTCTTCCAGT GACTgtgaag tctccagTTT TGCCTTCTGG GCATCATTTA CAGATTCCAG    600

CCCATGCTGA AGTGAAATCT GTACcagcgt catcattgcc tccttcagtg cagcaaaaga    660
tacttgcaac tgccaccacc agtacctcag gaatggttga ggcctcccaa atgccaaccg    720
ttatttatg                                                             729

(2) INFORMATION FOR SEQ ID NO:    44:

(i) SEQUENCE CHARACTERISTICS:
        (A) LENGTH: 802 base pairs
        (B) TYPE: nucleic acid
        (C) STRANDEDNESS: single
        (D) TOPOLOGY: linear (vii) IMMEDIATE SOURCE:
        (A) LIBRARY: KIDNTUT01
        (B) CLONE: 999663

(xi) SEQUENCE DESCRIPTION: SEQ ID NO: 44 :

taaggatgta atctacagtt ttcagatctg cagggtagtc ttgattggct aaaaacaaat     60
caattttctt cttggcataa agtgtttcat tattataggg gtgttcattt taaatagttt    120
aaaaacaatt gcagcacatt ctaagcataa gagaaagtta ttgacaacag gtaccttcct    180
aatctcccaa gacgtactta ctcatttgtg aagtattaaa gtaagaggta actcaagcag    240
aatgctggct atgaatgtag atattgaagc tattcataaa cactggaaat agaattttaa    300
gcttttagcc ttcagtggaa tgcacatatt ggacatgtgc atgtgaacac cttttttcagt    360 agcactcacg gatttccatt cgattgtata gaatgaatac aagtgtttta gtggaatttg    420
ctacttaatt tttaatcttg cgatgtccgt gattattaca tgcttactag tgttgtggac    480
attgaagaca aggtcattcg taggtgtcag attacaatgg agaacaaaaa tcgtttccc     540 cccacccaca tccaaacacc attctcgagg gagcatttct tgcaaaacac cttacattca    600
ttttctatct ttgcactttt tcttaagtac agaaaagttg tctttaagac ctagtttgaa    660
cttcatgcag taagagggac aaagggtaaa ccatgttggg gagttcacat tggtcagagc    720
atagtaaggg aaagtaccaa aaccccaatt ttcctngaat aattcagatg gttttaaaaa    780
cctcacttct aggccggnaa ca                                            802

(2) INFORMATION FOR SEQ ID NO:    45:

(i) SEQUENCE CHARACTERISTICS:
        (A) LENGTH: 2039 base pairs
        (B) TYPE: nucleic acid
        (C) STRANDEDNESS: single
        (D) TOPOLOGY: linear (vii) IMMEDIATE SOURCE:
        (A) LIBRARY: MENITUT03
        (B) CLONE: 1256053

(xi) SEQUENCE DESCRIPTION: SEQ ID NO: 45 :

AGCAGCCTGG GCGGCAGGGG CGGTGGCTGG AGCTCGGTAA AGCTCGTGGG ACCCCATTGG     60

GGGAATTTGA TCCAAGGAAG CGGTGATTGC CGGGGGAGGA GAAGCTCCCA GATCCTTGTG    120
```

-continued

```
TCCACTTGCA GCGGGGAGG CGGAGACGGC GGACGGGCCT TTTGGCGTCC ACTGCGCGGC      180

TGCACCCTGC CCCATCCTGC CGGGATCATG GTCTGCGGCA GCCCGGGAGG GATGCTGCTG      240

CTGCGGGCCG GGCTGCTTGC CCTGGCTGCT CTCTGCCTGC TCCGGGTGCC CGGGGCTCGG      300

GCTGCAGCCT GTGAGCCCGT CCGCATCCCC CTGTGCAAGT CCCTGCCCTG GAACATGACT      360

AAGATGCCCA ACCACCTGCA CCACAGCACT CAGGCCAACG CCATCCTGGC CATCGAGCAG      420

TTCGAAGGTC TGCTGGGCAC CCACTGCAGC CCCGATCTGC TCTTCTTCCT CTGTGCCATG      480

TACGCGCCCA TCTGCACCAT TGACTTCCAG CACGAGCCCA TCAAGCCCTG TAAGTCTGTG      540

TGCGAGCGGG CCCGGCAGGG CTGTGAGCCC ATACTCATCA AGTACCGCCA CTCGTGGCCG      600

GAGAACCTGG CCTGCGAGGA GCTGCCAGTG TACGACAGGG GCGTGTGCAT CTCTCCCGAG      660

GCCATCGTTA CTGCGGACGG AGCTGATTTT CCTATGGATT CTAGTAACGG AAACTGTAGA      720

GGGGCAAGCA GTGAACGCTG TAAATGTAAG CCTATTAGAG CTACACAGAA GACCTATTTC      780

CGGAACAATT ACAACTATGT CATTCGGGCT AAAGTTAAAG AGATAAAGAC TAAGTGCCAT      840

GATGTGACTG CAGTAGTGGA GGTGAAGGAG ATTCTAAAGT CCTCTCTGGT AAACATTCCA      900

CGGGACACTG TCAACCTCTA TACCAGCTCT GGCTGCCTCT GCCCTCCACT TAATGTTAAT      960

GAGGAATATA TCATCATGGG CTATGAAGAT GAGGAACGTT CCAGATTACT CTTGGTGGAA     1020

GGCTCTATAG CTGAGAAGTG GAAGGATCGA CTCGGTAAAA AAGTTAAGCG CTGGGATATG     1080

AAGCTTCGTC ATCTTGGACT CAGTAAAAGT GATTCTAGCA ATAGTGATTC CACTCAGAGT     1140

CAGAAGTCTG GCAGGAACTC GAACCCCCGG CAAGCACGCA ACTAAATCCC GAAATACAAA     1200

AAGTAACACA GTGGACTTCC TATTAAGACT TACTTGCATT GCTGGACTAG CAAAGGAAAA     1260

TTGCACTATT GCACATCATA TTCTATTGTT TACTATAAAA ATCATGTGAT AACTGATTAT     1320

TACTTCTGTT TCTCTTTTGG TTTCTGCTTC TCTCTTCTCT CAACCCCTTT GTAATGGTTT     1380

GGGGGCAGAC TCTTAAGTAT ATTGTGAGTT TTCTATTTCA CTAATCATGA GAAAACTGT      1440

TCTTTTGCAA TAATAATAAA TTAAACATGC TGTTACCAGA GCCTCTTTGC TGGAGTCTCC     1500

AGATGTTAAT TTACTTTCTG CACCCCAATT GGGAATGCAA TATTGGATGA AAAGAGAGGT     1560

TTCTGGTATT CACAGAAAGC TAGATATGCC TTAAAACATA CTCTGCCGAT CTAATTACAG     1620

CCTTATTTTT GTATGCCTTT TGGGCATTCT CCTCATGCTT AGAAAGTTCC AAATGTTTAT     1680

AAAGGTAAAA TGGCAGTTTG AAGTCAAATG TCACATAGGC AAAGCAATCA AGCACCAGGA     1740

AGTGTTTATG AGGAAACAAC ACCCAAGATG AATTATTTTT GAGACTGTCA GGAAGTAAAA     1800

TAAATAGGAG CTTAAGAAAG AACATTTTGC CTGATTGAGA AGCACAACTG AAACCAGTAG     1860

CCGCTGGGGT GTTAATGGTA GCATTCTTCT TTTGGCAATA CATTTGATTT GTTCATGAAT     1920

ATATTAATCA GCATTAGAGA AATGAATTAT AACTAGACAT CTGCTGTTAT CACCATAGTT     1980

TTGTTTAATT TGCTTCCTTT TAAATAAACC CATTGGTGAA AGTCAACAAA AAAAAAAA      2039
```

(2) INFORMATION FOR SEQ ID NO: 46:

(i) SEQUENCE CHARACTERISTICS:
        (A) LENGTH: 2484 base pairs
        (B) TYPE: nucleic acid
        (C) STRANDEDNESS: single
        (D) TOPOLOGY: linear (vii) IMMEDIATE SOURCE:
        (A) LIBRARY: SYNORAT05
        (B) CLONE: 1262948

(xi) SEQUENCE DESCRIPTION: SEQ ID NO: 46 :

-continued

```
gaagaagagc cctgtgggcc tccactttct gttcctcctg ggaccctgg gcctctttgg      60 gctgacgttg ccttcatcat ccaggaggac gagaccatct gctctgtccg ccgcttcctc     120 tgggcgtcc  tctttgcgct ctgcttctcc tgcctgctga ccaggcatg  gcgcgtgcgg     180 aggctggtgc ggcatggcac gggcccgcg  ggctggcagc tggtgggcct ggcgctgtgc     240
ctgatgctgg tgcaagtcat catcgctgtg gagtggctgg tgctcaccgt gctgcgtgac     300
acaaggccag cctgcgccta cgagcccatg gactttgtga tggccctcat ctacgacatg     360
gtactgcttg tggtcaccct ggggctggcc ctcttcactc tgtgcggcaa gttcaagagg     420
tggaagctga acggggcctt cctcctcatc acagccttcc tctctgtgct catctgggtg     480
gcctggatga ccatgtacct cttcggcaat gtcaagctgc agcaggggga tgCCTGGAAC     540

GACCCCACCT Tggccatcac gctggcggcc agcggctggg tctTCGTCAT CTTCCACGCC     600

ATCCCTGAGA TCCACTGCAC CCTTCTGCCA GCCCTGCAGG AGAACACGCC CAACTACTTC     660

GACACGTCGC AGCCCAGGAT GCGGGAGACG GCCTTCGAGG AGGACGTGCa gctgccgcgg     720
gcctatATGG AGAACAAGGC CTTCTCCATG GATGAACACA ATgcagctCT CCGAACAGCA     780

GGATTTCCCA ACGGCAGCTT GGGAAAAAGA CCCAGTGGCA GCTTGGGGAA AGACCCAGC     840

GCTCCGTTTA GAAGCAACGT GTATCAGCCA ACTGAGATGG CCGTCGTGCT CAACGGTGGG     900

ACCATCCCaa ctgctccgcC AAGTCACACA GGAAGACACC TTTGGTGAAA GACTTTAAGT     960

TCCAGAGAAT CAGAATTTCT CTTACCGATT TGCCTCCCTG GCTGTGTCTT TCTTGAGGGA    1020

GAAATCGGTA ACAGTTGCCG AACCAGGCCG CCTCACAGCC AGGAAATTTG GAAATCCTAG    1080

CCAAGGGGAT TTCGTGTAAA TGTGAACACT GACGAACTGA AAAGCTAACA CcgaCTGCCc    1140
gcccctcCCC TGCCACACAC ACAGACACGT AATACCAGAC CAACCtcaat ccccgcaaac    1200
taaagcaaag ctaattgcaa atagtattag gctcactgga aaatgtggct gggaagactg    1260
tttcatcctc tgggggtaga acagaaccaa attcacagct ggtgggccag actggtgttg    1320
gttggaggtg gggggctccc actcttatca cctctcccca gcaagtgctg gaccccaggt    1380
agcctcttgg agatgaccgt tgcgttgagg acaaatgggg actttgccac cggcttgcct    1440
ggtggtttgc acatttcagg ggggtcagga gagttaagga ggttgtgggt gggattccaa    1500
ggtgaggccc aactgaatcg tggggtgagc tttatagcca gtagaggtgg agggaccctg    1560
ggcatgtgcc aaagaagagg ccctctgggt gatgaagtga ccatcacatt tggaaagtga    1620
tcaaccactg ttccttctat gggggctctt gctctagtgt ctatggtgag aacacaggcc    1680 ccgcccttc  ccttgtagag ccatagaaat attctggctt ggggcagcag tcccttcttc    1740
ccttgatcat ctcgccctgt tcctacactt acgggtgtat ctccaaatcc tctcccaatt    1800
ttattccctt attcatTTCA AGAGCTCCAA TGGGGTCTCC AGCTGAaagc ccctCCGGGa    1860
ggcaggttgg aaggcaggcA CCACGGCAGG TTTTCCGCGA TGATGTCACC TAGCAGGGCT    1920

TCAGGGGTTC CCACTAGGAT GCAgagATGA CCTCTCGCTG CCTCACAAGC AGTGACACCT    1980

CGGGTCCTTT CCGTTGCTAT GGTGAAAatt cCTGGATGGA ATGGATCACA TGAGGGTTTC    2040

TTGTTGCTTT TGGAGGGTGT GGGGGATATT TTGTTTTGGT TTTTCTGCAG GTTCCATGAA    2100

AACAGCCCTT TTCCAAGCCC ATTGTTTCTG TCATGGTTTC CATCTGTCCT GAGCAAGTCA    2160

TTCCTTTGTT ATTTAGCAtt tCGAACAtct CGGCCATTCA AAGCCCCCAT GTTCTCTGCA    2220

CTGTTTGGCC AGCATAACCT CTAGCATCGA TTCAAAGCAG AGTTTTAACC TGACGGCATG    2280

GAATGTATAA ATGAGGGTGG GtcctTCTGC AGATACTCTA ATCACTACAT TGCTTTTTCT    2340
```

-continued

```
ATAAAACTAC CCATAAGCCT TTAACCTTTA AAGAAAAATG AAAAAGGTTA GTGTTTGGGG    2400

GCCGGGGGAG GACTGACCGC TTCATAAGCC AGTACGTCTG AGCTGAGTAT GTTTCAATAA    2460

Accttttgat atttctcaaa aaaa                                           2484
```

(2) INFORMATION FOR SEQ ID NO:   47:

(i) SEQUENCE CHARACTERISTICS:
        (A) LENGTH: 2077 base pairs
        (B) TYPE: nucleic acid
        (C) STRANDEDNESS: single
        (D) TOPOLOGY: linear (vii) IMMEDIATE SOURCE:
        (A) LIBRARY: TESTTUT02
        (B) CLONE: 1271435

(xi) SEQUENCE DESCRIPTION: SEQ ID NO: 47 :

```
ttggcggcna ntgcaacgat ctnnaaatgt gaatcagcca ggaaaggctg tatgagggac      60
aggcggctct tcttcgaatt ttccacctgc tgaattactc acgcccaag gagggtgatg     120 accggncgtt cttctggatg tttgagaatg ttgtagnctc gtgccgattc ggcagagggg    180
acatctcacg gttcctggag tgtaatccag tgatgattga tgccatcaaa gtttctgctg    240
ctcacagggc ccgatacttc tggggcaacc tacccgggat gaacaggccc gtgatagcat    300
caaagaatga taaactcgng ctgcaggact gcttggaata caataggata gccaagttaa    360
agaaagtaca gacaataacc accaagtcga actcgatcaa acaggggaaa aaccaacttt    420
tccctgttgt catgaatggc aaagaagatg tttngtggtg cactgagctc gaaaggntct    480 ttggcttttcc tgtgcactac acagacgtgt ccaacatggg ccgtggtgcc cgccagaagc    540
tgctgggaag gtcctggagc gtgcctgtca tccgacacct cttcgcccct ctgaaggact    600
actttgcatg tgaatagttc cagccagggc ccaagcccac tggggtgtgt ggcagagcca    660
ggacccagga ggtgtgattc ctgaaggcat ccccaggccc tgctcttcct cagctgtgtg    720
ggtcataccg tgtacctcag ttccctcttg ctcagtgggg gcagagccac ctgactcttg    780 cagggggtagc ctgaggtgcc gcctccttgt gcacaaatca gacctggctg cttggagcag    840
cctaacacgg tgctcatttt ttcttctcct aaaactttaa aacttgaagt aggtagcaac    900
gtggcttttt tttttttccct tcctgggtct accactcaga gaaacaatgg ctaagatacc    960
aaaaccacag tgccgacagc tctccaatac tcaggttaat gctgaaaaat catccaagac   1020
agttattgca agagtttaat ttttgaaaac tggctactgc tctgtgttta cagacgtgtg   1080
cagttgtagg catgtagcta caggacattt ttaagggccc aggatcgttt tttcccaggg   1140
caagcagaag agaaaatgtt gtatatgtct tttacccggc acattcccct tgcctaaata   1200
caagggctgg agtctgcacg ggacctatta gagtatttttc cacaatgatg atgatttcag   1260
cagggatgac gtcatcatca cattcagggc tattttttcc cccacaaacc caaggggcag   1320
gggccactct tagctaaatc cctccccgtg actgcaatag aaccctctgg ggagctcagg   1380 aaaggggggtg tgctgagttc tataatataa gctgccatat attttgtaga caagtatggc   1440
tcctccatat ctccctcttc cctaggaaga ggagtgTGAA GCAAGGAGCT TAGATAAGAC    1500

ACCCCCTCAA ACCCATTCCC TCTCCAGGAG ACCTACCCTC CACAGGCACA GGTCCCcaGA    1560

TGAGAagtcT GCTACCCTCA TTTCTCATCT TTTTACTAAA CTCAGAGGCA GTGACAGCAG    1620

TCAGGGACAG ACATACATTT CTCATACCTT CCCCACATCT GAGAGATGAC AGGGAAAACT    1680

GCAAAGCTCG GTGCTCCCTT TGGAGATTTT TTAATCCTTT TTTATTCCAT AAGAAGTCGT    1740
```

```
TTTTAGGGAG AACGGGAATT CAGACAAGCT GCATTTCAGA AATGCTGTCA TAATGGTTTT      1800

TAACACCTTT TACTCTTCTT ACTGGTGCTA TTTTGTAGAA TAAGGAACAA CGTTGACAAG      1860

TTTTGTGGGG CTTTTTATAC ACTTTTTAAA ATCTCAAACT TCTATTTTTA TGTTTAACGT      1920

TTTCATTAAA ATTTTTTtgT AACTGGAGCC ACGACGTAAC AAATATGGGG AAAAAACTGT      1980

GCCTTGTTTC AACAGTTTTT gctaattttt aggctgaaag atgacggatg cctagagttt      2040
accttatgtt taattaaaat cagtatttgt ctaaaaa                               2077

(2) INFORMATION FOR SEQ ID NO:    48:

(i) SEQUENCE CHARACTERISTICS:
        (A) LENGTH: 625 base pairs
        (B) TYPE: nucleic acid
        (C) STRANDEDNESS: single
        (D) TOPOLOGY: linear (vii) IMMEDIATE SOURCE:
        (A) LIBRARY: TESTTUT02
        (B) CLONE: 1271539

(xi) SEQUENCE DESCRIPTION: SEQ ID NO: 48 :

tttttagtta actttagata ttttaacaac acataaaatg agtggtaggg tatattgtat        60
tttactgtat aggacacctt cagataaatt ctaaaaataa tttgcatttc atgtaatgct       120
tttcacacaa agtaatggcc aaactttagg gtcagtttgc cctgcttcat accacatgca       180
gaacaaattt aagatggatt aggactccaa atagaaaaga aaaattctta ataaaaaact       240
attcaagatg gataaaagga ttaatttcaa gaaaaataaa actaataaaa tagaactatt       300
ctggtaaccc cagaaaccat aagagaaagg attaacagat tagctgcatt aaaatttcaa       360
atttattact tattcattca cccattcatg agataattgt ttttattgag gacatactat       420
gtggccacgc acccattcct gctgctgagg gcacagcaat gtactaaaca gccagcatca       480
ctgcncttgt ggcatgctgt atggnaacca aaacctaaac aaaacaggaa ganagtaata       540
gcntggagaa gttatttggc aaaatatttg ataagcaaac taagtatctg tagtaaacaa       600
gagctcgtna gncaagggaa aggga                                            625

(2) INFORMATION FOR SEQ ID NO:    49:

(i) SEQUENCE CHARACTERISTICS:
        (A) LENGTH: 1571 base pairs
        (B) TYPE: nucleic acid
        (C) STRANDEDNESS: single
        (D) TOPOLOGY: linear (vii) IMMEDIATE SOURCE:
        (A) LIBRARY: BLADTUT02
        (B) CLONE: 1314935

(xi) SEQUENCE DESCRIPTION: SEQ ID NO: 49 :

ttgcatgcca tgcaggtcga ctctagagga tcccccctcga ggttaaacat atgtatgacc       60
cagaaattcc acacttaggt agctattcaa ggggaatgaa atcaTATGTG CATAAAAAAA      120

TTGTATGCAA ATGTTCATAG TAGCACTATT CatagtagCC AAAAAGTAGA AACAATACAA      180

AGTTCCATTT ACTGATGAAT GGATAAATGA AATGTGGTAT ATCCATGCAA TGAAATATTA      240

TTCAGCAATA AAAATAAATG TAGTGCTGAT AcatGTTACA TCATGGAGGA ACCTTGAAAA      300

CATTTTGGTA AGTGAAAGAA GCCACTCACA AAAGACCACA TATCATATGA CCAATTGTGA      360

AGTGTCAAAA ATAGGTAAAT CCATAGCGGC AGAAACTCTA GTGGTTGCCT AGCTGGGTGG      420

TTGGGAGAAA ATGGGTAGTG ACTGTAAATG GATATAGGGT TTCTTTGTGG GGTGATGAAA      480
```

```
ATGTCCTAAA ATTGATTGTG GTCGTGGTTG CACGACTCTA TGAATATAAA TCTTGAATTG      540

TACACATTAG ATTGATTAAc aGTATGATAT GTGAATTATA TCTCTAAAAA GCTGTTATAA      600

AAACAAAAAA GAGATGCCAC AGGgcTTGTT TTCTATGAAA GAAGCTTGAA ATATGCTAGA      660

ATTAATGCTT TGCTCGCTGC TACCACATAA ATTCTGTGAG GACTTGGAGT TTAAGTCttt      720
gCTGTATCTA GAAATAGagg cACACAAATA GAATGCTGaa tgaGTCCCTG CATTGGTGGT      780

CCCcaAGACC ACTTGCaagG TTCTGTAAAT CTCTAGGagg aCTCCTAGGA CTCAGCATTG      840

TTATCTTCTG GTTCTGATTT GCTACAGTGA AAGAACACAA AGTAAAATCA ACATAGGGAA      900

AAGgagCATG GTGTGCAGTC TGGAGAAATC AGGAGTAAGC GTCCAAGAGt cctCTTCCAA      960

TGCAGTCACA CAGGATGCTC TTAGTTCCTT AAGCAACAAG CTGCGACAAc aaGTTTGAAG     1020

TGTTGCCTAC TAGGGCACTC ATTAGAGACT CAGTGCCCAA GGCTACTGCT GGGagcTGAT     1080

CTgcctAGCA CATACCCAAA TTCCAGACTC CCAGAAGGAA AGCAGGTGTT CAGCATAAAC     1140

CACACTGTTT GTACAAACAG GTGAGGCATA GTGGCCACTC TATAATTTAG GAAAAATGTC     1200

ATATTAGTGT AGGGAACTGT TTACCAGCTC CAATTCCCAG CTGCTAACCA AAGGCCAACA     1260

TTGCAAACAG GCCTTCTAAG GATAGGCCTT CTCGAGCCTG CTCTGTGTTA ACTCTTTTCT     1320

GCACAATGAA TAGAAGACTG CCAGGTTCCA AATTtctgta ttatatgcAA CAAGCCTATA     1380

TGTGCAAAAG GTGTTAGGAG GAGGATTCAG CATGCCGTGG GAAGAGTGCT GCCTTGCACA     1440

CAGCTGGCAA TACAATCCAT GCTCATCTCT GAGGAAGAAG AGTCTAGAGG GGAGTCTGCC     1500

CTCTGGATTT TCCTCCCGAT GCCCAGAAAC aagtgaatta agacttaaag taggccagga     1560
acggtggctc a                                                         1571

(2) INFORMATION FOR SEQ ID NO:    50:

(i) SEQUENCE CHARACTERISTICS:
           (A) LENGTH: 601 base pairs
           (B) TYPE: nucleic acid
           (C) STRANDEDNESS: single
           (D) TOPOLOGY: linear (vii) IMMEDIATE SOURCE:
           (A) LIBRARY: COLNTUT03
           (B) CLONE: 1339906

(xi) SEQUENCE DESCRIPTION: SEQ ID NO: 50 :

ctgggtggag acaccatgta cttggtccac ttgtgctctt cagccaggac accagacatg       60
gtccaaaccg ctgcagggct ggctgcagca actccctgac actcaggaag gcccaggctg      120
ggcaggcaat acctgctccc aacagccatc tcccaggaag gaccctgttg ctagtgtgga      180
gcaaagacga gtcaagttta tgggctggaa gtcctacccg gaggctgctc actgagctgt      240
gatggctaca aggacagatg gggggaaggg tgcagggtgc ccgagacctg gcccgctgga      300
gcctgtcacc taatggctgg ctggaagacc actacacacc agccagccct ggtccattct      360
ctcatttaga ggcctccccg gtggaggcag ggatacacaa aatgctttgg ggctggatgg      420
gcccgccttt cagtctaaac aagagatctc aacacagctg cccagaaaan gcagattacc      480
agaaatggat aaagctggct gggtggggga ctgtccgaag gcagccagca ntgaactccg      540
gctngttgta acaaacaagg atanntnttt caaaactgaa atttaaatca ngaaangana      600
t                                                                    601

(2) INFORMATION FOR SEQ ID NO:    51:
```

(i) SEQUENCE CHARACTERISTICS:
        (A) LENGTH: 1180 base pairs
        (B) TYPE: nucleic acid
        (C) STRANDEDNESS: single
        (D) TOPOLOGY: linear (vii) IMMEDIATE SOURCE:
        (A) LIBRARY: COLNTUT03
        (B) CLONE: 1340918

(xi) SEQUENCE DESCRIPTION: SEQ ID NO: 51 :

```
gttgattgtt  ttccttaaca  ctttgacaaa  aggaccagtg  gaccaatctg  acaaagccat      60
tctggttcct  ttccttgagt  gtactgagaa  tagttttaaa  gctatgcaga  aaagggagct     120
gttattcaca  ctgcccttat  tttgttgtag  aattatggag  ttaaaagaaa  atgtgattcc     180
gaactctacc  aatgtattcc  taggctgtga  gtactttccc  ggcccaaagt  gtgaaaatat     240
gtaaagaagc  tttgttatgc  tgctattgat  ctgccatgat  ttctatttat  tcttttatgg     300
catgtaatgg  tgtttagtaa  tatttttaatg  tagattttga  tttatttcag  caatagtaat     360
tttaagatat  tctttgaatg  aaagtgtctt  cgtttctatg  atacaggtca  ttttgtagta     420
tttaaccaat  taagatgcac  tgcttacttt  tctgagcact  atttaatgat  ggggtaaaaa     480
cccaattggc  tcaaccagct  agcataagga  ttagctgtga  ataatgctga  cagatatgat     540
ggttccttag  gaacaatcat  ttaagcttta  atggtaactc  aatcataagt  ccatagatta     600
tttttttcta  gctaaaattt  tagaaaatta  cttgtgaatt  acatacttgt  tttagtttgg     660
tcttagttttt  tagcataaag  aatgattggc  ttttgttgat  ctaaacatgc  ttcctggaca     720
gggtttctgc  ttctcatttt  agtgtcttct  attgctgtct  acctaattat  gtgtgaattg     780
tgcagaattc  agggaagctt  taatgtgtgg  aaattgtgca  ggaattcaag  ggnagcttat     840
aaggtttcna  tgctccaatt  gtggaatagg  ttgttttcac  caggtagtat  gtaaattaag     900
caaccaaaaa  tgaattccct  atgcaatcac  tgggacgggg  aagctatagt  ggggtacagn     960
gggtgctgac  accgggggag  gtgtnccggg  ggccccggga  cttccctaaa  ggggcggac    1020
ccgtagggtg  gattgcaccc  caagggtagg  cccagtgggc  ttcggtggac  agncggtcna    1080
ggggttcttg  aatcggaata  tgctttgggg  atgaanattt  gggggtaag  gggatancc    1140
caagggcct  tgnccaacta  attcacccta  agctagggng                           1180
```

(2) INFORMATION FOR SEQ ID NO:   52:

(i) SEQUENCE CHARACTERISTICS:
        (A) LENGTH: 1280 base pairs
        (B) TYPE: nucleic acid
        (C) STRANDEDNESS: single
        (D) TOPOLOGY: linear (vii) IMMEDIATE SOURCE:
        (A) LIBRARY: COLNTUT03
        (B) CLONE: 1341346

(xi) SEQUENCE DESCRIPTION: SEQ ID NO: 52 :

```
cagatcaggg  ctgcttctag  tttggaggaa  gaaacaacta  tggcctcagt  tcttcctgga     60
gcctgagaag  aaacagccct  gcccgctctg  gccAGCCTGT  GGGCTCTGCT  GCTTGTGgca    120
gggttgccCT  GGGCACCACT  Tggcagtgcc  ttctctccag  ccCCAGGTTC  ATCCACTGGG    180
AGGAACCAGG  CTTTGTTTAA  ACATCTGTCC  TGTCCCCAGA  GAAGCTTGGA  GGACCAAGTG    240
GTACAGCGAT  TGAGGAAAGA  TGCCCTGGTG  GAGGCATTTG  CTTTTGGTGG  GAGGAAATGG    300
ATGGACAGGA  TGACTCTCTA  GAGCTGTCTT  TCCCAGAGAA  GCCCAAGTAG  ATAATAAAGC    360
```

```
CATGTAGAAA ATAGGATTAA GGTAATGAAC AGGCAGGACA AAGTTTGATC TTTCAGTAAC      420

ACCAAAGCCT GACTGACAGG CCAATccgag aggtggagCA GCATTGCCgg caggacttgg      480
ggttgggcgg tgagcggtgC TGGATGgatt ctttgctttt aacctgtcac tgctgcaact      540
tgaggagcgc ctggattttc tcttttatgt atgtgccggg gcttgggcag agagcgggga      600
gtactggagg ggcagtttgc cctaagcatt gctataccct ggatgatggt ggggctggg      660 acacattcaa agctgtagcc acccactggg caccagcgct cccatcaggg gagctatcac      720
ccacgtctat gtgtgtctct cagctactca ccctcagaca gccaatgctg cttctcacag      780
aacctggacc cctttcaggg tcaccattgt tccctcagcc cctcattcca tcaagaccac      840
tagagactgt tctccttgca ggctgggctg aacagggat ggaggggcag ttgctagctg       900
gagcacacag gtcagaaggc agccacaggc acacagccgt tgcctaaatg gcaaggagct      960
tggctgtccc cttccccctt cctcnnnttt tttttttnnn nnnnnnnnn nnnnnnnnnn      1020 nnnnnnnnnn nnnnnnnnnn nnnnnnnnnn nnnnnnnnnn nnnnnnnnnn nnnnnnnnnn      1080
nnnnnnnnnn nnnnnnnnnn nnnnnnnnnn nnnnnnnnnn nnnnnttct tctagttCCT      1140

TTAAGGATTT CTCTAGCACA GGATCAGAGA GGATCTTGGT TATtagtgaC TGGTGAGATT      1200

CTGTTGGGTG TTTGGAAGCT TCAAATGCat gGAGCCACCC CTTAAAAATG TCTCActgga      1260
ggcaggcacg gtggcttatg                                                 1280

(2) INFORMATION FOR SEQ ID NO:    53:

(i) SEQUENCE CHARACTERISTICS:
        (A) LENGTH: 713 base pairs
        (B) TYPE: nucleic acid
        (C) STRANDEDNESS: single
        (D) TOPOLOGY: linear (vii) IMMEDIATE SOURCE:
        (A) LIBRARY: BSTMNON02
        (B) CLONE: 1373668

(xi) SEQUENCE DESCRIPTION: SEQ ID NO: 53 :

ctaccctcag aaagagacag aggagtgcat cgcagctgtg tgaacccggg gtggtggtgg        60
ttccagcagc ggggcacgtg gtggacgcaa gacggccccg ttGAGTTTT GCTGCTAGGT       120

GAcACGTAGA ACTTGAACTT CAGAGGGTGC TCCTTGGAGG CCCTGATGAG AGAGACACAG      180

AAGGGAAGGG AGACTGTTCC CATGGTCCTG CCTCTGCGGc agcGAGCCTG CTGCTCTTGC      240

AGCTGGGTGG CTGTTCGGTG CAGGGGCCG GTGAGGAACA CGGTGGGGAG CAGCCTGCGA       300

GGGCGCCGGG CTTTCAGCAC TCACTATACC TGCTGTTTGG TTTGGCCAGG ATGGCCTGGG      360

AGTCCCCAGG GCCGGGCAAA GACTGCCCCC AACAGACATG GGCGGAGGGA ACCGTCTCAC      420

CCCTGCCTCT TCTCCCTTCT CTAcgcagtg tcagtGGGAC GGGAGGGTGG TCTGCCCGGG     480

GCTTCAAGCT CCTGTCCAGG AACCGGACCC ATGTCGTACG CCAGTGCAGC CACACGGCCA     540

GCTTCGAGGT GCTCATGGAC GTCTCCAGGT GTGAGATGGG CATCTTCTTG TGGCCACTAT     600

GCCCGCTgag cctaccccca aacctgcccc tcctcaaact aaatcttcca ttctaagcgc     660
tttgaacgaa gcaaatcaac caattaaaaa aatatattcc caggaaaaaa aaa            713

(2) INFORMATION FOR SEQ ID NO:    54:

(i) SEQUENCE CHARACTERISTICS:
        (A) LENGTH: 804 base pairs
        (B) TYPE: nucleic acid
        (C) STRANDEDNESS: single
        (D) TOPOLOGY: linear
```

(vii) IMMEDIATE SOURCE:
              (A) LIBRARY: BRAITUT08
              (B) CLONE: 1381411

(xi) SEQUENCE DESCRIPTION: SEQ ID NO: 54 :

| | | | | | |
|---|---|---|---|---|---|
| aagccctaag | ggncccatcn | ccatcaggnc | catttggnag | gcacgggngc | cnttcctntc | 60 |
| cccgctggcg | aagggattcn | ccagggataa | ttggtacccc | cggttncccn | ncccgcgttt | 120 |
| aaacgcgcca | tgaatgaatt | tggggccctt | tggaggggtn | tgcgtccatg | cccgcgacgt | 180 |
| aagccggaaa | tcgaantcgg | gagagaagaa | cctagaggcc | tggtttgctt | tggtggcatt | 240 |
| gtaaaaagag | taagagaggt | ttggtttgtg | gtggtttgct | tTCTTTACCA | TAAGCAATCC | 300 |
| CTTGCCTTAA | CTCATCACCC | TTTTTCACTA | TGACCCTTAG | ACCCTGAGTA | TTTTCAAATA | 360 |
| TATGATTGCT | GATAGTAGTG | ACCAAAACTa | ctttgttcct | ttcttacCAC | TCTCTCCTGG | 420 |
| GGCCGACACG | TTGGGACagc | acaccatagc | ataaagctag | gggatgcatg | gaaatagcag | 480 |
| cttgaaacta | ggaggtaaca | agaaagcttc | taggaagtag | atgttccata | tcttcaaaat | 540 |
| gcctcctcca | attttgtaag | aatgctagct | aggtattcct | gggattatta | tactgagata | 600 |
| tatatatata | cacacacaca | cacatnnnnn | nnnnnnnnnn | nnnnnnnnnn | nnnnnnnnnn | 660 |
| nnnnnnnnnn | nnnnnnnnnn | nnnnnnnnnn | nntatacaca | cacgcacaca | tatatgttgc | 720 |
| tgcagcataa | agaaattgaa | ataaaagttt | aaaatagtac | ccggttcaat | gaaagagccn | 780 |
| taaacccatc | cttaacccca | gctt | | | | 804 |

(2) INFORMATION FOR SEQ ID NO:   55:

(i) SEQUENCE CHARACTERISTICS:
              (A) LENGTH: 1095 base pairs
              (B) TYPE: nucleic acid
              (C) STRANDEDNESS: single
              (D) TOPOLOGY: linear (vii) IMMEDIATE SOURCE:
              (A) LIBRARY: BRAITUT08
              (B) CLONE: 1383714

(xi) SEQUENCE DESCRIPTION: SEQ ID NO: 55 :

| | | | | | |
|---|---|---|---|---|---|
| aagngtcnca | nncggggccc | nagtcagcag | tncaggcctt | gcttccaacc | gccgcggact | 60 |
| cgcagggccc | ancaggcatc | gggcagtnac | cagggcttcc | agaggagctn | tgnacccnt | 120 |
| gcaaaggctc | ctgccctgcg | tccagcctat | ccggcgggga | ctcnacgtgc | accccctcct | 180 |
| nattgtcctt | gtctagggcn | gcggcggcaa | ggtccttgct | cccatGGCGT | GACTCCAGGG | 240 |
| TGCAGGAGCC | TGGGCTGAGC | AGGTGGAGTA | GGgtgagctc | cgcCAAGAAC | CCAGCGAGAg | 300 |
| tggcgcccca | gggcggcaca | ggaggccgca | tTTAACATGT | CAATCATCTG | AAAGATTTTA | 360 |
| TGGCATCTtt | TTTTTGACAT | CTTATAATAT | CTATAATGtt | tATTATATCT | TGTGATATAA | 420 |
| TTATTAACAC | CACTTCagtG | TGATTATTAT | GATTATTTTT | ATACCAACAC | ATCTTcaaTT | 480 |
| ATTAATATTC | CCAGTTGCTA | GAGAAAactG | AAAActaCTA | GTTTTgaaAG | CCTCActtct | 540 |
| gCCAATGGAA | GCACATTcca | GCATGTCgcc | AacgCAATCC | ACTTTCCACC | ACTTTCACAa | 600 |
| aaAACGTTAC | TGCACAATtt | tACTATCCTA | CCCtcaTATa | cttttTtttGT | GTGTGtgtac | 660 |
| ttgtatgcat | gtatgtcaca | tatgttatat | atatatatat | atatataaag | tatgCCAGAG | 720 |
| ATGAACAAGT | ATTAGAAAAT | TAAATGCaca | cgagTCATGT | CAGTGCTATG | TATAATGTGG | 780 |
| TGTACTAAGT | ATAGATGTTC | AACAGTGTGG | GATctaGGct | ggAACAAGAC | TCCTAGTCTT | 840 |
| AAGCAATTCT | TTCTAGGTTC | AGTCTCTGGA | AATAATGcct | TgaaTCAAAT | GTgtgAGAAA | 900 |

```
Atcaatgggt tttaaagaCT ATTCTATGTC AactaTAACA tttaatttgg ggatttctgt      960
cccttataat gtctacctca ttttggatgg aatccttgag gcctggttta tttttctttt     1020
cctttctaca gatcgctgct cagagtgagg aatggagttg tgttttgaat aaaatatcca     1080
cgcatccttt tgtga                                                     1095
```

(2) INFORMATION FOR SEQ ID NO:    56:

(i) SEQUENCE CHARACTERISTICS:
        (A) LENGTH: 1610 base pairs
        (B) TYPE: nucleic acid
        (C) STRANDEDNESS: single
        (D) TOPOLOGY: linear (vii) IMMEDIATE SOURCE:
        (A) LIBRARY: BRAITUT08
        (B) CLONE: 1396833

(xi) SEQUENCE DESCRIPTION: SEQ ID NO: 56 :

```
ttagccactc agttttaaag gacannccct ccccaccccc cacacatttc tcagtcctcc       60
tctctctttt tttaaaatta aaattaaaat nnnnnnnnnn nnnnnnnnnn nnnnnnnnnn      120
nnnnnnnnnn nnnnnnnnnn nnnnnnnnnn nnnnnnnnnn nnnnnnnnnn nnnnnnnnnn      180
nnnnnnnnnn nnnnnnnnna gaggtgtgag ccaacatgcc cggccagtcc tcctcctttc      240
ttttccctgc tttatttctt ccgtagcctg atcatgacct gacacgtgtt ttgttgatga      300
tctccactcg catgaatata aggttccaca aaggcagggg gtttgtctat tatgtttaca      360
ttcatagtaa tccccagtgc ctaggcatag aagtaggtgc ttaaggtttg ttgaatgaat      420
acctgaaaga tggcaggaac tgaagttctg ggctgatgca ggaaagggga gtgggccatg      480
aggtgaggac atcatcgctt tccttttttg ccaaatgaat gggttggcct agacacccaa      540
gagaccatga acccctggga attgcgtaca tcattgggtg agtctctgcc tccatgcatt      600
tttctggaac aagggtccct accttcttgc agacattgaa gagagcctgt gacctcccag      660
aggcgctaag cacccttcca gctctgacat cgtatagttg gctctaatag gtctcagttt      720
cctgccttcc tgggaagtgg ggaaaggctg agaggccccg tgctgggggt gaagctaatt      780
cattagttac gcctcaacaa ggaccgggtg cctgcagtgc cagcgtgatt catcatgatg      840
attgccccac tgccagcctg cgtgggcctg gaacgccagc acattttacc tttacccact      900
gagaagggcc tggtgggagg tgaaggtaca ggatctgccg agagcaagaa aaagactctg      960
agaaagaaga gggctggtcc tccatgctct cgggcccaag aagctctgcc aggctggtgc     1020
cggggtggag aggctcatgt gggctcatgt ggtgcttcct gtgctgatgg agcccaagaG     1080

GGCAGCCTGG CGCTGGGTGC CAGCCTGAGC ATGTGGCGAG CTGGGCTGc tgagcctcct     1140 cctccacagc caatgttccc tcaaactgct tggggtggg gggagggact catcctcatc     1200
ccattagcct ggctgggtat tccctacctt tctggtctct gagagactta cctcttccaa     1260
gaagtcctcc cgaatgagta aagggagag agctggattg gaacttaagt gacatctggg     1320
aggagcctga agcccctccg gttgggctg agactcctat accctaggtc tggtgtctgg     1380
gttccacctg ggtcctctac cttggcctgg attcctgcTT TCGTTTTGCC AGTCTctccc     1440
aggatggggg tgcatggctG GTTCGTGGCT CAGAGCAACA TCTGCCtctg tgtccccca      1500 tcATCTGTCC GCCCCCTAAC ACCTCTTGcc atattagaat tgctATTGCT CTGTCCTTTC     1560

ATTCATGTat ccaacaaata tatattatct ganannnnan annanaangg               1610
```

(2) INFORMATION FOR SEQ ID NO: 57:

(i) SEQUENCE CHARACTERISTICS:
        (A) LENGTH: 928 base pairs
        (B) TYPE: nucleic acid
        (C) STRANDEDNESS: single
        (D) TOPOLOGY: linear (vii) IMMEDIATE SOURCE:
        (A) LIBRARY: BRAITUT08
        (B) CLONE: 1396995

(xi) SEQUENCE DESCRIPTION: SEQ ID NO: 57 :

```
cggtagagac atgtatggta tctcgtatac acaggcatgc cttatttctt tgtcttctac    60
cccagtgcta cctacctaaa gacctctggt actcttccct ttcctgggaa agaaattcaa   120
tcttgttttc tcttttatta ttgtattctc tattctacag ttatgcccca atagtagcca   180
aaggaaaaag ggggaagatg atagtttgac taaacaaata ccagttcata cattcttggt   240
ccaataggag ttatgggagg aaaaattatt ccaagcaatc acacaggatc aaCTTTTTCT   300
CCTTGTAGAA TATGTGTCAT CACATTGGCA GAATCTCATC CAGTTCTTCA AAGTGGAAAA   360
ACAATTAAAA GCATTTCCTA TCAGATCAGT ACCAACTGTA GCAGACTTCA GAACAAGGTC   420
TCTGGGAAAT TTAAGCGGGt atgttccTGT AATTCTGTGA TTATCTACTT ACATCCTCTA   480
TATTCATGGT AATGACAGAT CCAATGAACT TTAGAATCCA GTAGCATATG CTTAGCATAC   540
TTCTCTAGCA GTTTGAGGTG CTAATTTTAG GTATACTTTC ACCTAAAGAA ATTCTCAGCT   600
CCCCCAAATT AGGTATCTCA GGAGGTGTAG TATCTGTTAT AttaggttctgtgctaCTAT   660
CCCTATAATG CCCAGgatgg aggagggggaaggcaggcct ttgaaaggag aactctaata   720
gcaatataac aagatatttt gtcccttcta gttgtattaa actagtatgt cgagttctgt   780
aaaatttagg tgactaactc ttctttacca tatatttcca catgtaaata gccatatgca   840
ggggaggcct agtgcttcac ttagttttcc ctctctgtct tcataatgag ncctgggttc   900
catttgtcta cagcctgncc agatctgg                                     928
```

(2) INFORMATION FOR SEQ ID NO: 58:

(i) SEQUENCE CHARACTERISTICS:
        (A) LENGTH: 246 base pairs
        (B) TYPE: nucleic acid
        (C) STRANDEDNESS: single
        (D) TOPOLOGY: linear (vii) IMMEDIATE SOURCE:
        (A) LIBRARY: BRAITUT08
        (B) CLONE: 1398524

(xi) SEQUENCE DESCRIPTION: SEQ ID NO: 58 :

```
cgctagtcag cagttaccag gctcatgagt aaacctgaag tatctagatt gacaaccaag    60
acacaggaca gcctcaaaaa ctaatcagca ggaaggatcc aaggaatcct tctaagctag   120
cattctagcc ttcttgggca ctcactgcag ccctcaactc tgctgtgctc ccctgtggct   180
cagagcaagc cctcctgctg atggtatgga gctggaattg atctttgttg ttacgcattt   240
tacctt                                                             246
```

(2) INFORMATION FOR SEQ ID NO: 59:

(i) SEQUENCE CHARACTERISTICS:
        (A) LENGTH: 401 base pairs
        (B) TYPE: nucleic acid
        (C) STRANDEDNESS: single
        (D) TOPOLOGY: linear (vii) IMMEDIATE SOURCE:
              (A) LIBRARY: LATRTUT02
              (B) CLONE: 1403508

(xi) SEQUENCE DESCRIPTION: SEQ ID NO: 59 :

| | | | | | |
|---|---|---|---|---|---|
| agggaatggg | tggcttatct | cttggcttta | taactggata | tcttcatctg | ctattcagtc | 60 |
| actcttttt | attatggaga | catgttttct | gggaaaatgc | taccatgaag | caggaccaat | 120 |
| ctccagttca | aggtacctct | tgatttgttc | attccaaagc | atccctgtt | aggaattagg | 180 |
| gctcagatca | tgggtcatc | tattctgtaa | gtaaaaggct | gacaaaaagt | ctgttacttc | 240 |
| actgctcttt | acattagggt | aatattaaca | atggaaatcc | agttcattca | ataaaacaag | 300 |
| tgtcgatgaa | gagtcnaact | cggtaaaata | ttttaagaga | cttattctga | gccaaatatg | 360 |
| agtgnccatg | gcacatgaca | cagccctaag | gngatcctga | g | | 401 |

(2) INFORMATION FOR SEQ ID NO:    60:

(i) SEQUENCE CHARACTERISTICS:
            (A) LENGTH: 3436 base pairs
            (B) TYPE: nucleic acid
            (C) STRANDEDNESS: single
            (D) TOPOLOGY: linear (vii) IMMEDIATE SOURCE:
              (A) LIBRARY: PANCTUT02
              (B) CLONE: 1466523

(xi) SEQUENCE DESCRIPTION: SEQ ID NO: 60 :

| | | | | | |
|---|---|---|---|---|---|
| cgtgatgcca | ccgcagaccc | agtcccccgg | gcagccggcc | cagcccgcgc | ccatggtgcc | 60 |
| actgcaccag | aagcagagcc | gcatcacccc | catccgaaag | ccgcggggcc | tcgaccctgt | 120 |
| ggagatcctg | caggagcgcg | agtacaggct | gcaggctcgc | atcgcacacc | gaattcagga | 180 |
| acttgaaaac | cttcccgggt | ccctggccgg | ggatttgcga | accaaagcga | ccattgagct | 240 |
| caaggccctc | aggctgctga | cttccagag | gcagctgcgc | caggaggtgg | tggtgtgcat | 300 |
| gcggagggac | acagcgctgg | agacagccct | caatgctaag | gcctacaagc | gcagaaagcg | 360 |
| cccagtccct | gcgcgaggCC | CGCATCACTG | AGAAGCTGGA | GAAGCAGCAG | AAGATCgagc | 420 |
| aggagcgcaa | gcgccgggca | gAAGCACCAG | GAATACCTCA | ATAGCATTCT | CCAGCATGCC | 480 |
| AAGGATTTCA | AGGAATATCA | CAGATCCGTC | ACAGGCAAAA | TCCAGAAGCT | GACCAAGGCA | 540 |
| GTGGCCACGT | ACCatgCCAA | CACGGAGCGG | GAGCAGAAGA | AAGAGAACGA | GCGGATCGAG | 600 |
| AAGGAGCGCA | TGCGGAGGCT | CATGGCTGAA | GATGAGGAGG | GGTACCGCAA | GCTCATCGAC | 660 |
| CAGAAGAAGG | ACAAGCGCCT | GGCCTACCTC | TTGCAGCAGA | CAGACGAGTA | CGTGGCTAac | 720 |
| ctCACGGagc | tggtgcggca | gcaCAAGGCT | GCCCAGGTCG | ccaaggagaa | aaagaagaaa | 780 |
| aagaaaaaga | agaagggcag | aaaatgcaga | aggacagacg | cctgccattg | ggccggatgg | 840 |
| cgagcctctg | gacgagacca | gccagatgag | cgacctcccg | gtgaaggtga | tccacgtgga | 900 |
| gagtgggaag | atcctcacag | gcacagatgc | ccccaaagcc | gggcagctgg | aggcctggct | 960 |
| cgagatgaac | ccggggtatg | aagtagctcc | gaggtctgat | agtgaagaaa | gtggctcagn | 1020 |
| nnnnnnnnn | nnnnnnnnnn | nnnnnnnnnn | nccgcaggag | ccacagcctc | ccaccctgcc | 1080 |
| cgtggaggag | aagaagaaga | ttccagatcc | agacagcgat | gacgtctctg | aggtggcacg | 1140 |
| cgcggcacat | cattgagaat | gccagcaag | atgtcgatga | tgaatatggc | gtgtcccagg | 1200 |
| cccttgcacg | tggcctgcag | tcctactatg | ccgtggccca | tgctgtcact | gagagagtgg | 1260 |
| acaagcagtc | agcgcttatg | gtcaatggtg | tcctcaaaca | gtaccagatc | aaaggtttgg | 1320 |

-continued

```
agtggctggt gtccctgtac aacaacaacc tgaacggcat cctggccgac gagatgggcc    1380
tggggaagac catccagacc atcgcgctca tcacgtacct catggagcac aaacgcatca    1440
atgggccctt cctcatcatc gtgcctctct caacgctgtc caactgggcg tacgagtttg    1500
acaagtgggc ccctccgtg gtgaaggtgt cttacaaggg atccccagca gcaagacggg     1560
cctttgtccc ccagctccgg agtgggaagt tcaacgtctt gctgacgacg tacgagtaca    1620
tcatcaaaga caagcacatc ctcgccaaga tccgttggaa gtacatgatt gtggacgaag    1680
gtcaccgcat gaagaaccac cactgcaagc tgacgcaggt gctcaacacg cactatgtgg    1740 cacccccgccg cctgctgctg acgggcacac cgctgcagaa caagcttccc gagctctggg   1800
cgctgctcaa cttcctgctg cccaccatct tcaagagctg cagcaccttc gagcagtggt    1860
ttaacgcacc ctttgccatg accggggaaa aggtggacct gaatgaggag gaaaccattc    1920
tcatcatccg gcgtctccac aaagtgctgc ggcccttctt gctccgacga ctcaagaagg    1980
aagtcgaggc ccagttgccc gaaaaggtgg agtacgtcat caagtgcgac atgtctgcgc    2040
tgcagcgagt gctctaccgc cacatgcagg ccaagggcgt gctgctgact gatggctccg    2100
agaaggacaa gaagggcaaa ggcggcacca agaccctgat gaacaccatc atgcagctgc    2160
ggaagatctg caaccacccc tacatgttcc agcacatcga ggagtccttt tccgagcact    2220
tggggttcac tggcggcatt gtccaagggc tggacctgta ccgagcctcg ggtaaatttg    2280
agcttcttga tagaattctt cccaaactcc gagcaaccaa ccacaaagtg ctgctgttct    2340
gccaaatgac ctccctcatg accatcatgg aagattactt tgcgtatcgc ggctttaaat    2400
acctcaggct tgatggaacc acgaaggccg gaggaccggg gcatgctgct gaaaaccttc    2460
aacgagcccg gctctgagta cttcatcttc ctgctcagca cccgggctgg ggggctcggc    2520
ctgaacctcc agtcggcaga cactgtgatc atttttgaca gcgactggaa tcctcaccag    2580
gacctgcaag cgcaggaccg agcccaccgc atcgggcagc agaacgaggt gcgtgtgctc    2640
cgcctctgca ccgtcaacag cgtggaggag aagatcctag ctgcagccaa gtacaagctc    2700
aacgtggacc agaaggtgat ccaggccggc atgttcgacc agaagtcctc cagccatgag    2760
cggcgcgcct tcctgcaggc catcctggag cacgaggagc aggatgagag cagacactgc    2820
agcacgggca gcggcagtgc cagcttcgcc cacactgccc ctccgccagc gggcgtcaac    2880
cccgacttgg aggagccacc tctaaaggag gaagacgagg tgcccgacga cgagaccgtc    2940
aaccagatga tcgcccggca cgaggaggag tttgatctgt tcatgcgcat ggacctgacc    3000
gcaggcgcga ggaggcccgc aaccccaagc ggaacccggc ctcanggagg acgacgagct    3060
cccctcgtgg atcatcaagg acgacgcgga gtggagcggc tgacctgtga ngangannan    3120
gagaagatgt tcggcccgtg gcttccggc naccggcnaa ggaggttnga cttacagcgn     3180
acttcnantg accgggganaa cccatttggt ncnaaaggcc attcncnang nangggcaac    3240
ctnggaccga agntttcnaa acaacggcan gttcccggca cgaaannaaa ttcctccacc    3300
cggaaancgn gcaaacngcg gaacaagcna aangccgggn ttcntccaaa cccccgacca    3360
acccaagnac cccggaancc cccgcacaaa nggncnccg gnaccaagaa acccnanaa      3420 aaccccgggg cgggcc                                                    3436
```

(2) INFORMATION FOR SEQ ID NO: 61:

(i) SEQUENCE CHARACTERISTICS:
        (A) LENGTH: 480 base pairs
        (B) TYPE: nucleic acid (C) STRANDEDNESS: single
                (D) TOPOLOGY: linear (vii) IMMEDIATE SOURCE:
                (A) LIBRARY: PANCTUT02
                (B) CLONE: 1466902

(xi) SEQUENCE DESCRIPTION: SEQ ID NO: 61 :

caaggataca gccgttgtat ttaaggggtt gagggacaaa gtagtgaaga actgtaagat     60
attcaatata gtgtattgat gaattagaat tgtatggaaa gataaaccgc agaaggtgag    120
agtcctgtat aagtaaatcc ttacacatat aactttgctc ccaagtaaca tggaacacga    180
ggaattctgt gtgaatcagt GAGGACCATA TCTCATAAGG CTAAAtactc ttactAACCG    240

ATAGCGCATA GTACCGTGAG GGAAAGGTGA AAAGAACCCC TGGAGGGGAG TGAAATAGAA    300

CCTGAAATTG TGTGCTTACA AGCGGTCAGA GCCCATTAGG GTGATGGCGT GCCTTTTGGA    360

GAATGATCCT GCGAGTTACG TTAAACGGCG AGGTTAAGTA TAACGgagcc gaagggaaac    420
cAAGTCTTAa tagggcgata tagtcgtttg gcgtagacgc gaaacctggt gatctaaacc    480

(2) INFORMATION FOR SEQ ID NO:    62:

(i) SEQUENCE CHARACTERISTICS:
                (A) LENGTH: 552 base pairs
                (B) TYPE: nucleic acid
                (C) STRANDEDNESS: single
                (D) TOPOLOGY: linear (vii) IMMEDIATE SOURCE:
                (A) LIBRARY: PANCTUT02
                (B) CLONE: 1468040

(xi) SEQUENCE DESCRIPTION: SEQ ID NO: 62 :

agaaatcaCC TTACAACCCA TTTCTCAGAA CATGTTTCTA TTGTTAAACA ACACACAACT     60

ATTTTATTTA TGTGTTTTAT TTATGCCTGA TCACCAATAT CAATAACTGA AACACAGCAG    120

TTTAGTAATA ATTTAATACA CACCATAACC TGCCTATTGA GAATGGCATT ATATTTGTTT    180

TCATTGTAGT GGCTCCATCC AAAATAAAAT GATTTTTTTC CTTCCTTCAG GATGAAGGCA    240

AGCATTTATT CCTACGGTCT GGATTCCTCA TATCACCTAC AAGTTAACTG CTTTTGTGTT    300

CTAAGAGAGG AAAAATGAAG TCAACCTTAT TGAAAAACAA GGAGGGAAAC TAAGGAACAT    360

GCTTTTGCTT TTGAGGTTCT AGGCCAGAAG TCATAAGCTG TAACTTGTCC AAGTTATGGC    420

CAAGCAGATA TGTTTTgttt ggcctacatg GAGTATATTT TTTCTAATTG AATCAACATT    480

TTAAAATATG Atgatttaat atttaaaact atanaancna aaaaaaaaaa gggcggccgc    540
cgactagtga gc                                                       552

(2) INFORMATION FOR SEQ ID NO:    63:

(i) SEQUENCE CHARACTERISTICS:
                (A) LENGTH: 595 base pairs
                (B) TYPE: nucleic acid
                (C) STRANDEDNESS: single
                (D) TOPOLOGY: linear (vii) IMMEDIATE SOURCE:
                (A) LIBRARY: LUNGTUT03
                (B) CLONE: 1472220

(xi) SEQUENCE DESCRIPTION: SEQ ID NO: 63 :

aancggncat gancncaccg caataatggg agtagctcac tcataggccc ccaggcttac     60
acnnnnnnnn nnnnnnnnnn nnnnnnnnnn nnnnnnnnnn nnnnnnnnnn nnnnnnnnnn    120

```
nnnnnnnnnn nnnnnnnnnn nnnnnnnnnn nnnnnnnnnn nnnnnnnnnn nnnnnnnnnn       180
nnnnnnnnnn nnnnnnnnnn nnnnnnnnnn nnnnnnnnnn nnnnnngggc acttGGAAAG       240

AATATGTATT CTGTTGTTCT TGGGTAGAGT GTTTTTTGTA AATGTCCATT ATATTAAACC       300

AGTTGATAAC GTTATCCAGG TTTGATATAT CCTTTTTGAT TTCCATCTAT TTGTTTATCA       360

GTCATTGAGA ATGGACTTAT TGAGTCTCCC AGTTATGACT GTGGATTTTT CCATATCTCT       420

TTTAGTTCTA TCAATTTTTG CTTCATTTAT TTTGgatctt tgttagttgc atattatatt       480
tcagtgttta tcttcttggt gaattgaccc ttttatcatt atgtaatttc cctatattta       540
tatctttata tttaaaatag gtttccttaa catttgagaa gtaaaaataa aataa            595

(2) INFORMATION FOR SEQ ID NO:    64:

(i) SEQUENCE CHARACTERISTICS:
        (A) LENGTH: 554 base pairs
        (B) TYPE: nucleic acid
        (C) STRANDEDNESS: single
        (D) TOPOLOGY: linear (vii) IMMEDIATE SOURCE:
        (A) LIBRARY: LUNGTUT03
        (B) CLONE: 1474862

(xi) SEQUENCE DESCRIPTION: SEQ ID NO: 64 :

catgccgccc ggaccccag cccaggacat catggtgccc agagagcgtg agccccaagg         60
gcattggcag gagctgccga ttccatctcc ctgggtgggt tccaggtggc acaggaaggg       120
tgggccggga ggcttggtga cctgggagct gcccttggag gctatttcca ggggcctcag       180
ggtgggccgt gggggatttg gagtcttctg cctgtgcagg gtcaggcagg gtcggttggg       240
ggntcggagg tagatgccat ggtatgctgg gcagcaagtg gctcaggaag cctctgggtg       300
tgagtcctcg ggggtcacca aggcaggang gggcagggat gtgcagggtc cgccctcgtc       360
tccccacgtc tggcncaggg aagcttctgc tcangtcttc gngaaacacg ttcaagaagc       420 aangggncg gtggggtntg nntgtgganc ccggagaccc tgcccccan ncttcctngg         480 aagccaggnt ggaagctgtg cccagaaagg ntttcgggga ncanaaagtt ctggagacaa       540
gttcaggcct caaa                                                         554

(2) INFORMATION FOR SEQ ID NO:    65:

(i) SEQUENCE CHARACTERISTICS:
        (A) LENGTH: 487 base pairs
        (B) TYPE: nucleic acid
        (C) STRANDEDNESS: single
        (D) TOPOLOGY: linear (vii) IMMEDIATE SOURCE:
        (A) LIBRARY: BRAITUT07
        (B) CLONE: 1502604

(xi) SEQUENCE DESCRIPTION: SEQ ID NO: 65 :

taagcagaaa tagaagaaat gggggcaatt tttctaatag actggagatt cacagcaacc        60
aatcaaggag ggcccagtca acctgagcca gcctaaagaa ccccttctgc tttaaccctt       120
acaaagaaag caacttgaaa taacctgatg ttgagcaaca cgctgttttg gtatcatgct       180
gatgctggct ctctagtcgt gggtgcattt ggtgttcaat gatattggtg aaggggcttt       240
ataatctcag ctctgtatac acccatcat ggcttccggg gccacgcttc ccctccttgg        300
acacaacaag tcatccatac cccagggcca ttgcactggc tttctctctg ttttgagatg       360
tagacacagc ttgtttcaac tctgcttcaa ngcttgatgn ttgagcttgc tcctccaaga       420
```

```
agccctctct gatcttctcc agagtcctgc tancctggtt ccctagtttt tggcttctag      480
tcctttc                                                                487

(2) INFORMATION FOR SEQ ID NO:    66:

(i) SEQUENCE CHARACTERISTICS:
        (A) LENGTH: 285 base pairs
        (B) TYPE: nucleic acid
        (C) STRANDEDNESS: single
        (D) TOPOLOGY: linear (vii) IMMEDIATE SOURCE:
        (A) LIBRARY: BRAITUT07
        (B) CLONE: 1504814

(xi) SEQUENCE DESCRIPTION: SEQ ID NO: 66 :

ganttcggct cgagaaaaaa aatggacacg tGAGCAATTC AAACTTTTGT CTCCAAGAAG       60

ATTGGTATGC TTATAAATTG ACTCACTCTT TGTTTCCATA TTGCTACATA TGCTCAAACC      120

TAATTCCACT CCTGGCTTTT AAGATCTGGC CTCTCCTGTA CTCTCCCCAA GACATTTGGG      180

CTCATAATTT TGTATGAATG GAGGGCTAAC CTAGTTAGAA AGTAAACTTC AGTCcgttca      240
attaaaacac aaaacaaaac aaaacaaaaa acagccgggc acagt                      285

(2) INFORMATION FOR SEQ ID NO:    67:

(i) SEQUENCE CHARACTERISTICS:
        (A) LENGTH: 715 base pairs
        (B) TYPE: nucleic acid
        (C) STRANDEDNESS: single
        (D) TOPOLOGY: linear (vii) IMMEDIATE SOURCE:
        (A) LIBRARY: BRAITUT07
        (B) CLONE: 1505025

(xi) SEQUENCE DESCRIPTION: SEQ ID NO: 67 :

ctggacacat ctgagggaat ggaaggagaa agccatgGCT ACAGAGGCAG Aacagaggcg       60
caggaagaaa gaagccattg gtttcacTAC GGAAGCACTG CAAGAAGCTT CAGCTgcagg      120
aagacccata tctGGAGTTT TCAATGATGT GAGAACAAAC TATTTCCTTC ATTATTCACG      180

TCAAGTTCGG GCTGCCTGGA GTGAAACACA TTCTAAAGCC AGTAGGTAGC ATCACAAGTG      240

CAAAATGAAA AAGGCACCCA CAGAACTGGG ACAAATTTTG TTTCATTGCA CTGAGACTAG      300

AAGGGACGAG ACAGCTCATG TGGTCTGTGT TCCTGCCTTC AAGGAGGAGT AGAATCAAGA      360

AATGGAAGAA GCCTTGGGGC TTTCaggtca CCCACGCCTG TGTCTGACCC TTGGCTGTAC      420

ACCAGATCAC CTGGGGAACT TTGTAAAAac agcttcctcc accCCATTCC AtTGCGTTGA      480

GCCAAAATCT CTAGGGtgga ggctcattat ctgttttcac aaactccaag tgattctgag      540

GGACCATCcc ttaacaactg tgaactttcc tttggtagaa ggaagcagca tagcagatcc      600
taatgctaat gccgacatca aattcaaagc actgaatgtg tgtatcatgg tcttagaagt      660
atgtataact catttctgaa tcactttatt gaagacccaa attaattaaa tactt           715

(2) INFORMATION FOR SEQ ID NO:    68:

(i) SEQUENCE CHARACTERISTICS:
        (A) LENGTH: 329 base pairs
        (B) TYPE: nucleic acid
        (C) STRANDEDNESS: single
        (D) TOPOLOGY: linear (vii) IMMEDIATE SOURCE:
```

(A) LIBRARY: BRAITUT07
(B) CLONE: 1505274

(xi) SEQUENCE DESCRIPTION: SEQ ID NO: 68 :

| | | | | | |
|---|---|---|---|---|---|
| gctcgaganc | aagaccctgt | ctcngaaagn | gagagaagng | aaaganntag | gagaaagaag | 60
| gaaaganaga | nagangaaac | annactgtTA | GCATCATATT | GACAACTAAA | TAGATAGGTC | 120
| GAAACGTTCT | GCCGTCCCAT | TTGGCATCCT | GGAGAGGTTA | ATGTTAATAG | TCAGTGGTTG | 180
| AGCCAGAGGC | ATGTTCCTAA | ATATCACCAT | GCTATGCAAA | GTCACACAAA | AAAACACACA | 240
| GGGCTTATGG | GAAAAAAAAA | AAGGAATTAT | GGCTGTAACA | CTTGGAAACA | TCACCTGTGA | 300
| acattaaaaa | aaaagataaa | gggcggccg | | | | 329

(2) INFORMATION FOR SEQ ID NO: 69:

(i) SEQUENCE CHARACTERISTICS:
        (A) LENGTH: 569 base pairs
        (B) TYPE: nucleic acid
        (C) STRANDEDNESS: single
        (D) TOPOLOGY: linear (vii) IMMEDIATE SOURCE:
        (A) LIBRARY: BRAITUT07
        (B) CLONE: 1505293

(xi) SEQUENCE DESCRIPTION: SEQ ID NO: 69 :

| | | | | | |
|---|---|---|---|---|---|
| ctccccagca | atcacagcac | acaggcgcat | tcagcctgcc | ccttgctttt | gtccctaaac | 60
| attgtcattt | ggcagcagtc | tgtatcagtc | cagaaagggt | ttcttctgct | ttctgttgca | 120
| gagaacttga | tcgtgtggct | gaactgtgat | ttattgatca | ggatccctct | tgagggatac | 180
| agaggttagt | tccagtgttc | acactggcct | aatcgaacct | ctttatactc | tttctccccc | 240
| tctgcagggt | ggccgtcgtg | acctgggggc | nncctgctta | aggtgagggg | ggtggccccc | 300
| cttcgagggc | cacggagatg | agcctggaac | ctggagaagg | agggcaggag | ccagccactg | 360
| gctggacagg | gaagaagacc | ccaggagncn | agcccanccc | ttcttgtgta | ggacggggga | 420
| caatnggctg | ttccnggaaa | atctnggnag | gggcctcggg | anatcttcan | ccgttctgga | 480
| anactgttaa | gatccattaa | gcctgnccag | ctntggttgt | naaaanaagg | aggaantttg | 540
| gaaaanaaaa | atnttggtga | aagggnttt | | | | 569

(2) INFORMATION FOR SEQ ID NO: 70:

(i) SEQUENCE CHARACTERISTICS:
        (A) LENGTH: 1203 base pairs
        (B) TYPE: nucleic acid
        (C) STRANDEDNESS: single
        (D) TOPOLOGY: linear (vii) IMMEDIATE SOURCE:
        (A) LIBRARY: BRAITUT07
        (B) CLONE: 1505958

(xi) SEQUENCE DESCRIPTION: SEQ ID NO: 70 :

| | | | | | |
|---|---|---|---|---|---|
| ccaaccaagc | tncaagtgct | tggctaacag | gcaacagcca | atgcccgaag | ccttgcccaa | 60
| gcaaancctt | gaggcttaaa | gcaagctnca | aggcccgaag | cggttnaaag | tcttcactga | 120
| gacccccccc | cagctttcgg | caccactggc | cagcattttc | cagctgcagg | atgcagacag | 180
| gagctgcctg | ctggcacacg | tccaccgcct | cCACCACGAG | GGCAGGTTCA | GAGAAGCAGC | 240
| CACGCTGGGc | acGACGTTGA | AGCTGCAGTC | GGAGCTTGGC | GTTGAAAAGA | TGAGCATCCC | 300
| ACTGCTCCTC | CAGGACAAGG | TGGCCCTCGT | GGAGCGCTAT | GTGGCCGGCT | TCCCGGACCT | 360

```
CCAGAGGAGG CTGCTGGTCC TCATGGATTC CTGGTGCCAG CCCGGCTTTG ACATCAAGGA    420

CGTTGCCaga cagtaccctg aggtgacctc cttgagcctg gagaagctga gtccgaaggc    480
gctgagcagg caggtcttgc gtctgcagga gcggtacggc gtaccccagc gctgtgtccc    540
aacgcggcca ttcagcagcg cctggcggcc ctgcggcacc tgtgcccaca agcggtttgt    600
ggagaagagc ctgtcacagg agaactggac cgaccatgtg cagggcctgg tggggcagag    660
cccgtggctt caggagcagc tgtctcagct gctggtctcc cacagtgacc cagtcacggc    720
cgcccagtgt gccatggacc tcttgctgcc cgaggagcgg ctgccggctc tttggggccg    780
naaggtnccn gtgaaanagg aanaggaaaa agggcccaaa gggncccccn nnccnncngg    840
tccccngggt tttgncccna annnccggnc aatnaantnc cccggggncc cngtggaaaa    900 agggtgcaa aaaccccggt aaaccttttc ccctntnaaa aaaggaaaat tttcnccggg    960
nggcncgngn gttttttncca aaaacggttn atttnttttn ncntgttncc caaaaccttt   1020 ttggggaaa aaacncccc anatgtgctc nncgggggga aaaatccnna anccnttttc    1080
naaaangttt tnttntttgg gggggcctct tgataaaaac cncaaaatng tgnggtgaca    1140
aanggnccct gganaacncn ttttncttt ncnanagggc nccccttttt gngggttttt    1200
tct                                                                 1203

(2) INFORMATION FOR SEQ ID NO:   71:

(i) SEQUENCE CHARACTERISTICS:
        (A) LENGTH: 759 base pairs
        (B) TYPE: nucleic acid
        (C) STRANDEDNESS: single
        (D) TOPOLOGY: linear (vii) IMMEDIATE SOURCE:
        (A) LIBRARY: BRAITUT07
        (B) CLONE: 1506088

(xi) SEQUENCE DESCRIPTION: SEQ ID NO: 71 :

gttcngggnt tacaggnntt atnaccgcnt ccagccaatg atttttcaaa ataatatttt     60
tngtaacaaa aagcacaaac cctggtaaag acatgTATTT ATTATAgcat tttgagCTTA    120

AAAGAATGTA TTACTACTAT GTCAGCAAAA TATGAGTTAT TTGCTAGGAT ACCCATGTAG    180

TCTCATAATG ATATTCTTTG AAATGCACGA TACCTGTAAA GTATAAGGAA AGACACAATT    240

ACGTTTGCAG AATTTCAGAA ATATTTCGCC CCACAGGAAC AGCAGTGTTT GCAATCCCAA    300

AAAACAACTC TAAGCTAACA AGTTTAATTC AAGAGGTTCC ATGGACCTTA ACCCACCTCC    360

TGTGGAAGCC CAGGTTTGTG TGCTAGGCTA TTTTGGAAGA GGCTATGCCG AAAAATAAAC    420

AAATGAGTGA ATAATAAGTT CACCAAAGGG TGCACTTCAt ctaagctaCC TTTAATCCAC    480

ATGTTCCACT CTGCACTGGT CTATTTAAGG TTCCTGCTCA GAGGAGCTCA TAACTTGTGA    540

CAGATACAAA CTTAATCTTA CCCTCAATGC ctagcatggt acACACTATA GATGCAGTTC    600

TCAAAGTCT GCTAAATGAA AGATTTTTTT Ttcagctgat tnnnnnnnn nnnnnnnnn    660 nnnnnnnnn nnnnnnnnn nnnnnnnnn nnnnnnnnn nnncaattt ccacaccaac    720 atacggggcc cggaagcctt aaagtggtaa agccctggg                          759

(2) INFORMATION FOR SEQ ID NO:   72:

(i) SEQUENCE CHARACTERISTICS:
        (A) LENGTH: 185 base pairs
        (B) TYPE: nucleic acid
        (C) STRANDEDNESS: single
        (D) TOPOLOGY: linear
```

(vii) IMMEDIATE SOURCE:
    (A) LIBRARY: BRAITUT07
    (B) CLONE: 1506303

(xi) SEQUENCE DESCRIPTION: SEQ ID NO: 72 :

| | | | |
|---|---|---|---|
| gtgtactcca tggcataact ttgctaagaa ccaactgata aagcatgtct gttgctttt | | | 60 |
| cttggtgata atctcagtct aacgtaggaa atcatatttc ttcatggcca aaggaagaat | | | 120 |
| ttgttttcc catgtagtta aaggtgatgg ctctggaggc aatggtatta gaatattaaa | | | 180 |
| atctg | | | 185 |

(2) INFORMATION FOR SEQ ID NO:    73:

(i) SEQUENCE CHARACTERISTICS:
        (A) LENGTH: 500 base pairs
        (B) TYPE: nucleic acid
        (C) STRANDEDNESS: single
        (D) TOPOLOGY: linear (vii) IMMEDIATE SOURCE:
        (A) LIBRARY: BRAITUT07
        (B) CLONE: 1506513

(xi) SEQUENCE DESCRIPTION: SEQ ID NO: 73 :

| | | | |
|---|---|---|---|
| ttccacctgc cctggtgttc acggtggcct ggtccctcct tgccgagaga gtgtcctggg | | | 60 |
| tcagggacgc agaggacgct cacagactcc agcccttgt taccgagagg acacttggca | | | 120 |
| aggtccagcg atggtccgga gtccacacac agactggcgg cagggcagga gggggacagt | | | 180 |
| TCTGTTGTGC TTGGTTGGAC AGTAAGAGGG TCTTGGCCAG TCCAGGGTGG GGGGCGGCAA | | | 240 |
| ACTCCATAAA GAACCAGAGG GtctgggCCC cggccacAGA GTCATCTGCC CAGCTCCTCT | | | 300 |
| GCTGCTGGCC AGTGGGAGTG GCACGAGGTG GGGCTTTGTG CCAGTAAAAC CACAGGCTGG | | | 360 |
| ATttgcctgc GGGCCATGGT CCCTGTCTAG GGCAGCAATT CTCAACCTTC TTGCTCTCAG | | | 420 |
| GACCCCAAAG AGCTTTCATT GTATCTATTG ATTTttacca cattagcaat taaaactgag | | | 480 |
| aaatgggccg ggcacggtgg | | | 500 |

(2) INFORMATION FOR SEQ ID NO:    74:

(i) SEQUENCE CHARACTERISTICS:
        (A) LENGTH: 1059 base pairs
        (B) TYPE: nucleic acid
        (C) STRANDEDNESS: single
        (D) TOPOLOGY: linear (vii) IMMEDIATE SOURCE:
        (A) LIBRARY: PANCTUT01
        (B) CLONE: 1516263

(xi) SEQUENCE DESCRIPTION: SEQ ID NO: 74 :

| | | | |
|---|---|---|---|
| gcttcacaag ttacagttcg tcctgacata tgtggctcct tggcagatgg cttggggttc | | | 60 |
| ttcgtttcac gtgtttgctc agctctttgc cattcctcat tctgccatgc ttttcttca | | | 120 |
| gacgattgcc acatcaatct tttctacccc attgagccca ttccttggga gtgtcatttt | | | 180 |
| catcacatca tatgtcaggc cagtgaaatt ctggagggcc tcttctagta caaggcgagt | | | 240 |
| ggataattcc aacacaagac tggcagtcca aattgaaaga gatccaggga atgatgacaa | | | 300 |
| caatctcaat tccatttttt atgaacactt gacaaggacc ctccaggagt ccctctgtgg | | | 360 |
| agacttagtt cttggacgtt ggggcaacta cagctctggc gattgcttta ttttggcttc | | | 420 |
| agatgacctc aatgcctttg ttcacctgat tgaaattgga aatggtcttg tcacctttca | | | 480 |

-continued

```
acttcgagga ctggaattcc gagagtataa tatactatat ggtaacgtct cccaaactcc      540
tctcctggat caaaaatgaa tcacttctga agtccctgca gcccttttgcc aagtggcatt     600 acattgagcg tgaccttgca atgttcaaca ttaacattga tgatgactac gtcccgtgtc     660 tccagggat cacacgagct agcttctgca atgtttatct agaatggatt caacactgtg      720
cacggaaaag acaagagcct tcaacgaccc tggacagtga cgaggactct cccttggtga     780
ctctgtcctt cgccctgtgc acctggggag gagagttctg ggaacagccg ctcacaatat      840
ggccatcagc ctggattctt tcctgtatgg cctcccatgt cctcttcaaa ggtgacttca     900
gaataacagc acntgacgag tgggtatttg ctgacatgga ctactgcatt aaagttgtag     960
ntccagctat caggatgtnc ctgaaacttn accaggacca gttcacttgn cctgacgagt    1020
atgaagaccc agcagtcttt acgngggcat ncagttctt                            1059
```

(2) INFORMATION FOR SEQ ID NO: 75:

(i) SEQUENCE CHARACTERISTICS:
        (A) LENGTH: 1567 base pairs
        (B) TYPE: nucleic acid
        (C) STRANDEDNESS: single
        (D) TOPOLOGY: linear (vii) IMMEDIATE SOURCE:
        (A) LIBRARY: BLADTUT04
        (B) CLONE: 1553234

(xi) SEQUENCE DESCRIPTION: SEQ ID NO: 75 :

```
atcttatgat taatgaatac acatttgagg acctagaact tttagcagta agatttgcat       60
acgcttttcc tattgaatta gaaaaaagaa aaaaaaaagt tcaaaattct gttagattaa      120
ttctgtgata tagtttataa tttggcataa gctggtagta gggaaatagt cacttcttta      180
tgcccatgat ttatataatg aaacaatctt ccattcactt agaagacaac ttcgatttaa      240
atatttagcc tccctagcaa ggcccagcca tgcaattttt tccctgttag aagaatttta     300
gcaacagtaa aaaaaattaa tatgtaagat tttgctattt ttattagttt tgaggactgc      360
ttgccttgta gtttaaaggg ggtaaaaagg atcattgttt acccatgnat atatatat      420 tattaatggt agattttttt ttttttttgg ttgatgtagg aactttggga gtagagcaga     480
aagcctattg acttccaaaa atagtgactc agggttggta taatcattag aaagcaggtt     540
gggaaaaatc ctaattccag acctcaagta gaatttagt atCAGAGTCA CTcctgttcc     600
ttaaatgtag atctcctgat ttcaggccat ttTTcattCT AATAGAATTA GAGAAGAAAA     660

ATAAAACCTG TCAACGAGGA CTATTTACCT CCTATAGATA GGATTGAGAC CTACTTTTCT    720

GTAACTTTTG AAGTTATTTT TGGGAAAAAT TTCCTTGGGT TGACTTTGCC CCCTTCACCC    780

AATGCATCTG TGTGATCAGG AAAAGGGAAA ACAAGATTTA ATTGTTAACT TTTAAAAAGT    840

CCTTTTGAAA GAAAagaATA TATACTGTCT TATATTGACA GAGAACCAAT TATTGGGTTA    900

CCTGCAACAc cgTATCCTCC ATTTAGTGCT GATAATCATA ATGTCCATAA TCTCCCAATA   960

AGATAAAATA ATAAAGAGGC TCTGAGGCAT GAACAGGGGT GGCTAAAGGA TCATTGAGAT    1020

AACTTTTAAA ATAATAATGA TTTATAGAAA TTGAGTTAAT ATTTGTTGAC CTTCTACAAA    1080

CTTTAAAACA GATAGAAGGT TTTAAGGTAT ATGTTTTGAA ATAATCCAAA CCAAATAAAT   1140

CTAAACTTAG AAATACCATA TTAGAAATAT ACAGTGAACA CACACAAGGT CAATTTTAAA    1200

AACAGCACTT AGCTTTGAGC GGATAATTTC TCCTTCACCC TGAATGCAAA TAATTTATTC    1260

AGCCCTTCTA TAACAAGCTT AGGGGATAAA AGAGGCAAAG GGCATGAGAA ATGAGTCTTT    1320
```

```
GGAAAATTAT TGTAACTAAC ACTAATGCTT ATTTAGCATC TTTCATTCAA AGACCTTCAG    1380

ACATTTCCTA ATTGAGTTCT GTAGTACTTC TGGAGTGTGG GTAAGGAACA TTTAGAGACT    1440

CCTGTGCCCA GTGCTGTAAG GCCTGCCATC Cccgtgtggc atgttgcagg gggatcctct    1500
agagcatcat attccctcct ggggccagag aatggaggag acagcgtttt caagctgaaa    1560
tcccaga                                                               1567

(2) INFORMATION FOR SEQ ID NO:   76:

(i) SEQUENCE CHARACTERISTICS:
        (A) LENGTH: 408 base pairs
        (B) TYPE: nucleic acid
        (C) STRANDEDNESS: single
        (D) TOPOLOGY: linear (vii) IMMEDIATE SOURCE:
        (A) LIBRARY: BLADTUT04
        (B) CLONE: 1553883

(xi) SEQUENCE DESCRIPTION: SEQ ID NO: 76 :

attgagggca tccctcttc tgtcctggtg cagatttcct ttttcttgga gaaagaaaac      60
gagccccctn gcagggagct tactaaggag dacctttca agacacacag cgtccctgcc     120 accccacca gcactcctgt gccgaaccct gaggccgagt ccagctccaa ggaaggagag     180
ctggacgcca gagacttgga aatgtctaag aaagtnaggc gttcctacag cnggctggag    240
acccngggct ctgcctctac ctccacccca ggncgccggt nntgntttgg cttcgagggg    300
ctgcnggggg cagaagantt gtncggaatc tcgncagtng tgtgctcaaa aatcacngag    360
gtcnccaagg tttgtgaaaa gccntgggcn nnagacatgn cttctnnt                 408

(2) INFORMATION FOR SEQ ID NO:   77:

(i) SEQUENCE CHARACTERISTICS:
        (A) LENGTH: 1042 base pairs
        (B) TYPE: nucleic acid
        (C) STRANDEDNESS: single
        (D) TOPOLOGY: linear (vii) IMMEDIATE SOURCE:
        (A) LIBRARY: BLADTUT04
        (B) CLONE: 1555118

(xi) SEQUENCE DESCRIPTION: SEQ ID NO: 77 :

cagagaaact ggaacagact tggggatttt tatcaaatcc atcattcatg gaggcgctgc     60
ttttaaggat ggtcgtctgc gaatgaatga ccagctgatt gcagttaatg gggaatctct    120
tttgggaaag tccaaccacg aagctatgga aacacttagg cggtcaatgt ccatggaggg    180
aaacatccga gggatgatcc agttggtgat tctgaggagg ccagagagac caatggagga    240
tcctgcagag tgtgggggcat tttccaagcc atgctttgag aactgtcaaa atgctgtaac    300
cacctctagg cgaaatgata atagtatcct gcatccactt ggcacttgca gtccacaaga    360
caaacagaaa ggtctattgc tgcccaatga cggatgggcc gagagtgaag ttccaccttc    420
tccaacacca cattCTGCTC TGGGattggg cctcgaAGAT TACaGCCACA GCTCTGGGGT    480

GGATTCAGCA GTATATTTTC CAGATCAGCA CATCAACTTC AGATCTGTGA CACCGGCCAG    540

GCAGCCTGAA TCAATTAATT TGAAAGCCTC GAAGAGCATG GACCTTGTGC CAGATGAAAG    600

CAAGGTTCAC TCATTGGCTG ACAAAAATC GGAATCTCCA AGCAAAGATT TTGGTCCAAC     660

TCTGGGTTTG AAAAAGTCCA GCTCCTTGGA GAGTCTGCAG ACTGCAGTGG CCGAGGTCAG    720

GAAGAATGAC CTTCCCTTTC ACAGGCCCCG GCCGCACATG GTTCGAGGCC GAGGCTGCAA    780
```

```
TGAGAGCTTT AGAGCAGCCA TTGACAAATC CTACGATGGA CCTGAAGAAA TAGAAGCTGA      840

CGGTCTGTCT GATAAGAGCT CTCACTCTGG CCAAGGAGCT CTGAATTGTG AGTCTGCCCC      900

TCAGGGAAT TCGGAGCTAG AGGACATGGA AAATAAAGCC AGGAAAGTCA AAAAAacgaa       960
agagaaggag aagaaaaagg aaaagggcaA ATTGAAAGTC AAGGAGAAAa agcgcaaaga      1020
ggagaatgaa gatccagaaa gg                                              1042
```

(2) INFORMATION FOR SEQ ID NO: 78:

(i) SEQUENCE CHARACTERISTICS:
        (A) LENGTH: 3090 base pairs
        (B) TYPE: nucleic acid
        (C) STRANDEDNESS: single
        (D) TOPOLOGY: linear (vii) IMMEDIATE SOURCE:
        (A) LIBRARY: BRAINOT14
        (B) CLONE: 1595762

(xi) SEQUENCE DESCRIPTION: SEQ ID NO: 78 :

```
ccnggatacg ttaaaccacg ggtccgcggc angtccgcac aatncctcgg tggacatgtg        60
cgagctcaaa agggacctcc ngctgctcag ccagttcctg aagcatcccc agaaggcctc       120
aaggaggccc tcggctgccc ccgccagcca gcagttcag agcctggagt cgaaactgac        180
ctctgtgaga ttcatggggg acatggtgtc cttcgaggag gaccggatca acgccacggt       240
gtggaagctc cagcccacag ccggcctcca ggacctgcac atccactccc ggcaggagga       300
ggagcagagc gagatcatgg agtactcggt gctgctgcct cgaacactct tccagaggac       360
gaaaggccgg agcggggagg ctgagaagag actcctcctg gtggacttca gcagccaagc       420
cctgttccag gacaagaatt ccagccaagt cctgggtgag aaggtcttgg ggattgtggt       480
acagaacacc aaagtagcca acctcacgga gcccgtggtg ctcaccttcc agcaccagct       540
acagccgaag aatgtgactc tgcaatgtgt gttctgggtt gaagacccca cattgagcag       600
cccggggcat tggagcagtg ctgggtgtga gaccgtcagg agagaaaccc aaacatcctg       660
cttctgcaac cacttgacct actttgcagt gctgatggtc tcctcggtgg aggtggacgc       720
cgtgcacaag cactacctga gcctcctctc ctacgtgggc tgtgtcgtct ctgccctggc       780
ctgccttgtc accattgccg cctacctctg ctccagggtg cccctgccgt gcaggaggaa       840
acctcgggac tacaccatca aggtgcacat gaacctgctg ctggccgtct tcctgctgga       900
cacgagcttc ctgctcagcg agccggtggc cctgacaggc tctgaggctg ctgccgagc       960 cagtgccatc ttcctgcact tctccctgct cacctgcctt tcctggatgg gcctcgaggg      1020
gtacaacctc taccgactcg tggtggaggt cttttggcacc tatgtccctg gctacctact      1080
caagctgagc gccatgggct ggggcttccc catctttctg gtgacgctgg tggccctggt      1140
ggatgtggac aactatggcc ccatcatctt ggctgtgcat aggactccag agggcgtcat      1200
ctacccttcc atgtgctgga tccgggactc cctggtcagc tacatcacca acctgggcct      1260
cttcagcctg gtgtttctgt tcaacatggg ccatgctagc caccatggtg gtgcagatcc      1320
tgcggctgcg cccccacacc caaaagtggg tcacatgtgc tgacactgct gggcctcagc      1380
ctggtccttg gcctgcctg gggccttgat cttcttctcc tttgcttctg gcaccttcca      1440
gcttgtcgtc ctctaccttt tcagcatcat cacctccttc caaggcttcc tcatcttcat      1500
ctggtactgg tccatgcggc tgcaggcccg gggtggcccc tcccctctga agagcaactc      1560
agacagcgcc aggctccccca tcagctcggg cagcacctcg tccagccgca tctaggcctc      1620
```

```
cagcccacct gcccatgtga tgaagcagag atgcggcctc gtcgcacact gcctgtggcc    1680
cccgagccag gcccagcccc aggccagtca gccgcagact ttggaaagcc caacgaccat    1740
ggagagatgg gccgttgcca tggtggacgg gactcccggg ctgggctttt gaattggcct    1800
tggggactac tcggctctca ctcagctccc acgggactca gaagtgcgcc gccatgctgc    1860
ctagggtact gtccccacat ctgtcccaac ccagctggag gcctggtctc tccttacaac    1920
ccctggggcc cagccctcat tgctggggc caggccttgg atcttgaggg tctggcacat    1980
ccttaatcct gtgcccctgc ctgggacaga aatgtggctc cagttgctct gtctctcgtg    2040
gtcaccctga gggcactctg catcctctgt cattttaacc tcaggtggca cccagggcga    2100
atggggccca gggcagacct tcagggccag agccctggcg gaggagaggc cctttgccag    2160
gagcacagca gcagctcgcc tacctctgag cccaggcccc ctccctccct cagcccccca    2220
gtcctccctc catcttccct ggggttctcc tcctctccca gggcctcctt gctccttcgt    2280
tcacagctgg ggggtccccg attccaatgc tgttttttgg ggagtggttt ccaggagctg    2340
cctggtgtct gctgtaaatg tttgtctact gcacaagcct cggcctgccc ctggagccag    2400
gctcGGTacc gATGCGTggg ctgggctagg tccctctgtc caTCTGGGCC TTTGTATGAG    2460

CTGCATTGCc ctTGCTCACC CTGACCAAGC ACACGCCTCA GAGggccct cagcCTCTCC    2520

TGAAGCCCTC TTGTGGCAAG AACTGTGGAC CATGCCAGTC CCGTCTGGTT TCCATCCCAC    2580

CACTCCAAGG ACTGAGACTG ACCTCCTCTG GTGACACTGG cctAgggCCT GACACTCTCC    2640

TAAGagtTC TCTCCAAGCC CCCAAATAGC TCCAGGCGCC CTCGGCCGCC CATCATGGTT    2700

AATTCTGTCC AACAAACACA CACGGGTAGA TTGCTGGCCT GTTGTAGGTG GTAGGGACAC    2760

AGATGACCGA CCTGGTCACT CCTCCTGCCA ACATTCAGTC TGGTATGTGA GGCGTGCGTG    2820

AAGCAAGAAC TCCTGGAGCT ACAGGGACAG GGAGCCATCA TTCCTGCCTG GGAATCCTGG    2880

AAGACTTCCT GCAGGAGTCA GCGTTCAATC TTGACCTTGA AGATGGGAAG GATGTTCTTT    2940

TTACGTACCA ATTCTTTTGT CTTTTGATAT TAAAAAGAAG TACATGTTCA TTGTAGAGAA    3000

TTTGGAAACT GTAGAAGAGA ATCAAGAAGA AAAATAAAAA TCAGCTGTTG TAatcgccta    3060
gccaaannng nnnnaganaa naaaaaaagg                                    3090

(2) INFORMATION FOR SEQ ID NO:    79:

(i) SEQUENCE CHARACTERISTICS:
         (A) LENGTH: 510 base pairs
         (B) TYPE: nucleic acid
         (C) STRANDEDNESS: single
         (D) TOPOLOGY: linear (vii) IMMEDIATE SOURCE:
         (A) LIBRARY: COLNTUT06
         (B) CLONE: 1610212

(xi) SEQUENCE DESCRIPTION: SEQ ID NO: 79 :

gcaagagagt gttgtaacct gatttatgtt tgaacagtat tgttttggct tctgtgtagt      60
gaaagaattg caggagacaa gagtggagct aacggcagtg gcccaggtga gagatgatgg    120
caggaaagtc cttggaccag gggcaagtgg aggtggaagg aggtggacag ctgtgtgatt    180
tttttttata aagagttcac aaaatgtaca tataattcaa agtagtggat gaggaagaga    240
gagaaatcag agnnantnat agatctggga cctgagcaac tgagtggatg ttggtgccac    300
ttccttgcct tcctagagga ggctcgggat ttggagagca acatgttaag cttggtggag    360
agaagcaagc tgaaaacagc atgccctctt ccttctcttg atctctccaa tcaggtcagt    420
```

| | |
|---|---|
| atctcnttng gagggaagac aagaaatngg gatcccatac tgtcttcatc ccatctgcta | 480 |
| taccaaaaaa aaacataaac tngggnggct | 510 |

(2) INFORMATION FOR SEQ ID NO: 80:

(i) SEQUENCE CHARACTERISTICS:
        (A) LENGTH: 2939 base pairs
        (B) TYPE: nucleic acid
        (C) STRANDEDNESS: single
        (D) TOPOLOGY: linear (vii) IMMEDIATE SOURCE:
        (A) LIBRARY: COLNTUT06
        (B) CLONE: 1611508

(xi) SEQUENCE DESCRIPTION: SEQ ID NO: 80 :

| | |
|---|---|
| tgcacccaaa nccagtgaa gtcccatgtg gagaagaagc actgtgtgcg cagcggcagc | 60 |
| agccacagac gtcccatgag gaanactccc agtgatgntc tgacatttac aattacccca | 120 |
| catggaaant taggggtttc tgaatcaagc ggctcgagta caGTTTCCAA Atagccattt | 180 |
| tgcagtgtat agtttcctta cAAAACTACC CCGCATTCAG TTTTCACATT ATCTGCAAGC | 240 |
| TGAAACTTAT TTTTAAGTTT TGTGTACAAG TTGACTGCTG TAAAGATATA TATTTTTGGG | 300 |
| TCAGTTTTTT TCCTTCATTA ACTTGGTGgt agaaaaaaat atatacttag aaatcctaaa | 360 |
| ttaaagccat gttttatata taagtcaggt aacattggtg tatagatgag aatgcaatta | 420 |
| aacctgatga gaatctactt gagaatatag aaagtctttc tctaaaggag atactgactc | 480 |
| cctggtttat tgcattaaaa tttatgttttg aggttacctc aacttgtttt aaaagattttt | 540 |
| gttttgtgaa tttgtactgt atatttgagt aactgtcagg cttttattta aaattgttta | 600 |
| acatgtacca tgtacatgtc attactatat ttcaatgcat catgcttgta acaggcattt | 660 |
| catttataat aagaatgagt tattcatttg taagccgttc agtaatttat ctactattcc | 720 |
| taaattggca taatgttaga taatctattt tgaatcacct ttaattacat gtcagaatgc | 780 |
| cttaactacc ctaacttgac aaaacagaat tctttggtag acgcggtggg ggcggggtgg | 840 |
| ggggtctgga cggagtctct atttaaggag aaatcatcat gctatgataa aacacagaag | 900 |
| catgagtggc aagtggcggg gtatttattt tgcacaaact atttgcagtc tctgtgtatt | 960 |
| taaaaagtaa agaaagttgc atccagaagg gttttgttag aatgaataca tttatattag | 1020 |
| gactgacaac ttcagctctt ttgtttaggt tttcaattat ttttggtaag agtatgtagc | 1080 |
| cttatgatct ggatatattt tgcattcatt ttccaacgcc tacatttaat tcctggtaag | 1140 |
| agcagtgctc gtcaagtttc tggtttttct ctgctctcat ttaacccgtc aaacacaatc | 1200 |
| tttgtaaagc tagattggtg gtgttttata caacttATTT ACTCAGctta ccttttttgag | 1260 |
| aaacgattgt taGaaattga cgatgtgttt gttccagtga tactgAAAGt agtggggca | 1320 |
| agaattgagt ttcacagtGG AATTGGCttt ggatctggcc tatagattag tgacaTAAAA | 1380 |
| TATTttctct attttcccct gttctttttg tgttatgcAC TTAATTTAT GACTGCCGGG | 1440 |
| GGGGTCAGCT GGAGTGCTGC TTAACAAGTA TCTCTCCTAC TCTCAGTGGT CAGAGGCTGT | 1500 |
| GTTGGACCCA TAGTAGAATT TTCCAGGTCA CAGACCCAAG CTTCCATGGG TTGTTACTGT | 1560 |
| GCTGTACCAC TTGGTGGGTC TGATTCTGAA CCTGATGTGT GTGTTAATTA TATTTTaagc | 1620 |
| annnnnnnnn nnnnnnnnnn nctcatGTAA TGGACTTTTA TAACAAAAGA AAAAATTTGG | 1680 |
| ATTTCTAATT TACAAATGGC AAATTATTTA TCCCTCTCTG GATGCACCAA AGACCAGTAA | 1740 |
| AGTTTATAGC TTTTCCATCT ATATTTATAA AGCAATACTG TATTATAAAA ATCAATATTT | 1800 |

```
TTATCACATG CTTGAAATTT TTATTTTGTT GTTTTAAAAT GTGCACTCTA AACATATCAG    1860

AACCTTATTT CTTCCTATGA ACTTAAGCTG CCTGcgcaca aaaaaaaaaa aaatttacca    1920
aatggagatg cagtagagtc cataggctct aaaaactaaa agaaatggga tgcaggggga    1980
acaagttatt tgtcctgagt tactgtactt gcttgacatg gttgttgggt actaaatcac    2040
aaaagaatcc attccaggta tgcatgtctg ggggttgggc tgtgtctaga ttagaaactg    2100
ggtttcaagc tttgcatgat gggagagcgt cctctcctct atcagcTGCG TGTGTTCTGG    2160

ATAGGACAGT AGCCCGGAGA Tgaaaccac cttcagtACC ATtagcccac cataccaagt     2220
aacAAGTTAG GCAGGAATCG TGGGAATTTA TTGAGTCAGC TTTGAGTGTT TGAGAGAATG    2280

TAAACAAGAT TGGCTCGAAT TGTAAACGTT TGTACTTTGG ATGAGTTCAT GGTTCTTTAG    2340

GTCACCTTAA TACCAGCTAT CTTTGGTAGa agcTACAGCA TTCAGTTTCT CTGGAAACTG    2400

TATCACATTt ttgCATttta AAAATTTTAC AGTATCAAAA AACCAAAATC TGCTTATGAA    2460

ACAAAACATG AAGCAGGACA TATTTGGATT CTATTTATTT AAAATTAAAT TCTTTGCAAA    2520

ATTGAACTTC TCAACTAAAA CGTGTCCATG TCAGAATTTT AACTGTTAGC AGGTAGTTTG    2580

TGGCAAAGAT GGCTAAATAA TGAAGCAAAT TAGAATCTGT GTGTATACTA ATGAGCTGCT    2640

TTTTTTCTGT TGAGACTATC ATTATTTGTC TTATTACCCA AGAGGCAATT ACCTGAATTT    2700

GGATGTCTGA ATTATAACTT ATGCAGGAAT AGTTCTGTAA ATACATTTAA ATAAACTGTA    2760

AAGATATTTA ATAAATATag tatttatact aaaannnaaa nanaangaag aaaaaaagnn    2820
nntnaannan nnnaagnaaa nctngnnnnn nannaannnn ggnnanannn nnanaaaaan    2880
nggggggnnc ccccngggg ggttcccagg ctttaccgnn ctcncnngtt ngggnnaag     2939

(2) INFORMATION FOR SEQ ID NO:    81:

(i) SEQUENCE CHARACTERISTICS:
        (A) LENGTH: 497 base pairs
        (B) TYPE: nucleic acid
        (C) STRANDEDNESS: single
        (D) TOPOLOGY: linear (vii) IMMEDIATE SOURCE:
        (A) LIBRARY: BRAITUT12
        (B) CLONE: 1616035

(xi) SEQUENCE DESCRIPTION: SEQ ID NO: 81 :

ggtagttgag gccatatctg gaggatcttt acttctaagc tgagtctgaa gttatctttc     60
tggggagtgg gaaattacaa atctttgagc tccactcaag agatggtttt gctaacaatg    120
gcaggacgac nnnnnnnnnn nnnnnnngaa actggtagca tgaattctaa ttgggtttct    180
gttattctag ccgagaaaat tggggaatgg actttcagta gaataataca gatctgggaa    240
tcaactgcat ggaggaggta gttataggtg atgagatgtc tcaggacaa agtttggtag     300 aaggagaaaa gatactaggc tgctacagaa ataattgctg tttttgccat tacttttaat    360
ggcaaaatcc gcaattactt ttgcaccaac ctaataggat gcaaacttcg gagccatctg    420
catcagaggg attgatgaag atccacaaag tttnggaaca caggganann ncccggggag    480
ggtaatgact tgagggc                                                   497

(2) INFORMATION FOR SEQ ID NO:    82:

(i) SEQUENCE CHARACTERISTICS:
        (A) LENGTH: 807 base pairs
        (B) TYPE: nucleic acid
        (C) STRANDEDNESS: single
```

(D) TOPOLOGY: linear (vii) IMMEDIATE SOURCE:
            (A) LIBRARY: BRAITUT12
            (B) CLONE: 1617155

(xi) SEQUENCE DESCRIPTION: SEQ ID NO: 82 :

```
tntgggggna aaagggnccc cnaantcccg gttttnccgg ggnccctttt nttttccggc      60
tttaatttta ccnccccaaa gccttgggcc cggaaaaagg gggggggaat ttttgccctt     120
gccaaagggg cccgaatttt aaagggtttg ggggnttaac ccggcccaag ggggnttttt    180
tccccccaag gtttcaccgg accctttttnt ttaaaaaacc ggaccgggcc ccnaggtgaa    240
atttggaant ttttangggg gacncacctt tttngaaagg gggcttattg accgttccgc    300
attgccaccg ccgttaccgt aaagcntcgg aaattccggc nncgggggtt naaaaccaaa    360
ggtttgctgg ggnaacatcc ccnngagtgt aagtttcagt taggtctggg gtgagacttt    420
taaaatttgt ACCTCTAATa agtttccaga TGATAGTGAT TTTGCTGGTC GGGAACCACA    480
CTGCAAAAAT TATTTGTATA GCTAAAACCT TGTCGGAGTG AATATGGGGG CAAGATCACT    540
GCTGAGAATT TTAAGCAACC AGCTGACCCT TGTATAATTT GCAGTGCGAA TTTAACGCTG    600
TGTAGGTgat ctaaaaaana aaagaaaaa gaattcccta aGATAATTTA TCCCCATAAT     660
GGCAGTATAC ATAGACTGGC AGTGAGTATC CCCAgactct tgtagaagct aacagaaatt    720
ctctttggag aaactcatct ccatcccaga gttgaaagtt ttcctagaaa taaaattcta    780
agtaagtagg aacaaactgt gatagtc                                        807
```

(2) INFORMATION FOR SEQ ID NO:    83:

(i) SEQUENCE CHARACTERISTICS:
            (A) LENGTH: 1542 base pairs
            (B) TYPE: nucleic acid
            (C) STRANDEDNESS: single
            (D) TOPOLOGY: linear (vii) IMMEDIATE SOURCE:
            (A) LIBRARY: BRAITUT12
            (B) CLONE: 1617156

(xi) SEQUENCE DESCRIPTION: SEQ ID NO: 83 :

```
acaagtaaca gtttacacat agatgtctgt atgctgctct ttctagtcac atccatttag     60
ctataacatg atgaagtcta attaattgaa gcttcaataa atggaaggac cagcttaaag    120
taaaataagc ctgtgaaaaa tcttggcaca attgaaattt cataaatatc tgtgaaagat    180
aattaggcat cttaaagtga aaagtcttca ttatgaactt attaatgaag atggatgttt    240
ttgaagtttg aaagaattct tgtcttaagg tagggtgtc cccaaggaga gggtaaatta     300
ttacctgtca aaggatatga caagaaagta cttactggtg aattttctgt gttcgaaagc    360
ctggctctgt agaactagaa attggtattg taagcccaac agtgggttca tttttagag    420
tagtctcaaa tttataaatc tcaaaaaaaa ggaactgtgt aaactagaat aacaatttac    480
tgattttcaa gtaagaaata cgacatgcat ttaattcaaa ctcatgcaaa tatttatgaa    540
gcacctatgt ccaggacact gtgctatgtg ttgaaaattt ggagttcaaa tttatcaaga    600
aagatatata ttgaaaaagt aaagtagga tgggtgttaa gaaagaggaa gtatgggagc     660
ttgtagaagc acgcacgagg tttataacct aggttagatg gtcaggaaga tctccaaaat    720
gatttttatct taagggaatg agaaattatt aaaaaggctt taaataggaa attagcatga    780
tcagatttgt cggctagaat atttgtgtaa tcggaaaggg taatgtttca aGAAGTGTAT    840
```

```
TAATGTCACT TTCTGGGTat acaacttaat caatccaagg CACCTTTCTG CTGAGGATTT      900

GGATTCTTGT ATAAAAAATA CAAAAGAAAT ATTTACTTTT TAACTTTCGA TATTAAATAT      960

AggATTTTTT AAATCGAGTT TTTAGGCTTC AAATCGAGGC ATTGTCAAGA CATAAAATGT     1020

AAATTTGTTT ATGGTTCAAC ATATCAAGGC TAGGCCTGGT GGACCAAATG ATAGGGTTTC     1080

TCCCATAGTA AAGACAAGGT ATCTTAGTCC AGTATGAAGG ATTTAGTCAG AGATTGATAT     1140

AAGGAAGGTG GTGGCTATGA AGTAGGTAAA GTAGAAGAAA ATCCTATTCT CTTTGGCTTG     1200

GAGAATTACG GGAAGGGGT AGAAGAGCTC AAGAAAGACA CCAGAAACAT TTTTACTGTT      1260

CCCACCCTGA AGATGTAGGG TGAGGGGTTG TGGCTTTAGA AATATCCAGA TTGGTGTGGG    1320

AAAACTCAAG GACAGAGAAA TTACTTTCCC AATTCTCAGA TATCTGGGAA GATATCAGGC     1380

TGAGCAGGAA CCACATTCCA GTAACCTTGA ACAGGGCGGA GACAGGGTAG GCATTGACTT     1440

TCCAGAGTGC TGTAAGTTTC TATGTACTGT TGAGACTCAG AAAACAATAC TCCCCTCctc    1500
caccaanaaa aaaagtacan nnangaggan gananaaaaa gg                        1542
```

(2) INFORMATION FOR SEQ ID NO: 84:

(i) SEQUENCE CHARACTERISTICS:
        (A) LENGTH: 1083 base pairs
        (B) TYPE: nucleic acid
        (C) STRANDEDNESS: single
        (D) TOPOLOGY: linear (vii) IMMEDIATE SOURCE:
        (A) LIBRARY: BRAITUT12
        (B) CLONE: 1617720

(xi) SEQUENCE DESCRIPTION: SEQ ID NO: 84 :

```
tgctaatatg ctcagattag tactcatccc ctcctcaaca taagtgaatt ttgcagtaga       60
agcttcagaa tagtgtgcgt aatcgCGTAT ATCAAAcatt cctaatgttt ccatggtccc      120
cttcaaGTTT TTTAGGTCAT GGCATCTTTG AAGATAATCT CAGAAGTGAc agggcaagaa     180
ttGATAATGA AAATGGATGG ATCCATTTTT ACTATCAGTA GTTGAGGTAG AGATgacctt      240
cttcacagtC TGTAATATGA GTAGCTTGCT TCAAGCATCT GTAGTttaag gacaggAATG      300

TAATATTAGA AATGTCATAT TATGgcttct gaagctTCTA AAGAAAGTGA TACCAAGTGT      360

CACTAGAATC AGCCTTAcgt CTTTTTTTTC TCTGTACATC AGTGCATTTC TTAAGTTTTC     420

CTGTCATCTT TAACAACTGA GTCATGAAGC TCACTTTTAG TGTTTCATTT GTAACATTTT     480

AATGCTCACA AACCAAATAA AGGTGAACTG TCCTTTGCTA TTGGGTTAAA TAGTAAAGAG    540

ACCACACCAC CTTTTACATT GTTTGTGTCA AGGGTTTTAG ACCCCTAACT TACTTAGAAA    600

TTAATCTGTT ACTTTGTCAA GTGACAAAAG ATGAGAGAAG ACTCTGCTTT TGTAAATTTT    660

ATTTAGAAAT TAGAGTTAAA Acagttatgt attgttgaaa tgtaataaag ttaagccatt    720
tttgttacta gtgtgaagct ttatgcccat taactatgtt ttaactttaa TTTGGAATAG    780

AAACCTGCAG GAAGTTACAA AAATAGTACA GAATTCAATG TAGCCTTCAC ACAGCTTCCT    840

CCAAATGTGA CACCTCATAT AACTAACTGT AATGTAATAT TAAAACCAGG ACATTGACAT     900

AGTTATATTA CTATTAACTA GATGACAGAA CTTAATGTCT TCACCATTAA AAAAAATGCA    960

TCTGTGTTTT TATGCTATTT GCccattgaC TTTTAAAACA TATTTGTTTT ATAGGAGTTT    1020

ATACAGAGAA ATCCTCTTCT TATCATTAGt gtctctagga agagagaata ttgatattgg    1080
taa                                                                  1083
```

(2) INFORMATION FOR SEQ ID NO: 85:

(i) SEQUENCE CHARACTERISTICS:
        (A) LENGTH: 1197 base pairs
        (B) TYPE: nucleic acid
        (C) STRANDEDNESS: single
        (D) TOPOLOGY: linear (vii) IMMEDIATE SOURCE:
        (A) LIBRARY: BRAITUT13
        (B) CLONE: 1622121

(xi) SEQUENCE DESCRIPTION: SEQ ID NO: 85 :

| | | | | | |
|---|---|---|---|---|---|
| caggtcgact | ctagaggatc | cccctatact | ggtacatatt | taatataga | agattattta    60 |
| tcaagtacaa | gaattatatt | ctgccatgtg | gtgacaaatg | atgccaagta | taaacctaaa   120 |
| tagtgatttc | aaaagtgctg | ggattacagg | cgtganctat | acttgattta | taagtacatc   180 |
| acaagtaatg | caacaaccta | cacacttgca | actacaaact | ttcagattat | ttccgtggct   240 |
| gactaacctc | cacattatca | gagccacatt | cttttatgga | aatatttagg | tttgtgcaaa   300 |
| agtAATTGCG | GTCTTTGCCA | TTAAAGTAAA | GGCAAAAACC | ACAATTACTT | TTGCACCAAT   360 |
| CTTTATATTT | ATATAATTCA | CTAGCTTGCA | GTAAAATCCC | ACAAGCTGAT | TACCAATTTT   420 |
| CTCTCTTTCA | GGAGTCCTCT | CTAACCTCTA | CCCTGATCTT | TGTTTGTGGA | TGTTGCTCTT   480 |
| GAGCTCCTGA | GTACACTCTT | ACTTCCCCCA | TTTCTAGGAt | ttTGGGCAAT | GGGGAAGACC   540 |
| TTGATTGTAA | CTAACATATA | TGAAAACCCG | TCTATACAAG | AGTTAAAGCT | GCACCTGTCT   600 |
| CCTACACAAA | AATTCCACCT | CATCCTAAGT | CAAAGACCCT | TCTTCTATAT | CATAGTcatC   660 |
| AAAACACTGT | ATGAATTTAT | TTTTATTTTT | TAATTTTTAT | TTTTTTAAGA | TAAGTAGAGA   720 |
| GTTTATTTGG | GCCAAGTtcg | AAGACTGCAA | TCCAAGAACA | TAGATTCAAA | TTGCCCTGAA   780 |
| TACACACTCC | CACTGCATTA | ATTTAGACAG | CACTAATGGA | AATTGCAACT | TTACATCTCC   840 |
| TCAGATGAGA | GTTTCACTTG | ATTTCTGTCA | GTCTTACACA | TAGGAATGCT | TAAGATGACC   900 |
| CTAGGGTAGT | AGAACAGTAT | TTCTCAGTTA | ACCATAATAA | ATGCCTGTCA | CACTCAAAGC   960 |
| TCCCCCTGCC | AAGAATTATG | GACCCTCTTA | CCAGCCTGGT | TGTCTTAAAA | TCCAGTCTGG  1020 |
| GTGATGTTCA | TTATaagctt | ttactTCAAG | AAAATcgctc | caactcAGAA | ATCTAACTTC  1080 |
| TTAAATCATa | agtaaaaacc | tcTTTTTATC | CTTGTAACTG | ATAAAGTGTT | TGaacttggc  1140 |
| cctagtttcc | aattaaatta | tctagcactc | ctaacccagc | tttctcctgt | gtcttgg     1197 |

(2) INFORMATION FOR SEQ ID NO:    86:

(i) SEQUENCE CHARACTERISTICS:
        (A) LENGTH: 1772 base pairs
        (B) TYPE: nucleic acid
        (C) STRANDEDNESS: single
        (D) TOPOLOGY: linear (vii) IMMEDIATE SOURCE:
        (A) LIBRARY: PROSTUT09
        (B) CLONE: 1646005

(xi) SEQUENCE DESCRIPTION: SEQ ID NO: 86 :

| | | | | | |
|---|---|---|---|---|---|
| CCCTGCTGTC | ATCAAAATAA | AAGCTTTCTG | AAGGTGGAGG | CATCTGATAC | CCAGAGTGCT    60 |
| GCTATCAGCC | GGCACGGTGG | GCCGCTGGTG | GCAGGAGCGT | CGAGAAGGCC | AGCTCGCTTC   120 |
| CTATCCGGGA | TTCAGAATCA | GCTATGGAAA | CTTGAGAGAC | CTAGAGAAAA | TAACTTCTTT   180 |
| CACTTTGAAC | TGATTCTTTG | CTTCATAAGA | AAGTATTAT | CCAGCCACAA | AAATGGTCAA   240 |
| AATTCAGATC | TACAAAAGCC | TGTCAGGCAG | AAACTGACCC | CACTTAGGCC | ACGCCAATGA   300 |
| GCAAGTCATC | AAAGCAGCCA | AGACAGGTCC | TGTGGGGGCC | ACCCATGCAC | AGGGCCCAGC   360 |

```
CTCGGGTCCT AACCCCGCCT ATGCTTTCCG CCACCATAAA GAGGCCCATC TGGGTAAGAC      420

CTGTCCCGCC TGCTGTGGGG TATTAGGGCA GATGGGGTCT GAGGGGTCTG AGGGCTCTGA      480

GAGCAGCTGG CAGCTCAAGG ACATCCGGAG TTGGAGGATG GAGCAATGCA GGCCCTTGTG      540

GTAAAGACAG TCCTGCAGCC GCGCAGGCAG GGATGCTGCA AGTGGAGTGC CAGGCGGGTG      600

CGGAGCCCTG TGGGACTGTG GAGGGGTCAG AGGGAAGCCA GGATTTTGGG GTCTCTGAGA      660

GTTTGGAGAA GGGGAAGAAG ATTAAAGCTT GTTTCAAAAG TTTCTAATCA GGTGGGCAGG      720

GCCAAGGGTG GCTGTGGGGT GAGACCCATG ACTCAGGGTG GCCCACTGTT ACTCTATTGA      780

TTTTTGGGCG TTTTTTTCCA AATTGATTAT TCTTGCTGAA TGAGACCTGA GTCCTTGACT      840

GTCCCCTTAA AGCCACCTGA CTTGTTTTCA GTTCCACTGG CCTGTCGGGC TGTTTTCTAC      900

TCAACTCCAC TCTTGCTTGT CTGCCCTCCC TGCCTGGGGC CCAGCCAGCA GTCAGCTCAA      960

GGGCCAGATG AATTGGGTGG CTGTGCTCTG CCCACTGGGA ATCGTGTGGA TGGTGGGTGA     1020

CCAGCCCCCT CAGGTGCTCA GCCAGGCCTC AAGCCTTGCT GTGTACCTCA GAGCAGCTCC     1080

GTACCCTGAT GTCACAGCAA AGAAACTTAG ACATGACACA AACTGTGGCT TCCCAAGGCA     1140

GCAAAGAATG GCCAGGGGTC ATGAGGGCCG TGCCCCACTT TTGGACAGAC CTACTCTAAA     1200

GTCACGCTAC CTGCGTGCAA ATCATAAAAT CAACACTTTT GAGGAGATCA CAGCTATGCC     1260

TTCGTAACAC AGCCCAGTCC GACCAGATAG ACGGTGCCTC GTGACCCGAA AACAAGCCCC     1320

CGGCCCCCCA CCATGTGTGT GAGCCTTACC TTGGACTGCA CGCTGAGGGA GCGGATGGAA     1380

GGGACAGCAA GGAGGCCGAA GCGCTCGTAG AGGTACTCAT GGAGGAGCT TCCCTTCAGG      1440

AGGGCGAAAG GAATGAGGTA GAGCTCCCCC TCCAGAACCA GGATGAGCTG CCGGTGCCGG     1500

CCCACGGGGC CGCTGGAGTG CATCAGGCCC TATGGAGCAA GCACGGAGAG GCTGACATGG     1560

GTGGCCCAGC AGGCAGGGGT TTCAGGCACC AGGACAACCC CTGAGCCCTA CCTGGATGAC     1620

ACCAGCACGA ACAGGTTAAG CCTGTTGGGG GTTTGGGGCG CCAATGGGGA ATGGGCCCAA     1680

GTGGCAAACC CTGCAGGAAC CGGGAACAAA CTTGGCATGC TCCGCTCGTT GAACTTGGCA     1740

AAGGGCTGGC CCTTGGAAGC ATTCAATCTT GC                                  1772

(2) INFORMATION FOR SEQ ID NO:   87:

(i) SEQUENCE CHARACTERISTICS:
            (A) LENGTH: 822 base pairs
            (B) TYPE: nucleic acid
            (C) STRANDEDNESS: single
            (D) TOPOLOGY: linear (vii) IMMEDIATE SOURCE:
            (A) LIBRARY: PROSTUT09
            (B) CLONE: 1649377

(xi) SEQUENCE DESCRIPTION: SEQ ID NO: 87 :

agcagactca caccagaact acattccctg gcccctgcc tgtgtgcttc tggccaggcc        60
ttggttggca agtctgaccc gagaaaagga tctgcagaaa atcagactat gggatcactt      120
tgtttgtgca ttgggaatga cattctttcc cacccccagga aaacctttgg gactttcaga     180
gacattgtgg ctagccaacc acatggtcag cctcaaagtt gagaggctca gtaaccctcc      240
tatccctaga gaattccaaa gtgtggatgt aatttaacta gaaagccatt ggtgactatc      300
tgtgatcctc tggaagtatg ctatgttgtg tatatcttgc atccaaagcc agagggaacc      360
acaatgacta gtaaaacggt ggtctcaatg cccacttagc ctctgcctct gaatttgacc      420
atagtggcgt tcagctgata gagcgggaag aagaaatatg cattttttat gaaaaaataa      480
```

```
atatccaaga gaagatgaaa ctaaatggag aaattgaaat acatctactg gaagaaaaga      540
tccaattcct gaaaatgaag attgctgaga agcaaagaca aatttgtgtg acccagaaat      600
tactgccagc caagaggtcc ctggatgccg acctagctgt gctccaaatt cagtttttcac    660 agtgtacaga cagaattaaa gacctggaga aacagttcgt aaagcctgat ggtgagatag     720
agctcggctc ccttccangg gaaagatctg accggaaaag naatgttcca aaaanttggc     780
caagctngga ctacaaattg gccaagaaag gnggagaagc tt                        822
```

(2) INFORMATION FOR SEQ ID NO: 88:

(i) SEQUENCE CHARACTERISTICS:
        (A) LENGTH: 410 base pairs
        (B) TYPE: nucleic acid
        (C) STRANDEDNESS: single
        (D) TOPOLOGY: linear (vii) IMMEDIATE SOURCE:
        (A) LIBRARY: PROSTUT08
        (B) CLONE: 1651564

(xi) SEQUENCE DESCRIPTION: SEQ ID NO: 88 :

```
aggcaagatc aagagagaga ggaaatactt tatttcgagc cactctcctt gcagtctcag       60
actgggttcc aatcttgctg tgccaagaat aaagtcaact tcatatttat atagttatat      120
tatccggaga tctgagaaag aatggacgtt acactgatct tctatgttct tttatttagt      180
ttctaacttc aatgttattt atatctaagt ctgaatgctg tctatattga aaatagttaa     240
tttattaaaa cattttttca cgtaagttta tggtcacagt acctaatctt tgctaaatgt     300
ttgatttatt ctaaaaagtc ttaaaatgat agtttatgag tgctctctta ttacncttaa     360
acttttgcct tttaaaatga cttgtagngg gggagnagag gcanacanca                410
```

(2) INFORMATION FOR SEQ ID NO: 89:

(i) SEQUENCE CHARACTERISTICS:
        (A) LENGTH: 2388 base pairs
        (B) TYPE: nucleic acid
        (C) STRANDEDNESS: single
        (D) TOPOLOGY: linear (vii) IMMEDIATE SOURCE:
        (A) LIBRARY: PROSTUT08
        (B) CLONE: 1652112

(xi) SEQUENCE DESCRIPTION: SEQ ID NO: 89 :

```
ggagcttcgt ccagcctgtg gatggagcct gactggctgc agatggaact tctgtgtcct       60
cccaccctag gtgggctaag gttctgctct cagagctgaa ttgacaggag gtgtgtgtgt     120
gtgctcactt gtgtgcacaa gcatgcgttt atgcatgttt tcacgcaacc agaagagcca     180
ttcgtgggat ttagccattt cgaggcacct aggagttgag gcagccagct gtgcagccag     240
gtgtgactgt tactggcagc attgtataaa agacacgact cagctgccgt agggaggact     300
gggttgtctg gaagtattag gctcatttta tatttgtgtc agaagaaatg tctgactttg     360
gggcagatga cacggtggct gcggaccagg catggctccc ctaggttgaa atcagggaaa     420
agctaatagt atcagacaga tatgcttttt ctttggtggc tgcaggattt ttgctggaaa     480
atgcactatt aatcagcact tgtccaagaa agacccatcc atttctgttg tcattcaagc     540
cacagttcct gatttactcg gcaagatact gggccagttc agtgtctcta gctgagcctg     600
acctcggggt ttgcgtctcg agtctgaaat cctgtttagt cctctgtgca tagttttgtc     660
```

-continued

| | | | | |
|---|---|---|---|---|
| tcattttaac | gactgcatct | tcttggcaca | tttattatac | tcacaactga atggcacaca | 720 |
| atagccttgt | gttaataaaa | gctaccgtgg | cgctgtgggt | gaaaccgctg ggttgaagtc | 780 |
| cgatggactc | tacggatgca | ggcatccaga | aatatgttgt | aactctacct ggctccctgc | 840 |
| cagcctggcc | tcctcctctg | ggagagctcc | tggcatggtc | ccaatgtgta cctgcatggg | 900 |
| aacaacagct | gcatgggcca | gctgtttcgg | atctaaAGAT | GTGCAGTGAa actcacattc | 960 |
| ccagattcac | atccctcatg | tttatttggg | tcatcatggt | ttagcatgtt gtatatatgt | 1020 |
| CTGGAGCACT | TCATACACCT | CTATCCACCA | CAGACACTCT | TAATCACAGT tctgtaaTAA | 1080 |
| TAAGGCAAAC | TATACGGCAA | AGAGAAGCAT | GTAAATATGT | ACCAAATCCT TATGAAGTTG | 1140 |
| TAATTGTTTA | TATGTAAAAA | GTATGTATAT | AGGAACGGGA | GAAGGTGCAA GGAATGTGCT | 1200 |
| GAATAACATC | CAAACTGCAT | CGCGTCTCTG | CCCCATTCCT | GAAAGCACAC ATCTAGTTGG | 1260 |
| AGCGTCAGTT | CCTCTCCTTA | GATatcattg | ttttcactcg | tctatCATAG GCACCTTCTT | 1320 |
| TACATCTGAT | TACAATACCC | AGCATTTCAG | AactgggtctTTGCCCCAA | ttgcccccaa aaaggtaaat | 1380 |
| atgagcattt | atcaCTGACT | CCTcctggtc | cagtgagcag | cagcaGAATT Caagtattta | 1440 |
| aaaataaggt | gcatttctaa | attgcaggct | ataccttctt | ttccaaacca atgggctaga | 1500 |
| gtgaatttcc | tccaagtact | tgggctgtct | tactgctagc | tcttctaaca ggggaagtct | 1560 |
| gtatgaatgc | atcacccct | aataaggcaa | gaggaaggac | cctgaaatgt tgccagaaat | 1620 |
| gtactgttac | atcaacattt | acattatatt | aacatcatca | cactctgtgt tcaacacaca | 1680 |
| gaacaacata | gatactttag | tttgtctaaa | gtaaaaatcc | acataaatag cagattcctt | 1740 |
| tgttgacacc | agtgtgttgt | ttacCTTGTG | CCCATGGTCC | AGATTTTGAG CTGGAGAAGG | 1800 |
| ACTATGGCTG | TTCCTTAAAG | TCTCTGCCct | TGCAGAATCT | GTAGCCTTCA GGATACCCCG | 1860 |
| AGTGCCTTAC | AGGGCTTGTG | AACACCGATA | CTAGAAGTCA | AAAAGAAGAG AGTGCCCAAG | 1920 |
| TGTGGGTTTG | GAGGCACTGA | CGCATTCGCc | aacTCACCGT | CATCCCATCC TTGAAACCCT | 1980 |
| GAGAGAGAGT | GTGTGTTTTA | TCACAGTAAT | GGAATTCAGT | TTAGCCTCAG GAAACTCATA | 2040 |
| TTGTGAATAT | AGGTATCAAA | TCATATATTT | GTTTACTGTA | TATTTTTAA AAAGCTTTAT | 2100 |
| TGTAAATTTA | TGCAAAAACT | AACCGGGCCT | GTTTTCTTAC | GGCGGCATGC CAGGTAGTGT | 2160 |
| GTGTATTCTC | CCAGGCACTC | CCTTCATAGT | CACcctctaa | cCACGTGaca ttccGTTCCA | 2220 |
| TGCTAAGCAG | TATTCACagg | cctaaaatag | gtttgtatgg | tgatctacaa gatttttacaa | 2280 |
| atatttttgt | attgtgattc | ctatgatata | taccagagaa | ttttttactc ggtttgtaaa | 2340 |
| ttattgtaca | gttttaataa | aaaatgtttt | aaatcttaaa | aaaaaaaa | 2388 |

(2) INFORMATION FOR SEQ ID NO: 90:

(i) SEQUENCE CHARACTERISTICS:
  (A) LENGTH: 861 base pairs
  (B) TYPE: nucleic acid
  (C) STRANDEDNESS: single
  (D) TOPOLOGY: linear (vii) IMMEDIATE SOURCE:
  (A) LIBRARY: PROSTUT08
  (B) CLONE: 1653770

(xi) SEQUENCE DESCRIPTION: SEQ ID NO: 90 :

| | | | | |
|---|---|---|---|---|
| aaaaaccctt | ngnnttngnc | aaatgaacaa | ttctgtgcna | ctttgggctc cagCAAGAAA | 60 |
| TTTAAGAGAA | AGGAGAGATT | TTTATTATGA | TTTTGATTTC | TTTACTACAA CATTGCATGT | 120 |
| GTCTGGAGTA | TAGCCATTAC | ACTTTATGAA | AAAGGCAAAA | TGGTCATTTG GGGTGTTTTA | 180 |

```
GGAAGTTTGC CAAAAGGCTC CTTTGTCATT ATAATCCTTC CTAAGCTGCC ATCCACGGGT      240
ttagGTCATG GATATGAAAA GTGAAAGGGT TTAGAGATGA AGTAGTGTCC CCTGAGTGCT      300

TACCAACCTG TTAATCTTTT TGAGATGTTA ATTTTTTCAT ATAGAGCCCC CTAAAATCTT      360

GATGGCTCTA GATCAGTCAA GCCTAAGAGA AGAcgTATTT ATggaaaaaa accanaaaac     420
aaaaaaacct tGCTGGATTG CTAGTAATAT CTACTTCTTG GAAATTAATA CTTCATATTT      480

TTTAAAAAAA TTATTGATGC ATTAGGAATA TTTTTTGCTT AGCAGTTaca aattttaaga     540
ggcacatata caccacggaa tactatgcag ggggatcctc tagagtcgac ctgtcctttg      600
tagggacatg gatgaagctg gaaccatca ttctcaacaa actatcgcca ggacaaacaa      660
ccaaacaccg catgttctca ctcacaggtg ggaactgaac agtgagaaca cttggacacg      720
ggaaggggaa catcacacac tggggcctgt cgtgggntng ggggngnnna nangnatagc      780
attaggagat atacctaatg taaatgatga gttaatgggt gcagcacacc aacatggcac      840
aggtatacat atgtaacaaa c                                                861
```

(2) INFORMATION FOR SEQ ID NO:   91:

(i) SEQUENCE CHARACTERISTICS:
        (A) LENGTH: 699 base pairs
        (B) TYPE: nucleic acid
        (C) STRANDEDNESS: single
        (D) TOPOLOGY: linear (vii) IMMEDIATE SOURCE:
        (A) LIBRARY: COLNNOT23
        (B) CLONE: 1693426

(xi) SEQUENCE DESCRIPTION: SEQ ID NO: 91 :

```
atttntatat aattcattat aacatatatt atatattata tataattcat tatatataaa       60
ttgtttttca aaataaaaa taaaacaAAG AATGTCAATG TTTCTGAAAG ACCACTGTCC      120

AGAAAGAAGG CAGAGCACAT TCAAGGCTTG AGTTGTCCAC TGGGTCATCA GCCACGTTGC      180

CCAGACACAG AcacctccAT gagCGCCTCC AGCGGCCGGT TGTTGTCCAG GTCGCGGCTG      240

AGCTGCAGTT CGCCCGTGGC GGGGTCCAGC AGCAACAGGc gcagctcgtt gccctggcac     300
gaAGGTGTAG TTGAGGCTGT CTGACACGTC GGGGTCATGG GCCGGGATGC GGCCGATCAC      360

GCCGGTGGGG AAACTGTTGG ACTTGTTGGT GACATAGTTG TTGAAGAGGA TCTGGAAGTC      420
gggcagcACA GGCGGGTTGT CATTCTGGTC Cacgagaagg atgtgcaccg tgGCTCGGCT      480

CACCAgcgga gccgacgtgg cctgcaccac cagcacatac tcccgcCGGA CCTCAAAGTc      540
cagctcgagc cgttcgagcn nnnnnnnnn nnnnnnnnn nnnnnnnnn nnnnnnnnn      600 nnnnnnnnn nnnnnnnnn nnaattcaat tcacttgggc cgtncttaa caaacgtcct      660 ngaactggga naaacctggc gttanccaac nttaatcgc                            699
```

(2) INFORMATION FOR SEQ ID NO:   92:

(i) SEQUENCE CHARACTERISTICS:
        (A) LENGTH: 1252 base pairs
        (B) TYPE: nucleic acid
        (C) STRANDEDNESS: single
        (D) TOPOLOGY: linear (vii) IMMEDIATE SOURCE:
        (A) LIBRARY: BLADTUT05
        (B) CLONE: 1700601

(xi) SEQUENCE DESCRIPTION: SEQ ID NO: 92 :

```
tcgactctag aggatccccc tttattaaag ttgaaagcag aaatcatttt tattgcagcc       60
```

```
taggagttac tcagcacatc tttttgaatc cccttcatgt gctatttagn nnnnnnnnnn    120
nnnnnnnnnn nnnnnnnnnn nnnnnnnnnn nnnnnnnnnn nngtcgactc tagaggatcc    180
ccctcccggc ccgaaactga agttgtttaa ttgagaagtt tcagggctgt gaaatgtacA    240

CTGAGCACAC ACCCTGCACA TTTCATCTTC Ccgcctttgt tttggatccT ATATCTtcag    300
tgcccttAAA GTGTGAaact CTCAATCAGA CCCCGCTTCC TGCACTGCTC CCCAGGTATC    360

TTACattcCt tgCAACATTT TAGACTGCAT GTACTATTTT GTACTCAATT ACATAATTTT    420

ATTTTGTTCA CTATTGTTTT ATCCTTGCTT GGGTGTTTTC CTCACTATGG GAAGAAGAAC    480

CCTAAGAATG AATCATCTCA CTGGGAAAGG AAGCATTTAA AACTTATTTa gtGTATTTTT    540

ATAATTGGGG AACTGTAAGT ATTTCTTTTA GCATTAATGC TTGTTTCCAA GAAATGGTGA    600

ACTTACCTAA ACTTAGTAAA TTTTTGTCAT AATAATAGAA TATTCACAAT TGTTTTTAAT    660

TTATAAAAAT gtAagttgCt ttcTACTAGG GTGTTATTTT AGGGGGGAAG ATTTGTAAAA    720

ATGttcAGTC AAAATATTGT CATGTTAATC GTATTtttcA AGATGTGCTA AAAATGATTT    780

CCCACTTAGA ACAAATTAGC TGGAGGCCAC CTTATCCCAC CTCCAGCCCC CTCTGCAACA    840

CCCTTCATAG CTAATtacCT GCTTTTCATT CCAAATTTTC TATGACAAGG TGTTCCTACC    900

TCAAcagGTG ATCACCATGG CAACGAGGTA GTCTGTTCTA TTTTTGGAGT ATGAAAGTAG    960

TGCCTTCTTA AATCTAATAA TAAATGAGAG TTCCAGAAAA CCAGTGCTTC AAACAAATTT   1020
gatTTACTTG AATTTTTTTT TATTTTAaat cacactttgg tttttaaaat ttttagggtt   1080
ccacaancTT tttnggggga nagggcTTTT aangggccag gaaaaagggg attcccacct   1140
ttgnaagggn cccccagggg gaggtttttg gaancaancc caaggccctt nggggggcn    1200 aaacaatttg gggtggaacc aaccttcntn gggtccncaa ttaaccaaag gg           1252

(2) INFORMATION FOR SEQ ID NO:    93:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (vii) IMMEDIATE SOURCE:
        (A) LIBRARY: BRSTTUT08
        (B) CLONE: 1729463

(xi) SEQUENCE DESCRIPTION: SEQ ID NO: 93 :

GAAAACCACA ACTGTGGGAT TGAAGTCAAC AGAAAAGGCC TGACAAGACA GTATTAGAAT     60

GAGTGGCCTG CC                                                        72

(2) INFORMATION FOR SEQ ID NO:    94:

(i) SEQUENCE CHARACTERISTICS:
        (A) LENGTH: 150 base pairs
        (B) TYPE: nucleic acid
        (C) STRANDEDNESS: single
        (D) TOPOLOGY: linear (vii) IMMEDIATE SOURCE:
        (A) LIBRARY: BRSTTUT08
        (B) CLONE: 1730680

(xi) SEQUENCE DESCRIPTION: SEQ ID NO: 94 :

GATTCAGCCC GTGATCCTTG ACTGGATCCT GGGTGAAAGC AAAAGCAGCT CTAAAGGACA     60

CTTTGCAGAC TAAATGTTAG CTAACACCAT TGTATCAGTG AGAAAGTGCA GAGTGTGGTG    120
```

```
AGTCCATTGA GGCTCTGTAG AAGAAAGTCC                                        150
```

(2) INFORMATION FOR SEQ ID NO:    95:

(i) SEQUENCE CHARACTERISTICS:
        (A) LENGTH: 1075 base pairs
        (B) TYPE: nucleic acid
        (C) STRANDEDNESS: single
        (D) TOPOLOGY: linear (vii) IMMEDIATE SOURCE:
        (A) LIBRARY: BRSTTUT08
        (B) CLONE: 1731419

(xi) SEQUENCE DESCRIPTION: SEQ ID NO: 95 :

```
ccactgtgcc cagcgcgcat tgttcttta acaaaagatt cgcctggccc ctgctttggc         60
tgggctccgc agAGATAGcg caggcctagt ggacaaggcc tctgtCTGAA CCGggcctat       120
actgtagtGG GACAgaaAGA CACCAAACAA TTTGCTTTCa cggggaagaa agtGGGGTGC       180
CAAAAATAAT GTGGGAGAAG GCCTTTGCAT ACAGGGTCAG AGACGGCCTC CCCAAAGAGA       240
TgacATTCCA CAGGATTCCT GTCTGAGAAG AGCATGGGGC AGAGGAAGGG CCTCAGCCAG       300
GGGGCTGGAG CAGGGAGGCA GGCtgtgacc ctggagCGGC AAAAGGACTC ACACCGCAGA       360
CTCCATGGAT GATGCGTGCA CAGCTCAGTG AACGTCATCC GCACAACCAG CTTCCCCACG       420
GCCAGATAAG CCCAGACGAG CAAAGCACAC ACCACCCCAa gcATTCCTGC TCTGGACATG       480
Ctcgcaggcc ccccagcAGC CTCCCCCGGA ACCCCTGCCA TGCTTCAAAC TGGAGGAGAG       540
GCCAGCCTCC CCAAGCCTAC TTTCCTGGCC TCCCGCACTG CTGGGCCTAG GCATGACCC        600
AAGCTGGGCC AGTCAGGTGC TCCTGCCCAA GTTTTCAAGG GACACAACTG tgacctcagA       660
AGGGGTGCAA AGCCAGTCCA GGTGGACACt gTCGGCCACC TGTGTCCAAG GCGCAGTGGA       720
GGCTGCTGCC TGACTCACTC ATTCTCTGGT ACCCTACTCC TGCCGCACCC TACTCCCACT       780
TCAGAACATG CTGGACTATC ATCCCCTCCA GGAAGGCTCC TCCTGggaca ccttctcccc       840
tctgccccca cctcACAGTA CTGCCCAGCA TATCTTGaca tagcccaatt cacacccctg       900
caccccaggc acccaggaca ggaggacaag tctacctcct tcagaagggt aactccaggg       960
cacgtgcacc agaggaaccc aggaaggcct ttgggggctt gctcatccca aagggcaggg      1020
ccagaggagg agagggggat cctctagagt cgnattgcca aggacttncc ctaaa           1075
```

(2) INFORMATION FOR SEQ ID NO:    96:

(i) SEQUENCE CHARACTERISTICS:
        (A) LENGTH: 93 base pairs
        (B) TYPE: nucleic acid
        (C) STRANDEDNESS: single
        (D) TOPOLOGY: linear (vii) IMMEDIATE SOURCE:
        (A) LIBRARY: LIVRTUT01
        (B) CLONE: 1751509

(xi) SEQUENCE DESCRIPTION: SEQ ID NO: 96 :

```
GTAGTTTTAA ATTGCATGCA TTATAGCCAA ATATTTTATT GCAACCCAGC CCTCCTCTAC        60
TGAGCCTTGT AAATGAGATA TTATATTAAG TGC                                    93
```

(2) INFORMATION FOR SEQ ID NO:    97:

(i) SEQUENCE CHARACTERISTICS:
        (A) LENGTH: 606 base pairs
        (B) TYPE: nucleic acid
        (C) STRANDEDNESS: single (D) TOPOLOGY: linear (vii) IMMEDIATE SOURCE:
         (A) LIBRARY: LIVRTUT01
         (B) CLONE: 1752114

(xi) SEQUENCE DESCRIPTION: SEQ ID NO: 97 :

gcctacagtg tactaaagca ctggggtaag gaaagattag tttgtacagg tttgcaaata     60
attcaaggca ataaataaaa tgtagggaca gtagtacaga gaaattatga agactggggg    120
tagaattagc tggcattaaa gctccagctt ggaactggag tattatggtg tctgacactc    180
aactgtgatc ccagtgttag gcttgatagc agcatatccc ttaggcattt aaggagagga    240
aagaagttag atggaggggc tcctgtcact gtccccactg actttgtagg cctcgtgaat    300
ccttaatatc acagacctaa tgagcattcc tatttttatt tttttttaag tatttagttt    360
tgtccaggca acaacatcaa aggatttcca gagttgtctt aaggacctgg gaaccatatt    420
gctatagaag ttaggaaggt actattaata gtttctaaa tagggaaact gaagattaaa     480
aattaaatat tttgggggct gggcaaaggt tcctcacgnc ctgtaatccc agcactttgg    540
ggaagctgaa ggtgagaaaa tccatttgac ccccagagnt tgagaccagc cgtaggcaac    600
atagcg                                                               606

(2) INFORMATION FOR SEQ ID NO:    98:

(i) SEQUENCE CHARACTERISTICS:
         (A) LENGTH: 724 base pairs
         (B) TYPE: nucleic acid
         (C) STRANDEDNESS: single
         (D) TOPOLOGY: linear (vii) IMMEDIATE SOURCE:
         (A) LIBRARY: GBLATUT01
         (B) CLONE: 1819891

(xi) SEQUENCE DESCRIPTION: SEQ ID NO: 98 :

aggagggaat gaagtcttat gctggggagg tgggcaagta tcaatttcct taatatcttg     60
aatcctgtgg gtccaaaatg tggcttggaa atcaagtag catgtggctt aattactaat    120
cccacccttt gctgttgcat cccagcccta ttcctggtgc atttatgccc agagaggtgg    180
cattatttcc tggggtggca ttcagctcct cttgagttgg tgccacagca tttgtgggct    240
ttgaagcaaa ggtacaggaa atgtcaaggg tgccaccccg gcaaccttga gcaagtcacc    300
cctcctattt gtaaaatgag gaaggaaagg taacaaactg tggagtcaga gagaagtagg    360
ttggaatcct ctttgtcatt tagtagctgt ttgacctaag gtggtttact gaacttctca    420
gtttctccat ctgtaaaatg agaattctag caactccgtt aagggtattt gtggagatgt    480
tgcatgcaaa gccccagca ccatgcctgt cctagcttaa gcacccacca ggtgtcgata     540
agtaattgtt cttccctgga ctgcctgcac atctagggca cccnaggaag attcaccgca    600
ctctgtttcg gggctcggct ctctgagggg agggcatcct gtatgggag gagggtctgg    660 accagagctg tccctgatcg ctagaatcaa cngcagaatt cttgttattt taataataat    720
taat                                                                 724

(2) INFORMATION FOR SEQ ID NO:    99:

(i) SEQUENCE CHARACTERISTICS:
         (A) LENGTH: 515 base pairs
         (B) TYPE: nucleic acid
         (C) STRANDEDNESS: single
         (D) TOPOLOGY: linear (vii) IMMEDIATE SOURCE:
        (A) LIBRARY: GBLATUT01
        (B) CLONE: 1822832

(xi) SEQUENCE DESCRIPTION: SEQ ID NO: 99 :

| | | | | | |
|---|---|---|---|---|---|
| agaggnattt | nngnttttcn | tnncaaannc | cnccntttc | ccncccacna | aaagttnang | 60 |
| gtgnnncttn | aaaggaaagg | naaaaagtnc | acggtnnnat | agngcaggaa | gaaaagaaan | 120 |
| cggagnanaa | gggggactt | cccaatangc | aggnaganga | accgnaactn | tnttgatgtn | 180 |
| atgnanntgg | atncagcggt | gtccatnntg | gntcagccct | tagaggagag | ccagnganag | 240 |
| agatagacag | tgAGAgagtc | ctggccctta | tgattAACAT | GGGATCTGCC | TGCAAATGCT | 300 |
| GTTTAGGgcc | attgcctcTT | CCTGTACTGC | TATTTTTGAG | AGTGATGCTC | CTGAGCCCCA | 360 |
| TGACCCAGTC | AAATTtcaTG | TCCCCttgAG | CCAGATTCAG | TGCTGGGAGT | CCAGTGTGAT | 420 |
| CTGCCTGGAT | CTTGCtgcat | tgagaacagg | ccagatcttg | accccaatac | aggggctgga | 480 |
| tatgaacagg | caatagctng | gtttctgagt | cagaa | | | 515 |

(2) INFORMATION FOR SEQ ID NO: 100:

(i) SEQUENCE CHARACTERISTICS:
        (A) LENGTH: 635 base pairs
        (B) TYPE: nucleic acid
        (C) STRANDEDNESS: single
        (D) TOPOLOGY: linear (vii) IMMEDIATE SOURCE:
        (A) LIBRARY: GBLATUT01
        (B) CLONE: 1823006

(xi) SEQUENCE DESCRIPTION: SEQ ID NO: 100 :

| | | | | | |
|---|---|---|---|---|---|
| acgcgtccgt | aagctcggaa | ttcggctcga | ccaaacacag | ggagaatttg | gggaacagtC | 60 |
| ACAGAATGTG | GAGGAATGAG | CTTCTAGGCT | CTGTGGCTGC | AGATTCTGTG | ACTGTTCCCC | 120 |
| AAACACAGGG | AGAATTTGCa | gaaaataagc | ccaaAAATCT | TGCCATTCTT | TGCAATAAAA | 180 |
| CCCCACATTA | CAAACTGCTG | AAAACAGGAT | TTTAGCCTGA | ATAGGTTGTT | CCTCTATTTG | 240 |
| AAAGCCTTTA | CAATTTCGGA | GGGAAGTTTC | CAAATCAATC | AGTAAGTACC | CCCCACTCCA | 300 |
| GGTTTATCCT | TATGTAAAGT | GCCCcctttg | cacatgcaag | attgaataaa | ccttgaaaat | 360 |
| attatgccta | agtgaaagaa | gccggtcnca | aaggaccaca | tggtatgtaa | ttccatttaa | 420 |
| ataaaatgtc | caaatagac | caacacatag | aaacagaaag | tagatttgtg | gtggcccagg | 480 |
| attaggggag | ttgggggaa | atggagggat | atggtgttta | cttcagggta | atgaaaatga | 540 |
| tctaaaattt | attgtggtga | tgtttgcata | acagtgcaaa | tatactgaaa | accactgaat | 600 |
| tttacacgtt | taaatcagtg | gcttctggtg | ggtat | | | 635 |

(2) INFORMATION FOR SEQ ID NO: 101:

(i) SEQUENCE CHARACTERISTICS:
        (A) LENGTH: 1689 base pairs
        (B) TYPE: nucleic acid
        (C) STRANDEDNESS: single
        (D) TOPOLOGY: linear (vii) IMMEDIATE SOURCE:
        (A) LIBRARY: BLADTUT07
        (B) CLONE: 1887573

(xi) SEQUENCE DESCRIPTION: SEQ ID NO: 101 :

| | | | | | |
|---|---|---|---|---|---|
| cctcggagac | ccccgcgctg | gggacgggag | gccggcgagc | ctcgggacct | ctgaaagcct | 60 |

-continued

```
tgaggaggcg cggggacacc atggccgagc ctctgaagga ggaagacggc gaggacggct      120
ctgcggancc cccgggcccg tgaaggccga acccgcccac accgctgcct ctgtagcggc      180
caagaacctg gccctgctta agcccgctc cttcgatgtg acctttgacg tgggcgacga       240
gtacgagatc atcgagacca taggcttta gGGAGCAGGA GTGCATCTGG TAATTGAGGG       300
TGGATGTTGT GTGTGCTGGG GaggGGTCCT TCTGTTTGGT GCTACCCTTG TCTACTctgc      360
ccctggatgg tgcggggtgc tttctccacc cccacactcc ctgctcagct cctcgtgctg      420
ccctgcatgc ccaggcttgt gagccaagct gcttttttggg gcaggGAGTA GCAGCAGGTG     480
GGAGGGGtta cccatcaGCC CTTGCAAGTC CCCCACTCAG GCCTCTGGAA GGTCCAGGGA     540
TGGGCTCTGA TGAGAGGGTA AAAGATGCTC AGGGAAACAC AGGCCTCAGC TGCCTAGagg     600
aCcctCCccc tGCCTTGCAG TGGGCTCGGG TAGAGCAGTA TCAGGAGCTA GGGTTGTCTG     660
CTGCCCACAC TCCTGCTTTT TGGGATATCT AACTGCTAAG GAGGGAGTTG ACATCCCCCT    720
TCTGGCTCAT GTGTCTGACA CCAACAACAT GGTCTCTGTC CCTCTCTCTT TGACTCTCCC   780
TTTGTCCTCC CCATAGAGCT GGGGTGGGGT GGATCCCTAT ACCTGGGGCA GGCAGCCCCA   840
AAGTGGGGGA GGGGGATGGC AGAgactGTA AAGGCGCCAC TGgaCTCTGG CAAGGCCTTT   900
ATTACCTTTA CTCCCCTCCC TCTCCCATCA CCAGCCTCAA GGCCTGAGGg gtGCAGgggc    960
tCCTGGCAGC TACTGGGTGA GGTTTCCTGG CACAGACTCA CCCTTCTTTC TGGCACCACC   1020
TCTTTCCCTT TTGAAGAGAC AGCAACAGCC GTAGCAAAAG CAGCTGCTGC TCCTGCTATG   1080
AGGGTGTATA TATTTTTTAC CCAAAGCTCT GGAATTGTAC ATTTATTTTT TAAAACTCAA   1140
AGAGGGAAAG AGCCTTGTAT CATATGTGAA CATTGTATCA TAGGTAATGT TGTACAGACC   1200
CTTTTATACA GTGATCTGTC TTGTTCCTGC AGCAAAAATC CTCTATGGAC ATAGGAGGTG   1260
CTGTGTCCCA TGCCCTCTTG CCCTGACAGT GTCCCATGGG CCCCCTTCTG CTCCCTGCCC   1320
CCTCCCTGCT ACTGCTGATG CACtctCCTC TCCCTGCAGC CCCTGGCTTC CCAGCCTTCC   1380
TCCTGACCCC TTCCAACAGC CTTGGAACTC CAGCTGCCAC CACCCTCTGG GTCGGAcact   1440
GGGACCcact GGCCCAGTCT TGGCTGCtgc tTACCCCTAG CCTTGATGCC TGCCCAGGGA   1500
CCCCCAGCCC CCTCCCGTTG CCCTGCAGCT TTAACAGAGT GAACCATGTG TATTGTACAG   1560
GCGCGGTTGT CATTGCAGAA ACCGCTGGGT GGAGAAGAAG CCGATAAAGt ctatgaatca   1620
acctgnttga gcaataaaag ggnngggccg nttntagtgg gatcccaagc ttanngnatn   1680
gtnattnnt                                                              1689
```

(2) INFORMATION FOR SEQ ID NO: 102:

(i) SEQUENCE CHARACTERISTICS:
        (A) LENGTH: 613 base pairs
        (B) TYPE: nucleic acid
        (C) STRANDEDNESS: single
        (D) TOPOLOGY: linear (vii) IMMEDIATE SOURCE:
        (A) LIBRARY: BLADTUT07
        (B) CLONE: 1888890

(xi) SEQUENCE DESCRIPTION: SEQ ID NO: 102 :

```
ggacaaggga cattttaaag ctttgtttaa aaactgtaat tcatagcaac gaacaaggca       60
ttaataacaa gtatagttag gtgctacttg tttcatgcta gagatccagc aattttatac      120
aacattgttt tgcctcatca gtgcaaatgt taacacaatg cgtataaaaa taattttgac      180
ctcattaatc tcttgaaagt gtttcaggga ccttcaagat tcaaagacca catttgcaga      240
```

```
actgctgata taatggacca gtgtggcgtt ccacatactg tgtcaatgtt tcaggtctct    300
atactgcatt ataatagggg tcaagagagt taacagaact ccagttaaaa ctctataagt    360
gtattccttt tgttcccatg tgggatctaa actgattctg gattttctcnt tttggaaatg   420 ggctggaaaa taaaatggcc atttccantt tggatgggct ttaataatcc tccacacctg    480
gnaaggcttg tggtccantc nngcttcnng gaaaaaaaaa aattaaccccn taggccgggt   540 ggcaagcaaa ccggccaant tgggtggtta cctgggcttg ggataaaagnt ttacnagtta   600 atccccncng gtc                                                       613

(2) INFORMATION FOR SEQ ID NO: 103:

(i) SEQUENCE CHARACTERISTICS:
        (A) LENGTH: 1143 base pairs
        (B) TYPE: nucleic acid
        (C) STRANDEDNESS: single
        (D) TOPOLOGY: linear (vii) IMMEDIATE SOURCE:
        (A) LIBRARY: BLADTUT07
        (B) CLONE: 1889526

(xi) SEQUENCE DESCRIPTION: SEQ ID NO: 103 :

ggcactgggc ggataccaga aattgcagaa gatcatgaag ccttgctttg gagacatgct     60
gtccttcacc ctgacggcct tcgttgagct gatggaccat ggcatagtgt cctgggatac    120
attttcggtg gcgttcatta agaagatagc aagttttgtg aacaagtcag ccatagacat    180
ctcgatcctg cagcggtcct tggccatttt ggagtcgatg gtgctcaata gccatgacct    240
ctaccagaaa gtggcgcagg agatcaccat cggccagctc attccacacc tgcaagggtc    300
agatcaagaa atccaaacct atactattgc agtgattaat gcgcttttcc tgaaggctcc    360
tgatgagagg aggcaggtaa gttgcatttc tttagtctta tggctatGTC AAGGCTAGGA    420

ACTTTGTGTG CAGAGAACGC CCTCTCCTTC TATTCAGGGA CTCATTGGGc ctcTCTGCta    480
tcctggccac agatggactc tccagagcag ctatgttccg ctgcacggct ggcccgctgg    540
ggtccttccc aaatccaggg gcaagtgggt agagatggat aagcccttga ctgatgaggg    600
atgctaggAG TGTTCCAGCA gtagagcctt ttcatgaaAT GAAATGCAAC CTGGAAGCCC    660

AGATGTAAAA AGATGAAAAC GCTGCTGTGG TGGAAGCAGA GTTAGGAGCC CCTGCcacct    720
cctgtCATTT CAtagGATGC TCACTAGGTT GAGGGAAGTG ccgTTCTCAT TTTCTGTATC    780

AGGAAACAGA CCCTGAGGGG TGCCATGTTT TTCCCAAGGA AGGAGGTGAT GGAAGGTAAG    840

AGGACAGGAG GGATAATATG CAGATGGCTG CTCCTTGTGG AGATAACTGC ATTCGTATGT    900

CAGAGGGGCT CCTTGCTTGG TGAGATTACT TACTTCTGTG TGTGGATGTG GCTGGGAAAT    960

TGGAGCCATC TGTTTCCTCT cctgtataaa aagannnnnn nnnnnnnnnn nnnnnnnnnn   1020
nnnnnnnnnn nnnnnnnnnn nnnnnnnnnn nnnnnnnnnn nnnnnnnnnn nnnnnnnnag   1080
gggtaccgaa ctcgaattcg gtaatcatgt caaaagctgt ttcccgtgtt naaattggta   1140
atc                                                                1143

(2) INFORMATION FOR SEQ ID NO: 104:

(i) SEQUENCE CHARACTERISTICS:
        (A) LENGTH: 476 base pairs
        (B) TYPE: nucleic acid
        (C) STRANDEDNESS: single
        (D) TOPOLOGY: linear (vii) IMMEDIATE SOURCE:
```

(A) LIBRARY: BLADTUT06
        (B) CLONE: 1900017

(xi) SEQUENCE DESCRIPTION: SEQ ID NO: 104 :

```
agggatcagc aggttgacct gtccctataa tacccaccct ggagcttact cagctaaaga      60
aacaaatttg gtcccatgtt aggtaaactc cctctgccac ctcccaggct cagagcacag     120
gtagccagac tctgatcatg gctctgagga ggagccctgg tagccctggc ccaggctggc     180
ctcccctctg tggctccctc tgcttactgc agttggactt ggcggtccca tttctgcctt     240
gccctcttgg gtggcatctt cttgaaagcc cctgggctgt gggcactact gtaactctct     300
caacacggtg ctggcataga cagacttaca gaatagaata ctgagcccag ataaaaacct     360
gctcgtacat ggtgaaatga tttttggtaa gggcgcctat cagtacacaa taagggnacg     420
tgagacccct caactctgcg tgcattcctt tggtgttttc atgggattgt ggcntt         476
```

(2) INFORMATION FOR SEQ ID NO: 105:

(i) SEQUENCE CHARACTERISTICS:
        (A) LENGTH: 986 base pairs
        (B) TYPE: nucleic acid
        (C) STRANDEDNESS: single
        (D) TOPOLOGY: linear (vii) IMMEDIATE SOURCE:
        (A) LIBRARY: PROSTUT04
        (B) CLONE: 1915946

(xi) SEQUENCE DESCRIPTION: SEQ ID NO: 105 :

```
ggaattttnn gnngcggaat aaaaaatttt ncaacnccgg gaaaaccngc ttnttnacca      60
tggnatgatt acgaattcga gctcggtacc cccatggccc cagcaggtgt ttatgctgga     120
cacccagtgC TCACCAAAGA CACCAAACaa ctttgacCAC GCTCagtcct gccagctcat     180
tattggagct GCCTCCTGat gaaaaaccaa atggacACAC CAAGAAAAGC GTGTCTTTCA     240
GGGAAATTGT GGTGAGCCTG CTGTCTCATC AGGTGTTACT CCAGAACTTA TATGACATCT     300
TGTTAGAAGA GTTTGTCAAA GGCCCCTCTC CTGGAGAGGA AAAGACGATA CAAGTGCCAG     360
AAGCCAAGCT GGCTGGCTTC CTCAGATACA TCTCTATGCA GAACTTGGCA GTCATATTCG     420
ACCTGCTGCT GGACTCTTAT AGGACTGCCA GGGAGTTTGA CACCAGCCCC GgcTGAAGTG     480
CCTGCTGAAG AAAGTGTCTG GCATCGGGGG CGCCGCCAAC CTCTACCGCC AGTCTGCGAT     540
GAGCTTTAAC ATTTATTTCC ACGCCCTGGT GTGTGCTGTT CTCACCAATC AAGAAACCAT     600
cacggccgag caagtgaaga aggtcctttt tgaggacgac gagagaagca cggattcttc     660
ccagcagtgt tcatctgagg atgaagacat ctttgaggaa accgcccagg tcagccctga     720
tctgctgttc agatcgtncc aatgtngact gagatgatcg cttcactggt ccatgttcan     780
tactnggagc cctgcnccag ctggacgtgg acntcatgaa aacantcagc actanccaaa     840
tctctgtcca tccaagtgca ntggactgga gantgtntgg aggnnctcca tnttcaaggg     900
ngacccgttc tttatcctgn cnngnttcna tccgagtatc aaccccatcc acggggggtt     960
tttgggaann aaaccttcg nggggg                                           986
```

(2) INFORMATION FOR SEQ ID NO: 106:

(i) SEQUENCE CHARACTERISTICS:
        (A) LENGTH: 447 base pairs
        (B) TYPE: nucleic acid
        (C) STRANDEDNESS: single
        (D) TOPOLOGY: linear (vii) IMMEDIATE SOURCE:
(A) LIBRARY: PANCTUT02
(B) CLONE: 1975013

(xi) SEQUENCE DESCRIPTION: SEQ ID NO: 106 :

| | | | | | |
|---|---|---|---|---|---|
| ataaagaggt | aagaaaaagt | aaagaagaga | aaattcagtt | tgtaatcaaa | aaatcgagtc | 60
| ttaatcgttt | ttatataatt | gattgcggac | tgcaatttca | caggcaaaac | gagttcaagg | 120
| gttttttgga | agaatatttc | aaggaccctg | aaaaaacaag | atggataaga | tgtgttgcat | 180
| cgtgaagatt | ttcatgtcga | agttcatcag | attcacaaga | gaaaggaaat | aagagcgaac | 240
| ggaggatgcc | taggcttCTG | GAGGCGAAGA | AGGACGCGGC | AAGCTGCGAA | AAGTCACGGG | 300
| TATCTGCAAG | CATGAAATGA | TCCGTGAATA | TCCGAATGGG | GCAACCCGTG | CAGGTGAAGC | 360
| Ctgcacacct | gaATAAATCA | GGGGCAgacg | cagggaactg | aaacatctta | gtacctgcag | 420
| gaaanaaaaa | naaaaaaggg | cggccgc | | | 447

(2) INFORMATION FOR SEQ ID NO: 107:

(i) SEQUENCE CHARACTERISTICS:
        (A) LENGTH: 3058 base pairs
        (B) TYPE: nucleic acid
        (C) STRANDEDNESS: single
        (D) TOPOLOGY: linear (vii) IMMEDIATE SOURCE:
        (A) LIBRARY: BRAITUT02
        (B) CLONE: 2103670

(xi) SEQUENCE DESCRIPTION: SEQ ID NO: 107 :

| | | | | | |
|---|---|---|---|---|---|
| gcggcgcccg | gtcccgggtc | cacagccgca | ctcactccgc | cgcgctctcc | gccaccgcca | 60
| ccactgcggc | caccgccaat | gaaacgcctc | ccgctcctag | tggttttttc | cactttgttg | 120
| aattgttcct | atactcaaaa | ttgcaccaag | acaccttgtc | tcccaaatgc | aaaatgtgaa | 180
| atacgcaatg | gaattgaagc | ctgctattgc | aacatgggat | tttcaggaaa | tggtgtcaca | 240
| atttgtgaag | atgataatga | atgtggaaat | ttaactcagt | cctgtggcga | aaatgctaat | 300
| tgcactaaca | cagaaggaag | ttattattgt | atgtgtgtac | ctggcttcag | atccagcagt | 360
| aaccaagaca | ggtttatcac | taatgatgga | accgtctgta | tagaaaatgt | gaatgcaaac | 420
| tgccatttag | ataatgtctg | tatagctgca | aatattaata | aaactttaac | aaaaatcaga | 480
| tccataaaag | aacctgtggc | tttgctacaa | gaagtctata | gaaattctgt | gacagatctt | 540
| tcaccaacag | atataattac | atatatagaa | atattagctg | aatcatcttc | attactaggt | 600
| tacaagaaca | acactatctc | agccaaggac | acccttteta | actcaactct | tactgaattt | 660
| gtaaaaaccg | tgaataattt | tgttcaaagg | gatacatttg | tagtttggga | caagttatct | 720
| gtgaatcata | ggagaacaca | tcttacaaaa | ctcatgcaca | ctgttgaaca | agctacttta | 780
| aggatatccc | agagcttcca | aaagaccaca | gagtttgata | caaattcaac | ggatatagct | 840
| ctcaaagttt | tcttttttga | ttcatataac | atgaaacata | ttcatcctca | tatgaatatg | 900
| gatggagact | acataaatat | atttccaaag | agaaaagctg | catatgattc | aaatggcaat | 960
| gttgcagttg | cattttttata | ttataagagt | attggtcctt | tgctttcatc | atctgacaac | 1020
| ttcttattga | aacctcaaaa | ttatgataat | tctgaagagg | aggaaagagt | catatcttca | 1080
| gtaatttcag | tctcaatgag | ctcaaaccca | cccacattat | atgaacttga | aaaaataaca | 1140
| tttacattaa | gtcatcgaaa | ggtcacagat | aggtatagga | gtctatgtgc | attttggaat | 1200
| tactcacctg | ataccatgaa | tggcagctgg | tcttcagagg | gctgtgagct | gacatactca | 1260

```
aatgagaccc acacctcatg ccgctgtaat cacctgacac attttgcaat tttgatgtcc   1320
tctggtcctt ccattggtat taaagattat aatattctta caaggatcac tcaactagga   1380
ataattattg cactgatttg tcttgccata tgcattttta ccttctggtt cttcagtgaa   1440
attcaaagca ccaggacaac aattcacaaa atctttggc tgtagcctat ttcttgctga    1500
acttgttttt cttgttggga tcaatacaaa tactaataag ctcttctgtt caatcattgc   1560
cggactgcta cactacttct ttttagctgc ttttgcatgg atgtgcattg aaggcataca   1620
tctctatctc attgttgtgg gtgtcatcta caacaaggga tttttgcaca agaatttta    1680 tatctttggc tatctaagcc cagccgtggt agttggattt tcggcagcac taggatacag   1740
atattatggc acaaccaaag tatgttggct tagcaccgaa aacaacttta tttggagttt   1800
tataggacca gcatgcctaa tcattcttgt taatctcttg gcttttggag tcatcatata   1860
caaagttttt cgtcacactg cagggttgaa accagaagtt agttgctttg agaacataag   1920
gtcttgtgca agagggagcc ctcgctcttc tgttccttct cggcaccacc tggatctttg   1980
gggttctcca tgttgtgcac gcatcagtgg ttacagctta cctcttcaca gtcagcaatg   2040 cttttccaggg gatgttcatt tttttattcc tgtgtgtttt atctagaaag attcaagaag   2100
aatattacag atTGTTCAAa aatgtcccct gtTGTTTTGG ATGTTTAagg taaacataGA   2160

GAATGGTGGA TAATTACAAC TGCACAAAAA TAAAAATTCC AAGCTGTGGA TGACCAATGT   2220

ATAAAAATGA CTCATCAAAT TATCCAATTA TTAACTACTA GACAAAAAGT ATTTTAAATC   2280

AGTTTTTCTG TTTATGCTAT AGGAACTGTA GATAATAAGG TAAAATTATG TATCATATAG   2340

ATATACTATG TTTTTCTATG TGAAATAGTT CTGTCAAAAA TAGTATTGCA GATATTTGGA   2400

AAGTAATTGG TTTCTCAGGA GTGATATCAC TGCACCCAAG GAAAGATTTT CTTTCTAACA   2460

CGAGAAGTAT ATGAATGTCC TGAAGGAAAC CACTGGCTTG ATATTTCTGT GACTCGTGTT   2520

GCCTTTGAAA CTAGTCCCCT ACCACCTCGG TAATGAGCTC CATTACAGAA AGTGGAACAT   2580

AAGAGAATGA AGGGGCAGAA TATCAAACAG TGAAAAGGGA ATGATAAGAT GTATTTTGAA   2640

TGAACTGTTT TTTCTGTAGA CTAGCTGAGA AATTGTTGAC ATAAAATAAA GAATTGAAGA   2700

AACACATTTT ACCATTTTGT GAATTGTTCT GAACTTAAAT GTCCACTAAA ACAACTTAGA   2760

CTTCTGTTTG CTAAATCTGT TTCTTTTTCT AATATtctaa aaaaaaaaaa aaggtttaCC   2820

TCcacaaatt gaaaaaaaaa aagtgaaaaa atctgtTTCT AAGGTTAGAC TGAGATATAT   2880

ACTATTTCCT TACTTATTTC ACAGATTGTG ACTTTGGATA GTTAATCAGT AAAATATAAA   2940

TGtgtcaaga tataatattg tttataccta tcaatgtaaa aacagtgtaa taaagctgaa   3000
gtattctatt accttcaaaa nnnagnngan naagnagana nnnantanat gannattt     3058
```

(2) INFORMATION FOR SEQ ID NO: 108:

(i) SEQUENCE CHARACTERISTICS:
        (A) LENGTH: 2009 base pairs
        (B) TYPE: nucleic acid
        (C) STRANDEDNESS: single
        (D) TOPOLOGY: linear (vii) IMMEDIATE SOURCE:
        (A) LIBRARY: BRSTNOT07
        (B) CLONE: 2124411

(xi) SEQUENCE DESCRIPTION: SEQ ID NO: 108 :

```
CCGAGCTGCG GAGTCCGGGA CTGGAGCTGC CCGGGCGGGT TCGCGCCCCG AAGGCTGAGA    60

GCTGGCGCTG CTCGTGCCCT GTGTGCCAGA CGGCGGAGCT CCGCGGCCGG ACCCCGCGGC   120
```

```
CCCGCTTTGC TGCCGACTGG AGTTTGGGGG AAGAAACTCT CCTGCGCCCC AGAGGATTTC      180

TTCCTCGGCG AAGGGACAGC GAAAGATGAG GGTGGCAGGA AGAGAAGGGC GCTTTCTGTC      240

TGCCGGGGTC GCAGCGCGAG AGGGCAGTGC CATGTTCCTC TCCATCCTAG TGGCGCTGTG      300

CCTGTGGCTG CACCTGGCGC TGGGCGTGCG CGGCGCGCCC TGCGAGGCGG TGCGCATCCC      360

TATGTGCCGG CACATGCCCT GGAACATCAC GCGGATGCCC AACCACCTGC ACCACAGCAC      420

GCAGGAGAAC GCCATCCTGG CCATCGAGCA GTACGAGGAG CTGGTGGACG TGAACTGCAG      480

CGCCGTGCTG CGCTTCTTCC TCTGTGCCAT GTACGCGCCC ATTTGCACCC TGGAGTTCCT      540

GCACGACCCT ATCAAGCCGT GCAAGTCGGT GTGCCAACGC GCGCGCGACG ACTGCGAGCC      600

CCTCATGAAG ATGTACAACC ACAGCTGGCC CGAAAGCCTG GCCTGCGACG AGCTGCCTGT      660

CTATGACCGT GGCGTGTGCA TCTCGCCTGA AGCCATCGTC ACGGACCTCC GGAGGATGT       720

TAAGTGGATA GACATCACAC CAGACATGAT GGTACAGGAA AGGCCTCTTG ATGTTGACTG      780

TAAACGCCTA AGCCCCGATC GGTGCAAGTG TAAAAAGGTG AAGCCAACTT GGCAACGTA      840

TCTCAGCAAA AACTACAGCT ATGTTATTCA TGCCAAAATA AAAGCTGTGC AGAGGAGTGG      900

CTGCAATGAG GTCACAACGG TGGTGGATGT AAAAGAGATC TTCAAGTCCT CATCACCCAT      960

CCCTCGAACT CAAGTCCCGC TCATTACAAA TTCTTCTTGC CAGTGTCCAC ACATCCTGCC     1020

CCATCAAGAT GTTCTCATCA TGTGTTACGA GTGGCGTTCA AGGATGATGC TTCTTGAAAA     1080

TTGCTTAGTT GAAAAATGGA GAGATCAGCT TAGTAAAAGA TCCATACAGT GGGAAGAGAG     1140

GCTGCAGGAA CAGCGGAGAA CAGTTCAGGA CAAGAAGAAA ACAGCCGGGC GCACCAGTCG     1200

TAGTAATCCC CCCAAACCAA AGGGAAAGCC TCCTGCTCCC AAACCAGCCA GTCCCAAGAA     1260

GAACATTAAA ACTAGGAGTG CCCAGAAGAG AACAAACCCG AAAAGAGTGT GAGCTAACTA     1320

GTTTCCAAAG CGGAGACTTC CGACTTCCTT ACAGGATGAG GCTGGGCATT GCCTGGGACA     1380

GCCTATGTAA GGCCATGTGC CCCTTGCCCT AACAACTCAC TGCAGTGCTC TTCATAGACA     1440

CATCTTGCAG CATTTTTCTT AAGGCTATGC TTCAGTTTTT CTTTGTAAGC CATCACAAGC     1500

CATAGTGGTA GGTTTGCCCT TTGGTACAGA AGGTGAGTTA AAGCTGGTGG AAAAGGCTTA     1560

TTGCATTGCA TTCAGAGTAA CCTGTGTGCA TACTCTAGAA GAGTAGGGAA ATAATGCTT      1620

GTTACAATTC GACCTAATAT GTGCATTGTA AAATAAATGC CATATTTCAA ACAAAACACG     1680

TAATTTTTTT ACAGTATGTT TTATTACCTT TTGATATCTG TTGTTGCAAT GTTAGTGATG     1740

TTTTAAAATG TGATCGAAAA TATAATGCTT CTAAGAAGGA ACAGTAGTGG AATGAATGTC     1800

TAAAAGATCT TTATGTGTTT ATGGTCTGCA GAAGGATTTT TGTGATGAAA GGGGATTTTT     1860

TGAAAAATCT AGAGAAGTAG CATATGGAAA ATTATAATGT GTCTTTTTTA CAATGACTTC     1920

AGCTCTGTTT TTAGCTAGAA ACTCTAAAAA CAAAAATAAT AATAAAGAAA AATAAAAAAA     1980

AAGGAGAGGC AGAAAAAAAG CAAAAAAAA                                      2009
```

(2) INFORMATION FOR SEQ ID NO: 109:

(i) SEQUENCE CHARACTERISTICS:
        (A) LENGTH: 2225 base pairs
        (B) TYPE: nucleic acid
        (C) STRANDEDNESS: single
        (D) TOPOLOGY: linear (vii) IMMEDIATE SOURCE:
        (A) LIBRARY: ENDCNOT01
        (B) CLONE: 2133755

(xi) SEQUENCE DESCRIPTION: SEQ ID NO: 109 :

-continued

```
gcgtccgagc tccttcacca gcttggtggt gggcgtgttc gtggtctacg tggtgcacac      60
ctgctgggtc atgtacggca tcgtctacac ccgcccgtgc tccggcgacg ccaactgcat     120
ccagccctac ctggcgcggc ggcccaagct gcagctgagc gtgtacacca cgacgaggtc     180
ccacctgggt gctgagaaca acatcgacct ggtcttgaat gtggaagact ttgatgtgga     240
gtccaaattt gaaaggacag ttaatgtttc tgtaccaaag aaaacgagaa acaatgggac     300
gctgtatgcc tacatcttcc tccatcacgc tggggtcctg ccgtggcacg acgggaagca     360
ggtgcacctg gtcagtcctc tgaccaccta catggtcccc aagccagaag aaatcaacct     420
gctcaccggg gagtctgata cacagcagat cgaggcggag aagaagccga cgagtgccct     480
ggatgagcca gtgtcccact ggcgaccgcg gctggcgctg aacgtgatgg cggacaactt     540
tgtctttgac gggncctccc tgcctgccga tgtgcatcgg tacatgaaga tgatccagct     600
ggggaaaacc gtgcattacc tgcccatcct gttcatcgac cagctcagca accgcgtgaa     660
ggacctgatg gtcataaacc gctccaccac cgagctgccc ctcaccgtgt cctacgacaa     720
ggtctcactg gggcggctgc gcttctggat ccacatgcag gacgccgtgt actccctgca     780
gcagttcggg ttttcagaga aagatgctga tgaggtgaaa ggaatttttg tagataccaa     840
cttatacttc ctggcgctga ccttctttgt cgcagcgttc catcttctct ttgatttcct     900
ggcctttaaa aatgacatca gtttctggaa gaagaagaag agcatgatcg gcatgtccac     960
caaggcagtg ctctggcgct gcttcagcac cgtggtcatc tttctgttcC TGCtggacga    1020
gcagacgagc ctGCTGGTGC TGGTCCCGGC gggtGTTGGA GCCGCCATTG AGCTGTGGAA    1080
AGTGAAGAAG GCATTGAAGA TGACTATTTT TTGGAGAGGC CTGATGCCCG AATTTCAGtt    1140
tgGCACTTAC AGCGAATCTG AGAGGAAAAC CGAGGAGTAC GATACTCAGG CCATGAAGTA    1200
CTTGTCATAC CTGCTGTAcC CTCTCTGTGT CGGGGGTGCT GTCTATTCAC TCCTGAATAT    1260
CAAATataag agctggtact cctggttaat caacagcttc gtcaacgggg tctatgcctt    1320
tggtttcctc ttcatgctgc cccagctctt tgtgaactac aagttgaagt cagtggcaca    1380
tctgccctgg aaggccttca cctacaaggc tttcaacacc ttcattgatg acgtctttgc    1440
cttcatcatc accatgccca cgtctCACCG gctggcctgc ttccgggacg acgtggtgtt    1500
tctggTCTAC CTgtaccagc ggtgGCTTTA TCCTGTGGAT AAACGCAGAG TGAACGAGtt    1560
tgGGGAGTCC tacgaggaga aggccacgcg gGCGCCCCAC ACGGACTGaa ggcccgcccg    1620
gggctgcCGC CAGCCAAGTG CaactTGAAT TGTCAATGAG TATTTTTGGA AGCATTTGGA    1680
GGAATTCCTA GACATTGCGT TTTCTGTGTT GCCAAAATcc ctTCGGACAT TTCTCAGACA    1740
TCTCCCAAGT TCCATCACG TCAGATTTGG AGCTGGTAGC GCTTACGATG CCCCCACGTG    1800
TGAACATCTG TCTTGGTCAC AGAGCTGGGT GCTGCCGGTC ACCTTGAGCT GTGGTGGCTC    1860
CCGGCACACG AGTGTCCGGG GTTCGGCCAT GTCCTCACGC GGGCAGGGGT GGGAGCCCTC    1920
ACAGGCAAGG GGGCTGTTGG ATTTCCATTT CAGGTGGTTT TCTAAGTGCT CCTTATGTGA    1980
ATTTCAAACA CGTATGGAAT TCATTCCGCA TGGACTCTGG GATCAAAGGC TCTTTCCTCT    2040
TTTGTTTGAG AGTTGGTTGT TTTAAAGCTT AATGTATGTT TCTATTTTAA AATAAATTTT    2100
TCTGGCTgtg gcatttttct tgacctggta taatgaaagt atttcagata tttgagttta    2160
accctttttcc agaaagtaat acatgatatg gatttattta tgcattaaaa gncaaattta    2220
aagcc                                                                2225
```

(2) INFORMATION FOR SEQ ID NO: 110:

(i) SEQUENCE CHARACTERISTICS:
    (A) LENGTH: 839 base pairs
    (B) TYPE: nucleic acid
    (C) STRANDEDNESS: single
    (D) TOPOLOGY: linear (vii) IMMEDIATE SOURCE:
    (A) LIBRARY: SINTFET03
    (B) CLONE: 2206642

(xi) SEQUENCE DESCRIPTION: SEQ ID NO: 110 :

| | | | | | |
|---|---|---|---|---|---|
| cgcgtgggct | natatcccaa | atcacttgac | atattatcca | acgttggatg | tgcactgtct | 60 |
| gttactggtc | tggctctcac | agttatattt | cagattgtca | ccaggaaagt | cagaaaaacc | 120 |
| tcagtaacct | gggttttggt | caatctgtgc | atatcaatgt | tgattttcaa | cctcctcttt | 180 |
| gtgtttggaa | ttgaaaactc | caataagaac | ttgcagacaa | gtgatggtga | catcaataat | 240 |
| attgactttg | acaataatga | catacccagg | acagacacca | ttaacatccc | gaatcccatg | 300 |
| tgcactgcga | ttgccgcctt | actgcactat | tttctgttag | tgacatttac | ctggaacgca | 360 |
| ctcagcgctg | cacagctcta | ttaccttcta | ataaggacca | tgaagcctct | tcctcggcat | 420 |
| ttcattcttt | tcatctcatt | aattggatgg | ggagtcccag | ctatagtagt | ggctataaca | 480 |
| gtgggagtta | tttattctca | gaatggaaat | aatccacagt | gggaattaga | ctaccggcaa | 540 |
| gagaaaatct | gctggctggc | aattccagaa | cccaatggtg | ttataaaaag | tccgctgttg | 600 |
| tggtcattca | tcgtacctgt | aaccattatc | ctcatcagca | atgttgttat | gtttattaca | 660 |
| atctcgattc | aaagtgctgt | ggaagaataa | ccagaacctg | acaagcacaa | aaaaagtttc | 720 |
| atccatgaag | aagattgtta | gcacattatc | tgttgcagtt | gttttggat | taaccgtgga | 780 |
| ttccagcata | cngatgccag | ttaatgatga | tagcatcagg | ttcgtcttca | gctacatat | 839 |

(2) INFORMATION FOR SEQ ID NO: 111:

(i) SEQUENCE CHARACTERISTICS:
        (A) LENGTH: 801 base pairs
        (B) TYPE: nucleic acid
        (C) STRANDEDNESS: single
        (D) TOPOLOGY: linear (vii) IMMEDIATE SOURCE:
        (A) LIBRARY: SINTFET03
        (B) CLONE: 2211526

(xi) SEQUENCE DESCRIPTION: SEQ ID NO: 111 :

| | | | | | |
|---|---|---|---|---|---|
| ATTCGGCTCG | AGGAACAAGG | CAGCGGCTCC | TTGGTAAAGC | TACTCCTTGA | TCGATCCTTT | 60 |
| GCACCGGATT | GTTCAAAGTG | GACCCCAGGG | GAGAAGTCGG | AGCAAAGAAC | TTACCACCAA | 120 |
| GCAGTCCAAG | AGGCCCAGAA | GCAAACCTGG | AGGTGAGACC | CAAAGAAAGC | TGGAACCATG | 180 |
| CTGACTTTGT | ACACTGTGAG | GACACAGAGT | CTGTTCCTGG | AAAGCCCAGT | GTCAACGCAG | 240 |
| ATGAGGAAGT | CGGAGGTCCC | CAAATCTGCC | GTGTATGTGG | GGACAAGGCC | ACTGGCTATC | 300 |
| ACTTCAATGT | CATGACATGT | GAAGGATGCA | AGGGCTTTTT | CAGGAGGGCC | ATGAAACGCA | 360 |
| ACGCCCGGCT | GAGGTGCCCC | TTCCGGAAGG | GCGCCTGCGA | GATCACCCGG | AAGACCCGGC | 420 |
| GACAGTGCCA | GGCCTGCCGC | CTGCGCAAGT | GCCTGGAGAG | CGGCATGAAG | AAGGAGATGA | 480 |
| TCATGTCCGA | CGAGGCCGTG | GAGGAGAGGC | GGGCCTTGAT | CAAGCGGAAG | AAAAGTGAAC | 540 |
| GGACAGGGAC | TCAGCCACTG | GGAGTGCAGG | GGCTGACAGA | GGAGCAGCGG | ATGATGATCA | 600 |
| GGGAGCTGAT | GGACGCTCAG | ATGAAAACCT | TTGACACTAC | CTTCTCCCCA | TTTTCAAGGA | 660 |
| TTTCCGGCTG | CCAGGGGTGC | TTAGCAGTGG | CTGCGAGTTT | GCAGAGTCTC | TGCANGCCCC | 720 |

| | |
|---|---|
| ATCGAGGGGA AGAAGCTGCC AAGTGGAAGC CGGTCCCGGA AGATCTGTGC TCTTTGAAGT | 780 |
| CTCTCTGCAG CTGCGGGGGG A | 801 |

(2) INFORMATION FOR SEQ ID NO: 112:

(i) SEQUENCE CHARACTERISTICS:
        (A) LENGTH: 2713 base pairs
        (B) TYPE: nucleic acid
        (C) STRANDEDNESS: single
        (D) TOPOLOGY: linear (vii) IMMEDIATE SOURCE:
        (A) LIBRARY: SINTFET03
        (B) CLONE: 2214608

(xi) SEQUENCE DESCRIPTION: SEQ ID NO: 112 :

| | |
|---|---|
| gtgnntggag tttcagctgc tattgactat aagagctatg aacagaaaaa agcttgctgg | 60 |
| cttcatgttg ataactactt tatatggagc ttcattggac ctgttacctt cattattctg | 120 |
| ctaaatatta tcttcttggt gatcacattg tgcaaaatgg tgaagcattc aaacactttg | 180 |
| aaaccagatt ctagcaggtt ggaaaacatt aagtcttggg tgcttggcgc tttcgctctt | 240 |
| ctgtgtcttc ttggcctcac ctggtccttt gggttgcttt ttattaatga ggagactatt | 300 |
| gtgatggcat atctcttcac tatatttaat gctttccagg gagtgttcat tttcatcttt | 360 |
| cactgtgctc tccaaaagaa agtacgaaaa gaatatgggc aagtgcttca gacactcata | 420 |
| ctgctgtgga ggcctcccaa ctgagagtcc ccacagttca gTGAAGcat caaccaccag | 480 |
| aaccagtgct cgctattcct ctggcaCACA gagtcgtaTA AGAAGAATGT GGAATGATAC | 540 |
| TGTGAGAAAA CAATCAGAAT CTTCTTTTAT CTCAGGTGAC ATCAATAGCA CTTCAACACT | 600 |
| TAAtcaaggt ggcataaatc ttaatatatt attacaggac tgacatcaca tggtctgaga | 660 |
| gcccatcttc aagatttata tcatttagag gacaTTCACT GAACAatgcc agggataCAA | 720 |
| GTGCCATGGA TACTCTACCG CTAAATGGTA ATTttaacaa cagctacTCG CTGCACAAGG | 780 |
| GTGACTATAA TGACAGCGTG CAAGTTGTGG ACTGTGGACT AAGTCTGAAT GATACtgctt | 840 |
| ttgagaaaat gatcatttca gaattagtgc acaacaactt acggggcagc agcaagactc | 900 |
| acaacctcga gctcacgcta ccagtcaaac ctgtgattgg aggtagcagc agtgaagatg | 960 |
| atgctattgt ggcagatgct tcatctttaa tgcacagcga caacccaggg gctgggagct | 1020 |
| ccatcacaaa gaactcgagg caccacttat tcctcagcgg actcactccc ttctgtacca | 1080 |
| accccagaag aaagtgaagt ccgagggaac tgacagctat gtctcccaac tgacagcaga | 1140 |
| ggctgaagat cacctacagt cccccaacag agactctctt tatacaagca tgcccaatct | 1200 |
| tagagactct ccctatccgg agagcagccc tgacatggaa gaagacctct ctccctccag | 1260 |
| gaggagtgag aatgaggaca tttactataa aagcatgcca aatcttggag ctggccatca | 1320 |
| gcttcagatg TGCTACCAGA TCAGCAGGGG CAATAGTGAT GGTTATATAA TCCCCATTAA | 1380 |
| CAAAGAAGGG TGTATTCCAG AAGGAGATGT TAGAGAAGGA CAAATGCAGC TGGTTACAAG | 1440 |
| TCTTTAATCA TACAGCTAAG GAATTCCAAG GGCCACATGC GAGTATTAAT AAATAAAGAC | 1500 |
| ACCATTGGCC TGACGCAGCT CCCTCaaacT CTGCTTGAAG AGATGACTCT TGACCTGTGG | 1560 |
| TTCTCTGGTG TAAAaaagAT GACTGAACCT TGCAGTTCTG TGAATTTTTA TAAAACATAC | 1620 |
| AAAAACTTTG TATATACACA GAGTATACTA AAGTGAATTA TTTGTTACAA AGAAAAGAGA | 1680 |
| TGCCAGCCAG GTATTTTAAG ATTCTGCTGC TGTTTAGAGA AATTGTGAAA CAAGCAAAAC | 1740 |
| AAAACTTTCC AGCCATTTTA CTGCAGCAGT CTGTGAACTA AATTTGTAAA TATGGCTGCA | 1800 |

```
CCATTTTTGT AGGCCTGCAT TGTATTATAT ACAAGACGTA GGCTTTAAAA TCCTGTGGGA    1860

CAAATTTACT GTACCTTACT ATTCCTGACA AGACTTGGAA AAGCAGGAGA GATATTCTGC    1920

ATCAGTTTGC AGTTCACTGC AAATCTTTTA CATTAAGGCA AAGATTGAAA ACATGCTTAA    1980

CCACTAGCAA TCAAGCCACA GGCCTTATTT CATATGTTTC CTCAACTGTA CAATGAACTA    2040

TTCTCATGAA AAATGGCTAA AGAAATTATA TTTTGTTCTA TTGCTAGGGT AAAATAAATa    2100
catttgtgtc caactgaaat ataattgtca ttAAAATAAT TTTAAAGAGT GAAGAAAATA    2160

TTGTGAAAAG CTCTTGGTTG CACATGTTAT GAAATGTTTT TTCTTACACT TTGTCATGGT    2220

AAgttcTACT CATTTTCACT TCTTTTCCAC TGTATACAGT GTTCTGCTTT GACAAAGTTA    2280

GTCTTTATTA CTTACATTTA AATTTCTTAT TGCCAAAAGA ACGTGTTTTA TGGGGAGAAA    2340

CAAACTCTTT GAAGCCAGTT ATGTCATGCC TTGCACAAAA GTGATGAAAT CTAGAAAAGA    2400

TTGTGTGTCA CCCCTGTTTA TTCTTGAACA GAGGGCAAAG AGGGCACTGG GCACTTCTCA    2460

CAAACTTTCT AGTGAACAAA AGGTGCctat tcttttttaa aaaaataaaa taaaacaTAA    2520

ATATTACTCT TCCATATTCC TTctgcctat atttagtAAT TAATTTATTT TATGATAAAG    2580

TTCTAATGAA ATGTAAATTG TTTCAGCAAA ATTCTGCTTT TTTTTCATCC CTTTGTGTAA    2640

ACCTGTTAAT AATGAGCCCA TCACTAATAT CCAGTGTAAA GTTAACACG GTTTGACagt     2700 aaataaatgt gaa                                                       2713

(2) INFORMATION FOR SEQ ID NO:   113:

(i) SEQUENCE CHARACTERISTICS:
        (A) LENGTH: 1796 base pairs
        (B) TYPE: nucleic acid
        (C) STRANDEDNESS: single
        (D) TOPOLOGY: linear (vii) IMMEDIATE SOURCE:
        (A) LIBRARY: ISLTNOT01
        (B) CLONE: 2375244

(xi) SEQUENCE DESCRIPTION: SEQ ID NO: 113 :

ttttttnaac ccaacctttt tnaaggggcc cttncccgg ggnctcccnn ttantggntt       60 ngtgggggg aaaaatttng gtggcccncg gganntcaac cnaattttnt caaccncggg     120
ggnaaaaccn nggttttttg accggggttt ncccggantt tccgnaggct gggntccccc    180
cccnggaant tcggcccgga gaatttatgt cctttgctta ttttttctatt aaaatgttat   240 cccctatctg cttttatttt taaaattcat ttactgtata taattacata aacaataCCT    300

TTATTCTTTT CAATTATTCT GTTCTAGGAT AGCATTTCTC AAGACCTGac ttatggagca    360

CTTGTAACCT GAGATATTTC AGTTGAAGGA AGAAATAGCT CTTCTCCTAA GATGGAATCT    420

GTGGTTTGGG AATGTGGTTG ATCAACTTGA TATGTTGGCC AAATGTGCCC CATGTAATAA    480

AATGAAAAGA AGAGACAAGA TGATGTCATT TTCCCATATT GTGAAACCAA AAACAAACGC    540

CTTTTGTGAG ACCAAGCTAA CAAACCTCTG ACGGTGCGAA GAGTATTTAA CTGTTTGAAG    600

AATTTAACAG TAAGATACAG AAGAAGTACC TTCGAGCTGA GACCTGCAGG TGTATAAATA    660

TCTAAAATAC ATATTGAATA GGCCTGATCA TCTGAATCTC CTTCAGACCC AGGAAGGATG    720

GCTATGACTT GgaTTGTCTT CTCTCTTTGG CCCTTGACTG TGTTCATGGG GCATATAGGT    780

GGGCACAGTT TGTTTTCTTG TGAACCTATT ACCTTGAGGA TGTGCCAAGA TTTGCCTTAT    840

AATACTACCT TCATGCCTAA TCTTCTGAAT CATTATGACC AACAGACAGC AGCTTTGGCA    900

ATGGAGCCAT TCCACCCTAT GGTGAATCTG GATTGTTCTC GGGATttccg gccttttctt    960
```

```
tgtgcactct acgctcctat ttgtatggaa tatggACGTG TCACACTTCC CTGTCgtagg    1020
ctgTGTCAGC GGGCTTACAG TGAGTGTTCG AAGCTCATGG AGATGTTTGG TGTTCCTTGG    1080

CCTGAAGATA TGGAATGCAG TaggtTCCCA GATTGTGATG AGCCATATCC TCGACTTGTG    1140

GATCTGAATt tagCTGGAGA ACCAACTGAA GGAGCCCCAG TGGCAGTGCA GAGAGACTAT    1200

GGTTTTTGGT GTCCCCGAGA GTTAAAAATT GATCCTGATC TGGGTTATTC TTTTCTGCAT    1260

GTGCGTGATT GTTCACCTCC TTGTCCAAAT ATGTACTTCA GAAGAGAAGA ACTGTCATTT    1320

GCTCGCTATT TCATAGGATT GATTTCAATC ATTTGCCTCT CGGCCACATT GTTTACTTTT    1380

TTAACTTTTT TGATTGATGT CACAAGAttc CGTTATCCTG AAAGGCCTAT TATATTTTAT    1440

GCAGTCTGCT ACATGATGGT ATCCTTAATT TTCTTCATTG GATTtttgCT TGAAGATCGA    1500

GTAGCCTGCA ATGCATCCat cCCTGCACAA TATAAGGCTT CCACAGTGAC acaaggatct    1560
cataATAAAG CCTGTACCAT GCTTTTTATG ATACTCTATT TTTTTACTAT GGCTGGCAGT    1620

GTATGGTGGG TAATTCTTAC CATCACATGG TTTTTAGCAG CTGTGCCAAA GTGGGGTAGT    1680

GAAGCTATTG AGAAGAAAGC ATTGCTGTTT CACGCCAGTG CATGGGGCAT CCCCGGAACT    1740

CTAACCATCA TCCTTTTAGC GATGAATAAA ATTGAAGGtg acaataaaaa natgtt       1796
```

(2) INFORMATION FOR SEQ ID NO: 114:

(i) SEQUENCE CHARACTERISTICS:
        (A) LENGTH: 711 base pairs
        (B) TYPE: nucleic acid
        (C) STRANDEDNESS: single
        (D) TOPOLOGY: linear (vii) IMMEDIATE SOURCE:
        (A) LIBRARY: LIVRTUT04
        (B) CLONE: 2512629

(xi) SEQUENCE DESCRIPTION: SEQ ID NO: 114 :

```
gcagagtatc cagagggccg gcatgtggtc tgcagaagag gaggacgtgg ctgggtggca     60
nggctggtct ccaaggacga gtaagatcct gcagctgcgg gcttcaggaa gtctcctggg    120
gctatcagat ggctccttct tgtagcagca gctgtggggt ccactggccc tgagccctca    180
gaggggcggc cgtggggggac ctcctgtctt ttgccttgca agggcctcag ttgtgctttt    240
tccctctagg cagccatggg tgccaggcag tgctgagagc agtggggcat ggctgcagcc    300
ctgcaggtcc tgccccgctt ggcccgagcc cccttgcatc cactcctctg gcggggctca    360
gtggcccgtc tggccagcag catggccttg gcagagcagg ccaggcagct gtttgagagt    420
gctgtaggtg cagtgctgcc gggcccatg ctgcaccggg cactatcctt ggaccctggt    480
ggcagacagc tgaaggtgcg ggaccggaac tttcagctga ggcaaaacct ctacctggtg    540
ggctttggca aggctgtgct gggtatggca gctgcagctg aggaactact gggccagcat    600
cttgtgcagg gcgtgatcan cgttcccaag gggatcngtg ctgccatnga acgtgccgnc    660
aancaggaga tgctgctgaa acnacatagc cgtgtcnagg tantcgaggg t              711
```

(2) INFORMATION FOR SEQ ID NO: 115:

(i) SEQUENCE CHARACTERISTICS:
        (A) LENGTH: 592 base pairs
        (B) TYPE: nucleic acid
        (C) STRANDEDNESS: single
        (D) TOPOLOGY: linear (vii) IMMEDIATE SOURCE:
        (A) LIBRARY: LIVRTUT04
        (B) CLONE: 2512827

(xi) SEQUENCE DESCRIPTION: SEQ ID NO: 115 :

```
aggcctccct ccacctgtct tctcagagca gataatggca agcatggctg ccgtgctcac    60
ctgggctctg gctcttcttt cagcgttttc ggccacccag gcacggaaag gcttctggga   120
ctacttcagc cagaccagcg gggacaaagg cagggtggag cagatccatc agcagaagat   180
ggctcgcgag cccgcgaccc tgaaagacag ccttgagcaa gacctcaaca atatgaacaa   240
gttcctggaa aagctgaggc ctctgagtgg gagcgaggct cctcggctcc cacaggaccc   300
ggtgggcatg cggcggcagc tgcaggagga gttggagagt gtgaaggctc gcctccagcc   360
ctacatggca gaggcgcacg agctggtggg ctggaatttg gagggcttgc ggcagcaact   420
gaagccctac acgatggatc tgatggagca ggtggccctg cgcgtgcagg agctgcagga   480
gcagttgcgc gtggtggggg aagacaccaa ggcccagttg ctgggggcg tggacgaggc   540
ttgggctttg ctgcagggac tgcttcagaa gcccgcgttg ttgcanccac ac           592
```

(2) INFORMATION FOR SEQ ID NO: 116:

(i) SEQUENCE CHARACTERISTICS:
        (A) LENGTH: 255 base pairs
        (B) TYPE: nucleic acid
        (C) STRANDEDNESS: single
        (D) TOPOLOGY: linear (vii) IMMEDIATE SOURCE:
        (A) LIBRARY: BRAITUT21
        (B) CLONE: 2518961

(xi) SEQUENCE DESCRIPTION: SEQ ID NO: 116 :

```
ctttctcaga cccacgtttc ggccttctct cctaattccc ggtgtcgggt ccctagtctg    60
attttttct gccctcaatc tccaaggccc cggttcccct cctcggcacg ctttggttgt   120
ggtggagccg gccctatttt ccttgccgga cgcctctcgc ggccttcagc gcgacccatc   180
gcgttctttg cgggcgccgg ggcctggtcc cacgcccgta gcaggccatt cattgattta   240
ttgcgctgac caaca                                                    255
```

(2) INFORMATION FOR SEQ ID NO: 117:

(i) SEQUENCE CHARACTERISTICS:
        (A) LENGTH: 716 base pairs
        (B) TYPE: nucleic acid
        (C) STRANDEDNESS: single
        (D) TOPOLOGY: linear (vii) IMMEDIATE SOURCE:
        (A) LIBRARY: BRAITUT21
        (B) CLONE: 2520839

(xi) SEQUENCE DESCRIPTION: SEQ ID NO: 117 :

```
ttatctgtgg ctgcttatcc caacatggaa tggtgctagg tggcagtgct tctgttatgg    60
taactacttc tacaatttt attgatttct tcttgccact ttttgcttgt agttgcagcc   120
ttcaaaacta tcttcttcta atccagtTTT CTTCAGAACA GAGGCTGAGC TCGAAGCGCC   180
GGGCAGTACA GTGAGGGAGA GCCGAGGGAA CCAGCGCGGT GCCTAGCGGA ACTCCAGGGC   240
TGGAATCCCG AGACACAAGT GCATCTGCTA GCTGTTAGCA CTTGGCAGAC GGAGTTCTCC   300
TCTAGGGTAG TTCTAACTTT GGGTAATAAT GTTTGTCAGC TACCTGATAT TAACATTGCT   360
CCACGTTCAA ACAGCAGTGT TAGCAAGACc tgggggagag agcattggct gtgatgacta   420
cttaggctcc gacaaagtcg tggacaaatg tggggtgtnt ggaggagaca acacgggctg   480
```

-continued

| | | |
|---|---|---|
| tcaggnngca tcgggcgtgt ntaagcatgc cctccaccan nctgggctaa caccgcgtcn | 540 |
| tggagatccc gagggagcca cgaaaatcaa acatcacaga gntgtncaag agcaanaact | 600 |
| atntggccct gagaagtngt ttcttgangg ttccatcatc aanggggaa tggggcantt | 660 |
| gatcgaccag gnaaataacg agggcnggna gggaccntgt ttcancnnca nagcgt | 716 |

(2) INFORMATION FOR SEQ ID NO: 118:

(i) SEQUENCE CHARACTERISTICS:
        (A) LENGTH: 664 base pairs
        (B) TYPE: nucleic acid
        (C) STRANDEDNESS: single
        (D) TOPOLOGY: linear (vii) IMMEDIATE SOURCE:
        (A) LIBRARY: BRAITUT21
        (B) CLONE: 2525666

(xi) SEQUENCE DESCRIPTION: SEQ ID NO: 118 :

| | | |
|---|---|---|
| gggagaccaa gggtgccctg ctcaatgtca gccctgactc tgtgccacgt gcactcagct | 60 |
| ctgccacgga ggtgcatggc tctgtagacg tggacggtga gctggggagg aagtggtct | 120 |
| tggagagaaa tgccccatgg ggagctgaga cccaagggtg ccctgctcaa tgtcagccct | 180 |
| gactctgtgc cacgtgcact cagctctgcc acggaggtgc atggctctgt agacgtggac | 240 |
| gcctgcaggt cggaagtcca aaccaaggtg ctggaagggc tggttccttc cggacccttc | 300 |
| aggggagaat ctttctgcct cttggcttc ttgaggcccc ttcctggcat tgcttcttc | 360 |
| tccactgact cctaccatca gcgctgagtc ctgcctgcct cttataagat cttcagaggc | 420 |
| cacctgggat gtcagaagct tccaggaacc aggaggtagc tgcatctcct gtcccttccc | 480 |
| tgagtcacct tgctggactc cacagtgtgg tgcagacaag aagctgcagg ggacaacatg | 540 |
| gaaggaagcg gggatggagg agatgggatg ggatgggctc tgggccggcc agcagagcag | 600 |
| gatagggctg agagtcatct gagcacaggt ggttcaaatg gcagagaagc tccagctgga | 660 |
| gcgg | 664 |

(2) INFORMATION FOR SEQ ID NO: 119:

(i) SEQUENCE CHARACTERISTICS:
        (A) LENGTH: 787 base pairs
        (B) TYPE: nucleic acid
        (C) STRANDEDNESS: single
        (D) TOPOLOGY: linear (vii) IMMEDIATE SOURCE:
        (A) LIBRARY: THYMNOT03
        (B) CLONE: 2557294

(xi) SEQUENCE DESCRIPTION: SEQ ID NO: 119 :

| | | |
|---|---|---|
| gcagcagcag ngaagagaga tgttgaaatt taagagagga agacagagaa gaaaaatcca | 60 |
| ctggatacct tatgtgtaat tcaccaatct gttggaacac ttctgccacg tgtgaagagt | 120 |
| tttggcagac caaatccaca tgcctgaagt gatgcccacc aacaaagaca taAAAATTTT | 180 |
| CAACATTTCA ACAGCCATGT TGGAATCATC TGCAGAATAc cgaaaagtg ccCAGttgga | 240 |
| gatttcataa aaataacagg CAATCACACA CGTTGCAGGA ACTGTgtaca gtactgagaa | 300 |
| caccccaatc TTGACCATCA GTCTTTCTAA CTTGTCtgtc tttgtccCAT CCTTTTGAAG | 360 |
| ATTTGACCGA ATTTTGAACa aggccaccaa acctgcagca atgaacaaag ttccaatgac | 420 |
| caaataagta aagaggggag ccaccacgaa cccggtgagg gcatcgagat tttggtttcc | 480 |
| aacatagcac aagccagtca gttcatctgc atccaccagt ctcataatca agatgacaat | 540 |

```
ggttttcact gcggggatgg cccaggctgc aatgtggaaa taagagctgt gcatttcaat    600
ggcttcatga ccccatttga gtcctgctgc caaaaaccaa gtgagtgtca gaataaccca    660
ccaaatggag ctggccattc caaaaaagta catcagctag aaaattattg cacatcctgt    720
gttcttaagt cttcttggat gagaacaggt tctgctgcct cttcaaaatc acaggatatc    780
tttcccg                                                              787

(2) INFORMATION FOR SEQ ID NO:   120:

(i) SEQUENCE CHARACTERISTICS:
          (A) LENGTH: 378 base pairs
          (B) TYPE: nucleic acid
          (C) STRANDEDNESS: single
          (D) TOPOLOGY: linear (vii) IMMEDIATE SOURCE:
          (A) LIBRARY: PROSTUT12
          (B) CLONE: 2628541

(xi) SEQUENCE DESCRIPTION: SEQ ID NO: 120 :

anggaggttt ctcctggcgg gaaggctgtg accctgctga gctgtggaga aacagcttga     60
taaccagggc tttcctgggg cacccttcct ggtgcacttc ggaagacccc ggactgatga    120
tagggctctc ttgatttcac ctaaagcaag actgtaacct ctgggcagcc tgatgccagg    180
cttggaggca aaccctcaga aaacagctcc cctcagtgag ggaatgggag cctgtttgaa    240
ttaacgtgga gaattctcca agaacccgca gactggggagg cattctcacg gcgagtcagt   300
gcagtcctct tatgtttacc gcaattaagg tgagcatgag agcagcctgc ctctcttctg    360
ttctcccagc catggaag                                                  378

(2) INFORMATION FOR SEQ ID NO:   121:

(i) SEQUENCE CHARACTERISTICS:
          (A) LENGTH: 515 base pairs
          (B) TYPE: nucleic acid
          (C) STRANDEDNESS: single
          (D) TOPOLOGY: linear (vii) IMMEDIATE SOURCE:
          (A) LIBRARY: LUNGTUT08
          (B) CLONE: 2639842

(xi) SEQUENCE DESCRIPTION: SEQ ID NO: 121 :

aggcctcgcc tggcatcccc cagctgtaga tgggggcaga gcaagacttg ctgccaacct     60
gcctggctct gtggtccctg ctccctctcc cgttctgctg cgtcaccac ccctccttca     120 gaactctcta tggaattgca ttctagtctc tcctgcttct gcttatgcat gtgaaagcca    180
gatgcccctt ctctctctct cttttttttt ttttgatang gagttttnnn cttgttgccc    240
aagattnggc nantgntatc nagcctgggn nanagngcag gaccctgtcn cnatttnana    300
anttaaaaaa ggctgggttt ggtggctnan accctataan ccnaannntt ntggnttgac    360 aagttttnntt taacccnngg aattcaagtc naantcnggg nnaaaatggg ggnaanccct   420
agtttaacat aaanaatttc catggntgnt gaaatggttt tngtttgggn acacttggan    480
ttggtngtng tgaatccagn tntccggaag ggcna                               515

(2) INFORMATION FOR SEQ ID NO:   122:

(i) SEQUENCE CHARACTERISTICS:
          (A) LENGTH: 517 base pairs
          (B) TYPE: nucleic acid
```

(C) STRANDEDNESS: single
        (D) TOPOLOGY: linear (vii) IMMEDIATE SOURCE:
        (A) LIBRARY: LUNGTUT08
        (B) CLONE: 2642108

(xi) SEQUENCE DESCRIPTION: SEQ ID NO: 122 :

```
agctttcaaa gtccactcaa aaattatctt tcttgaagtc acccatgact gaaacgtctc      60
cccatcagat cttcagtgac tcttttcaga aattgccatt aggcaaagaa ctgccaggat     120
ctttactagc aatggtagtt cttcctccca aaaatgtgga aaggctttga gataaaagca     180
cttatcttta cacctgcaat gactaggaca agaaaatgtc actgccagca gttgatgctt     240
caccagcgtg ttgtaatata tgatgtgcat tttacatgtg gactctcatt taaattctta     300
aaacatatcc gttagtcaga taacatcatc tcactttgca ctggaggaaa ccaagttcag     360
ataggatata taccattgaa tgaccaagag gttaataaat attgatgatg taaggaaaa      420 ttatttctca gcagccaagt actaaaactt tgtaactgga gaagatgtat tcctttcta     480 antggntgct annaaannaa ttanttggac ngggngg                              517
```

(2) INFORMATION FOR SEQ ID NO:   123:

(i) SEQUENCE CHARACTERISTICS:
        (A) LENGTH: 518 base pairs
        (B) TYPE: nucleic acid
        (C) STRANDEDNESS: single
        (D) TOPOLOGY: linear (vii) IMMEDIATE SOURCE:
        (A) LIBRARY: LUNGTUT08
        (B) CLONE: 2643475

(xi) SEQUENCE DESCRIPTION: SEQ ID NO: 123 :

```
gttccctgtg tgtctgtgcg tgcctgcaat tgggggtggt gtccaggggc tcagcaaggc      60
atgtacacct gggctggggt gtgtcagacg ctgtcagtga caagcacctt ccctcagagc     120
ccggttcctg gagaatgtgg cggcagcaga aacagagaag caggttgcgc tggcccaggg     180
ccgggcagag acacttgccg gggccatgcc caatgaggcg ggtggacacc cagatgcccg     240
gcaactctgg gactccccag agacagcccc tgcagccaga acaccccaga gccctgcccc     300
ctgtgtcctg ctccgggccc agcgaagctt gcaccagagc ccaaggagcc atgataccag     360
caagccccaa ggctgagccc atctgggagc tccctaaccc gtgcanccag gctctctant     420
ggggacctgg acttttcagt ctaggggang atgaagacca ggacatgctg aatgtagagt     480
ctgtggaggc tgggaanaca tcccagntcc cntacatt                             518
```

(2) INFORMATION FOR SEQ ID NO:   124:

(i) SEQUENCE CHARACTERISTICS:
        (A) LENGTH: 516 base pairs
        (B) TYPE: nucleic acid
        (C) STRANDEDNESS: single
        (D) TOPOLOGY: linear (vii) IMMEDIATE SOURCE:
        (A) LIBRARY: ESOGTUT02
        (B) CLONE: 2668731

(xi) SEQUENCE DESCRIPTION: SEQ ID NO: 124 :

```
agagcaaagt cagctgaact tctccttgct gtcctctgaa aggcttttcc tgctgctgct      60
tttgagagta aaactggggc atccagcata ttatgccttt ctggcctact aagatgtaaa     120
```

```
tattgtaaaa ttgattctcc tggatggaga gacttagctt gattagaaag cttctaacct     180
gttgctgagc ccatcaaacc atgtatcatt ctgttcctag agaagggaa gtactggtca      240 cacagcaact cacaaacatc ctagcaagtc ttttttcttt ttgccatcaa atatagtcac     300
cctttaaaat aattttgatg agactaattt aaactggtga aaaaccagcc acctagaaaa    360
actaatttga ctgagcctac atcaacttgg ctgtccaggt ctccagtttc ttattgggca    420
tgaagatgtg tgcacagtgg agtggacagg atacaggcta acacagaggt caaggctctg    480
ctcccacttt ctccctaaat ggctctgtga cgtcat                              516
```

(2) INFORMATION FOR SEQ ID NO: 125:

(i) SEQUENCE CHARACTERISTICS:
        (A) LENGTH: 669 base pairs
        (B) TYPE: nucleic acid
        (C) STRANDEDNESS: single
        (D) TOPOLOGY: linear (vii) IMMEDIATE SOURCE:
        (A) LIBRARY: THYRNOT09
        (B) CLONE: 2715440

(xi) SEQUENCE DESCRIPTION: SEQ ID NO: 125 :

```
actttcatca gctatattgg gtgtggaata tctgctattt tttcagcagc aactctcctg     60
acatatgttg cttttgagaa attgcgaagg gattatccct ccaaaatctt gatgaacctg    120
agcacagccc tgctgttcct gaatctcctc ttcctcctag atggctggat cacctccttc    180
aatgtggatg gactttgcat tgctgttgca gtcctgttgc atttcttcct tctggcaacc    240
tttacctgga tggggctaga agcaattcac atgtacattg ctctagttaa agtatttaac    300
acttacattc gccgatacat tctaaaattc tgcatcattg gctgggtttt gcctgcctta    360
gtggtgtcag ttgttctagc gagcagaaac aacaatgaag tctatggaaa agaaagttat    420
gggaaagaaa aaggtgatga attctgttgg attcaagatc cagtcatatt ttatgtgacc    480
tgtgctgggt attttggagt catgttttt ctgaacattg ccatgttcat tgtggtaatg    540
gtgcagatct gtgggaggaa tggcaagaga agcaaccgga ccctgagaga agaagtgtta    600
anggacctgc gcatgtggtt agcttganct tctgttgggc atgacatggg gnttgcatct    660
tgccctggg                                                            669
```

(2) INFORMATION FOR SEQ ID NO: 126:

(i) SEQUENCE CHARACTERISTICS:
        (A) LENGTH: 247 base pairs
        (B) TYPE: nucleic acid
        (C) STRANDEDNESS: single
        (D) TOPOLOGY: linear (vii) IMMEDIATE SOURCE:
        (A) LIBRARY: OVARTUT05
        (B) CLONE: 2728317

(xi) SEQUENCE DESCRIPTION: SEQ ID NO: 126 :

```
GTGGATGACA TTGGCCTACA GCTGAACTTT TCAAACACGA CTATAAGTCT AACCTCCCCT    60

TCTTTGGCTC TGGCTGTGAT CAGAGTGAAT GCCAGTAGTT TCAACACAAC TACCTTTGTG   120

GCCCAAGACC CTGCAAATCT TCAGGTTTCT CTGGAAACCC AAGCTCCTGA GAACAGTATT   180

GGCACAATTA CTCTTCCTTC ATCGCTGATG AATAATTTAC CAGCTCATGA CATGGAGCTA   240

GCTTCCA                                                             247
```

(2) INFORMATION FOR SEQ ID NO: 127:

(i) SEQUENCE CHARACTERISTICS:
        (A) LENGTH: 2815 base pairs
        (B) TYPE: nucleic acid
        (C) STRANDEDNESS: single
        (D) TOPOLOGY: linear (vii) IMMEDIATE SOURCE:
        (A) LIBRARY: COLANOT02
        (B) CLONE: 2767250

(xi) SEQUENCE DESCRIPTION: SEQ ID NO: 127 :

```
AGGACAAGAT GAGGCCCGGC CTCTCATTTC TCCTAGCCCT TCTGTTCTTC CTTGGCCAAG      60

CTGCAGGGGA TTTGGGGGAT GTGGGACCTC CAATTCCCAG CCCCGGCTTC AGCCCTTTCC     120

CAGGTGTTGA CTCCAGCTCC AGCTTCAGCT CCAGCTCCAG GTCGGGCTCC AGCTCCAGCC     180

GCAGCTTAGG CAGCGGAGGT TCTGTGTCCC AGTTGTTTTC CAATTTCACC GGCTCCGTGG     240

ATGACCGTGG GACCTGCCAG TGCTCTGTTT CCCTGCCAGA CACCACCTTT CCCGTGGACA     300

GAGTGGAACG CTTGGAATTC ACAGCTCATG TTCTTTCTCA GAAGTTTGAG AAAGAACTTT     360

CCAAAGTGAG GGAATATGTC CAATTAATTA GTGTGTATGA AAAGAAACTG TTAAACCTAA     420

CTGTCCGAAT TGACATCATG GAGAAGGATA CCATTTCTTA CACTGAACTG GACTTCGAGC     480

TGATCAAGGT AGAAGTGAAG GAGATGGAAA AACTGGTCAT ACAGCTGAAG GAGAGTTTTG     540

GTGGAAGCTC AGAAATTGTT GACCAGCTGG AGGTGGAGAT AAGAAATATG ACTCTCTTGG     600

TAGAGAAGCT TGAGACACTA GACAAAAACA ATGTCCTTGC CATTCGCCGA GAAATCGTGG     660

CTCTGAAGAC CAAGCTGAAA GAGTGTGAGG CCTCTAAAGA TCAAAACACC CCTGTCGTCC     720

ACCCTCCTCC CACTCCAGGG AGCTGTGGTC ATGGTGGTGT GGTGAACATC AGCAAACCGT     780

CTGTGGTTCA GCTCAACTGG AGAGGGTTTT CTTATCTATA TGGTGCTTGG GGTAGGGATT     840

ACTCTCCCCA GCATCCAAAC AAAGGACTGT ATTGGGTGGC GCCATTGAAT ACAGATGGGA     900

GACTGTTGGA GTATTATAGA CTGTACAACA CACTGGATGA TTTGCTATTG TATATAAATG     960

CTCGAGAGTT GCGGATCACC TATGGCCAAG GTAGTGGTAC AGCAGTTTAC AACAACAACA    1020

TGTACGTCAA CATGTACAAC ACCGGGAATA TTGCCAGAGT TAACCTGACC ACCAACACGA    1080

TTGCTGTGAC TCAAACTCTC CCTAATGCTG CCTATAATAA CCGCTTTTCA TATGCTAATG    1140

TTGCTTGGCA AGATATTGAC TTTGCTGTGG ATGAGAATGG ATTGTGGGTT ATTTATTCAA    1200

CTGAAGCCAG CACTGGTAAC ATGGTGATTA GTAAACTCAA TGACACCACA CTTCAGGTGC    1260

TAAACACTTG GTATACCAAG CAGTATAAAC CATCTGCTTC TAACGCCTTC ATGGTATGTG    1320

GGGTTCTGTA TGCCACCCGT ACTATGAACA CCAGAACAGA AGAGATTTTT TACTATTATG    1380

ACACAAACAC AGGGAAAGAG GGCAAACTAG ACATTGTAAT GCATAAGATG CAGGAAAAAG    1440

TGCAGAGCAT TAACTATAAC CCTTTTGACC AGAAACTTTA TGTCTATAAC GATGGTTACC    1500

TTCTGAATTA TGATCTTTCT GTCTTGCAGA AGCCCCAGTA AGCTGTTTAG GAGTTAGGGT    1560

GAAAGAGAAA ATGTTTGTTG AAAAAATAGT CTTCTCCACT TACTTAGATA TCTGCAGGGG    1620

TGTCTAAAAG TGTGTTCATT TTGCAGCAAT GTTTAGGTGC ATAGTTCTAC CACACTAGAG    1680

ATCTAGGACA TTTGTCTTGA TTTGGTGAGT TCTCTTGGGA ATCATCTGCC TCTTCAGGCG    1740

CATTTTGCAA TAAAGTCTGT CTAGGGTGGG ATTGTCAGAG GTCTAGGGGC ACTGTGGGCC    1800

TAGTGAAGCC TACTGTGAGG AGGCTTCACT AGAAGCCTTA AATTAGGAAT TAAGGAACTT    1860

AAAACTCAGT ATGGCGTCTA GGGATTCTTT GTACAGGAAA TATTGCCCAA TGACTAGTCC    1920

TCATCCATGT AGCACCACTA ATTCTTCCAT GCCTGGAAGA AACCTGGGGA CTTAGTTAGG    1980
```

```
TAGATTAATA TCTGGAGCTC CTCGAGGGAC CAAATCTCCA ACTTTTTTTT CCCCTCACTA    2040

GCACCTGGAA TGATGCTTTG TATGTGGCAG ATAAGTAAAT TTGGCATGCT TATATATTCT    2100

ACATCTGTAA AGTGCTGAGT TTTATGGAGA GAGGCCTTTT TATGCATTAA ATTGTACATG    2160

GCAAATAAAT CCCAGAAGGA TCTGTAGATG AGGCACCTGC TTTTTCTTTT CTCTCATTGT    2220

CCACCTTACT AAAAGTCAGT AGAATCTTCT ACCTCATAAC TTCCTTCCAA AGGCAGCTCA    2280

GAAGATTAGA ACCAGACTTA CTAACCAATT CCACCCCCCA CCAACCCCCT TCTACTGCCT    2340

ACTTTAAAAA AATTAATAGT TTTCTATGGA ACTGATCTAA GATTAGAAAA ATTAATTTTC    2400

TTTAATTTCA TTATGGACTT TTATTTACAT GACTCTAAGA CTATAAGAAA ATCTGATGGC    2460

AGTGACAAAG TGCTAGCATT TATTGTTATC TAATAAAGAC CTTGGAGCAT ATGTGCAACT    2520

TATGAGTGTA TCAGTTGTTG CATGTAATTT TTGCCTTTGT TTAAGCCTGG AACTTGTAAG    2580

AAAATGAAAA TTTAATTTTT TTTTCTAGGA CGAGCTATAG AAAAGCTATT GAGAGTATCT    2640

AGTTAATCAG TGCAGTAGTT GGAAACCTTG CTGGTGTATG TGATGTGCTT CTGTGCTTTT    2700

GAATGACTTT ATCATCTAGT CTTTGTCTGT TTTTCCTTTG ATGTTCAAGT CCTAGTCTAT    2760

AGGATTGGCA GTTAAATGC  TTTACTCCCC CTTTTTAAAA TAAATGATTA AAATG         2815

(2) INFORMATION FOR SEQ ID NO:  128:

(i) SEQUENCE CHARACTERISTICS:
        (A) LENGTH: 728 base pairs
        (B) TYPE: nucleic acid
        (C) STRANDEDNESS: single
        (D) TOPOLOGY: linear (vii) IMMEDIATE SOURCE:
        (A) LIBRARY: LNODNOT05
        (B) CLONE: 3124538

(xi) SEQUENCE DESCRIPTION: SEQ ID NO: 128 :

agtggccatt tctgcagcct ccaggcctca cctttatgga acaccttccc gctgctggct      60
ccaaccagaa aagggattta tatgggcttt ccttggacct gtctgcgcca tcttctctgt     120
gaatttagtt ctctttctgg tgacTCTCTG GATTTTGAAA AACAGACTCT CCTCCCTCAA     180

TAGTGAAGTG TCCACCCTCC GGAACACAAG GATGCTGGCA TTTAAAGcga cagctcagCT     240

GTTCATCCTG GGCTGCACGT GGTGTCTGGG CATCTTGCAG GTGGGTCCGG ctgcccgggc     300
catgGCCTAC CTCTTCACCA TCATCAACAG CCTGCAGGGT GTCTTCATCT TCCTGGTGTA     360

CTGCCTCCTC AGCCAGCAGG TCCGGGAGCA ATATGGGAAA TGGTCCAAAG GGATCAGGAA     420

ATTGAAAACT GAGTCTGAGA TGCACACACT CTCCAGCAGT GCTAAGGCTG ACACCTCCAA     480

ACCCAGCacg gtaagatcaa cgcattgctc cagagcactt cactaaccga cccacctgag     540
gagcatgtgc ctatcacaca aggaaacctg ggaatacagc aggcaatgcc ctagaaaggc     600
tcgcatctga gtacgccttg actcattaac cattagcaat gatctcagtt taaatgtttt     660 ttttttaatca gtcatagcct gtcatcccgg natcactgtc atcccagcat ttgggaggnc     720
taggcaag                                                              728

(2) INFORMATION FOR SEQ ID NO:  129:

(i) SEQUENCE CHARACTERISTICS:
        (A) LENGTH: 1356 base pairs
        (B) TYPE: nucleic acid
        (C) STRANDEDNESS: single
        (D) TOPOLOGY: linear
```

```
       (vii) IMMEDIATE SOURCE:
             (A) LIBRARY: HNT2AZS07
             (B) CLONE: 3143858

(xi) SEQUENCE DESCRIPTION: SEQ ID NO: 129 :

tgcccgcgcg tcctcaaggt gccatcctat ctcagctaca agtttctggg cgagcgtgat      60
tgtgctgcgc cctgcgaacc tgcgcggccc gatggttcca tgttcttctc acaggaggag     120
acgcgtttcg cgcgcctctg gatcctcacc tggtcggtgc tgtgctgcgc ttccaccttc     180
ttcactgtca ccacgtactt ggtagacatg cagcgcttcc gctacccaga gcggcctatc     240 attttctgt cgggctgcta caccatggtg tcggtggcct acatcgcggg cttcgtgctc      300
caggagcgcg tggtgtgcaa cgagcgcttc tccgaggacg gttaccgcac ggtggtgcag     360
ggcaccaaga aggagggctg caccatcctc ttcatgatgc tctacttctt cagcatggcc     420
agctccatct ggtgggtcat cctgtcgctc acctggttcc tggcagccgg catgaagtgg     480
ggccacgagg ccatcgaggc caactctcag tacttccacc tggccgcctg ggccgtgccg     540
ggccgtcaag accatcacca tcctggccat gggccagatc gacggcgacc tgctgagcgg     600
cgtgtgcttc gtaggcctca acagcctgga cccgctgcgg ggcttcgtgc tagcgccgct     660
cTTCGTGTac ctgTTCATCG GCACGTCCTT CCTCCTGGCC GGCTTCGTGT CGCTCttccg     720
gaatccGCAC CATCATGAAG CACGACGGCA CCAAGACCGA AAAGCTGGAG CGGCTCATGG     780

TGCGCATCGG CGTCTTCTCC GTGCTCTACA CAGTGCCCGC CACCATCGTC ATCGCTTGCT     840

ACTTCTACGA GCAGGCCTTC CGCGAGCACT GGGAGCGCTC GTGGGTGAGC CAGCACTGCA     900

AGAGCCTGGC CATCCCGTGC CCGGCGCACT ACACGCCGCG CATGTCGCCC GACTTCACGG     960

TCTACATGAT CAAATACCTC ATGACGCTCA TCGTGGGCAT CACGTCGGGC TTCTGGATCT    1020

GGTCGGGCAA GACGCTGCAC TCGTGGAGGA AGTTCTACAC TCGCCTCACC AACAGCcgac    1080
acggtgagac caccgtgtga gggacgcccc caggccggaa ccgcgcggcg ctttcctccg    1140
cccggggtgg ggcccctaca gactccgtat tttatttttt taaataaaaa acgatcgaaa    1200
ccatttcact tttaggttgc ttttaaaag agaactctct gcccaacacc cccacaaggt     1260
ttgtaattaa nactgtaaat agtctttgta aatttaatta tatatatttt ctatttaaaa    1320
gaanaaagga gaaaaaaaaa caggggtgtg ggcgcc                              1356

(2) INFORMATION FOR SEQ ID NO:   130:

(i) SEQUENCE CHARACTERISTICS:
           (A) LENGTH: 1937 base pairs
           (B) TYPE: nucleic acid
           (C) STRANDEDNESS: single
           (D) TOPOLOGY: linear (vii) IMMEDIATE SOURCE:
             (A) LIBRARY: OVARTUN01
             (B) CLONE: 3256211

(xi) SEQUENCE DESCRIPTION: SEQ ID NO: 130 :

gactctagag gatccccccc agaacttcat tccctccatc ttcattgcct tagctccttt      60
tgtCTTTAAG TATTCACTCA CTAAGTCAag aaaatattgg aggggggtg gggcaAAACA     120

ACTAGGCTTT Aaaggtgggg gattACCCAG ATCAACACAA GTCTCCCACT TGAACAACTG     180

CTCTTTGAcg cCTGTACCCT GAGATGTGAC TATGGATTAA AGTCATAGCA CCCCTGCCTC     240

CAGGTTGGAA AGTTTTATGG AAAATGAACA TATTTTATTA GAAGACAATG AGAACTTCCT     300

GGAGCAGATG AGTAAACACA CCCTCATGTT TACCTGATAA CTGAAATCAA AGATGAGGTG     360
```

```
TAGCCTCTGG TTTGAAATGT TACAAAGTGT AAAATTAAGA TAAAGGCAGA AAAATGAAAA    420

GGAAATAGCC AGTTTTGAAG CAGAAGAACT CAGTGGGACA GGggccaaat cagTGAAAGA    480

GGTGCTGCTC AGATACCAGA TTTAATGACA ACCAAAGTGG CCCAAATATC CataAAAAAT    540

TGCGCTTCTG AAAACCAGTA GGAGGTTGCA GTGGACTAAA GATGGCCACA AAATTTTTAT    600

CGTTTTCCCC GTCAAGAATG GGAGTTTATT TTTCATCATC TTGAATCTGG CCCTGTGACT    660

GCATCACCAA GAAGACACTG CAGAAGTGAT GCTCTGCCAG TTCTGGTTCT AGTCTTTTAG    720

AAGACTGTTA GCCTCtactt cctctttctt caaATGAGCT CTCTTGGGAC ACCCTCTCTC    780

AGAACCAAAC CACCATGCAT GGGgcatgtg tggcctcttc actcaggagc ccccagcagg    840
agcaacccag cCAGTACTGA GCATCAAGTG CCAGTcatGT GAATGAGCCA TCTAGGAtgt    900
tctttggtca AGTCTATACA AAagaactta ccagctGAGC CCAGCCAACA CATAGAATTA    960

TGAAATAGTA AAATGATTAT TGTTTAAAGT CATGAAATTT Tgcagttttt ttaatatagc    1020

AATAGATAAC CAAAATCAAG ATTAAATAAA ATATCAGATG ATTAAAATGG AGCATGAAAA    1080

TGGAGTTAAC TTTgtaagaa gaaccACAAC CCCAatgatc atGACTTAGA GGAAAGTTCa    1140
gtaaataaaa cagaAAATAT TGAAAAAGGC TGTtttcattt taaacctGTG TCAAGCTCCT    1200

AGACCTAaaa tGACACTTGA AATTGTCCTC CATTAGAATT CATTGTGCTA CAGATTTTCT    1260

CTCATTCTGT TACATATATT TATTTAATGA AGTAGAGAAA TTCTTCTCTC ATAAGCTAAT    1320

GCTGCAAGGT GTTTTTATAT GTATTATATG TATATGTACA Tacatatatt ttttatatta    1380
acataacagt ttATAATAAA TGTTTAAGTG TTTTATAATA ATATTTATAC ATTTatcacc    1440
atatatacaC ACACACAAAT ATAtgtatnn nnnnnnnnnn nnnnnnnnnn naatgtCTGG    1500

GGATAGAAAG TGAGACCCtc agaatcttgg ATGTAGCCTG ACTGCTCTGC ACCCaactgg    1560
ggaggagtgA GGGGAGAAGA AAGTAGAGTT ccagccagaa aggtgacaga AGACTGCcca    1620
aagcttcatg taaccaatcc ctcaagcctg cggaaaagtt actaaatgtt tggtgccagt    1680
gccttcctgc agagtcagtg atgcttatgc ttggtactga atcagagaca gcaccttcaa    1740
ccatagtcac acgtctgcaa aagacagaaa atccagtct gatagctttg ttctatgtat    1800
ttgttcgtgt ttacaccaag gattgtagcc tgcagctcct gatcttttat tctgaaacgt    1860
tctggaagta gtaaaggcta ctctataaca tacttgtttt aataaatgta ttctccattt    1920
tttaatgcaa aacctgg                                                   1937
```

(2) INFORMATION FOR SEQ ID NO: 131:

(i) SEQUENCE CHARACTERISTICS:
        (A) LENGTH: 784 base pairs
        (B) TYPE: nucleic acid
        (C) STRANDEDNESS: single
        (D) TOPOLOGY: linear (vii) IMMEDIATE SOURCE:
        (A) LIBRARY: PTHYNOT03
        (B) CLONE: 3324895

(xi) SEQUENCE DESCRIPTION: SEQ ID NO: 131 :

```
tggagatgtg tgccttcacg atttcactgg aaaacagcac atgtttaacg agaaggaaga     60
ttcctgcaat gggaaaggcc gtatggctct cagaaggact tcaaagcggg gaagcttaca    120
ctttattgag caaatgtgat tcctttcttc taaaatcaaa gcatgatgct tgacagtgtg    180
aaatgtccaa ttttacctttt tacacaatgt gagatgtatg aaaatcaact cattttattc    240
tcggcaacat ctggagaagc ataagctaat taagggcgat gattattatt ccaagangaa    300
```

```
accangacat tacaccntgg tttttagac atttctgant tggtgtctta actntcattt     360
ttatnanncg gttggtttn accnatacac tnagantgac tcctatanag nnaacaaana     420
cnggtagtgn nctgtnnact natctttat aaaggctggg tgntcnttgg atnacctcat     480
atnnnccnnc tgttgacntn nggccacntn ggtngatct taggnntnna tngccttttg     540
ntngntncta atnccnatt tctcngngnn ccacnntngt nnaaaactct tacttcnacc     600 atttgncnc cacctgngtt tggttctttt ccnagncct tgtttgggnn ngnaggtgnt     660
tncngttcnt tggcccngan ccctttgga tngngtctnt ctntacaang ntggaaaaat     720
ttttnatttt gggccccat anttggtcnc anaaacaang ctanttnc nnccttttt      780 tttt                                                               784

(2) INFORMATION FOR SEQ ID NO:  132:

(i) SEQUENCE CHARACTERISTICS:
        (A) LENGTH: 3167 base pairs
        (B) TYPE: nucleic acid
        (C) STRANDEDNESS: single
        (D) TOPOLOGY: linear (vii) IMMEDIATE SOURCE:
        (A) LIBRARY: PTHYNOT03
        (B) CLONE: 3324971

(xi) SEQUENCE DESCRIPTION: SEQ ID NO: 132 :

agaaaattct gaagtcggcg aggggatct gccctttctc tgtttctttt ttaccctta      60 tctcttttc tgacaccctt ggatattc ttataattaa ngtgtcatct tgcctggctt     120
tccagaaccc tctccatagc atgccatggt tacagggtct cctgattgtt tcatcactgc    180
ttttcttgca tttactttc tgtgctccta attgcattt ccaaatactt atgttcctca     240
aattgaagca cctttgtttt cagtctaact tatgtaaaag ttctaaataa gtcttcacat    300
tcggttttct gttttatttg ccttatttca tggttttgct tttaggggct cataggtgaa    360
gtagggggtt gaaggtata atgtttgtaa taaaatgaaa tatatactgT TGTGCAAAAG    420
ctcaaacttt taaaacatgg gttaaCAGAT TATAAGATGA AAACATAGCA AAAATTTAAA   480

TTGTCAGACC ACTTATAAAT GATCTTAAAC TTAGGCTTTT GTTAGTGAAA ATAAACATAA   540

ACTTCAGTTA CTTTGTACCC TGATACACTG ATTATGCTAA CTTTAGAAAA GAAGGGTAGT   600

ATTTGTATGA AGTATAcatt ttggtaaaat tgaATGCTAA TAATatgaat ttttccttt    660 tgatttgtga tCACTGAaac ttgtttgcct gtgtaatttt ttaacttggc ttaaTTTTTG   720

TCTTTCTCTG TAACTGTTAG TTTTTGTGTG TCCTGGGACC TTGAAAGCAA TTGTGGACTC   780

ACCATGTATA TATGAAGCTG AACAAAAGGC GGGTGCTTGG TGCAAGGACC CTCTtcaggc   840
tgcagataaa atttatttca tgccctggac tccctatcgt accgatactt taatagaata    900
tgcttcttta gaagatttcc aaaatagtcg ccaaacaaca acatataaac ttccaaatcg    960
agtagatggt actggatttg tggtgtatga tggtgctgtc ttctttaaca agaaagaac   1020 gaggaatatt gtgaaatttg acttgaggac tagaattaag agtggcgagg ccataATTAA   1080

CTATGCCAAC TACCATGATA CCTCACCATA CAGATGGGGA GGAAAGACTG ATATCGACCT   1140

AGCAGTTGAT GAAAATGGTT TATGGGTCAT TTACGCCACT GAACAGAACA ATGGAATGAT   1200

AGTTATTAGC CAGCTGAATC CATACACTCT TCGATTTgaA GCAACGTGGG AGACTgtATA   1260

CGACAAACGT GCCGCATCAA ATGCTTTTAT GATATGCGGA GTCCTCTATG TGGTTAGGTC   1320

AGTTTATCAA GACAATGAAA GTGAAACAGG CAAGAACTCA ATTGATTACA TTTATAATAC   1380
```

```
CCGATTAAAC CGAGGAGAAT ATGTAGATGT TCCCTTCCCC AAccagTATC AGTATATTGC   1440

TGCAGTGGAT TACAATCCAA GAGATAACCA ACTTTACGTG TGGAACAATA ACTTCATTTT   1500

ACGATATTCT CTGGAGTTTG GTCCACCTGA TCCTGCCCAA GGTAAGCGTG TTTACTTGCT   1560

AATGCTTATG TCATtttgTG AAAAGCATTT TTCTTTTTAA AGACTTCTTA ATTTTTTttt   1620
cCTATTTTCT TCCCCTTTTC ATAGTTAAAG GACAAAGGAC AATGTTGTGG TACATTTTAG   1680

CCTTATTATG GTTCGTTTTC TTTTTCTCAA TTTCTTCATT TTAATGTTGG CTTCAAGAAA   1740

TTGTGGCATT ATTAGTCAGC TTAAACTTTT TTCATTGCTA AAAATATAAT ACTAACCAGA   1800

AACCTGTTAG CAGTGTTTTT TTGTTTGGTT GTTTTCCCCT ACTTGACTGC TGAATTGATT   1860

ACAATCTATG TTCAGACCTT TTAACTTCTT GGCGCCAGTG GTTAAAGGAA acgtGTGTTA   1920

GGAAGTCCCA GGAGAATGGC TAGGCTTGAT GTACAATGCC AGATATATGC GTTCTAAAGT   1980

TTTGGTGTCT GTTCTCTCAG TAGGAGAGGG AGCCATCCAA TATTTTTCTA GATTATCATG   2040

TAAAATTACa tgtttttatt ttctgaTAAA TTAGTGACAG TTTGAAGTCA ATATTTCTGT   2100

Gactttaacg atCACATGAA CCAAACTTTA AATGATCCCA AGTGATGACT TGTGATGACA   2160

GATATGCAAG CATTGTGTGA TTTGTATTCT CTTTATGGAG GATCATTACT TTAGAAAGTA   2220

ATGCTAAATT TTTGGAAATA TACTTTGGTT TATTAAGTGA GTTCAGTTTT GTGGGAAATA   2280

ATTTTTGATG ATAAACGAAT ACTTCATTAA AACAAGATTA TCTCATACTC ATGATGAAAG   2340

AATAATTTGT TAATGTATTA TTATAGAGCT TGCACTGTTT ATAAGTCTTC TATTTGAACA   2400

GTGTTTGTTT AAggtCTGAA TATCCTAATT TACTGAGTTA ATCTTGAAAT TATTGCATTA   2460

TTTCGAAATT TTAGGAACTA GAAAGTTCTT TGGAGTGATT AAATTAATAT CCTCAATAGG   2520

GTGGGGCAGA GACTAATATA TTTTTTTCTT CTCTTAAAGC AATGCAAGTA CACACACTTA   2580

AATATGTTCA TAACaaacAC ATACCCATAC ATATTTAAG ATATGCTGTT AATCAGTTTT    2640

AAATATTGTC ATACGGTCAG GACCTCAAAA GCAGAAGTCA CAGCTCTTTG TCATGGAATT   2700

TCTAATTTGA GTCATTGTAG AATACCAAAA TACATGAGTT TTGTTCATAT AATAACAATA   2760

ATGATCCACT GACTTAGTGT ACATCCCCTT TTTCCCTAaA TCAGGTTATG TTtgtatttt   2820
ttggctTATA GTTGTAGCAG TAATGTTcat tgttaaattt ataacaatGA AATCTTCTTT   2880

TAGGGCATAT AATTTTATTG ATAGtatctt agaatcattt atttaaaaat gtattcatat   2940
gtttgctcat gaggcagcag tttggtttgt ttcatctatt tcaattgttt ttccaaaagc   3000
tgctactaca atagtgcttc tttatcctat aggtttgtca aaaggcaaac ttaaggcatt   3060
gacagacttg tattggcatt ggctaaaatt gtattgatcc ttatgttaac cttttttgtag  3120 cctgtattag tctcacagtt gttagatttg tcttggntag cagtaat               3167

(2) INFORMATION FOR SEQ ID NO:   133:

(i) SEQUENCE CHARACTERISTICS:
        (A) LENGTH: 2499 base pairs
        (B) TYPE: nucleic acid
        (C) STRANDEDNESS: single
        (D) TOPOLOGY: linear (vii) IMMEDIATE SOURCE:
        (A) LIBRARY: PTHYNOT03
        (B) CLONE: 3325283

(xi) SEQUENCE DESCRIPTION: SEQ ID NO: 133 :

GGGCGCTGGA GGCAGCTCGA GGCGCGATGT CGGTGCCGCT GCTCAAGATC GGGGTCGTGC    60

TGAGCACCAT GGCCATGATC ACTAACTGGA TGTCCCAGAC GCTGCCCTCG CTGGTGGGCC   120
```

-continued

```
TCAACACCAC CAAGCTCTCG GCGGCCGGCG GCGGGACGCT GGACCGCAGC ACCGGCGTGC      180

TGCCCACCAA CCCTGAGGAG AGCTGGCAGG TGTACAGCTC TGCCCAGGAC AGCGAGGGCA      240

GGTGTATCTG CACAGTGGTC GCCCCACAGC AGACCATGTG TTCACGGGAT GCCCGCACAA      300

AACAGCTGAG GCAGCTACTG GAGAAGGTGC AGAACATGTC TCAATCCATA GAGGTCTTGG      360

ACAGGCGGAC CCAGAGAGAC TTGCAGTACG TGGAGAAGAT GGAGAACCAA ATGAAAGGAC      420

TGGAGTCCAA GTTCAAACAG GTGGAGGAGA GTCATAAGCA ACACCTGGCC AGGCAGTTTA      480

AGGCGATAAA AGCGAAAATG GATGAACTTA GGCCTTTGAT ACCTGTGTTG GAAGAGTACA      540

AGGCCGATGC CAAATTGGTA TTGCAGTTTA AGAGGAGGT CCAGAATCTG ACGTCAGTGC       600

TTAACGAGCT GCAAGAGGAA ATTGGCGCCT ATGACTACGA TGAACTTCAG AGCAGAGTGT      660

CCAATCTTGA AGAAAGGCTC CGTGCATGCA TGCAAAAACT AGCTTGCGGG AAGTTGACGG      720

GCATCAGTGA CCCCGTGACT GTCAAGACCT CCGGCTCGAG GTTCGGATCC TGGATGACAG      780

ACCCTCTCGC CCCTGAAGGC GATAACCGGG TGTGGTACAT GGACGGCTAT CACAACAACC      840

GCTTCGTACG TGAGTACAAG TCCATGGTTG ACTTCATGAA CACGGACAAT TTCACCTCCC      900

ACCGTCTCCC CCACCCCTGG TCGGGCACGG GGCAGGTGGT CTACAACGGT TCTATCTACT      960

TCAACAAGTT CCAGAGCCAC ATCATCATCA GGTTTGACCT GAAGACAGAG ACCATCCTCA     1020

AGACCCGCAG CCTGGACTAT GCCGGTTACA ACAACATGTA CCACTACGCC TGGGGTGGCC     1080

ACTCGGACAT CGACCTCATG GTGGACGAGA GCGGGCTGTG GGCCGTGTAC GCCACCAACC     1140

AGAACGCTGG CAACATCGTG GTCAGTAGGC TGGACCCCGT GTCCCTGCAG ACCCTGCAGA     1200

CCTGGAACAC GAGCTACCCC AAGCGCAGCG CCGGGGAGGC CTTCATCATC TGCGGCACGC     1260

TGTACGTCAC CAACGGCTAC TCAGGGGGTA CCAAGGTCCA CTATGCATAC CAGACCAATG     1320

CCTCCACCTA TGAATACATC GACATCCCAT TCCAGAACAA ATACTCCCAC ATCTCCATGC     1380

TGGACTACAA CCCCAAGGAC CGGGCCCTGT ATGCCTGGAA CAACGGCCAC CAGATCCTCT     1440

ACAACGTGAC CCTCTTCCAC GTCATCCGCT CCGACGAGTT GTAGCTCCCT CCTCCTGGAA     1500

GCCAAGGGCC CACGTCCTCA CCACAAAGGG ACTCCTGTGA AACTGCTGCC AAAAAGATAC     1560

CAATAACACT AACAATACCG ATCTTGAAAA ATCATCAGCA GTGCGGATTC TGACATCGAG     1620

GGATGGCATT ACCTCCGTGT TTCTCCCTTT CGAGCCGGCG GGCCACAGAC GTCGGAAGAA     1680

ACTCCCGTAT TTGCAGCTGG AACTGCAGCC CACGGCGCCC CGGTTTTCCT CCCCGCCCTG     1740

TCCCTCTCTG GTCAAACAAC ATACTAAAGA GGCGAGGCAA TGACTGTTGG CCAGTTCTCA     1800

CCGGGGAAAA ACCCACTGTT AGGATGGCAT GAACATTTCC TTAGATCGTG GTCAGCTCCG     1860

AGGAATGTGG CGTCCAGGCT CTTTGAGAGC CATGGGCTGC ACCCGGCCGT AGGCTAGTGT     1920

AACTCGCATC CCATTGCAGT GCCGTTTCTT GACTGTGTTG CTGTCTCTTA GATTAACCGT     1980

GCTGAGGCTC CACATAGCTC CTGGACCTGT GTCTAGTACA TACTGAAGCG ATGGTCAGAG     2040

TGTGTAGAGT GAAGTTGCTG TGCCCACATT GTTTGAACTC GCGTACCCCG TAGATACATT     2100

GTGCAACGTT CTTCTGTTAT TCCCTTGAGG TGGTAACTTC GTATGTTCAG TTTATGCGAT     2160

GATTGTTGTA AATGCAATGC CGTAGTTTGG ATTAATAAGT GGATGGTTTT TGTTTCTAAA     2220

AAGAAAAAAA AAATCAGTGT TCACCCTTAT AGAGACATAG TCAAGTTCAT GTTGATAATA     2280

ATCAAAGGAA TTACTCTCTT CTTGTTAAAT TAGCTAAATC ATGTAACCGC AGATAGGAAG     2340

GGCTCGCCTG GGAAACTCT GGTTTCCGAT GGGACAGGAA AGTCATACGG CAACAGTAT       2400

GCGGAAAGTA CGTTTTTTAA GTAAAAAACA AAGGCAAACT TTGTACTATC CAGTTATCTA     2460

AGGAACAATA AAAACATTAG GAGATAAAAA AAAAAAAA                              2499
```

```
(2) INFORMATION FOR SEQ ID NO:  134:

(i) SEQUENCE CHARACTERISTICS:
        (A) LENGTH: 298 base pairs
        (B) TYPE: nucleic acid
        (C) STRANDEDNESS: single
        (D) TOPOLOGY: linear (vii) IMMEDIATE SOURCE:
        (A) LIBRARY: DRGTNOT01
        (B) CLONE: 3603093

(xi) SEQUENCE DESCRIPTION: SEQ ID NO: 134 :

CCACCGGCNC CGCGCNGTGC ACCGTGGTCT TCTTGCTGGT CTACTTCTTC GGCATGGCCA        60

GCTCCANCTG GTGGGTGATC TTGTCGCTCA CATGGTTCCT GGNGGCCGGT ATGAAGTGGG       120

GCAACGAAGC CATCGCNGGC TACTCGCAGT ACTTCCACCT GGCCGCGTGG CTTGTGCCCA       180

GCGTCAAGTC CATCGCGGTG CTNGCGCTTC ANCTCNGTGG ACNGCGACCC GGNNGCGNGC       240

ATCTNCTACG TGGGCAACCA GANCCTGGAA CAACCTGCGC NGCTTCGTNC NGNCNCCG         298
```

COMPOSITION FOR THE DETECTION OF GENES ENCODING RECEPTORS AND PROTEINS ASSOCIATED WITH CELL PROLIFERATION

This application claims the benefit of U.S. Provisional application Ser. No. 60/079,677, our Docket No. PL-0008 P, filed on Mar. 27, 1998.

FIELD OF THE INVENTION

The present invention relates to a composition comprising a plurality of polynucleotide probes for use in research and diagnostic applications.

BACKGROUND OF THE INVENTION

DNA-based arrays can provide a simple way to explore the expression of a single polymorphic gene or a large number of genes. When the expression of a single gene is explored, DNA-based arrays are employed to detect the expression of specific gene variants. For example, a p53 tumor suppressor gene array is used to determine whether individuals are carrying mutations that predispose them to cancer. The array has over 50,000 DNA probes to analyze more than 400 distinct mutations of p53. A cytochrome p450 gene array is useful to determine whether individuals have one of a number of specific mutations that could result in increased drug metabolism, drug resistance, or drug toxicity.

DNA-based array technology is especially relevant for the rapid screening of expression of a large number of genes. There is a growing awareness that gene expression is affected in a global fashion. A genetic predisposition, disease, or therapeutic treatment may affect, directly or indirectly, the expression of a large number of genes. In some cases the interactions may be expected, such as where the genes are part of the same signaling pathway. In other cases, such as when the genes participate in separate signaling pathways, the interactions may be totally unexpected. Therefore, DNA-based arrays can be used to investigate how genetic predisposition, disease, or therapeutic treatment affect the coregulation and expression of a large number of genes.

It would be advantageous to prepare DNA-based arrays that can be used for monitoring the expression of a large number of proteins associated with cell proliferation or receptors. Proteins associated with cell proliferation include cytokines, hormones, growth and differentiation factors, G and ras-related proteins, lectins, oncogenes and their suppressors, and the like. Receptors include G protein coupled, four transmerrmbrane, tyrosine kinase, and nuclear receptors. Some of these proteins may be secreted and typically include signal sequences that direct proteins to their cellular or extracellular destination.

The present invention provides for a composition comprising a plurality of polynucleotide probes for use in detecting changes in expression of a large number of genes which encode proteins associated with cell proliferation and receptors. Such a composition can be employed for the diagnosis and for monitoring the treatment of any disease—a cancer, an immunopathology, a neuropathology and the like—where a defect in the expression of a gene which encodes a protein associated with cell proliferation or a receptor is involved.

SUMMARY OF THE INVENTION

In one aspect, the present invention provides a composition comprising a plurality of polynucleotide probes, wherein each of said polynucleotide probes comprises at least a portion of a gene which encodes a protein associated with cell proliferation or a receptor.

In one preferred embodiment, the plurality of polynucleotide probes can comprise at least a portion of one or more of the sequences (SEQ ID NOS:1–134) presented in the Sequence Listing. In a second preferred embodiment, the composition comprises a plurality of polynucleotide probes comprising at least a portion of a gene coding for a protein associated with cell proliferation. In a third preferred embodiment, the composition comprises a plurality of polynucleotide probes comprising at least a portion of a gene coding for a receptor. In a fourth preferred embodiment, the composition comprises a plurality of polynucleotide probes comprising at least a portion of at least one or more of the sequences of SEQ ID NOS:1–22. In a fifth preferred embodiment, the composition comprises a plurality of polynucleotide probes comprising at least a portion of at least one or more of the sequences of SEQ ID NOS:23–134.

The composition is particularly useful as hybridizable array elements in a microarray for monitoring the expression of a plurality of target polynucleotides. The microarray comprises a substrate and the hybridizable array elements. The microarray can be used, for example, in the diagnosis and treatment of a cancer, an immunopathology, a neuropathology, and the like.

In another aspect, the present invention provides an expression profile that can reflect the expression levels of a plurality of target polynucleotides in a sample. The expression profile comprises a microarray and a plurality of detectable complexes. Each detectable complex is formed by hybridization of at least one of said target polynucleotides to at least one of said polynucleotide probes and further comprises a labeling moiety for detection.

DESCRIPTION OF THE SEQUENCE LISTING AND TABLES

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

The Sequence Listing is a compilation of nucleotide sequences obtained by sequencing clone inserts (isolates) of different DNA libraries. Each sequence is identified by a sequence identification number (SEQ ID NO), by the clone number from which it was obtained and by the DNA library from which the sequence was obtained.

Table 1 is a list of the exemplary sequences disclosed herein. By column, the first (3rd, 5th, and 7th) page of the table contains: 1) SEQ as shown in the Sequence Listing; 2) Incyte CLONE number as shown in the Sequence Listing; 3) PRINT reflects the designation of the relevant PROSITE group, 4) the SIGNATURE of that group; 5) the SCORE to the group, where >1300 is strong and 1000 to 1300 is suggestive; 6) STRENGTH reports the degree of correlation to the group, >1300 is strong and 1000 to 1300 is weak; and 7) HITS, number of similar molecules in the group. The second (4th, 6th and 8th) page of the table contains: 8) SEQ (repeated); 9) DESCRIPTION of the molecule/ORGANISM; 10) GenBank identifier; 11) p value; and 12) designation as cell proliferation or receptor category as determined using PRINTS and/or BLAST. The table is arranged so that SEQ ID NOS:1–22 contain at least a portion of a gene coding for a cell proliferation protein and SEQ ID NOS:23–134 contain at least a portion of a gene coding for a receptor.

DESCRIPTION OF THE INVENTION

Definitions

The term "microarray" refers to an ordered arrangement of hybridizable array elements. The array elements are arranged so that there are preferably at least one or more different array elements, more preferably at least 100 array elements, and most preferably at least 1,000 array elements, on a 1 cm$^2$ substrate surface. The maximum number of array elements is unlimited, but is at least 100,000 array elements. Furthermore, the hybridization signal from each of the array elements is individually distinguishable. In a preferred embodiment, the array elements comprise polynucleotide probes.

A "polynucleotide" refers to a chain of nucleotides. Preferably, the chain has from about 50 to 10,000 nucleotides, more preferably from about 100 to 3,500 nucleotides. The term "probe" refers to a polynucleotide sequence capable of hybridizing with a target sequence to form a polynucleotide probe/target complex. A "target polynucleotide" refers to a chain of nucleotides to which a polynucleotide probe can hybridize by base pairing. In some instances, the sequences will be complementary (no mismatches) when aligned. In other instances, there may be up to a 10%. mismatch.

A "plurality" refers preferably to a group of at least one or more members, more preferably to a group of at least about 100, and even more preferably to a group of at least about 1,000, members. The maximum number of members is unlimited, but is at least about 100,000 members.

A "portion" means a stretch of at least about 100 consecutive nucleotides. A "portion" can also mean a stretch of at least about 100 consecutive nucleotides that contains one or more deletions, insertions or substitutions. A "portion" can also mean the whole coding sequence of a gene. Preferred portions are those that lack secondary structure as identified by using computer software programs such as OLIGO 4.06 software (National Biosciences, Plymouth MN), LASERGENE software (DNASTAR, Madison Wis.), MACDNASIS (Hitachi Software Engineering Co., S.San Francisco Calif.) and the like.

The term "gene" or "genes" refers to polynucleotide sequence of a gene which may be the partial or complete and may comprise regulatory, untranslated, or coding regions. The phrase "genes coding for a protein associated with cell proliferation or a receptor" refers to genes comprising sequences that contain conserved protein motifs or domains that were identified by employing Hidden Markov Models (HMMs; Krogh et al. (1994) J. Mol. Biol. 235:1501–1531; Collin et al. (1993) Protein Sci. 2:305–314), BLAST (Basic Local Alignment Search Tool; Altschul (1993) J. Mol. Evol. 36:290–300; and Altschul et al. (1990) J. Mol. Biol. 215:403–410) or other analytical tools. Additionally, "genes coding for proteins associated with cell proliferation or receptors" refers to genes which may produce proteins with signal sequences which direct secretion or destination within the cell.

The Invention

The present invention provides a composition comprising a plurality of polynucleotide probes comprising at least a portion of genes coding for proteins associated with cell proliferation or receptors. Preferably, the plurality of polynucleotide probes comprise at least a portion of one or more of the sequences (SEQ ID NOS:1–134) presented in the Sequence Listing. In one preferred embodiment, the composition comprises a plurality of polynucleotide probes, wherein each polynucleotide probe comprises at least a portion of a sequence selected from the group consisting of SEQ ID NOS:1–22. In a second preferred embodiment, the composition comprises a plurality of polynucleotide probes, wherein each polynucleotide probe comprises at least a portion of a sequence selected from the group consisting of SEQ ID NOS:23–134.

The microarray can be used for large scale genetic or gene expression analysis of a large number of target polynucleotides. The microarray can also be used in the diagnosis of diseases and in the monitoring of treatments where altered expression of genes coding for proteins associated with cell proliferation or receptors cause disease, such as cancer, an immunopathology, neuropathology, and the like. Further, the microarray can be employed to investigate an individual's predisposition to a disease, such as cancer, an immunopathology, or a neuropathology. Furthermore, the microarray can be employed to investigate cellular responses to infection, drug treatment, and the like.

When the composition of the invention is employed as hybridizable array elements in a microarray, the array elements are organized in an ordered fashion so that each element is present at a specified location on the substrate. Because the array elements are at specified locations on the substrate, the hybridization patterns and intensities (which together create a unique expression profile) can be interpreted in terms of expression levels of particular genes and can be correlated with a particular disease or condition or treatment.

The composition comprising a plurality of polynucleotide probes can also be used to purify a subpopulation of mRNAs, cDNAs, genomic fragments and the like, in a sample. Typically, samples will include target polynucleotides of interest and other nucleic acids which may enhance the hybridization background; therefore, it may be advantageous to remove these nucleic acids from the sample. One method for removing the additional nucleic acids is by hybridizing the sample containing target polynucleotides with immobilized polynucleotide probes under hybridizing conditions. Those nucleic acids that do not hybridize to the polynucleotide probes are washed away. At a later point, the immobilized target polynucleotide probes can be released in the form of purified target polynucleotides.

Method for Selecting Polynucleotide Probes

This section describes the selection of probe sequences for the plurality of polynucleotide probes. In one embodiment, the probe sequences are selected based on the presence of shared signal sequence motifs. For example, signal sequences generally contain the following features. The signal sequence is composed of 15 to 60 amino-acids which Ere located in the N-terminal region of the protein. Adjacent to the N-terminus is located an n-region which is composed of one to five amino acids which usually carry a positive charge. The second region, the h-region, is composed of 7 to 15 hydrophobic amino acids, creating a hydrophobic core. The third region, the c region, is located between the h-region and the cleavage site and is composed of three to seven polar, but mostly uncharged, amino acids.

Receptor sequences are recognized by one or more hydrophobic transmembrane regions, cysteine disulfide bridges between extracellular loops, an extracellular N-terminus, and a cytoplasmic C-terminus. For example, in G protein-coupled receptors (GPCRs), the N-terminus interacts with ligands, the disulfide bridge interacts with agonists and antagonists, the second cytoplasmic loop has a conserved, acidic-Arg-aromatic triplet which may interact with the G proteins, and the large third intracellular loop interacts with G proteins to activate second messengers such as cyclic AMP, phospholipase C, inositol triphosphate, or ion channel proteins (Watson and Arkinstall (1994) *The G-protein Linked Receptor Facts Book*, Academic Press, San Diego Calif.). Other exemplary classes of receptors such as the tetraspanins (Maecker et al. (1997) FASEB J. 11:428–442), calcium dependent receptors (Speiss (1990) Biochem. 29:10009–18) and the single transmembrane receptors may be similarly characterized relative to their intracellular and extracellular domains, known motifs, and interactions with other molecules.

Proteins associated with cell proliferation may act directly as inhibitors or as stimulators of cell proliferation, growth, attachment, angiogenesis, and apoptosis, or indirectly by modulating the expression of transcription, transcription factors, matrix and adhesion molecules, and cell cycle regulators. In addition, cell proliferation molecules may act as ligands or ligand cofactors for receptors which modulate cell growth and proliferation. These molecules may be identified by sequence homology to molecules whose function has been characterized, and by the identification of their conserved domains. Proteins associated with cell proliferation may be characterized using programs such as BLAST or PRINTS. The characterized, conserved regions of proteins associated with cell proliferation and receptors may be used as probe sequences.

Probe sequences can be selected by screening a large number of clones from a variety of cDNA libraries to discover sequences with conserved protein regions, domains and motifs common to genes coding for proteins associated with cell proliferation and receptors. Multiple sequences which are identified from the cDNA libraries are screened to identify those gene sequences using the BLOCK 2 Bioanalysis program (Incyte Pharmaceuticals, Palo Alto Calif.). This motif analysis program is based on sequence information contained in the SWISS-PROT database and PROSITE and is useful for determining the function of uncharacterized proteins translated from genomic or cDNA sequences (Bairoch et al. (1997) Nucleic Acids Res. 25:217–221; Attwood et al. (1997) J. Chem. Inf. Comput. Sci. 37:417–424, both references herein incorporated by reference). PROSITE is particularly useful to identify functional or structural domains that cannot be detected using motifs due to extreme sequence divergence. The method, which is based on weight matrices, calibrates the motifs against the SWISS-PROT database to obtain a measure of the chance distribution of the matches. Similarly, databases such as PRINTS store conserved motifs useful in the characterization of proteins (Attwood et al. (1998) Nucleic Acids Res 26:304–308). These conserved motifs are used in the selection and design of probe sequences. The PRINTS database can be searched using the BLIMPS search program. The PRINTS database of protein family "fingerprints" complements the PROSITE database and exploits groups of conserved motifs within sequence alignments to build characteristic signatures of different polypeptide families. Alternatively, HMMs can be used to find shared motifs, specifically consensus sequences (Pearson and Lipman (1988) Proc. Natl. Acad. Sci. 85:2444–2448; Smith and Waterman (1981) J. Mol. Biol. 147:195–197). Although HMMs were initially developed to examine speech recognition patterns, they have been used in biology to analyze protein and DNA sequences and to model protein structure (Krogh, supra; Collin, supra). HMMs have a formal probabilistic basis and use position-specific scores for amino acids or nucleotides. The algorithms are flexible in that they incorporate information from newly identified sequences to build even more successful patterns.

In another embodiment, Incyte sequences can be searched for homology using BLAST against GenBank and SWISS-PROT databases. Then the descriptions of the sequence matches may be scanned using keywords such as receptor, transmembrane, oncogene, inhibitor, growth, etc.

Sequences identified by the methods described above are provided in SEQ ID NOS:1–134 in the Sequence Listing. Table 1 provides the annotation for the referenced PROSITE and GenBank sequences. The resulting composition can comprise polynucleotide probes that are not redundant, i.e., there is no more than one polynucleotide probe to represent a particular gene. Alternatively, the composition can contain polynucleotide probes that are redundant, i.e., a gene is represented by more than one polynucleotide probe.

The selected polynucleotide probes may be manipulated further to optimize their performance as hybridization probes. Probes which may not hybridize effectively under hybridization conditions due to secondary structure are avoided. To optimize probe selection, the sequences are examined using a computer algorithm to identify portions of genes without potential secondary structure. Such computer algorithms are well known in the art, such as OLIGO 4.06 software (National Biosciences) or LASERGENE software (DNASTAR). These programs can search nucleotide sequences to identify stem loop structures and tandem repeats and to analyze G+C content of the sequence; those sequences with a G+C content greater than 60% are excluded. Alternatively, the probes can be optimized by trial and error. Experiments can be performed to determine whether probes and complementary target polynucleotides hybridize optimally under experimental conditions.

Where the greatest numbers of different polynucleotide probes are desired, the probe sequences are extended to assure that different polynucleotide probes are not derived from the same gene, i.e., the polynucleotide probes are not redundant. The probe sequences may be extended utilizing the partial nucleotide sequences derived from clone isolates by employing various methods known in the art. For example, one method which may be employed, "restriction-site" PCR, uses universal primers to retrieve unknown sequence adjacent to a known locus (Sarkar (1993) PCR Methods Applic. 2:318–322).

Polynucleotide Probes

This section describes the polynucleotide probes. The polynucleotide probes can be genomic DNA or cDNA or mRNA, or any RNA-like or DNA-like material, such as peptide nucleic acids, branched DNAs and the like. The polynucleotide probes can be sense or antisense polynucleotide probes. Where target polynucleotides are double stranded, the probes may be either sense or antisense strands. Where the target polynucleotides are single stranded, the nucleotide probes are complementary single strands.

In one embodiment, the polynucleotide probes are cDNAs. The size of the DNA sequence of interest may vary and is preferably from 100 to 10,000 nucleotides, more preferably from 150 to 3,500 nucleotides.

In a second embodiment, the polynucleotide probes are plasmids. In this case, the size of the DNA sequence of interest, i.e., the insert sequence excluding the vector DNA and its regulatory sequences, may vary from about 100 to 10,000 nucleotides, more preferably from about 150 to 3,500 nucleotides.

The polynucleotide probes can be prepared by a variety of synthetic or enzymatic schemes which are well known in the art. The probes can be synthesized, in whole or in part, using chemical methods well known in the art Caruthers et al. (1980) Nucleic Acids Res. Symp. Ser. 215–233). Alternatively, the probes can be generated, in whole or in part, enzymatically.

Nucleotide analogues can be incorporated into the polynucleotide probes by methods well known in the art. The only requirement is that the incorporated nucleotide analogues must serve to base pair with target polynucleotide sequences. For example, certain guanine nucleotides can be substituted with hypoxanthine which base pairs with cytosine residues. However, these base pairs are less stable than those between guanine and cytosine. Alternatively, adenine nucleotides can be substituted with 2,6-diaminopurine which can form stronger base pairs than those between adenine and thymidine.

Additionally, the polynucleotide probes can include nucleotides that have been derivatized chemically or enzymatically. Typical chemical modifications include derivatization with acyl, alkyl, aryl or amino groups.

The polynucleotide probes can be immobilized on a substrate. Preferred substrates are any suitable rigid or semi-rigid support including membranes, filters, chips, slides, wafers, fibers, magnetic or nonmagnetic beads, gels, tubing, plates, polymers, microparticles and capillaries. The substrate can have a variety of surface forms, such as wells, trenches, pins, channels and pores, to which the polynucleotide probes are bound. Preferably, the substrates are optically transparent.

Probes can be synthesized, in whole or in part, on the surface of a substrate using a chemical coupling procedure and a piezoelectric printing apparatus, such as that described in PCT publication WO95/251116 (Baldeschweiler et al.). Alternatively, the probe can be synthesized on a substrate surface using a self-addressable electronic device that controls when reagents are added (Heller et al. U.S. Pat. No. 5,605,662).

Complementary DNA (cDNA) can be arranged and then immobilized on a substrate. The probes can be immobilized by covalent means such as by chemical bonding procedures or UV. In one such method, a cDNA is bound to a glass surface which has been modified to contain epoxide or aldehyde groups. In another case, a cDNA probe is placed on a polylysine coated surface and then UV cross-linked (Shalon et al. PCT publication WO95/35505, herein incorporated by reference). In yet another method, a DNA is actively transported from a solution to a given position on a substrate by electrical means (Heller et al. U.S. Pat. No. 5,605,662). Alternatively, individual DNA clones can be gridded on a filter. Cells are lysed, proteins and cellular components degraded, and the DNA coupled to the filter by UV cross-linking.

Furthermore, the probes do not have to be directly bound to the substrate, but rather can be bound to the substrate through a linker group. The linker groups are typically about 6 to 50 atoms long to provide exposure to the attached polynucleotide probe. Preferred linker groups include ethylene glycol oligomers, diamines, diacids and the like. Reactive groups on the substrate surface react with one of the terminal portions of the linker to bind the linker to the substrate. The other terminal portion of the linker is then functionalized for binding the polynucleotide probe.

The polynucleotide probes can be attached to a substrate by dispensing reagents for probe synthesis on the substrate surface or by dispensing preformed DNA fragments or clones on the substrate surface. Typical dispensers include a micropipette delivering solution to the substrate with a robotic system to control the position of the micropipette with respect to the substrate. There can be a multiplicity of dispensers so that reagents can be delivered to the reaction regions simultaneously.

Sample Preparation

In order to conduct sample analysis, a sample containing target polynucleotides is provided. The samples can be any sample containing target polynucleotides and obtained from any bodily fluid (blood, urine, saliva, phlegm, gastric juices, etc.), cultured cells, biopsies, or other tissue preparations.

DNA or RNA can be isolated from the sample according to any of a number of methods well known to those of skill in the art. For example, methods of purification of nucleic acids are described in Tijssen (1993) *Laboratory Techniques in Biochemistry and Molecular Biolcoy: Hybridization With Nucleic Acid Probes, Part I. Theory and Nucleic Acid Preparation*, Elsevier, New York N.Y. In one case, total RNA is isolated using the TRIZOL reagent (Life Technologies, Gaithersburg Md.), and mRNA is isolated using oligo d(T) column chromatography or glass beads. Alternatively, when target polynucleotides are derived from an mRNA, the target polynucleotides can be a cDNA reverse transcribed from an mRNA, an RNA transcribed from that cDNA, a DNA amplified from that cDNA, an RNA transcribed from the amplified DNA, and the like. When the target polynucleotide is derived from DNA, the target polynucleotide can be DNA amplified from DNA or RNA reverse transcribed from DNA. In yet another alternative, the targets are target polynucleotides prepared by more than one method.

When target polynucleotides are amplified it is desirable to amplify the nucleic acid sample and maintain the relative abundances of the original sample, including low abundance transcripts. Total mRNA can be amplified by reverse transcription using a reverse transcriptase and a primer consisting of oligo d(T) and a sequence encoding the phage T7 promoter to provide a single stranded DNA template. The second DNA strand is polymerized using a DNA polymerase and a RNAse which assists in breaking up the DNA/RNA hybrid. After synthesis of the double stranded DNA, T7 RNA polymerase can be added, and RNA transcribed from the second DNA strand template (Van Gelder et al. U.S. Pat. No. 5,545,522). RNA can be amplified in vitro, in situ or in vivo (See Eberwine U.S. Pat. No. 5,514,545).

It is also advantageous to include quantitation controls within the sample to assure that amplification and labeling procedures do not change the true distribution of target polynucleotides in a sample. For this purpose, a sample is spiked with a known amount of a control target polynucleotide and the composition of polynucleotide probes includes reference polynucleotide probes which specifically hybridize with the control target polynucleotides. After hybridization and processing, the hybridization signals obtained should reflect accurately the amounts of control target polynucleotide added to the sample.

Prior to hybridization, it may be desirable to fragment the nucleic acid target polynucleotides. Fragmentation improves hybridization by minimizing secondary structure and cross-hybridization to other nucleic acid target polynucleotides in the sample or noncomplementary polynucleotide probes. Fragmentation can be performed by mechanical or chemical means.

The target polynucleotides may be labeled with one or more labeling moieties to allow for detection of hybridized probe/target polynucleotide complexes. The labeling moieties can include compositions that can be detected by spectroscopic, photochemical, biochemical, bioelectronic, immunochemical, electrical, optical or chemical means. The labeling moieties include radioisotopes, such as $^{32}$P, $^{33}$P or $^{35}$S, chemiluminescent compounds, labeled binding proteins, heavy metal atoms, spectroscopic markers, such as fluorescent markers and dyes, magnetic labels, linked enzymes, mass spectrometry tags, spin labels, electron transfer donors and acceptors, and the like.

Exemplary dyes include quinoline dyes, triarylmethane dyes, phthaleins, azo dyes, cyanine dyes and the like. Preferably, fluorescent markers absorb light above about 300 nm, preferably above 400 nm, and usually emit light at wavelengths at least greater than 10 nm above the wavelength of the light absorbed. Preferred fluorescent markers include fluorescein, phycoerythrin, rhodamine, lissamine, and C3 and C5 available from Amersham Pharmacia Biotech (Piscataway N.J.).

Labeling can be carried out during an amplification reaction, such as polymerase chain and in vitro transcription reactions, or by nick translation or 5' or 3'-end-labeling reactions. In one case, labeled nucleotides are used in an in vitro transcription reaction. When the label is incorporated after or without an amplification step, the label is incorporated by using terminal transferase or by kinasing the 5' end of the target polynucleotide and then incubating overnight with a labeled oligonucleotide in the presence of T4 RNA ligase.

Alternatively, the labeling moiety can be incorporated after hybridization once a probe/target complex has formed. In one case, biotin is first incorporated during an amplification step as described above. After the hybridization reaction, unbound nucleic acids are rinsed away so that the only biotin remaining bound to the substrate is that attached to target polynucleotides that are hybridized to the polynucleotide probes. Then, an avidin-conjugated fluorophore, such as avidin-phycoerythrin, that binds with high affinity to biotin is added. In another case, the labeling moiety is incorporated by intercalation into preformed target/polynucleotide probe complexes. In this case, an intercalating dye such as a psoralen-linked dye can be employed.

Under some circumstances it may be advantageous to immobilize the target polynucleotides on a substrate and have the polynucleotide probes bind to the immobilized target polynucleotides. In such cases the target polynucleotides can be attached to a substrate as described above.

Hybridization and Detection

Hybridization causes a denatured polynucleotide probe and a denatured complementary target to form a stable duplex through base pairing. Hybridization methods are well known to those skilled in the art (See, e.g., Ausubel (1997; *Short Protocols in Molecular Biology*, John Wiley & Sons, New York N.Y., units 2.8–2.11, 3.18–3.19 and 4-6-4.9). Conditions can be selected for hybridization where exactly complementary target and polynucleotide probe can hybridize, i.e., each base pair must interact with its complementary base pair. Alternatively, conditions can be selected where target and polynucleotide probes have mismatches but are still able to hybridize. Suitable conditions can be selected, for example, by varying the concentrations of salt in the prehybridization, hybridization and wash solutions, or by varying the hybridization and wash temperatures. With some membranes, the temperature can be decreased by adding formamide to the prehybridization and hybridization solutions.

Hybridization can be performed at low stringency with buffers, such as 6×SSPE with 0.005% Triton X-100 at 37° C., which permits hybridization between target and polynucleotide probes that contain some mismatches to form target polynucleotide/probe complexes. Subsequent washes are performed at higher stringency with buffers, such as 0.5×SSPE with 0.005% Triton X-100 at 50° C., to retain hybridization of only those target/probe complexes that contain exactly complementary sequences. Alternatively, hybridization can be performed with buffers, such as 5×SSC/0.2% SDS at 60° C. and washes are performed in 2×SSC/0.2% SDS and then in 0.1×SSC. Background signals can be reduced by the use of detergent, such as sodium dodecyl sulfate, Sarcosyl or Triton X-100, or a blocking agent, such as salmon sperm DNA.

Hybridization specificity can be evaluated by comparing the hybridization of specificity-control polynucleotide probes to specificity-control target polynucleotides that are added to a sample in a known amount. The specificity-control target polynucleotides may have one or more sequence mismatches compared with the corresponding polynucleotide probes. In this manner, whether only complementary target polynucleotides are hybridizing to the polynucleotide probes or whether mismatched hybrid duplexes are forming is determined.

Hybridization reactions can be performed in absolute or differential hybridization formats. In the absolute hybridization format, target polynucleotides from one sample are hybridized to the probes in a microarray format, and signals detected after hybridization complex formation correlate to target polynucleotide levels in a sample. In the differential hybridization format, the differential expression of a set of genes in two biological samples is analyzed. For differential hybridization, target polynucleotides from both biological samples are prepared and labeled with different labeling moieties. A mixture of the two labeled target polynucleotides is added to a microarray. The microarray is then examined under conditions in which the emissions from the two different labels are individually detectable. Probes in the microarray that are hybridized to substantially equal numbers of target polynucleotides derived from both biological samples give a distinct combined fluorescence (Shalon et al. PCT publication WO95/35505). In a preferred embodiment, the labels are fluorescent labels with distinguishable emission spectra, such as a lissamine conjugated nucleotide analog and a fluorescein conjugated nucleotide analog. In another embodiment, C3/C5 fluorophores (Amersham Pharmacia Biotech) are employed.

After hybridization, the microarray is washed to remove nonhybridized nucleic acids, and complex formation between the hybridizable array elements and the target polynucleotides is detected. Methods for detecting complex formation are well known to those skilled in the art. In a preferred embodiment, the target polynucleotides are labeled with a fluorescent label, and measurement of levels and patterns of fluorescence indicative of complex formation is accomplished by fluorescence microscopy, preferably confocal fluorescence microscopy. An argon ion laser excites the fluorescent label, emissions are directed to a photomultiplier, and the amount of emitted light is detected and quantitated. The detected signal should be proportional to the amount of probe/target polynucleotide complex at each position of the microarray. The fluorescence microscope can be associated with a computer-driven scanner device to generate a quantitative two-dimensional image of hybridization intensity. The scanned image is examined to determine the abundance/expression level of each hybridized target polynucleotide.

In a differential hybridization experiment, target polynucleotides from two or more different biological samples are labeled with two or more different fluorescent labels with different emission wavelengths. Fluorescent signals are detected separately with different photomultipliers set to detect specific wavelengths. The relative abundances/expression levels of the target polynucleotides in two or more samples is obtained.

Typically, microarray fluorescence intensities can be normalized to take into account variations in hybridization intensities when more than one microarray is used under similar test conditions. In a preferred embodiment, individual polynucleotide probe/target complex hybridization intensities are normalized using the intensities derived from internal normalization controls contained on each microarray.

Expression Profiles

This section describes an expression profile using the composition of this invention. The expression profile can be used to detect changes in the expression of genes implicated in disease. These genes include genes whose altered expression is correlated with cancer, immunopathology, apoptosis and the like.

The expression profile comprises the polynucleotide probes of the invention. The expression profile also includes a plurality of detectable complexes. Each complex is formed by hybridization of one or more polynucleotide probes to one or more complementary target polynucleotides. At least one of the polynucleotide probes, preferably a plurality of polynucleotide probes, is hybridized to a complementary target polynucleotide forming, at least one, preferably a plurality of complexes. A complex is detected by incorporating at least one labeling moiety in the complex. The labeling moiety has been described above. The expression profiles provide "snapshots" that can show unique expression patterns that are characteristic of a disease or condition.

After performing hybridization experiments and interpreting detected signals from a microarray, particular polynucleotide probes can be identified and selected based on their expression patterns. Such polynucleotide probe sequences can be used to clone a full length sequence for the gene or to produce a polypeptide.

Utility of the Invention

The composition comprising a plurality of polynucleotide probes can be used as hybridizable elements in a microarray. Such a microarray can be employed in several applications including diagnostics, prognostics and treatment regimens, drug discovery and development, toxicological and carcinogenicity studies, forensics, pharmacogenomics and the like.

In one situation, the microarray is used to monitor the progression of disease. Researchers can assess and catalog the differences in gene expression between healthy and diseased tissues or cells. By analyzing changes in patterns of gene expression, disease can be diagnosed at earlier stages before the patient is symptomatic. The invention can also be used to monitor the efficacy of treatment. For some treatments with known side effects, the microarray is employed to "fine tune" the treatment regimen. A dosage is established that causes a change in genetic expression patterns indicative of successful treatment. Expression patterns associated with undesirable side effects are avoided. This approach may be more sensitive and rapid than waiting for the patient to show inadequate improvement, or to manifest side effects, before altering the course of treatment.

Alternatively, animal models which mimic a disease, rather than patients, can be used to characterize expression profiles associated with a particular disease or condition. This gene expression data may be useful in diagnosing and monitoring the course of disease in a patient, in determining gene targets for intervention, and in testing novel treatment regimens.

The expression of genes coding for proteins associated with cell proliferation or receptors is closely associated with cancers; in fact, ~73% of the sequences of the Sequence Listing were expressed in cancerous tissues. In particular, the microarray and expression profile is useful to diagnose a cancer such as adenocarcinoma, leukemia, lymphoma, melanoma, myeloma, sarcoma and teratocarcinoma. Such cancers include, but are not limited to, cancers of the adrenal gland, bladder, bone, bone marrow, brain, breast, cervix, colon, gall bladder, ganglia, gastrointestinal tract, heart, kidney, liver, lung, muscle, ovary, pancreas, parathyroid, penis, prostate, salivary glands, skin, spleen, testis, thymus, thyroid and uterus.

The expression of genes coding for proteins associated with cell proliferation or receptors is also closely associated with the immune response. Therefore, the microarray can be used to diagnose immunopathologies including, but not limited to, AIDS, Addison's disease, adult respiratory distress syndrome, allergies, anemia, asthma, atherosclerosis, bronchitis, cholecystitus, Crohn's disease, ulcerative colitis, atopic dermatitis, dermatomyositis, diabetes mellitus, emphysema, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, and autoimmune thyroiditis; complications of cancer, hemodialysis, extracorporeal circulation; viral, bacterial, fungal, parasitic, and protozoal infections; and trauma.

Neuronal processes are also affected by the expression of genes coding for proteins associated with cell proliferation or receptors; in fact, ~38% of the sequences of the Sequence Listing were expressed in neuronal tissues. Thus, the microarray can be used to diagnose neuropathologies including, but not limited to, akathesia, Alzheimer's disease, amnesia, amyotrophic lateral sclerosis, bipolar disorder, catatonia, cerebral neoplasms, dementia, depression, Down's syndrome, tardive dyskinesia, dystonias, epilepsy, Huntington's disease, multiple sclerosis, neurofibromatosis, Parkinson's disease, paranoid psychoses, schizophrenia, and Tourette's disorder.

Also, researchers can use the microarray to rapidly screen large numbers of candidate drug molecules, looking for ones that produce an expression profile similar to those of known therapeutic drugs, with the expectation that molecules with the same expression profile will Likely have similar therapeutic effects. Thus, the invention provides the means to determine the molecular mode of action of a drug.

It is understood that this invention is not limited to the particular methodology, protocols, and reagents described, as these may vary. It is also understood that the terminology used herein is for the purpose of describing particular embodiments only and is not intended to limit the scope of the present invention which will be limited only by the appended claims. The examples below are provided to illustrate the subject invention and are not included for the purpose of limiting the invention.

EXAMPLES

For purposes of example, the preparation and sequencing of the BRAITUT07 cDNA library, from which Incyte Clones 1506513, 1506303, 1506088, 1505958, 1505293, 1505274, 1505025, 1504814, and 1502604 is described. Preparation and sequencing of cDNAs in libraries in the LIFESEQ database (Incyte Pharmaceuticals) have varied over time, and the gradual changes involved use of kits, plasmids, and machinery available at the particular time the library was made and analyzed.

I BRAITUT07 cDNA Library Construction

The BRAITUT07 cDNA library was constructed from cancerous brain tissue obtained from a 32-year-old Caucasian male (specimen #0263A) during excision of cerebral meningeal lesion following diagnosis of cerebral glioma. Pathology indicated a low grade desmoplastic neuronal neoplasm, type not specified. The lesion formed a firm, circumscribed cyst-associated mass involving both white and cortical matter. No definite glial component was evident, and although the intricate vascular pattern mimicked henangioblastoma, that diagnosis was not supported by other studies. The patient presented with nausea, vomiting and headache. Patient history included alcohol, tobacco use, and marijuana use twice a week for six years. Family history included atherosclerotic coronary artery disease in the grandparent(s).

The frozen tissue was homogenized and lysed using a Polytron homogenizer (PT-3000; Brinkmann Instruments, Westbury N.J.) in guanidinium isothiocyanate solution. The lysate was centrifuged over a 5.7 M CsCl cushion using an SW28 rotor in a L8-70M ultracentrifuge (Beckman Instruments, Fullerton Calif.) for 18 hours at 25,000 rpm at ambient temperature. The RNA was extracted with acid phenol pH 4.7, precipitated using 0.3 M sodium acetate and 2.5 volumes of ethanol, resuspended in RNAse-free water, and treated with DNase at 37° C. Extraction and precipitation were repeated as before. The mRNA was isolated with the OLIGOTEX kit (QIAGEN; Santa Clarita Calif.) and used to construct the cDNA library.

The mRNA was handled according to the recommended protocols in the SUPERSCRIPT plasmid system (Life Technologies). The cDNAs were fractionated on a SEPHAROSE CL4B column (Amersham Pharmacia Biotech), and those cDNAs exceeding 400 bp were ligated into pINCY 1 Plasmid (Incyte Pharmaceuticals) which was subsequently transformed into DH5α competent cells (Life Technologies).

II Isolation and Sequencing of cDNA Clones

Plasmid DNA was released from the cells and purified using the REAL Prep 96 olasmid kit (QIAGEN). This kit enabled the simultaneous purification of 96 samples in a 96-well block using multi-channel reagent dispensers. The recommended protocol was employed except for the following changes: 1) the bacteria were cultured in 1 ml of sterile Terrific Broth (Life Technologies) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs were prepared using a MICROLAB 2200 (Hamilton, Reno Nev.) in combination with DNA ENGINE thermal cyclers (PTC200; M. J. Research, Watertown Mass.) and sequenced by the method of Sanger (1975, J. Mol. Biol. 94:441f) using ABI 377 DNA sequencing systems (Perkin-Elmer, Norwalk Conn.).

III Homology Searching of cDNA Clones and their Deduced Proteins

As used herein, "homology" refers to nucleic acid or amino acid sequence similarity when compared with at least a portion of a reference sequence. The GenBank databases which contain previously identified and annotated sequences, were searched for regions of homology using BLAST (Altschul (1993 and 1990) supra).

BLAST involves: 1) finding similar segments between the query sequence and a database sequence, 2) evaluating the statistical significance of any matches that are found, and 3) reporting only those matches that satisfy a user-selectable threshold of significance. BLAST produces alignments of both nucleotide and amino acid sequences to determine sequence similarity. The fundamental unit of the BLAST algorithm output is the High scoring Segment Pair (HSP). An HSP consists of two sequence fragments of arbitrary, but equal lengths, whose alignment is locally maximal and for which the alignment score meets or exceeds a threshold or cutoff score set by the user.

The basis of the search is the product score, which is defined as:

$$\% \text{ sequence identity} \times \% \text{ maximum BLAST score}/100$$

The product score takes into account both the degree of similarity (identity) between two sequences and the length of the sequence match as reflected in the BLAST score. The BLAST score is calculated by scoring +5 for every base that matches in an HSP and −4 for every mismatch. For example, with a product score of 40, the match will be exact within a 1% to 2% error, and, with a product score of 70, the match will be exact. Homologous molecules are usually identified by selecting those which show product scores between 15 and 40, although lower scores may identify related molecules. The P-value for any given HSP is a function of its expected frequency of occurrence and the number of HSPs observed against the same database sequence with scores at least as high. Percent sequence identity refers to the percentage of sequence similarity found in a comparison of two or more amino acid or nucleic acid sequences. Percent identity can be determined electronically, e.g., by using the MEGALIGN program (DNASTAR). The percentage similarity between two amino acid sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no homology between the two amino acid sequences are not included in determining percentage similarity.

IV Selection of Sequences

The sequences found in the Sequence Listing were selected because they possessed motifs, descriptions, domains, regions or other patterns consistent with genes coding for proteins associated with cell proliferation or receptors. HMM was employed along with the Swiss-Prot database (Release 34) to build the models for identification of these sequences. All eukaryotic sequences that were annotated with the words such as "receptor, oncogene, growth factor, and signal peptide" were picked. Sequences with the words "potential", "probable" or "by similarity" were excluded. A nonredundant dataset was created. For the sequences with signal peptides, the first 25 amino acids after the cleavage site of each protein sequence that contained a signal peptide were obtained. A BLAST alignment of these sequences against themselves was performed. A cluster analysis with a BLAST score threshold of 80 was performed and from every resulting cluster one representative sequence was selected. After removing redundancies, sequences of 11 to 90 amino acids in length were selected. About ⅔ of these sequences were used to develop the model, and about ⅓ of these sequences were used to test the model. The HMM was built using HMMER software (Eddy (1996) Curr. Opin. Struct. Biol. 6:361–365), and a bootstrapping evaluation was performed to test the model. For the final selection those sequences containing an N-terminal methionine that were at least 20 to 50 amino acids in length were selected.

Sequences with conserved protein motifs may be searched using the BLOCKS search program. This program analyses sequence information contained in the Swiss-Prot Database and PROSITE and is useful for determining the classification of uncharacterized proteins translated from genomic or cDNA sequences (Bairoch, supra; Attwood, supra). PROSITE is a useful source for identifying functional or structural domains that are not detected using motifs due to extreme sequence divergence. Using weight matrices, these domains are calibrated against the SWISS-PROT database to obtain a measure of the chance distribution of the matches.

The PRINTS database can be searched using the BLIMPS search program to obtain protein family "fingerprints". The PRINTS database complements the PROSITE database by exploiting groups of conserved motifs within sequence alignments to build characteristic signatures of different polypeptide families.

For both BLOCKS and PRINTS analyses, the cutoff scores for local similarity were: >1300=strong, 1000–1300= suggestive; for global similarity were: p<exp−3; and for strength (degree of correlation) were: >1300=strong, 1000–1300=weak.

V Selection Based on Functional Hierarchies

Incyte sequences were searched for homology using BLAST against GenBank and SWISS-PROT databases. The sequences were placed in a relational database which organizes the sequences according to protein function, the relational database is disclosed in copending patent application entitled "Database System Employing Protein Function Hierarchies for Viewing Biomolecular Sequence Data", Ser. No. 08/812,290, now U.S. Pat. No. 6,023,659 herein incorporated by reference. Those sequences containing GenBank and SWISS-PROT annotations were screened electronically using a PERL regular expression file to identify proteins associated with cell proliferation and receptors. The protein groupings screened included extracellular messengers (including cytokines, growth factors, hormones, neuropeptides, oncogenes, and vasomediators), receptors (including GPCRs, tetraspannins, receptor kinases and nuclear receptors), and proteins associated with signaling cascades (including kinases, phosphatases, C proteins, and second messengers such as cyclic AMP, phospholipase C, inositol triphosphate, or ion channel proteins).

VI Preparation of Microarrays

A single 22×22 cm nylon membrane suitable for standard hybridization protocols is spotted with human cDNA clones as follows. The clones are robotically picked and arrayed into 384-well culture dishes. The cultures are gridded, using a Q-BOT robot (Genetix Ltd, Christchurch), onto the nylon membrane at a density up to 36,864 spots per membrane which includes one or more examples of individual genes and at least 38 controls spotted in duplicate. These membranes are suitable for standard hybridization protocols.

Several membranes are placed on LB plates with carbenicillin in bioassay trays and grown for about 16 hours at 42° C. The membranes are placed (colony side up) for 4 minutes on top of Whatman filter paper (Whatman, Lexington Mass.) previously saturated with prewarmed (95° C. to 100° C.) denaturing buffer (1.5M NaCl, 0.5M NaOH). Excess denaturing buffer is removed, and the membranes are saturated for 4 minutes with neutralizing buffer (1.5M NaCl, 1M Tris (Tris[hydroxymethyl] aminomethane) pH 8.0) by placing them (colony side up) on top of Whatman filter paper (Whatman) previously saturated with neutralizing buffer. The membranes are dried until no liquid is visible on their surfaces.

Next the membranes are submerged, colony side down, in 100 ml prewarmed (42° C.) proteinase K buffer which consists of 0.1 M NaCl, 50 mM EDTA pH 8.5, 50 mM Tris pH 8.0, Sarkosyl (1% N-lauroyl sarcosine), and 1 mg/ml proteinase K (Sigma, St. Louis Mo.). After one hour, the membranes are retrieved and placed on Whatman filter paper (Whatman) to dry overnight. Finally, the membranes are exposed to UV light (254 nm for 40 seconds) in a GS Gene Linker UV Chamber (Bio-Rad Laboratories, Hercules Calif.) which cross-links the DNA to the membranes.

Five $\mu$g mRNA and 2 $\mu$l random hexamer (0.5 mg/ml; Life Technologies) are combined in a 1.5 ml RNase-free microcentrifuge tube. The sample is incubated at 70° C. for 10 minutes, placed on ice for five minutes, lyophilized to dryness, and then dissolved in the following: 1.6 $\mu$l 5× first strand buffer, 0.8 $\mu$l 0.1 M DTT, 0.4 $\mu$l 10 mM dA/dCG/dT mix, 4.0 $\mu$l [$^{32}$P] dCTP (3000 Ci/mmol, 10 uCi/$\mu$l) and 1.2 $\mu$l SUPERSCRIPT II RT (200 U/$\mu$l; Life Technologies).

The sample is centrifuged and incubated at 42° C. for 1 to 2 hours and then diluted with 42 Ml of sterile water. Unincorporated nucleotides are removed with a PROBEQUANT G-50 microcolumn (Amersham Pharmacia Biotech). The purified sample is boiled at 95° C. for 3 minutes and then put on ice. To degrade mRNA, 12.5 $\mu$l of 1N NaOH are added to the sample which then is incubated at 37° C. for 10 minutes. The sample is neutralized by addition of 12.5 $\mu$l 1M Tris pH 6.8 and 10 $\mu$l 1M HCl. Degraded RNA is removed with a PROBEQUANT G-50 sicrocolumn.

The hybridization procedure described by Scares et al. (1994; PNAS 91:9228–9232) is followed. Ten mls prewarmed (42° C.) hybridization buffer (0.75 M NaCl, 0.1 M NaPO$_4$, 0.1% (w/v) NaP$_2$O$_7$, 0.15 M Tris pH 7.5, 5× Denhardt solution (Ausubel, supra), 2% sodium dodecyl sulfate (SDS), sheared salmon sperm DNA (100 $\mu$g/ml), 50% formamide) are added to the membranes in hybridization bags for greater than 2 hours to overnight for prehybridization. Radiolabelled probe ($^{32}$P; USB, Cleveland Ohio) is added to a new 10 ml aliquot of the prewarmed hybridization buffer, and hybridization is allowed to proceed at 42° C. for 14 to 16 hours.

After hybridization, membranes are rinsed with 200 ml 2× SSC at room temperature for 5 minutes, washed once with prewarmed 2× SSC plus 1% SDS for 20 minutes at 68° C., and then washed two more times with prewarmed 0.6× SSC plus 1% SDS for 30 minutes at 68° C. Damp membranes are exposed to XOKAT AR film (Eastman Kodak, Rochester N.Y.) for two nights in a PHOSPHOIMAGER cassette (Molecular Dynamics) and developed.

TABLE I

| SEQ | CLONE | PRINT | SIGNATURE | SCORE | STRENGTH | HITS | DESCRIPTION/ORGANISM | GENBANK | p value | CLASS |
|---|---|---|---|---|---|---|---|---|---|---|
| SEQ ID NO:1 | 843193 | PR00049D | WILM'S TUMOR PROTEIN | 1199 | 1459 | 4 | fibroblast growth factor 8 | g1399443 | 8.00E-58 | cell prol |
| SEQ ID NO:2 | 1417346 | PR00375B | HUNTINGTON SIGNATURE | 1255 | 1373 | 2 | BAI 1 [H. sapiens] | g2653432 | 2.70E-46 | cell prol |
| SEQ ID NO:3 | 1450775 | PR00497E | NEUTROPHIL CYTOSOL FACT | 1289 | 1289 | 9 | similar to hyaluronoglucosaminidase | g861300 | 5.90E-90 | cell prol |
| SEQ ID NO:4 | 1472268 | PR00466B | CYTOCHROME B-245 HEABY | 1337 | 1294 | 6 | MG(2+) transport ATPase, P-type | g530433 | 0.999999 | cell prol |
| SEQ ID NO:5 | 1514169 | PR00493A | BREAST CANCER TYPE I | 1327 | 1472 | 1 | very large tegument protein | g1869859 | 0.22 | cell prol |
| SEQ ID NO:6 | 1647183 | PR00640F | GASTRIN-RELEAS. PEPTIDE | 1142 | 1243 | 1 | nonstructural protein 53 | g393258 | 0.95 | cell prol |
| SEQ ID NO:7 | 1730180 | PR00755A | AFLATOXIN BIOSYNTHESIS | 1282 | 1272 | 3 | Ig mu-chain V-region (V-D-J) precurs | g185157 | 1 | cell prol |
| SEQ ID NO:8 | 1753826 | PR00375B | HUNTINGTON SIGNATURE | 1284 | 1350 | 6 | coded for by C. elegans cDNA cm21c7 | g861366 | 1.60E-56 | cell prol |
| SEQ ID NO:9 | 1773002 | PR00498B | NEUTROPHIL CYTOSOL FACT | 1254 | 1033 | 1 | ORF73a [Pinus thunbergiana] | g1262615 | 0.9996 | cell prol |
| SEQ ID NO:10 | 1810626 | PR00708C | ALPHA-1-ACID GLYCOPROT | 1243 | 1399 | 1 | protein-tyrosine phosphatase | g243550 | 0.68 | cell prol |
| SEQ ID NO:11 | 2158529 | PR00375B | HNTINGTON SIGNATURE | 1222 | 1373 | 1 | BAI 1 [H. sapiens] | g2653432 | 5.60E-38 | cell prol |
| SEQ ID NO:12 | 2236316 | PR00763G | COAGULIN SIGNATURE | 1376 | 1414 | 1 | KIAA0317 [H. sapiens] | g2224575 | 1.00E-26 | cell prol |
| SEQ ID NO:13 | 2237722 | PR00324B | NISIN SIGNATURE | 1281 | 1148 | 1 | apoferodoxin | g58086 | 0.8 | cell prol |
| SEQ ID NO:14 | 2314835 | PR00641B | EB11 ORPHAN RECEPTOR | 1264 | 1354 | 3 | platelet-endothelial tetraspan antig | g541613 | 2.70E-42 | cell prol |
| SEQ ID NO:15 | 2519631 | PR00049D | WILM'S TUMOUR PROTEIN | 1274 | 1459 | 4 | unknown [M. musculus] | g2564953 | 4.60E-13 | cell prol |
| SEQ ID NO:16 | 2526432 | PR00652F | 5-HYDROXYTRYPTAMINE 7 | 1351 | 1488 | 3 | secreted frizzled-related protein | g2213819 | 1.70E-160 | cell prol |
| SEQ ID NO:17 | 2742507 | PR00333A | HERPSEVIRUS INTEGRAL | 1038 | 1038 | 1 | protein kinase [A. thaliana] | g166888 | 1 | cell prol |
| SEQ ID NO:18 | 2883288 | PR00405B | HIV REV INTERACT PROT | 1237 | 1254 | 2 | decaprenyl diphosphate synthase | g1845555 | 8.30E-39 | cell prol |
| SEQ ID NO:19 | 2952523 | PR00249G | SECRETIN-LIKE GPCR | 1292 | 1454 | 4 | BAI 1 [H. sapiens] | g2653432 | 1.70E-106 | cell prol |
| SEQ ID NO:20 | 3190833 | PR00402B | TEC/BTK DOMAIN SIGNAT | 1289 | 1370 | 1 | latrophilin-related protein 1 | g2213659 | 6.20E-64 | cell prol |
| SEQ ID NO:21 | 3245612 | PR00249G | SECRETIN-LIKE GPCR | 1292 | 1454 | 4 | BAI 1 [H. sapiens] | g2653432 | 7.10E-104 | cell prol |
| SEQ ID NO:22 | 3270974 | PR00448D | NSF ATTACHMENT PROTEIN | 1321 | 1368 | 4 | BAI 1 [H. sapiens] | g2653432 | 1.90E-84 | cell prol |
| SEQ ID NO:23 | 150629 | PR00489C | FRIZZLED PROTEIN | 1822 | 1494 | 7 | transmembrane receptor [M. muscul | g1151256 | 0 | receptor |
| SEQ ID NO:24 | 158253 | PR00398A | STEROID HORMONE REC | 1294 | 1786 | 2 | seven transmembrane-domain receptor | g2117161 | 1.10E-47 | receptor |
| SEQ ID NO:25 | 172065 | PR00561C | BETA-1 ADRENERGIC REC | 1210 | 1422 | 1 | Numblike [M.musculus] | g2149943 | 0.00032 | receptor |
| SEQ ID NO:26 | 319854 | PR00249C | SECRETIN-LIKE GPCR | 1315 | 1404 | 4 | EMR1 gene product [H. sapiens] | g784994 | 1.60E-229 | receptor |
| SEQ ID NO:27 | 320551 | PR00249G | SECRETIN-LIKE GPCR | 1331 | 1454 | 2 | EMR1 gene product [H. sapiens] | g784994 | 7.00E-35 | receptor |
| SEQ ID NO:28 | 491493 | PR00322E | G10 PROTEIN SIGNATURE | 1585 | 1319 | 2 | latrophilin-related protein 1 | g2213659 | 4.00E-146 | receptor |
| SEQ ID NO:29 | 614640 | PR00652F | 5-HYDROXYTRYPTAMINE 7 | 1262 | 1488 | 3 | p53 transformation associated protei | g1399880 | 1 | receptor |
| SEQ ID NO:30 | 615769 | PR00652F | 5-HYDROXYTRYPTAMINE 7 | 1226 | 1488 | 4 | gtg start codon [Wolinella succin | g48526 | 1 | receptor |
| SEQ ID NO:31 | 713784 | PR00571G | ENDOTHELIN-B RECEPTOR | 1225 | 1420 | 1 | superoxide dismutase [Nocardia aster | g620118 | 0.0013 | receptor |
| SEQ ID NO:32 | 714029 | PR00641B | EB11 ORPHAN RECEPTOR | 1303 | 1354 | 2 | galectin-5 [Rattus sp.] | g727176 | 5.60E-17 | receptor |
| SEQ ID NO:33 | 746308 | PR00553A | ADENOSINE A2A RECEPTOR | 1291 | 1380 | 1 | similar to non-specific endonuclease | g2105496 | 2.70E-33 | receptor |
| SEQ ID NO:34 | 746982 | PR00643H | G10D ORPHAN RECEPTOR | 1278 | 1453 | 7 | nitric oxide synthase [R. norveg | g854727 | 0.999 | receptor |
| SEQ ID NO:35 | 791314 | PR00643H | G10D ORPHAN RECEPTOR | 1355 | 1454 | 3 | GTP-binding protein [A. thaliana] | g807577 | 0.99994 | receptor |
| SEQ ID NO:36 | 832357 | PR00642B | EDG1 ORPHAN RECEPTOR | 1144 | 1218 | 4 | unknown [S. pombe] | g984217 | 0.26 | receptor |
| SEQ ID NO:37 | 838871 | PR00652F | 5-HYDROXYTRYPTAMINE 7 | 1251 | 1488 | 3 | CR3 [Trypanosoma brucei] | g1142588 | 1 | receptor |
| SEQ ID NO:38 | 838872 | PR00560D | ALPHA-2C ADRENERGIC | 1219 | 1642 | 2 | No definition line [C. elegans] | g1825739 | 0.21 | receptor |
| SEQ ID NO:39 | 859761 | PR00643H | G10D ORPHAN RECEPTOR | 1244 | 1453 | 2 | CR3 [T. brucei] | g1142588 | 0.41 | receptor |
| SEQ ID NO:40 | 859956 | PR00565D | DOPAMINE 1A RECEPTOR | 1121 | 1369 | 1 | gamma fibrinogen [Canis latrans] | g1916262 | 0.91 | receptor |
| SEQ ID NO:41 | 867581 | PR00539C | MUSCARINIC M2 RECEPTOR | 1205 | 1365 | 1 | lipoprotein [Mycoplasma hyorhinis] | g581327 | 0.00042 | receptor |
| SEQ ID NO:42 | 936117 | PR00559A | ALPHA-2B ADRENERGIC | 1362 | 1409 | 2 | seven transmembrane-domain receptor | g2117161 | 1.20E-27 | receptor |
| SEQ ID NO:43 | 996903 | PR00636C | AT2 ANGIOTENSIN II REC | 1263 | 1317 | 1 | gastric mucin [Sus scrofa] | g915208 | 0.0075 | receptor |
| SEQ ID NO:44 | 999663 | PR00643H | G10D ORPHAN RECEPTOR | 1254 | 1453 | 3 | muscarinic acetylcholine receptor | g211068 | 0.97 | receptor |
| SEQ ID NO:45 | 1256053 | PR00647I | SENR ORPHAN RECEPTOR | 1407 | 1293 | 1 | frezzled [H. sapiens] | g1688095 | 7.50E-179 | receptor |
| SEQ ID NO:46 | 1262948 | PR00599A | ALPHA-2B ADRENERGIC | 1298 | 1292 | 1 | coded for by C. elegans cDNA yk13e10 | g1072155 | 8.10E-09 | receptor |
| SEQ ID NO:47 | 1271435 | PR00547F | X OPIOID RECEPTOR | 1285 | 1290 | 2 | metallothionein [Balaena mysticetus] | g2460320 | 0.9996 | receptor |
| SEQ ID NO:48 | 1271539 | PR00641F | EB11 ORPHAN RECEPTOR | 1234 | 1292 | 1 | A420L [Paramecium bursaria Chlorella | g1620092 | 1 | receptor |
| SEQ ID NO:49 | 1314935 | PR00522G | CANNABINOID RECEPTOR | 1284 | 1341 | 3 | ORF4 gene product [R. norvegicus] | g56590 | 2.70E-17 | receptor |

| SEQ | CLONE | PRINT | SIGNATURE | SCORE | STRENGTH | HITS | DESCRIPTION/ORGANISM | GENBANK | p value | CLASS |
|---|---|---|---|---|---|---|---|---|---|---|
| SEQ ID NO:50 | 1339906 | PR00537C | MU OPIOID RECEPTOR | 1232 | 1348 | 2 | S [Hepatitis B virus] | g2654220 | 0.94 | receptor |
| SEQ ID NO:51 | 1340918 | PR00647I | SENR ORPHAN RECEPTOR | 1250 | 1293 | 4 | cell wall hydroxyproline-rich glyco | g170454 | 0.25 | receptor |
| SEQ ID NO:52 | 1341346 | PR00571A | ENDOTHELIN-B RECEPTOR | 1242 | 1357 | 1 | small proline rich protein | g338423 | 0.24 | receptor |
| SEQ ID NO:53 | 1373668 | PR00587A | SOMATOSTATN RECEPTOR | 1317 | 1312 | 2 | Sim. to *D. melanogaster* cadherin | g1665821 | 2.30E-08 | receptor |
| SEQ ID NO:54 | 1381411 | PR00595B | P2Y PURINOCEPTOR | 1232 | 1435 | 2 | hypothetical protein [Synechocystis] | g1652005 | 0.99993 | receptor |
| SEQ ID NO:55 | 1383714 | PR00642C | EDG1 ORPHAN RECEPTOR | 1242 | 1193 | 3 | Gcap1 gene product [*M. musculus*] | g862343 | 0.97 | receptor |
| SEQ ID NO:56 | 1396833 | PR00594D | P2U PURINOCEPTOR | 1249 | 1397 | 1 | prpL_2 gene product [*H. sapiens*] | g762951 | 0.1 | receptor |
| SEQ ID NO:57 | 1396995 | PR00665G | OXYTOCIN RECEPTOR | 1226 | 1246 | 2 | unknown [*Methanobacterium thermo*] | g2622854 | 0.999996 | receptor |
| SEQ ID NO:58 | 1398524 | PR00643G | G10D ORPHAN RECEPTOR | 1200 | 1383 | 2 | Bright [*M. musculus*] | g1401348 | 0.86 | receptor |
| SEQ ID NO:59 | 1403508 | PR00522G | CANNABINOID RECEPTOR | 1203 | 1341 | 2 | This CDS feature is included to show | g347362 | 1 | receptor |
| SEQ ID NO:60 | 1466523 | PR00559A | ALPHA-2B ADRENERGIC | 1385 | 1409 | 4 | hSNF2b [*H. sapiens*] | g505088 | 0 | receptor |
| SEQ ID NO:61 | 1466902 | PR00240D | ALPHA-1A ADRENERGIC | 1271 | 1470 | 3 | ORF 3 product [*Haemophilus paragall*] | g303575 | 0.998 | receptor |
| SEQ ID NO:62 | 1468040 | PR00586B | PROSTANOID EP4 RECEPT | 1301 | 1452 | 2 | a652R [*P. bursaria* Chlorella virus 1] | g2447179 | 1 | receptor |
| SEQ ID NO:63 | 1472220 | PR00522G | CANNABINOID RECEPTOR | 1198 | 1341 | 6 | pot. ORF I [*H. sapiens*] | g1335196 | 0.2 | receptor |
| SEQ ID NO:64 | 1474862 | PR00553F | ADENOSINE A2A RECEPTOR | 1194 | 1307 | 1 | spliceosome SAP62 [*M. musculus*] | g633251 | 0.00063 | receptor |
| SEQ ID NO:65 | 1502604 | PR00563C | BETA-3 ADRENERGIC REC | 1201 | 1188 | 1 | slow skeletal muscle troponin T | g339783 | 0.95 | receptor |
| SEQ ID NO:66 | 1504814 | PR00795E | RYANODINE RECEPTOR | 1208 | 1587 | 1 | No definition line [*C. elegans*] | g1334996 | 0.0091 | receptor |
| SEQ ID NO:67 | 1505025 | PR00530C | HISTAMINE H1 RECEPTOR | 1225 | 1317 | 2 | envelope glycoprotein V1V2 region [H | g924359 | 0.995 | receptor |
| SEQ ID NO:68 | 1505274 | PR00490F | SECRETIN RECEPTOR | 1222 | 1239 | 1 | hypothetical protein [*Schizosaccharo*] | g2414582 | 0.67 | receptor |
| SEQ ID NO:69 | 1505293 | PR00522G | CANNABINOID RECEPTOR | 1176 | 1341 | 3 | homeo box 2.6 (Hox-2.6) gene prod | g193944 | 0.13 | receptor |
| SEQ ID NO:70 | 1505958 | PR00643G | G10D ORPHAN RECEPTOR | 1252 | 1383 | 1 | pro-alpha-1 type II collagen [*M. mus*] | g200217 | 1.00E-05 | receptor |
| SEQ ID NO:71 | 1506088 | PR00258C | SPERACT RECEPTOR | 1234 | 1210 | 2 | beta 1,3-glucanase [*Triticum aestivu*] | g924953 | 1 | receptor |
| SEQ ID NO:72 | 1506303 | PR00555F | ADENOSINE A3 RECEPTOR | 1187 | 1259 | 1 | calcium-activated potassium channel | g493571 | 0.21 | receptor |
| SEQ ID NO:73 | 1506513 | PR00575E | RED/GREEN-SENSITIVE OP | 1208 | 1449 | 1 | KIAA0303 [*H. sapiens*] | g2224547 | 0.018 | receptor |
| SEQ ID NO:74 | 1516263 | PR00596D | URIDINE NUCLEOTIDE REC | 1296 | 1255 | 1 | KIAA0435 [*H. sapiens*] | g2262151 | 8.30E-125 | receptor |
| SEQ ID NO:75 | 1553234 | PR00642G | EDG1 ORPHAN RECEPTOR | 1289 | 1242 | 2 | rps3 [*Plasmodium falciparum*] | g1171597 | 1 | receptor |
| SEQ ID NO:76 | 1553883 | PR00645A | LCR1 ORPHAN RECEPTOR | 1277 | 1446 | 1 | glycoprotein gX [Suid herpesvirus 1] | g1304439 | 0.03 | receptor |
| SEQ ID NO:77 | 1555118 | PR00663G | GALANIN RECEPTOR | 1312 | 1160 | 10 | NO definition line [*C. elegans*] | g495696 | 4.40E-10 | receptor |
| SEQ ID NO:78 | 1595762 | PR00249G | SECRETIN-LIKE GPCR | 1286 | 1454 | 4 | 7 transmembrane-domain receptor | g2117161 | 1.80E-31 | receptor |
| SEQ ID NO:79 | 1610212 | PR00512E | 5-HYDROXYTRYPTAMINE 1A | 1273 | 1218 | 2 | naringenin 3-dioxygenase [*Medicago s*] | g475959 | 0.91 | receptor |
| SEQ ID NO:80 | 1611508 | PR00643H | G10D ORPHAN RECEPTOR | 1267 | 1453 | 2 | alpha-amylase/alpha-galactosidase fu | g207854 | 0.9999 | receptor |
| SEQ ID NO:81 | 1616035 | PR00047C | C4-TYPE STEROID RECEPT | 1205 | 1373 | 1 | virion component IV [*Canine adenovir*] | g1477677 | 1 | receptor |
| SEQ ID NO:82 | 1617155 | PR00514D | 5-HYDROXYTRYPTAMINE 1D | 1236 | 1252 | 3 | cyanogen bromide [*Bos taurus*] | g457187 | 0.025 | receptor |
| SEQ ID NO:83 | 1617156 | PR00652F | 5-HYDROXYTRYPTAMINE 7 | 1260 | 1488 | 4 | pF66L [African swine fever virus] | g780504 | 0.71 | receptor |
| SEQ ID NO:84 | 1617720 | PR00497E | NEUTROPHIL CYTOSOL FACT | 1313 | 1289 | 1 | IRLB [*Homo sapiens*] | g33969 | 0.01 | receptor |
| SEQ ID NO:85 | 1622121 | PR00574D | LATERAL EYE OPSIN SIG | 1236 | 1263 | 6 | ZK265.8 [*C. elegans*] | g1667332 | 1 | receptor |
| SEQ ID NO:86 | 1646005 | PR00537C | MU OPIOID RECEPTOR | 1310 | 1348 | 5 | predicted ORF [*Mycobacterium tubercu*] | g1679850 | 1.60E-05 | receptor |
| SEQ ID NO:87 | 1649377 | PR00571G | ENDOTHELIN-B RECEPTOR | 1288 | 1420 | 1 | Ski2 [*X. laevis*] | g1890290 | 0.39 | receptor |
| SEQ ID NO:88 | 1651564 | PR00484C | PHEROMONE ODORANT REC | 1182 | 1272 | 5 | ORF for SH12 [Human herpesvirus 6] | g221458 | 1 | receptor |
| SEQ ID NO:89 | 1652112 | PR00576F | OPSIN RH1/RH2 SIGNAT | 1259 | 1348 | 2 | ORF YNL337w [*S. cerevisiae*] | g1302465 | 0.9992 | receptor |
| SEQ ID NO:90 | 1653770 | PR00643C | G10D ORPHAN RECEPTOR | 1237 | 1286 | 3 | unknown protein [*H. sapiens*] | g119431 | 1.90E-13 | receptor |
| SEQ ID NO:91 | 1693426 | PR00497E | NEUTROPHIL CYTOSOL FACT | 1397 | 1289 | 2 | Sim. to *D. melanogaster* cadherin | g1665821 | 9.90E-41 | receptor |
| SEQ ID NO:92 | 1700601 | PR00578C | LATERAL EYE OPSIN SIG | 1240 | 1102 | 1 | prion protein {intervening sequence | g1911644 | 0.999999 | receptor |
| SEQ ID NO:93 | 1729463 | PR00490F | SECRETIN RECEPTOR | 1167 | 1239 | 2 | carbamyl phosphate synthetase | g203576 | 1 | receptor |
| SEQ ID NO:94 | 1730680 | PR00552B | ADENOSINE A1 RECEPTOR | 1135 | 1353 | 1 | trehalose-6-phosphate synthase | g535003 | 0.68 | receptor |
| SEQ ID NO:95 | 1731419 | PR00581E | PROSTANOID EP2 RECE | 1293 | 1195 | 5 | small proline-rich protein [*O. aries*] | g1296429 | 0.0022 | receptor |
| SEQ ID NO:96 | 1751509 | PR00652F | 5-HYDROXYTRYPTAMINE 7 | 1283 | 1488 | 1 | methyltransferase [*Archaeoglobus ful*] | g2650202 | 0.9991 | receptor |
| SEQ ID NO:97 | 1752114 | PR00553F | ADENOSINE A2A RECEPTOR | 1233 | 1307 | 1 | URF (58 AA) [*Thermoproteus tenax pl vir*] | g62163 | 0.8 | receptor |
| SEQ ID NO:98 | 1819891 | PR00559A | ALPHA-2B ADRENERGIC REC | 1210 | 1409 | 2 | type II small proline-rich protein | g1296427 | 0.16 | receptor |
| SEQ ID NO:99 | 1822832 | PR00554F | ADENOSINE A2B RECEPTOR | 1185 | 1132 | 3 | YSPL-1 form 4 [*M. musculus*] | g1002427 | 0.7 | receptor |

TABLE I-continued

| SEQ | CLONE | PRINT | SIGNATURE | SCORE | STRENGTH | HITS | DESCRIPTION/ORGANISM | GENBANK | p value | CLASS |
|---|---|---|---|---|---|---|---|---|---|---|
| SEQ ID NO:100 | 1823006 | PR00003D | 4-DISULPHIDE CORE | 1243 | 1084 | 1 | Yer119cp [S. cerevisiae] | g603358 | 0.99996 | receptor |
| SEQ ID NO:101 | 1887573 | PR00244H | NEUROKININ RECEPTOR | 1305 | 1780 | 1 | BMK1 alpha kinase [H. sapiens] | g973307 | 4.80E-18 | receptor |
| SEQ ID NO:102 | 1888890 | PR00539E | MUSCARINIC M2 RECEPTOR | 1220 | 1322 | 3 | T13H5.1 [C. elegans] | g1044846 | 1 | receptor |
| SEQ ID NO:103 | 1889526 | PR00652F | 5-HYDROXYTRYPTAMINE 7 | 1232 | 1488 | 1 | ORF_ID:o341#6; sim. to SwissProt P46 | g1736568 | 0.97 | receptor |
| SEQ ID NO:104 | 1900017 | PR00581E | PROSTANOID EP2 RECEPT | 1251 | 1195 | 2 | UL25 FAMILY [Human cytomegalovirus] | g59630 | 0.56 | receptor |
| SEQ ID NO:105 | 1915946 | PR00581E | LYSOZYME G SNGATURE | 1230 | 1195 | 2 | Sec7p [S. cerevisiae] | g1326010 | 0.11 | receptor |
| SEQ ID NO:106 | 1975013 | PR00554D | ADENOSINE A2B RECEPTOR | 1312 | 1208 | 1 | 50S ribosomal protein L33 | g1185259 | 0.35 | receptor |
| SEQ ID NO:107 | 2103670 | PR00553E | ADENSOINE A2A RECEPTOR | 1361 | 1393 | 1 | latrophilin-related protein 1 | g2213659 | 2.70E-87 | receptor |
| SEQ ID NO:108 | 2124411 | PR00543A | OESTROGEN RECEPTOR | 1297 | 1388 | 1 | frpHE [H. sapiens] | g2476420 | 1.70E-203 | receptor |
| SEQ ID NO:109 | 2133755 | PR00527I | GASTRIN RECEPTOR | 1309 | 1633 | 2 | T13H5.2 [C. elegans] | g1044848 | 4.80E-123 | receptor |
| SEQ ID NO:110 | 2206642 | PR00564D | BURKITT'S LYMPHOMA REC | 1236 | 1295 | 1 | 7 transmembrane-domain receptor | g2117161 | 8.70E-18 | receptor |
| SEQ ID NO:111 | 2211526 | PR00047A | C4-TYPE STEROID REC | 1372 | 1480 | 6 | orphan nuclear receptor of steroid/t | g410518 | 3.00E-33 | receptor |
| SEQ ID NO:112 | 2214608 | PR00249G | SECRETIN-LIKE GPCR | 1286 | 1454 | 2 | latrophilin-related protein 1 | g2213659 | 1.50E-110 | receptor |
| SEQ ID NO:113 | 2375244 | PR00489B | FRIZZLED PROTEIN | 1832 | 1391 | 4 | frizzled-3 [M. musculus] | g1151180 | 9.30E-197 | receptor |
| SEQ ID NO:114 | 2512629 | PR00361F | CALCITONIN RECEPTOR | 1241 | 1490 | 1 | cuticle collagen [C. briggsae] | g1814029 | 0.00034 | receptor |
| SEQ ID NO:115 | 2512827 | PR00547B | X OPIOID RECEPTOR | 1280 | 1482 | 1 | apolipoprotein A-IV [Macaca fascicul. | g38051 | 1.20E-15 | receptor |
| SEQ ID NO:116 | 2518961 | PR00647I | SENR ORPHAN RECEPTOR | 1165 | 1293 | 5 | immed-early protein [Equine herpesvi | g330911 | 0.046 | receptor |
| SEQ ID NO:117 | 2520839 | PR00641B | EBI1 ORPHAN RECEPTOR | 1319 | 1354 | 3 | KIAA0366 [H. sapiens] | g2224673 | 0.00029 | receptor |
| SEQ ID NO:118 | 2525666 | PR00587A | SOMATOSTATIN RECEPTOR | 1239 | 1312 | 1 | ORF99 gene product [Alcaligenes eutr | g580706 | 0.097 | receptor |
| SEQ ID NO:119 | 2557294 | PR00489C | FRIZZLED PROTEIN | 1782 | 1494 | 5 | transmembrane receptor [M. musculus] | g1151254 | 1.40E-121 | receptor |
| SEQ ID NO:120 | 2628541 | PR00493C | BREAST CANCER TYPE I | 1202 | 1304 | 1 | RIL protein [M. musculus] | g1565269 | 0.98 | receptor |
| SEQ ID NO:121 | 2639842 | PR00562F | BETA-2 ADRENERGIC REC | 1218 | 1360 | 3 | variant-specific surface protein | g886380 | 0.25 | receptor |
| SEQ ID NO:122 | 2642108 | PR00641B | EBI1 ORPHAN RECEPTOR | 1305 | 1354 | 1 | replication origin binding protein | g1139674 | 1 | receptor |
| SEQ ID NO:123 | 2643475 | PR00240D | ALPHA-1A ADRENERGIC | 1246 | 1470 | 5 | F02D10.1 [C. elegans] | g1066924 | 7.00E-05 | receptor |
| SEQ ID NO:124 | 2668731 | PR00201D | 5-HYDROXYTRYPTAMINE 1D | 1186 | 1252 | 3 | envelope glycoprotein [HIV type 1] | g305465 | 1 | receptor |
| SEQ ID NO:125 | 2715440 | PR00201D | ANNEXIN TYPE V | 1265 | 1578 | 1 | seven transmembrane-domain receptor | g2117161 | 1.60E-68 | receptor |
| SEQ ID NO:126 | 2728317 | PR00409H | PHTHALATE DIOXYGENASE | 1318 | 1118 | 1 | seven transmembrane-domain receptor | g2117161 | 2.00E-36 | receptor |
| SEQ ID NO:127 | 2767250 | PR00594B | P2U PURINOCEPTOR | 1255 | 1452 | 1 | olfactomedin [Rana catesbiana] | g294502 | 1.40E-101 | receptor |
| SEQ ID NO:128 | 3124538 | PR00249G | SECRETIN-LIKE GPCR | 1276 | 1454 | 2 | EMR1 gene product [H. sapiens] | g784994 | 1.20E-46 | receptor |
| SEQ ID NO:129 | 3143858 | PR00489B | FRIZZLED PROTEIN | 1881 | 1391 | 8 | polarity gene; put. [H. sapiens] | g736679 | 3.90E-200 | receptor |
| SEQ ID NO:130 | 3256211 | PR00490C | SECRETIN RECEPTOR | 1336 | 1238 | 2 | Gcap1 gene product [M. musculus] | g862343 | 0.87 | receptor |
| SEQ ID NO:131 | 3324895 | PR00515C | 5-HYDROXYTRYPTAMINE 1F | 1238 | 1353 | 3 | seven transmembrane-domain receptor | g2117161 | 6.10E-20 | receptor |
| SEQ ID NO:132 | 3324971 | PR00005C | APPLE DOMAIN SIGNATURE | 1252 | 1104 | 5 | Ca-independent alpha-latrotoxi rece | g2239297 | 2.40E-116 | receptor |
| SEQ ID NO:133 | 3325283 | PR00512F | 5-HYDROXYTRYPTAMINE 1A | 1326 | 1388 | 1 | neuronal olfactomedin-related ER loc | g442370 | 1.90E-246 | receptor |
| SEQ ID NO:134 | 3603093 | PR00247D | CAMP-TYPE GPCR SIGNAT | 1229 | 1210 | 2 | transmembrane receptor [M. musculus] | g1151260 | 1.50E-30 | receptor |

What is claimed is:

1. A composition comprising a plurality of polynucleotide probes comprising a nucleotide sequence of SEQ ID NOs:1–134.

2. A composition of claim 1, wherein each of the polynucleotide probes comprises a nucleotide sequence coding for proteins associated with cell proliferation.

3. A composition of claim 1, wherein each of the polynucleotide probes comprises a nucleotide sequence coding for receptors.

4. The composition of claim 1, wherein each of the polynucleotide probes comprises a nucleotide sequence of SEQ ID NOs:1–22.

5. The composition of claim 1, wherein the polynucleotide probes comprise a nucleotide sequence of SEQ ID NOs:22–134.

6. The composition of claim 1, wherein the polynucleotide probes are immobilized on a substrate.

7. The composition of claim 6, wherein the polynucleotide probes are hybridizable array elements in a microarray.

* * * * *